US012736526B2

(12) United States Patent
Tekin et al.

(10) Patent No.: US 12,736,526 B2
(45) Date of Patent: Sep. 15, 2026

(54) THREE-DIMENSIONAL HUMAN NEURAL TISSUES FOR CRISPR-MEDIATED PERTURBATION OF DISEASE GENES

(71) Applicants: THE BROAD INSTITUTE, INC., Cambridge, MA (US); MASSACHUSETTS INSTITUTE OF TECHNOLOGY, Cambridge, MA (US)

(72) Inventors: Halil Tekin, Cambridge, MA (US); Feng Zhang, Cambridge, MA (US)

(73) Assignees: The Broad Institute, Inc., Cambridge, MA (US); Massachusetts Institutes of Technology, Cambridge, MA (US)

( * ) Notice: Subject to any disclaimer, the term of this patent is extended or adjusted under 35 U.S.C. 154(b) by 415 days.

(21) Appl. No.: 16/584,546

(22) Filed: Sep. 26, 2019

(65) Prior Publication Data

US 2020/0018746 A1 Jan. 16, 2020

Related U.S. Application Data

(63) Continuation of application No. 16/353,899, filed on Mar. 14, 2019, now abandoned.

(60) Provisional application No. 62/642,920, filed on Mar. 14, 2018.

(51) Int. Cl.

| | |
|---|---|
| ***G01N 33/50*** | (2006.01) |
| ***C12N 5/00*** | (2006.01) |
| ***C12N 5/079*** | (2010.01) |
| ***C12N 5/0793*** | (2010.01) |
| ***G16B 20/00*** | (2019.01) |

(52) U.S. Cl.

CPC ....... *G01N 33/5058* (2013.01); *C12N 5/0062* (2013.01); *C12N 5/0619* (2013.01); *C12N 5/0622* (2013.01); *G16B 20/00* (2019.02); *C12N 2502/086* (2013.01); *C12N 2513/00* (2013.01); *C12N 2533/74* (2013.01); *C12N 2533/80* (2013.01)

(58) Field of Classification Search

CPC ........... G01N 33/5058; G01N 2800/28; C12N 5/0062; C12N 5/0619; C12N 5/0622; C12N 2502/086; C12N 2513/00; C12N 2533/74; C12N 2533/80; C12N 2501/06; C12N 2502/99; C12N 2506/02; C12N 2533/90; G16B 20/00; G16B 40/30; G16B 25/10

See application file for complete search history.

(56) References Cited

PUBLICATIONS

Han et al., Lab on a Chip, 12:2305-2308, 2012 (Year: 2012).*
Meli et al., Stem Cell Research, 13:36-47, 2014 (Year: 2014).*
Brännvall et al., J Neurosci Res, 85:2138-2146, 2007 (Year: 2007).*
Mehrotra et al., J Biomaterial Sci Polym Ed. 23(0); 2012 (Year: 2012).*
Mehrotra et al., J Biomater Sci Polym Ed. 2012 ; 23(0): 1-27 (Year: 2012).*
Schizas et al., J Biomaterial Application, Feb. 2014;28(6):825-36 (Year: 2014).*
Simao et al., Recapitulation of Human Neural Microenvironment Signatures in iPSC-derived NPC 3D Differentiation, Stem Cell Reports 11:552-564, 2018 (Year: 2018).*
Murphy et al., Acta Biomaterialia, 54:1-20, published Mar. 1, 2017.*
Yue et al., Acta Biomaterialia, 58:337-345 Aug. 2017.*
Bian et al., Colloids and Surfaces B: Biointerfaces, 140:392-402, (Year: 2016).*
Engler, A. J. et al.. Matrix elasticity directs stem cell lineage specification. Cell, 126(4), 677-689. (Year: 2006).*
Leipzig, N. D., & Shoichet, M. S. The effect of substrate stiffness on adult neural stem cell behavior. Biomaterials, 30(36), 6867-6878. (Year: 2009).*
Lourenço, T. et al. Modulation of oligodendrocyte differentiation and maturation by combined biochemical and mechanical cues. Scientific Reports, 6, 21563. (Year: 2016).*
Chaudhuri et al., Nature Materials, 13: 970-978, Jun. 15, 2014.*
Corning® Matrigel® Product No. 356237 pamphlet (Year: 1994).*
Saarai et al, J Mechanical Behav of Biomed Materials, 18:152-166, (Year: 2013).*
Zheng, et al., "Massively Parallel Digital Transcriptional Profiling of Single Cells", Nature Communication, vol. 8, Jan. 16, 2017, 12 pages.
Qian, et al., "Brain-Region-Specific Organoids Using Mini-bioreactors for Modeling ZIKV Exposure", Cell, vol. 165, No. 5, Apr. 22, 2016, 1238-1254.
Quadrato, et al., "Cell Diversity and Network Dynamics in Photo-sensitive Human Brain Organoids", Nature,vol. 545, No. 7652, 2017, 48-53.
Quadrato, et al., "The Promises and Challenges of Human Brain Organoids as Models of Neuropsychiatric Disease", Nature Medicine, vol. 22, No. 11, Nov. 2016, 1220-1228.
Renton, et al., "State of Play in Amyotrophic Lateral Sclerosis Genetics", Nature Neuroscience, vol. 17, No. 1, Jan. 2014, 17-23.
Robinson, et al., "Characterization of a Novel Glycoprotein Isolated from the Basement Membrane Matrix of the Engelbreth-Holm-Swarm Tumor", Journal on Biological Chemistry, vol. 264, No. 9, Mar. 25, 1989, 5141-5147.
Satija, et al., "Spatial Reconstruction of Single-Cell Gene Expression", Nature Biotechnolgy, vol. 33, No. 5, May 2015, 495-502.
Schwartz, et al., "Human Pluripotent Stem Cell-Derived Neural Constructs for Predicting Neural Toxicity", Proceedings of the National Academy of Sciences, vol. 112, No. 40, Oct. 6, 2015, 12516-12521.

(Continued)

*Primary Examiner* — Stacey N Macfarlane
(74) *Attorney, Agent, or Firm* — F. Brent Nix, Esq.; Johnson, Marcou, Isaacs & Nix, LLC; Drew P. Harding

(57) ABSTRACT

Described herein are tissue cultures and methods for culturing stem-cell derived neurons in three-dimensional culture. Also provided are methods for screening therapeutic agents, developing cell line models, identifying genes associated with a neurological disease, and identifying genes associated with neuronal cell phenotypes.

34 Claims, 60 Drawing Sheets

Specification includes a Sequence Listing.

(56) References Cited

PUBLICATIONS

Seidlits, et al., "The Effects of Hyaluronic acid Hydrogels with Tunable Mechanical Properties on Neural Progenitor Cell Differentiation", Biomaterials, vol. 31, 2010, 3930-3940.
Shaltouki, et al., "Efficient Generation of Astrocytes from Human Pluripotent Stem Cells in Defined Conditions", Stem Cells, vol. 31, No. 5, May 2013, 941-952.
Shekhar, et al., "Comprehensive Classification of Retinal Bipolar Neurons by Single-Cell Transcriptomics", Cell, vol. 166, No. 5, Aug. 25, 2016, 1308-1323.
Subramanian, et al., "GSEA-P: A Desktop Application for Gene Set Enrichment Analysis", Bioinformatics, vol. 23, No. 23, Dec. 1, 2007, 3251-3253.
Tang, et al., "Astroglial Cells Regulate the Developmental Timeline of Human Neurons Differentiated from Induced Pluripotent Stem Cells", Stem Cell Research, vol. 11, No. 2, Sep. 2013, 743-757.
Tang-Schomer, et al., "Bioengineered Functional Brain-like Cortical Tissue", Proceedings of the National Academy of Sciences of the United States of America, vol. 111, No. 38, Sep. 23, 2014, 13811-13816.
Yi, et al., "Autism-Associated SHANK3 Haploinsufficiency Causes I-h Channelopathy in Human Neurons", Science, vol. 352, No. 6286, 2016, 24 pages.
Zaman, et al., "Migration of tumor cells in 3D matrices is governed by matrix stiffness along with cell-matrix adhesion and proteolysis", Proceedings of the National Academy of Sciences of the United States of America ,vol. 103, No. 29, Jul. 18, 2006, 10889-10894.
Zetsche, et al., "Cpf1 is a Single RNA-Guided Endonuclease of a Class 2 CRISPR-Cas System", Cell, vol. 163, No. 3, Oct. 22, 2015, 759-771.
Zetsche, et al., "Multiplex Gene Editing by CRISPR-Cpf1 using a Single crRNA Array", National Biotechnology, vol. 35, No. 1, Jan. 2017, 31-34.
Zhang, et al., "Rapid Single-Step Induction of Functional Neurons from Human Pluripotent Stem Cells", Neuron, vol. 78, No. 5, May 29, 2013, 785-798.
Tekin, et al., "Effects of 3D Culturing Conditions on the Transcriptomic Profile of Stem-Cell-Derived Neurons," Nature Biomedical Engineering, 2018, https://doi.org/10.1038/s41551-018-0219-9, all enclosed pages cited.
Abel, et al., "Alsod: A user-Friendly Online Bioinformatics Tool for Amyotrophic Lateral Sclerosis Genetics", Human Mutation, vol. 33, No. 9, Sep. 2012, 1345-1351.
Back, et al., "Hyaluronan Accumulates in Demyelinated Lesions and Inhibits Oligodendrocyte Progenitor Maturation", Nature Medicine, vol. 11, No. 9, Jul. 2005, 966-972.
Bennett, et al., "New Tools for Studying Microglia in the Mouse and Human CNS", Proceedings in the National Academy of Sciences, vol. 113, No. 12, Feb. 16, 2016, E1738-E1740.
Bozza, et al., "Neural Differentiation of Pluripotent Cells in 3D Alginate-Based Cultures", Biomaterials, vol. 35, No. 16, 2014, 4636-4645.
Brannvall, et al., "Enhanced Neuronal Differentiation in a Three-Dimensional Collagen-Hyaluronan Matrix", Journal of Neuroscience Research, vol. 85, Aug. 1, 2007, 2138-2146.
Brigham, et al., "Mechanically Robust and Bioadhesive Collagen and Photocrosslinkable Hyaluronic Acid Semi-Interpenetrating Networks", Tissue Engineering, vol. 15, No. 7, Jul. 2009, 1645-1653.
Burdick, et al., "Hyaluronic Acid Hydrogels for Biomedical Applications", Advanced Materials, vol. 23, No. 12, Mar. 25, 2015, H41-H56.
Busskamp, "Rapid Neurogenesis Through Transcriptional Activation in Human Stem Cells", Molecular Systems Biology,vol. 10, No. 760, Nov. 17, 2014, 21 pages.
Camp, et al., "Human Cerebral Organoids Recapitulate Gene Expression Programs of Fetal Neocortex Development", Proceedings of the National Academy of Sciences, vol. 112, No. 51, Dec. 22, 2015, 15672-15677.
Carlson, et al., "Generation and Transplantation of Reprogrammed Human Neurons in the Brain Using 3D Microtopographic Scaffolds", Nature Communications, vol. 7, 2016, 10 pages.
Catanzano, et al., "Alginate-hyaluronan Composite Hydrogels Accelerate Wound Healing Process", Carbohydrate Polymers, vol. 131, 2015, 407-414.
Cauwenberghe, et al., "The Genetic Landscape of Alzheimer Disease: Clinical ilmplications and Perspectives", Genetics in Medicine , vol. 18, No. 5, May 2016, 421-430.
Chanda, et al., "Generation of Induced Neuronal Cells by the Single Reprogramming Factor ASCL1", Stem Cell Reports, vol. 3, Aug. 12, 2014, 282-296.
Chaudhuri, et al., "Extracellular Matrix Stiffness and Composition Jointly Regulate the Induction of Malignant Phenotypes in Mammary Epithelium", Nature Materials, vol. 13, Oct. 13, 2014, 970-978.
Chaudhuri, et al., "Hydrogels with Tunable Stress Relaxation Regulate Stem Cell Fate and Activity", Nature Materials , vol. 15, No. 3, 2016, 326-334.
Chojnacki, et al., "Production of Neurons, Astrocytes and Oligodendrocytes from Mammalian CNS Stem Cells", Nature Protocols, vol. 3, No. 6, 2008, 935-940.
D'Angelo, et al., "Realistic Modeling of Neurons and Networks: Towards Brain Simulation", Functional Neurology, vol. 28, No. 3, Jul. 1, 2013, 153-166.
Dimos, et al., "Induced Pluripotent Stem Cells Generated from Patients with ALS can be Differentiated into Motor Neurons", Science , vol. 321, Aug. 29, 2008, 1218-1221.
Dobin, et al., "STAR: Ultrafast Universal RNA-seq Aligner", Bioinformatics, vol. 29, Issue 1, 2013, 15-21.
Ehrlich, et al., "Rapid and Efficient Generation of Oligodendrocytes from Human Induced Pluripotent Stem Cells Using Transcription Factors", Proceedings in The National Academy of Sciences, vol. 14, No. 11, 2017, E2243-E2252.
Freischmidt, et al., "Haploinsufficiency of TBK1 Causes Familial ALS and Fronto-Temporal Dementia", Nature Neuroscience, vol. 18, 2015, 20 pages.
Gandhi, et al., "Genome-Wide Association Studies: the Key to Unlocking Neurodegeneration?", Nature Neuroscience, vol. 13, 2010, 789-794.
Gao, et al., "Engineered Cpf1 Variants with Altered PAM Specificities", Nature Biotechnology, vol. 35, No. 8, 2017, 789-792.
Gerhard, et al., "On the Stability and Dynamics of Stochastic Spiking Neuron Models: Nonlinear Hawkes Process and Point Process GLMs", PLOS Computational Biology, vol. 13, No. 2, e1005390, Feb. 24, 2017, 31 pages.
Grealish, et al., "Human ESC-Derived Dopamine Neurons Show Similar Preclinical Efficacy and Potency to Fetal Neurons when Grafted in a Rat Model of Parkinson's Disease", Cell Stem Cell, vol. 15, No. 5, Sep. 17, 2014, 653-665.
Habib, et al., "Massively Parallel Single-Nucleus RNA-seq with DroNc-seq", Nature Methods, vol. 14, No. 10, Oct. 2017, 955-958.
Huang, et al., "ApoE4 Differentially Stimulate APP Transcription and Aβ Secretion", Cell, vol. 168, No. 3, 2017, 427-441.
Huebsch, et al., "Harnessing Traction-Mediated Manipulation of the Cell/Matrix Interface to Control Stem-Cell Fate", Nature Materials, vol. 9, No. 6, Jun. 2010, 518-526.
Katz, et al., "Combined Fulminant Frontotemporal Dementia and Amyotrophic Lateral Sclerosis Associated with an I113T SOD1 Mutation", Amyotrophic Lateral Sclerosis, vol. 13, No. 6, Oct. 2012, 567-569.
Khetan, et al., "Degradation-Mediated Cellular Traction Directs Stem Cell Fate in Covalently Crosslinked Three-Dimensional Hydrogels", Nature Materials, vol. 12, No. 5, May 2013, 458-465.
Kim, et al., "Anisotropically Organized Three-Dimensional Culture Platform for Reconstruction of a Hippocampal Neural Network", Nature Communications, vol. 8, Feb. 1, 2017, 16 pages.
Korzhevskii, et al., "Brain Microglia and Microglial Markers", Neuroscience and Behavioral Physiology, vol. 46, No. 3, Jan. 25, 2016, 284-290.
Kraehenbuehl, et al., "Three-Dimensional Biomaterials for the Study of Human Pluripotent Stem Cells", Nature Methods, vol. 8, No. 9, Aug. 30, 2011, 731-736.

(56) References Cited

PUBLICATIONS

Lam, et al., "Functional Maturation of Human Stem Cell-Derived Neurons in Long-Term Cultures", Plos One, vol. 12, No. 1, Jan. 4, 2017, 26 pages.
Lancaster, et al., "Cerebral Organoids Model Human Brain Development and Microcephaly", Nature, vol. 501, No. 7467, Sep. 19, 2013, 373-379.
Lau, et al., "Opinion—Pathophysiology of the Brain Extracellular Matrix: a New Target for Remyelination", Reviews Neuroscience, vol. 14, Oct. 2013, 722-729.
Li, et al., "RSEM: Accurate Transcript Quantification From RNA-Seq Data With or Without a Reference Genome", BMC Bioinformatics, vol. 12, Issue 323, Aug. 4, 2011, 16 pages.
Lill, et al., "Keeping up with Genetic Discoveries in Amyotrophic Lateral Sclerosis: the ALSoD and ALSGene Databases", Amyotrophic Lateral Sclerosis, vol. 12, No. 4, Jul. 2011, 238-249.
Love, et al., "Moderated Estimation of Fold Change and Dispersion for RNA-seq Data with DESeq2", Genome Biology, vol. 15, No. 12, 2014, 21 pages.
Mackenzie, et al., "TDP-43 and FUS in Amyotrophic Lateral Sclerosis and Frontotemporal Dementia", Lancet Neurology, vol. 9, 2010, 995-1007.
Margolis, et al., "Glycosaminoglycans of Brain During Development", Biochemistry, vol. 14, No. 1, 1975, 85-88.
Mccarrol, et al., "Genome-Scale Neurogenetics: Methodology and Meaning", Nature Neuroscience,vol. 17,No. 6, May 2014, 756-763.
Nalls, et al., "Large-Scale Meta-Analysis of Genome-Wide Association Data Identifies Six New Risk Loci for Parkinson's Disease", Nature Genetics, vol. 46, No. 9, Sep. 2014, 989-993.
Nowakowski, et al., "Spatiotemporal Gene Expression Trajectories Reveal Developmental Hierarchies of the hHuman Cortex", Science, vol. 358, No. 6368, Dec. 8, 2017, 1318-1323.
Pandya, et al., "Differentiation of Human and Murine Induced Pluripotent Stem Cells to Microglia-like Cells", Nature Neurocience, vol. 20, No. 5, 2017, 753-759.
Pang, et al., "Induction of Human Neuronal Cells by Defined Transcription Factors", Nature, vol. 476, No. 7359, May 26, 2011, 220-223.
Pasca, et al., "Functional Cortical Neurons and Astrocytes from Human Pluripotent Stem Cells in 3D Culture", Nature Methods, vol. 12, No. 7, 2015, 671-678.
Patel, et al., "Single-cell RNA-seq Highlights Intratumoral Heterogeneity in Primary Glioblastoma", Science, vol. 344, Issue. 6190, Jun. 20, 2014, 1396-1401.
Picelli, et al., "Full-Length RNA-Seq From Single Cells Using Smart-seq2", Nature Protocols, vol. 9, No. 1, 2014, 171-181.
Pollen, et al., "Molecular Identity of Human Outer Radial Glia during Cortical Development", Cell, vol. 163, No. 1, Sep. 24, 2015, 55-67.

* cited by examiner

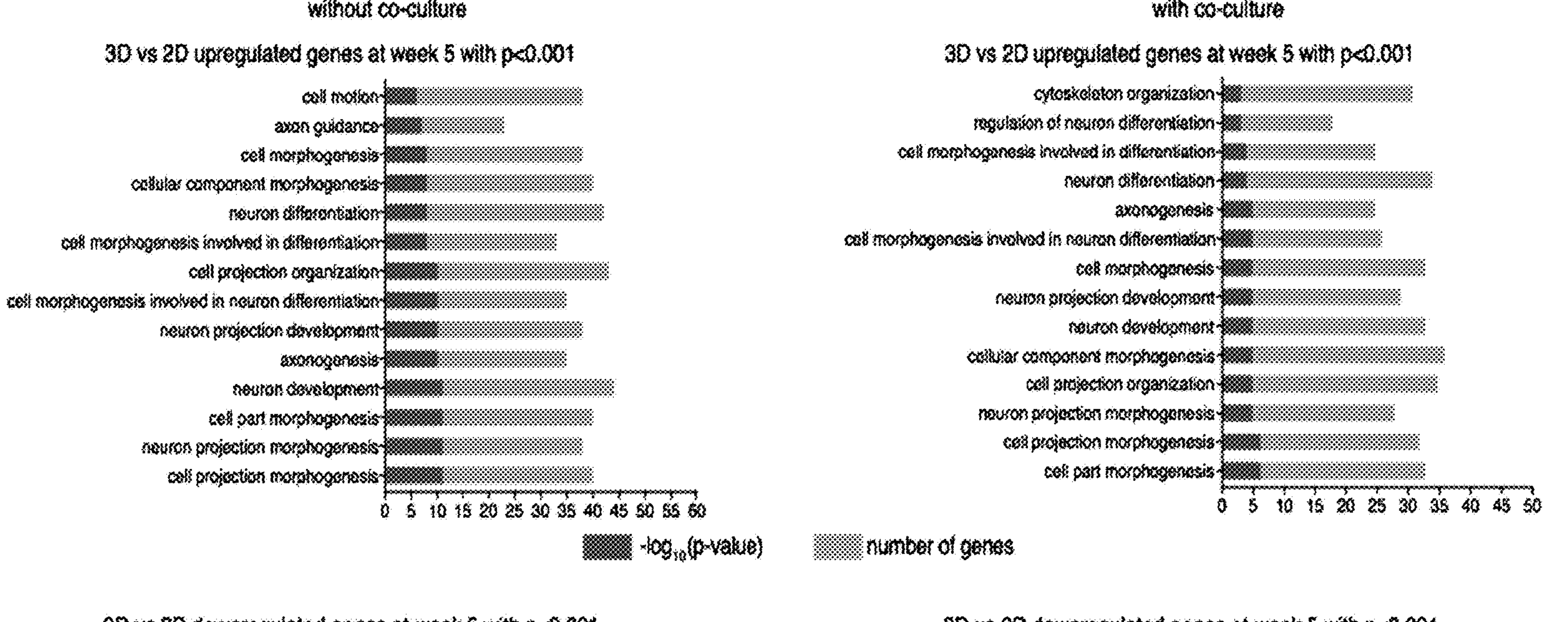
FIG. 1F
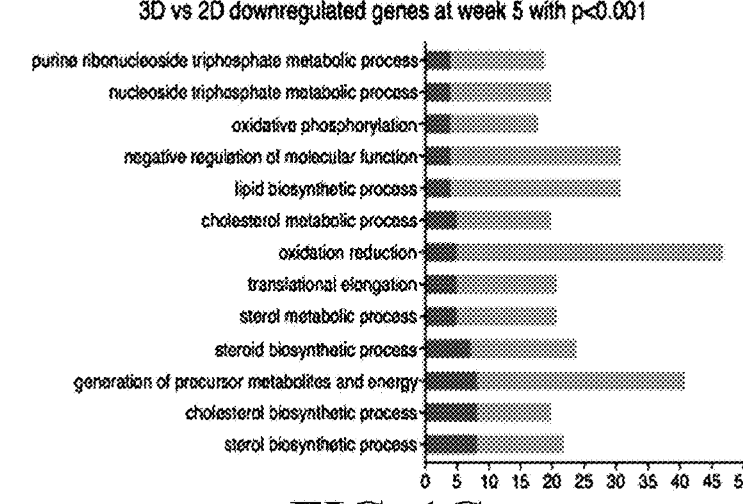
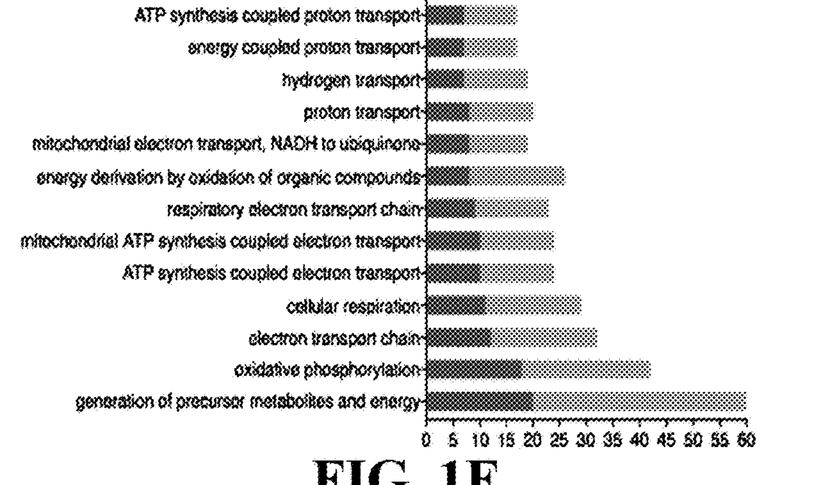
FIG. 1G

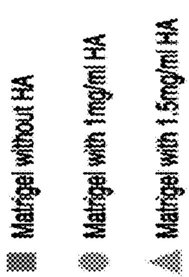
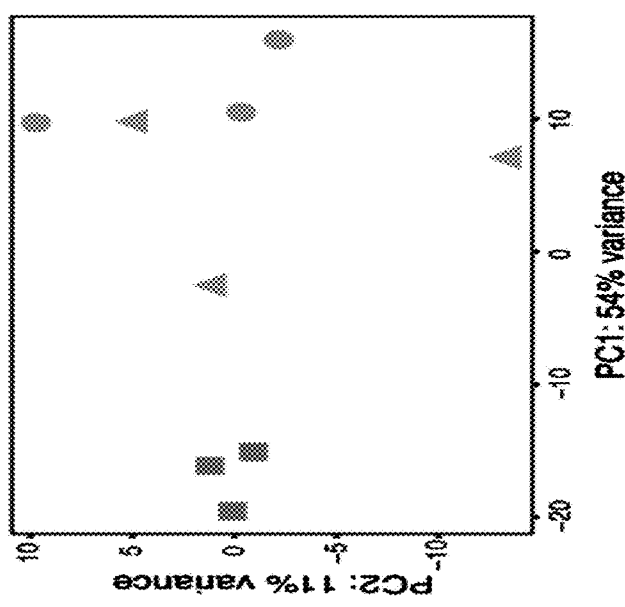
FIG. 2B
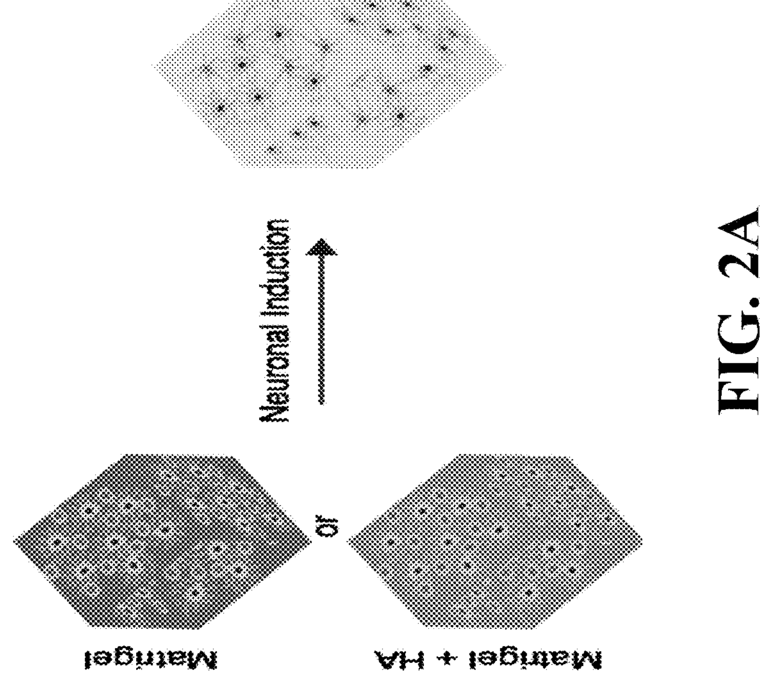
FIG. 2A

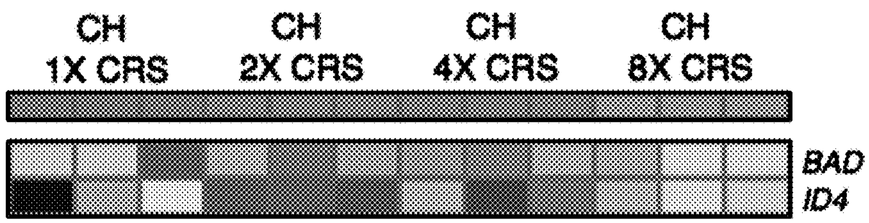
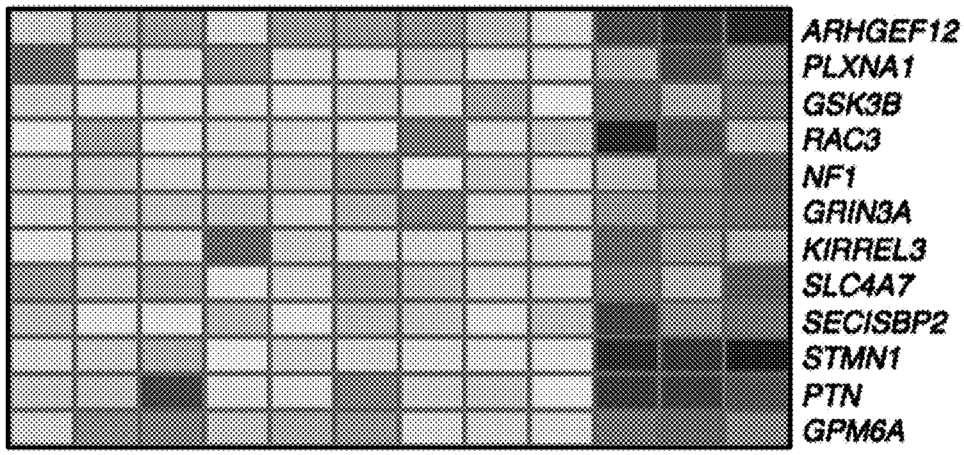
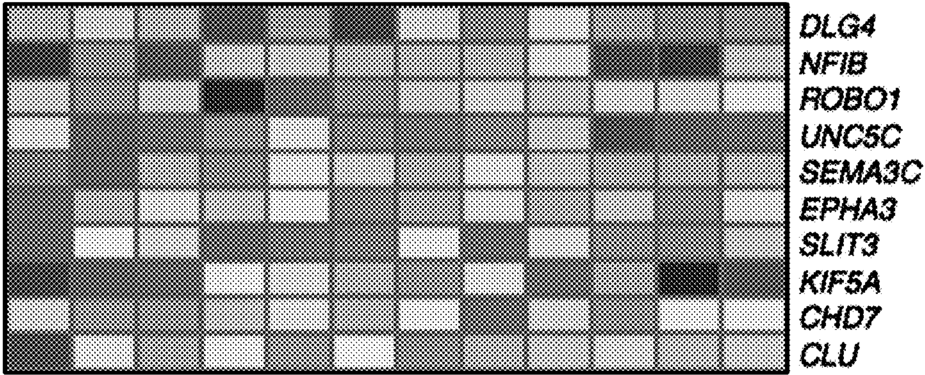
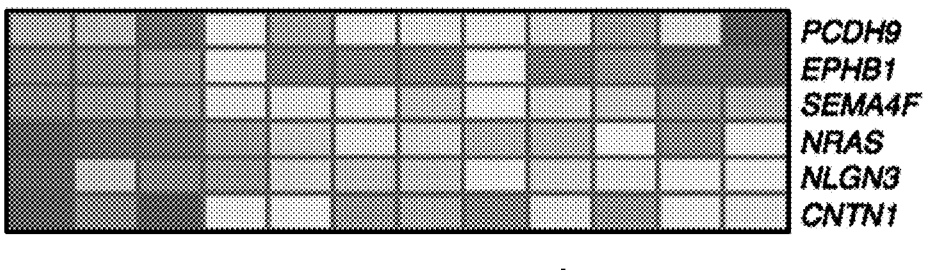
FIG. 3D

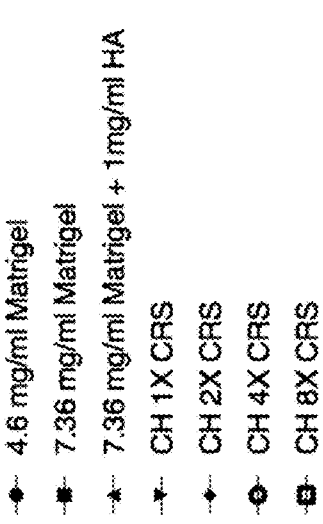
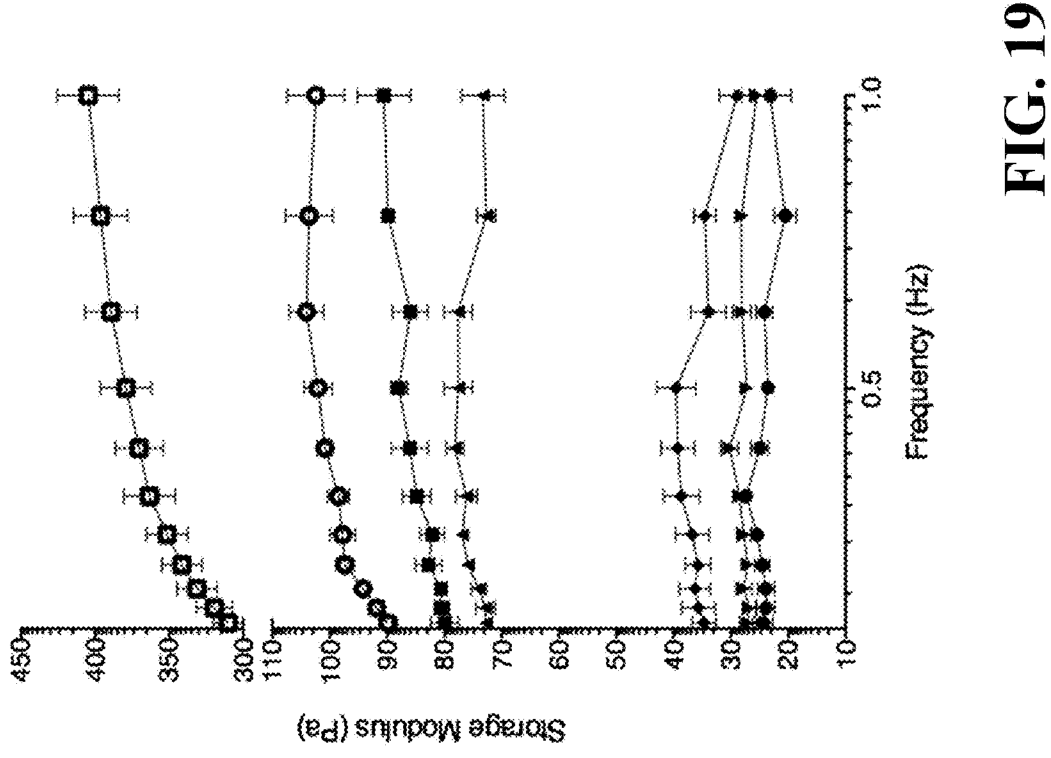
FIG. 19

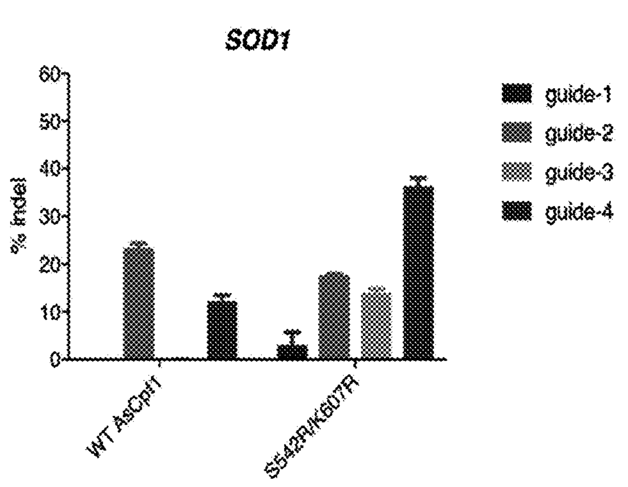

SEQ ID NOS: 1-4

SOD1

| | PAM | Target Sequence |
|---|---|---|
| guide-1 | GCCC | TTCAGCACGCACACGGCCTTCGT |
| guide-2 | TTTC | TGGATAGAGGATTAAAGTGAGGA |
| guide-3 | ACCG | TGTTTTCTGGATAGAGGATTAAA |
| guide-4 | TTCA | ATAGACACATCGGCCACACCATC |

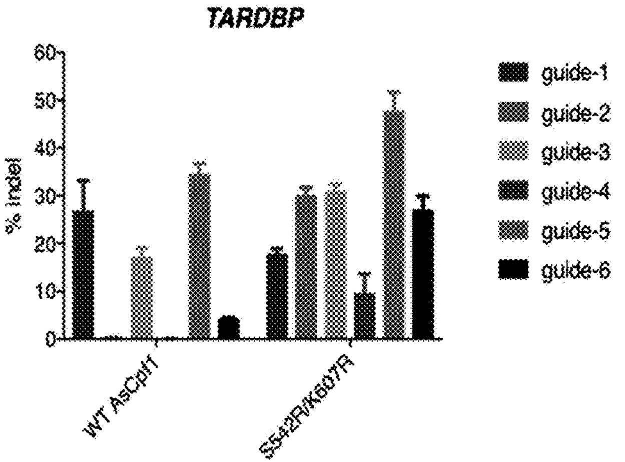

SEQ ID NOS: 5-10

TARDBP

| | PAM | Target Sequence |
|---|---|---|
| guide-1 | TTTC | TCTTTAGGAAAAGTAAAAGATGT |
| guide-2 | ACCC | GAATATATTCAGACATCTTTTAC |
| guide-3 | TTCG | GTTACCCGAATATATTCAGACAT |
| guide-4 | TCCA | GAAAACATCCGATTTAATAGTGT |
| guide-5 | TTCC | ATGGGAGACCCAACACTATTAAA |
| guide-6 | TTCG | GTTGTTTTCCATGGGAGACCCAA |

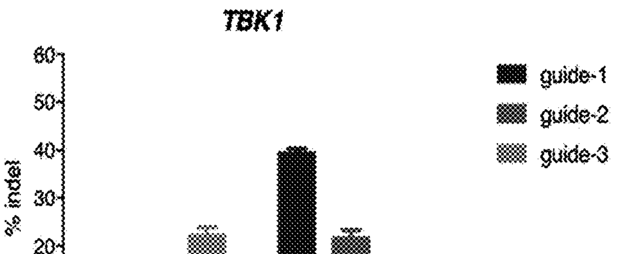

SEQ ID NO: 11-13

TBK1

| | PAM | Target Sequence |
|---|---|---|
| guide-1 | TCCA | GCCAAGATGCAGAGCACTTCTAA |
| guide-2 | GCCA | CAGATGATTAGAAGTGCTCTGCA |
| guide-3 | TTTA | ATAACATAAGCTTCCTTCGTCCA |

FIG. 27

SEQUENCE LISTING

```
<160> NUMBER OF SEQ ID NOS: 34

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1

ttcagcacgc acacggcctt cgt                                              23


<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 2

tggatagagg attaaagtga gga                                              23


<210> SEQ ID NO 3
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 3

tgttttctgg atagaggatt aaa                                              23


<210> SEQ ID NO 4
```

<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 4
atagacacat cggccacacc atc 23

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
tctttaggaa aagtaaaaga tgt 23

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6
gaatatattc agacatcttt tac 23

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 7
gttacccgaa tatattcaga cat 23

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 8
gaaaacatcc gatttaatag tgt 23

<210> SEQ ID NO 9
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 9
atgggagacc caacactatt aaa 23

<210> SEQ ID NO 10
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 10
gttgttttcc atgggagacc caa 23

<210> SEQ ID NO 11
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 11
gccaagatgc agagcacttc taa 23

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 12
cagatgatta gaagtgctct gca 23

<210> SEQ ID NO 13
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 13
ataacataag cttccttcgt cca 23

<210> SEQ ID NO 14
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 14
caaagatggt gtggccgatg tgtctattga agatt 35

<210> SEQ ID NO 15
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 15
aatcttcaat agacacatcg gccacaccat ctttg 35

<210> SEQ ID NO 16
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 16
ccgatttaat agtgttgggt ctcccatgga aaaca 35

<210> SEQ ID NO 17
<211> LENGTH: 35
<212> TYPE: DNA

<213> ORGANISM: Artificial Sequence
<220> FEATURE:
<223> OTHER INFORMATION: Synthetic Oligonucleotide

<400> SEQUENCE: 17
tgttttccat gggagaccca acactattaa atcgg 35

<210> SEQ ID NO 18
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 18
tactaatctt cacgagacgt agaaccgacc tagtc 35

<210> SEQ ID NO 19
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 19
gactaggtcg gttctacgtc tcgtgaagat tagta 35

<210> SEQ ID NO 20
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 20
tgctgacaat ggtgtggccg atgtgtctat tgaa 34

<210> SEQ ID NO 21
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 21
tgctgacaaa gatgtggccg atgtgtctat tgaa 34

<210> SEQ ID NO 22
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 22
tgctgacaaa gaggccgatg tgtctattga a 31

<210> SEQ ID NO 23
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 23
tgctgacaaa gattggccga tgtgtctatt gaa 33

<210> SEQ ID NO 24
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 24
tgctgacaga tggtgtggcc gatgtgtcta ttgaa 35

<210> SEQ ID NO 25
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 25
aaacatccgt gttgggtctc ccatggaa 28

<210> SEQ ID NO 26
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 26
aaacatccga tgttgggtct cccatggaa 29

<210> SEQ ID NO 27
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 27
aaacatccga ttaatgttgg gtctcccatg gaa 33

<210> SEQ ID NO 28
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 28
aaacatccga tgtgttgggt ctcccatgga a 31

<210> SEQ ID NO 29
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 29
aaacatccgg ttgggtctcc catggaa 27

<210> SEQ ID NO 30
<211> LENGTH: 27
<212> TYPE: DNA
<213> ORGANISM: Artificial Sequence
<220> FEATURE:

```
<223> OTHER INFORMATION: Synthetic Oligonucleotide

<400> SEQUENCE: 30

tccagccaag atgcagagca tctgtgg                                    27


<210> SEQ ID NO 31
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 31

tccagccaag atgcagagca ctaatcatct gtgg                            34


<210> SEQ ID NO 32
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 32

tccagccaag atgcagagct aatcatctgt gg                              32


<210> SEQ ID NO 33
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 33

tccagccaag atgcagagca ccatctgtgg                                 30


<210> SEQ ID NO 34
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 34

tccagccaag atgcagatca tctgtgg                                    27
```

THREE-DIMENSIONAL HUMAN NEURAL TISSUES FOR CRISPR-MEDIATED PERTURBATION OF DISEASE GENES

CROSS-REFERENCE TO RELATED APPLICATIONS

This application is a continuation of prior U.S. patent application Ser. No. 16/353,899, filed Mar. 14, 2019, which claims the benefit of U.S. Provisional Application No. 62/642,920, filed Mar. 14, 2018. The entire contents of the above-identified application are hereby fully incorporated herein by reference.

STATEMENT REGARDING GOVERNMENT SUPPORT

This invention was made with government support under Grant Nos. MH100706 and 1RO1-MH110049 granted by the National Institutes of Health. The government has certain rights in the invention.

REFERENCE TO AN ELECTRONIC SEQUENCE LISTING

The contents of the electronic sequence listing ("BROD-2475US-CON_ST25.txt"; Size is 7,153 bytes and it was created on Nov. 18, 2022) is herein incorporated by reference in its entirety.

TECHNICAL FIELD

Described herein are compositions and methods for generating a tractable neural tissue culture and uses thereof.

BACKGROUND

There is increasing evidence that many neurological diseases are caused by or impacted by genetic changes (Bulik-Sullivan, B. et al. *Nature Genetics* 47, 1236 (2015); Quadrato, G., et al. *Nature Medicine* 22, 1220-1228, (2016); Lambert, J. C. et al. *Nature Genetics* 45, 1452-U1206, (2013)). Although advances in next-generation sequencing have led to extensive catalogs of the genetic variation involved in these diseases, understanding the mechanistic outcomes of these mutations has been difficult because we lack tractable genetic models in which to systematically interrogate them (Quadrato, G., et al. *Nature Medicine* 22, 1220-1228, (2016); McCarro, S. A., et al. *Nature Neuroscience* 17, 756-763, (2014); Gandhi, S. et al. *Nature Neuroscience* 13, 789-794, (2010)). A realistic modeling method using microcircuits has been reported for investigating brain functions (D'Angelo et al., *Funct. Neurol.* 28(3), 153-166 (2013)). Statistical frameworks have also been developed to model spiking activity in single-neurons and neuronal networks (Gerhard et al., *PLoS Comput. Biol.,* 13(2), e1005390 (2017)). Yet current approaches do not accurately reflect the cellular state. In particular, it is unclear how the global transcriptome of neural cells in engineered tissues relates to the human brain and how the gene expression profiles of these cells respond to various culturing conditions. There is a need for novel neural tissue culture.

SUMMARY

Neural tissues have the potential to be tractable models for studying the human brain and neurological disorders, but to achieve this potential, they must closely reflect the cell composition, ECM, and gene expression profiles of the human brain. The present disclosure shows that the transcriptome of iN cells in 3D tissues correlates to the human brain transcriptome and is affected by a number of tissue engineering variables. Without being bound by theory, the 3D neural tissue culture of the present disclosure provides a novel system that is spacially and temporally controllable, and loyal to match neural state of cell. In particular, it more accurately captures the gene expression profiles of the human developing brain than currently available models. For example, the transcriptome of the present 3D neural tissue culture shows higher correlation to the developing human bran transcriptome than brain organoids at similar culture time. Controllability of the present 3D neural tissue culture also allows fine tuning of the neuronal transcriptome and precise gene perturbations, as the amount and type of cells in the 3D tissue culture can be determined. Furthermore, described herein is an approach to generate co-cultured iN and astrocytic cells derived from hESCs in a 3D matrix that can be tuned to reflect different transcriptomic states of the human developing brain transcriptome, which allows rapid generation of complex neurological disease models.

The first aspect of the disclosure relates to a tractable neural tissue culture, comprising neuronal and/or glial cells derived from a stem cell and a three dimensional (3D) matrix comprising a biological supporting material configured to decrease the distance in expression space of the neural tissue culture as compared to a target tissue. In some embodiments, the expression space is over one or more genes, 10 or more genes, 20 or more genes, 30 or more genes, 40 or more genes, 50 or more genes, 100 or more genes, 500 or more genes, or 1000 or more genes. In some embodiments, the expression space is over a set of genes. In some embodiments, the set of genes defines a cell pathway. In some embodiments, the expression space is over an entire transcriptome. In some embodiments, distance is measured by a Euclidean distance, pearson coefficient, spearman coefficient, or combination thereof. In some embodiments, changes in the distance in expression space are determined from single cell sequencing data from the neural tissue culture, target tissue, or both.

Another aspect of the disclosure relates to a tractable neural tissue culture, comprising neuronal and/or glial cells derived from a stem cell and a 3D matric comprising a biological supporting material configured to generate a statistically significant shift in gene expression distribution of the neural tissue culture as compared to a target tissue. In some embodiments, the statistically significant shift is over one or more genes, 10 or more genes, 20 or more genes, 30 or more genes, 40 or more genes, 50 or more genes, 100 or more genes, 500 or more genes, or 1000 or more genes. In some embodiments, the statistically significant shift in gene expression distribution is over a set of genes. In some embodiments, the set of genes defines a cell pathway. In some embodiments, the statistically significant shift is measured by a Fisher's exact test, Likelihood ratio test, negative binomial model, beta binomial model, two-stage poisson model, or combination thereof. In some embodiments, the statistically significant shift is least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%.

In some embodiments, the target tissue is a healthy neural tissue or a diseased tissue. In some embodiments, the diseased tissue is representative of tissues associated with a brain cancer, a neurodegenerative disease, a psychiatric or cognitive disorder, or an autoimmune disease. In some embodiments, the diseased tissue is representative of tissues associated with Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), or spinal and bulbar muscular atrophy (SBMA).

In some embodiments, the biological supporting material is selected from the group consisting of one or more extracellular matrix proteins, a basement membrane matrix, collagen, laminin, gelatin, protoglycans, alginate, polyethylene glycol, agarose, chitosan and silk protein-based and other porous scaffolds. In some embodiments, the 3D matrix further comprises a crosslinker. In some embodiments, the glial cell is a human astrocyte. In some embodiments, the 3D matrix further comprises hyaluronic acid. In some embodiments, the neuronal cells are selected from the group consisting of glutamatergic neurons, GABAergic neurons, dopaminergic neurons, microglia, oligodendrocytes, motor neurons, and bipolar neurons. In some embodiments the 3D matrix further comprises a proliferation inhibitor which suppresses proliferation of undifferentiated stem cells. In some embodiments, the proliferation inhibitor is 1-β-D-Arabinofuranosylcytosin (Ara-C).

In some embodiments, increasing the volume of the 3D matrix increases the expression of one or more genes associated with forebrain development, axon guidance, and/or neuron development biological processes.

In the embodiments that comprise hyaluronic acid, neuronal cells express one or more genes involved in neuron and forebrain development, axon guidance, and channel activity, at an increased level compared to the neuronal cells in a tissue culture without hyaluronic acid. In some embodiments, the one or more genes relate to neuronal development, included those listed in FIGS. 3C and 3D and supplemental figures. In certain example embodiments, the one or more gene expressed at an increased level comprise CDK5, RAC3, EPHB1, SOD1, PTEN, DLG4, GRIN3A, NF1, NME1, GSK3B, CHD5, or any combination thereof.

In embodiments that comprise crosslinkers, changing the concentration of the crosslinkers in the 3D matrix alters the expression of one or more genes associated with forebrain development, axon guidance, and neuron development biological processes in the neuronal cells. In further embodiments, increasing the concentration of the crosslinkers in the 3D matrix decreases the expression of one or more of JUN, BDNF, LHX2, OTX1, SIX3, RHOA, SEMA7A, POU4F1, RTN4, and CHN1 in the neuronal cells. In one embodiment, increasing the concentration of the crosslinkers in the 3D matric decreases the expression of NFIB, REGLN, SEMA3C, ROBO1, ROBO1, NTNG1, NLGN3, SEMA3E, LHZ1 or any combination thereof. In some embodiments, increasing the concentration of the crosslinkers in the 3D matrix results in a positive correlation of the transcriptome of the neuronal cells to the transcriptome of human primary visual cortex (V1C), dorsolateral prefrontal cortex (DFC), primary auditory cortex (core), or primary motor cortex (MIC) subregion at the fetal developmental stage of 19 post-conceptual weeks (pcw). In some embodiments, increasing the concentration of the crosslinkers in the 3D matrix results in a positive correlation of the transcriptome of the neuronal cells to the transcriptome of human V1C, DFC, primary auditory cortex (core), or MIC subregion at the fetal developmental stage of 37 pcw.

In some embodiments, the neuronal cells have been modified to express a CRISPR-Cas protein. In some embodiments, the CRISPR-Cas protein is Cas9, Cas13, or Cpf1.

Further aspects of the disclosure relate to methods for generating a tractable neural tissue culture, comprising culturing a sem cell on a two-dimensional plate, inducing differentiation of the stem cell into neuronal and/or glial cells, and detaching and encapsulating the neuronal and/or glial cells in a 3D matrix comprising a biological supporting material configured to decrease the distance in expression space of the neural tissue culture as compared to a target tissue. In some embodiments, the biological supporting material is selected from the group consisting of one or more extracellular matrix proteins, a basement membrane matrix, collagen, laminin, gelatin, proteoglycans, alginate, polyethylene glycol, agarose, chitosan and silk protein-based and other porous scaffolds. In some embodiments, the 3D matrix further comprises a crosslinker. In some embodiments, the tissue culture further comprises hyaluronic acid. In some aspects, the method further comprises co-culturing the neuronal cells with astrocytes. In some embodiments, the neuronal cells are selected from the group consisting of glutamatergic neurons, GABAergic neurons, dopaminergic neurons, microglia, oligodendrocytes, motor neurons, and bipolar neurons. In some embodiments the 3D matrix further comprises a proliferation inhibitor which suppresses proliferation of undifferentiated stem cells. In some embodiments, the proliferation inhibitor is 1-β-D-Arabinofuranosylcytosin (Ara-C).

In some embodiments, the hESCs express one or more transcription factors selected from the group consisting of NGN1, NGN2, Neurod1, ASCl1, Dlx2, SOX10, OLIG2, NKX6.2, ISL1, Lhx3, Phox2a, Brn2, Myt1l, Neurogenin-1, and Neurogenin-2.

Some aspects of the disclosure relate to methods of generating human astrocytic cells, comprising: providing a sample of hESCs, expressing transcription factors NGN1, NGN2, morphogen (ciliary neurotrophic factor) in the hESCs, and culturing the hESCs in fetal bovine serum for a sufficient time for the hESCs to differentiate to astrocytic cells.

Additional aspects of the disclosure relate to methods of identifying a candidate agent for treating a neurological disease, comprising: providing a 3D neural tissue culture comprising neuronal cells derived from hESCs and a 3D matrix comprising a biological supporting material, contacting the 3D neural tissue culture with a test compound, and detecting the expression and/or activity of one or more genes associated with the neurological disease, wherein an increase or decrease of one or more genes associated with the neurological disease indicates that the agent is effective for treating the neurological disease. In some embodiments, the biological supporting material is selected from the group consisting of one or more extracellular matrix proteins, a basement membrane matrix, gelatin, and silk protein-based porous scaffolds. In some embodiments, the 3D matrix further comprises alginate and/or crosslinkers, which form CH with the biological supporting material. In some embodiments, the tissue culture further comprises hyaluronic acid. In some aspects, the method further comprises co-culturing the neuronal cells with astrocytes. In some embodiments, the neurological disease is Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), or spinal and bulbar muscular atrophy (SBMA).

Some aspects of the disclosure relate to kits for screening a candidate agent for treating a neurological disease, comprising: a 3D neural tissue culture comprising neuronal cells derived from hESCs and a 3D matrix comprising a biological supporting material, wherein one or more genes associated with the neurological disease in the neuronal cells have been disrupted. In some embodiments, the biological supporting material is selected from the group consisting of one or more extracellular matrix proteins, a basement membrane matrix, gelatin, and silk protein-based porous scaffolds. In some embodiments, the 3D matrix further comprises alginate and/or crosslinkers, which form CH with the biological supporting material. In some embodiments, the tissue culture further comprises hyaluronic acid. In some aspects, the method further comprises co-culturing the neuronal cells with astrocytes. In some embodiments, the neurological disease is Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), or spinal and bulbar muscular atrophy (SBMA).

In the embodiments wherein the neurological disease is FTD, the one or more genes are SOD1, TARDBP, and TBK1. In the embodiments wherein the neurological disease is ASD, the one or more genes are CLU, TRIP12, UBE3A, CACNA1C, CHD8, SETD5, PTEN, SCN2A, MECP2, SMARCA2, and C12orf57. In the embodiments wherein the neurological disease is ALS, the one or more genes are ZSWIM7, SOD1, NTNG1, LHFP, C9orf72, TARDBP, TBK1, and CNTF. In the embodiments wherein the neurological disease is AD, the one or more genes are CLU, SLC24A4, PARK7, BIN1, PICALM, FERMT2, CELF1, and ABCA7. In the embodiments wherein the neurological disease is AD, the one or more genes are CLU, SLC24A4, PARK7, BIN1, PICALM, FERMT2, CELF1, and ABCA7. In the embodiments wherein the neurological disease is PD, the one or more genes are SNCA, STK39, DLG2, ASH1L, BCKDK, MAPT, TMEM229B, and LRRK2.

Some aspects of the disclosure relate to methods of constructing a cell line model for a neurological disease, comprising (a) providing the tractable neural tissue culture according to any of the proceeding embodiments; (b) identifying differences in one or more cell types and/or cell states between the tractable neural tissue culture and an in vivo system; (c) modulating the density or stiffness of the biological supporting material of the matrix to decrease the distance in expression space between the tractable neural tissue culture and the in vivo system. In some embodiments, identifying differences in one or more cell types and/or cell states comprises comparison of differentially expressed genes. In some embodiments, the biological supporting material is selected from the group consisting of one or more extracellular matrix proteins, a basement membrane matrix, gelatin, and silk protein-based porous scaffolds. In some embodiments, the 3D matrix further comprises alginate and/or crosslinkers, which form CH with the biological supporting material. In some embodiments, the tissue culture further comprises hyaluronic acid. In some aspects, the method further comprises co-culturing the neuronal cells with astrocytes. In some embodiments, the method further comprises mutating an endogenous gene by a CRISPR-Cas system. In some embodiments, the method further comprises transcriptionally activating expression of an endogenous gene by a CRISPR-Cas system. In some embodiments, the method further comprises transcriptionally repressing expression of an endogenous gene by a CRISPR-Cas system. In some embodiments, the method further comprises introducing an exogenous gene by a CRISPR-Cas system. Further aspects of the disclosure relate to a cell line model for a neurological disease obtained by any one of the methods of constructing a cell line model described herein. In some embodiments, the one or more genes associated with the neurological disease are selected from the group consisting of CLU3, TRIP12, UBE3A, CACNA1C, ZSWIM7, SOD1, NTNG1, CLU, SLC24A, SNCA, STK39, and DLG2.

Some aspects of the disclosure relate to methods for identifying a gene associated with a neurological disease comprising: introducing one or more guide RNAs into a 3D neural tissue culture comprising neuronal cells derived from hESCs and a 3D matrix comprising a biological supporting material, wherein the neuronal cells have been modified to express a CRISPR-Cas protein, wherein the neuronal cells either are expressing a CRISPR-Cas9 protein or have had the CRISPR-Cas9 protein or a nucleic acid encoding the CRISPR-Cas9 protein introduced simultaneously or sequentially with guide RNAs, wherein the guide RNAs target one or more endogenous genes; and assaying for a phenotype indicative of a neurological disease in the modified neuronal cells to identify a gene associated with the neurological disease. In some embodiments, the biological supporting material is selected from the group consisting of one or more extracellular matrix proteins, a basement membrane matrix, gelatin, and silk protein-based porous scaffolds. In some embodiments, the 3D matrix further comprises alginate and/or crosslinkers, which form CH with the biological supporting material. In some embodiments, the tissue culture further comprises hyaluronic acid. In some aspects, the method further comprises co-culturing the neuronal cells with astrocytes.

Some aspects of the disclosure relate to methods for identifying a gene associated with a phenotype of neuronal cells, comprising: introducing a library of guide RNAs into a 3D neural tissue culture comprising neuronal cells derived from hESCs and a 3D matrix comprising a biological supporting material, wherein the neuronal cells have been modified to express a CRISPR-Cas protein, wherein the neuronal cells either are expressing a CRISPR-Cas9 protein or have had the CRISPR-Cas9 protein or a nucleic acid encoding the CRISPR-Cas9 protein introduced simultaneously or sequentially with guide RNAs, wherein the guide RNAs target a plurality of endogenous genes; selecting the neuronal cells based on a pre-determined phenotype; and sequencing guide RNAs present in the selected neuronal cells, wherein the enrichment or depletion of guide RNAs are quantified and/or ranked to identify a gene associated with the pre-determined phenotype. In some embodiments, the biological supporting material is selected from the group consisting of one or more extracellular matrix proteins, a basement membrane matrix, gelatin, and silk protein-based porous scaffolds.

In certain example embodiments, methods for astrocyte generation produce low amounts of inhibitory neurons.

Unless otherwise defined, all technical and scientific terms used herein have the same meaning as commonly understood by one of ordinary skill in the art to which this invention belongs. Nonlimiting methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

All references disclosed herein are incorporated by reference. Inhibitory neurons are being generated—Day 15-Day 30, must faster generation compared to organoids.

BRIEF DESCRIPTION OF THE DRAWINGS

FIGS. 1A-G. 3D cultures and co-cultures of hESC-derived human iN cells within Matrigel show enriched neuronal processes compared to 2D cultures and co-cultures. Schematic for generation of (FIG. 1A) 3D and 2D neuronal cultures of human iN cells derived directly from hESCs by transcriptional activation (see also FIGS. 6A and 6B) and (FIG. 1B) 3D and 2D neuronal co-cultures of human iN cells and mouse astrocytes. (FIG. 1C) PCA of gene expression values derived from whole transcriptome sequencing data of 3D and 2D cultured iN cells at 1 week and 5 weeks (n=3 for each condition). For 3D cultures, human iN cells (at a concentration of 10×106 cells/ml) were encapsulated in Matrigel (4.6 mg/ml). (FIG. 1D) PCA of gene expression values derived from whole transcriptome sequencing data of 3D and 2D co-cultured iN cells at 1 week and 5 weeks (n=3 for each condition). For 3D co-cultures, human iN cells and mouse astrocytes (at a concentration of 20×106 cells/ml) were encapsulated in Matrigel (4.6 mg/ml). (FIG. 1E) Venn diagram showing number of differentially upregulated genes with $p<0.05$ for 3D vs 2D cultures and co-cultures and overlap of genes at week 5 (adjusted p value is 0.05). (FIG. 1F) Gene ontology (GO) analysis for differentially upregulated and downregulated genes with $p<0.001$ for 3D vs 2D cultures and (FIG. 1G) co-cultures (adjusted p value is 0.05).

FIGS. 2A-2F: Incorporating HA within Matrigel leads to enriched non-neuronal biological processes in 3D co-cultured human iN cells and decreases gene expression correlation to the human brain developmental transcriptome. (FIG. 2A) Schematic showing human iN cells and mouse astrocytes (at a concentration of $30\times10^6$ cells/ml) encapsulated in Matrigel with or without HA trapped within the Matrigel. (FIG. 2B) PCA of gene expression values derived from whole transcriptome sequencing data of 3D co-cultured iN cells in Matrigel with or without HA at week 5 of culture (n=3 for each condition). (FIG. 2C) GSEA of six enriched non-neuronal biological processes and signaling pathways in iN cells co-cultured in Matrigel doped with HA relative to without HA. (FIG. 2D) Gene expression clusters for iN cells co-cultured in Matrigel with or without HA. GO terms for genes in each cluster are shown. Differentially expressed genes with $p<0.01$ and $\log_2$(fold change)<−1 or $\log_2$(fold change)>1 were used. (FIG. 2E) Relative expression of upregulated genes in iN cells under HA conditions with $p<0.05$ compared to without HA that are associated with neuron development, forebrain development, central nervous system development, and channel activity (see also FIG. 12). (FIG. 2F) Pearson's correlation between RNA-sequencing data of iN cells with/without HA at 5 weeks and human brain transcriptome data of 4 different subregions at 4 fetal developmental stages from the BrainSpan database (http://www.brainspan.org). V1C: primary visual cortex (striate cortex, area V1/17); DFC: dorsolateral prefrontal cortex; A1C: primary auditory cortex (core); M1C: primary motor cortex (area M1, area 4). pcw: post-conceptual weeks. Bars show mean correlation±SEM.

FIGS. 3A-3E: Composite hydrogels (CHs) alter the correlation of gene expression profiles in 3D co-cultured human iN cells to the human brain developmental transcriptome and modulate the expression levels of individual neuronal genes. (FIG. 3A) Schematic showing human iN cells and mouse astrocytes (at a concentration of $20\times10^6$ cells/ml) encapsulated in Matrigel (4.6 mg/ml) or in a CH of Matrigel (4.6 mg/ml) and alginate (5 mg/ml) with varying amounts of the crosslinker (CRS) $CaCl_2$ (1×: 3.125 mM; 2×: 6.25 mM; 4×: 12.5 mM; 8×: 25 mM). (FIG. 3B) PCA based on whole-transcriptome data of co-cultured iN cells at week 5 of culture (n=3 for each condition). (FIG. 3C) Gene expression clusters for iN cells co-cultured for 5 weeks in Matrigel and CH. Heatmaps show selected neuronal genes in each cluster involved in forebrain development, axon guidance, and neuron development, and genes in each cluster associated with neurological diseases (ASD, autism spectrum disorder; ALS, amyotrophic lateral sclerosis), and their relative expression among 3D hydrogel conditions (see also FIGS. 13A-13D, 14A, 14B). Differential expression was performed between co-cultures in CH and co-culture in Matrigel with $p<0.01$ and $\log_2$ (fold change)<−1 or $\log_2$ (fold change)>1 used as cut-offs. (FIG. 3D) Relative expression of neuronal genes across increasing amounts of CRS in CH (see also FIG. 15). Differential expression was performed between co-cultures in CH with 2×, 4× and 8×CRS and co-culture in CH with 1×CRS with $p<0.05$ and $\log_2$ (fold change)<−0.75 or $\log_2$ (fold change)>0.75 used as cut-offs. (FIG. 3E) Pearson's correlation analysis of RNA-sequencing data of co-cultured human iN cells in Matrigel and CH with varying amounts of CRS compared to human brain transcriptome data of 4 different subregions at 4 fetal developmental stages. V1C: primary visual cortex (striate cortex, area V1/17); DFC: dorsolateral prefrontal cortex; A1C: primary auditory cortex (core); M1C: primary motor cortex (area M1, area 4); pcw: post-conceptual weeks. Bars show mean correlation±SEM.

(FIG. 4A) PCA based on whole-transcriptome data of iN cells cultured/co-cultured in a variety of 3D conditions at 5 weeks (symbols are shown at the bottom of the figure) (n=3 for each condition). (FIG. 4B) Storage modulus at 0.5 Hz of different encapsulating hydrogels (n=3 for each condition) (see also FIG. 19). Dots represent storage modulus values for each hydrogel condition. Bars show mean±SEM. (FIG. 4C) Pearson's correlations between RNA-sequencing data of human iN cells cultured/co-cultured in different 3D conditions at 5 weeks and human brain transcriptome data of 2 different subregions at 3 fetal developmental stages. V1C: primary visual cortex (striate cortex, area V1/17); DFC: dorsolateral prefrontal cortex; pcw: post-conceptual weeks (see also FIG. 20*a*). Dots represent correlation values between a 3D condition and a brainspan sample. Each brainspan timepoint-region pair has 1 sample except for 12 pcw, which had 3 samples available for each subregion. Bars show mean correlation±SEM. (FIG. 4D) Expression levels of selected disease-related genes across various 3D conditions encapsulating human iN cells (ASD, autism spectrum disorder; ALS, amyotrophic lateral sclerosis; AD, Alzheimer's disease; PD, Parkinson's disease) (see also FIG. 20*b*) (Abel, 2012 #52). Color schemes are based on z-score distribution.

(FIG. 5A) Astrocytic cells were derived from hESCs using a combination of transcription factors used for neural induction (NGN1 and NGN2), a morphogen (cntf, ciliary neurotrophic factor), and fetal bovine serum (fbs). Expression levels of marker genes for a variety of cell types across different conditions of differentiation protocols at different time points. Undifferentiated hESCs were used as a negative control and human primary astrocytes (huPAst) were used as positive control. Astro: Astrocyte marker genes; RG: Radial Glia marker genes; NE: Neuroepithelial cells marker genes; IPC: Intermediate Progenitor Cells marker genes; ExcN: Excitatory Neurons marker genes; InhbN: Inhibitory Neurons marker genes. Color schemes are based on z-score distribution. (n=3 for all conditions). (see also FIGS. 21A, 21B, 22, 23A-23C, 24B, and 24C). (FIG. 5B) Schematic showing generation of 3D human neural tissues composed of human iN cells and human astrocytic cells both directly derived from hESCs. (FIG. 5C) PCA based on whole-transcriptome data of iN cells cultured alone or co-cultured with either human primary astrocytes (iN–huPAst) or human astrocytic cells (iN–huAstC) in Matrigel (7.36 mg/ml) at 5 weeks. (n=3 for each condition, $10^3$ iN cells were sorted from each replicate for each condition)(see also FIGS. 24D, 24E). (FIG. 5D) Venn diagram showing number of differentially upregulated genes with p<0.05 for iN–huPAst vs only iN and iN–huAstC vs only iN and overlap of genes at week 5 (adjusted p value is 0.05). (FIG. 5E) GO analysis for differentially upregulated genes with p<0.05 for iN–huPAst vs only iN and iN–huAstC vs only iN. FDR: False Discovery Rate. (FIG. 5F) A t-distributed stochastic embedding (tSNE) plot of single-cell RNA sequencing (scRNA-seq) profiles from iN cells co-cultured with mouse astrocytes (iN–mAst) and from co-culture of iN cells and human astrocytic cells (iN+huAstC). Cells are colored by condition membership. Both cultures were performed in CH 4×CRS. (n=3 for each condition). (FIG. 5G) A tSNE plot showing identified clusters of distinct cell types with cells colored by cluster membership and (FIG. 5H) number of cells in each cell type for each condition for scRNA-seq profiles shown in FIG. 25F (see also FIGS. 25A-25G). (FIG. 5I) Pearson's correlations between the average gene expression in cell type clusters shown in FIG. 5G for each condition (rows) and cell types defined by scRNA-seq in the human fetal cortex[39] (columns) (see also FIGS. 26A, 26B). Excitatory: Excitatory Neurons; Newborn Excitatory: Newborn Excitatory Neurons; Inhibitory: Inhibitory Neurons; Newborn Inhibitory: Newborn Inhibitory Neurons; IPC: Intermediate Progenitor Cells. (FIG. 5J) Pearson's correlations between the average gene expression in cell type clusters shown in FIG. 5G for each condition (rows) and cell types defined by scRNA-seq in the human fetal cortex[38] (columns) (see also FIG. 25E). Int-Neu: Interneurons; IPC: Intermediate Progenitor Cells; RG: Radial Glia cells. (FIG. 5K) Pearson's correlations between the average gene expression in cell type clusters shown in FIG. 5G for each condition (rows) and cell types (Excitatory Neurons, Inhibitory Neurons, and Astrocytes) defined by DroNC-seq (single-nucleus RNA sequencing with droplet technology) in the adult post-mortem human brain tissue[40] (columns) (see also FIG. 25F). (FIG. 5L) Pearson's correlations between the average gene expression in cell type clusters shown in FIG. 5G for each condition (rows) and main clusters and forebrain subclusters defined by scRNA-seq in six-month-old human brain organoids[16] (columns) (see also FIG. 25G). Forebrain subclusters were derived from forebrain cluster shown in main clusters. IPC: Intermediate Progenitor Cells (FIG. 6*a*) Schematic showing neural tissue formation by encapsulating hESCs within a 4.6 mg/ml Matrigel hydrogel and activating transcription factors (NGN2 and NGN1) by delivering doxycyclin to cells in the matrix. Image of calcein stained 3D cultured cells at day 5 show encapsulated cells form aggregates. (FIG. 6*b*) Schematic showing neural tissue formation by first inducing neurons from hESCs on 2D cultures by activating transcription factors (NGN2 and NGN1) followed by drug selection (puromycin), and then encapsulation of iN cells within a 4.6 mg/ml Matrigel hydrogel. (FIG. 6*c*) Phase image of encapsulated cells following neural induction on 2D cultures. Arrows point to cell aggregates formed in the hydrogel matrix within 2 days. (FIG. 6*d*) Cell aggregates formed in 3D (4.6 mg/ml) Matrigel hydrogels resulted in spheroids at day 30 which are shown by fluorescent images of cells stained with antibodies against MAP2 and PAX6. (FIG. 6*e*) Initial neural induction on 2D cultures was modified by performing stronger drug selection (puromycin) following transcription activation (NGN2 and NGN1) in the presence of a proliferation inhibitor (Ara-C) introduced into culture medium after encapsulating cells in 3D (4.6 mg/ml Matrigel) matrix. Confocal z-stack images (with 10×, 20×, and 63× objectives) of pure 3D neural tissue at day 40 without cell aggregates formed by culturing iN cells in 4.6 mg/ml Matrigel (with MAP2 and DAPI staining).

(FIG. 7*a*) Gene set enrichment analysis (GSEA) of representative enriched biological processes or signaling pathways in 3D (red) and 2D (blue) cultured iN cells at week 5 (represented in FIGS. 1A, 1C). Normalized Enrichment Scores and nominal p values are shown as well as $\log_2$ (fold change) (bottom) of genes contributing to core enrichment for each plot. (FIG. 7*b*) qPCR validation of selected genes from RNA-sequencing data at 5 weeks. (n=3 for all conditions).

(FIG. 8*a*) Principal component analysis (PCA) of whole transcriptome data of 3D and 2D cultured iN cells at 1 week and 5 weeks (n=3 for each condition). For 3D cultures, human iN cells (at a concentration of $10\times10^6$ cells/ml) were encapsulated in Matrigel (4.6 mg/ml) from two different batches, Batch-1 Matrigel and Batch-2 Matrigel. (FIG. 8*b*) Venn diagrams showing number of differentially upregulated genes with p<0.05 for 3D vs 2D cultures of iN cells using two different batches of Matrigel and overlap genes at week 5 (adjusted p value is 0.05). (FIG. 8*c*) Gene ontology (GO) analysis for differentially upregulated and downregulated genes with p<0.05 for 3D vs 2D cultures of iN cells using two different batches of Matrigel (adjusted p value is 0.05). (FIG. 8*d*) PCA of whole transcriptome data of 3D cultured iN cells cultured (at $10\times10^6$ cells/ml) in either 4.6 mg/ml or 7.36 mg/ml Matrigel (from same batch) at 1 week and 5 weeks (n=3 for each condition). (FIG. 8*e*) GO analysis for upregulated genes with p<0.05 in iN cells cultured within either 4.6 mg/ml or 7.36 mg/ml Matrigel at week 5. Differential expression analysis between 3D cultures in 4.6 mg/ml and 7.36 mg/ml Matrigel was performed by taking adjusted p value 0.05.

(FIG. 9*a*) Relative expression of genes associated with channel activity and channel complexes showing significant ($p<0.05$) upregulation in iN cells cultured either within 4.6 mg/ml or 7.36 mg/ml Matrigel compared to 2D cultured iN cells at 5 weeks (n=3 for each condition). (FIG. 9*b*) iN cells cultured in 7.36 mg/ml Matrigel at 36 days exhibit neuronal excitability and spontaneous excitatory postsynaptic currents (sEPSCs) (n=6 iN cells). 3 out of 6 patched 3D cultured iN cells showed spontaneous activity. iN cells were patched while they were in the 3D matrix; 2D cultured iN cells at same time point could not be patched. (FIG. 9*c*) Representative phase images at week 5 of 2D cultured iN cells and 3D cultured iN cells (in 7.36 mg/ml Matrigel).

(FIG. 10*a*) We compare the number of mouse genes expressed to the number of human genes expressed in each sample, as well as comparing the number of reads mapping to mouse (excluding those mapping to Rn45s) to the number of reads mapping to human. Note these results are based on running RSEM using a joint human and mouse transcriptome. We see that samples consisting only of mouse cells have very little contaminating human reads and vice versa, while mixed samples contain both. (FIG. 10*b*) PCA for whole-transcriptome data of iN cells in 3D co-cultures (iN cells+mouse astro) or pure iN cells cultures (just iN cells) at 1 week and 5 weeks (n=3 for each condition). For co-cultures, iN cells derived from hESCs and mouse astrocytes (1:1 ratio at total $20\times10^6$ cells/ml) were co-cultured in 3D (4.6 mg/ml Matrigel) hydrogels. For pure iN cells cultures, iN cells (at $10\times10^6$ cells/ml) were cultured in 3D (4.6 mg/ml Matrigel) hydrogels. (FIG. 10*c*) Relative expression of genes significantly ($p<0.05$) upregulated in 3D co-cultured iN cells compared to 3D pure cultures of iN cells at 5 weeks associated with neurological processes.

(FIG. 11*a*) Plots demonstrating excitability iN cells co-cultured with mouse astrocytes (Neuron+Astro) in a 3D hydrogel (7.36 mg/ml Matrigel) or on a 2D surface. (FIG. 11*b*) Absolute resting membrane potential and membrane capacitance for iN cells co-cultured with mouse astrocytes (Neuron+Astro) either in 3D or on 2D and 3D only iN cell cultures (Neuron) are shown. (FIG. 11*c*) Plots showing representative sEPSCs of human iN cells co-cultured with mouse astrocytes (Neuron+Astro) in 3D hydrogels (7.36 mg/ml Matrigel) (n=6 iN cells were measured for spontaneous activity) or on 2D surfaces (n=5 iN cells were measured for spontaneous activity). 6 out of 6 3D co-cultured iN cells showed spontaneous activity, while 5 out of 5 2D co-cultured iN cells showed spontaneous activity.

(FIG. 13*a*) Storage modulus at 0.5 Hz of 4.6 mg/ml Matrigel and CH formed with varying amounts of crosslinker (CRS), $CaCl_2$ (1×: 3.125 mM; 2×: 6.25 mM; 4×: 12.5 mM; 8×: 25 mM) (n=3 for each condition). Relative expression of genes associated with (FIG. 13*b*) forebrain development process, (FIG. 13*c*) axon guidance pathway, and (FIG. 13*d*) neuron development process in iN cells co-cultured within either Matrigel (4.6 mg/ml) or CH formed with varying amounts of CRS. Differential expression was processed between co-cultures in CHs and co-culture in Matrigel. Differentially expressed genes with $p<0.01$ and $\log_2$ (fold change)<−1 or $\log_2$ (fold change)>1 were used for intersecting with the gene sets of neuronal processes.

(FIG. 16*a*) Schematic showing generation of 3D co-cultures of human iN cells and mouse astrocytes (at a concentration of $30\times10^6$ cells/ml) to evaluate the addition of HA (either at 1 mg/ml or at 1.5 mg/ml concentration) within a CH of Matrigel (4.6 mg/ml) and alginate (5 mg/ml) with varying amounts of $CaCl_2$ (1×: 3.125 mM; 2×: 6.25 mM; 4×: 12.5 mM; 8×: 25 mM). (FIG. 16*b*) PCA based on whole-transcriptome data of co-cultured iN cells in CHs without HA at week 5 (n=3 for each condition). (FIG. 16*c*) Pearson's correlation analysis comparing RNA-sequencing data of co-cultured human iN cells in CH with/without two different concentrations of HA with varying amounts of CRS to human brain transcriptome data of 4 different subregions at 4 fetal developmental stages. V1C: primary visual cortex (striate cortex, area V1/17); DFC: dorsolateral prefrontal cortex; A1C: primary auditory cortex (core); M1C: primary motor cortex (area M1, area 4). pcw: post-conceptual weeks. Bars show mean correlation±SEM.

(FIG. 17*a*) Schematic showing generation of 3D co-cultures of human iN cells and mouse astrocytes (with $30\times10^6$ cells/ml) in either 200 μl or 50 μl CH (4.6 mg/ml Matrigel and 5 mg/ml alginate) with 2×CRS (6.25 mM $CaCl_2$). (FIG. 17*b*) PCA based on whole-transcriptome data of co-cultured iN cells at week 5 in two different volumes of CHs (n=3 for each condition). (FIG. 17*c*) GO analysis for differentially upregulated and downregulated genes with $p<0.05$ for co-culture of iN cells in 200 μl CH vs co-culture of iN cells in 50 μl CH (adjusted p value is 0.05). FDR: False Discovery Rate. (FIG. 17*d*) Pearson's correlation analysis of RNA-sequencing data of co-cultured human iN cells in two different volumes of CHs with or without two different concentrations of HA compared to human brain transcriptome data of 4 different subregions at 4 fetal developmental stages. V1C: primary visual cortex (striate cortex, area V1/17); DFC: dorsolateral prefrontal cortex; A1C: primary auditory cortex (core); M1C: primary motor cortex (area M1, area 4). pcw: post-conceptual weeks. Bars show mean correlation±SEM.

FIG. 19: Frequency dependent rheology of various encapsulating hydrogels. Frequency dependent rheology of Matrigel at two different concentrations, Matrigel with HA, and CHs with varying amounts of CRS, $CaCl_2$ (1×: 3.125 mM; 2×: 6.25 mM; 4×: 12.5 mM; 8×: 25 mM) (n=3 for each condition). Bars show mean±SEM.

(FIG. 20*a*) Pearson's correlations between RNA-sequencing data of human iN cells cultured/co-cultured in different 3D conditions at 5 weeks (n=3 for each condition) (symbols are shown at the bottom of the figure) and human brain transcriptome data of 2 different subregions at 3 fetal developmental stages. A1C: primary auditory cortex (core); M1C: primary motor cortex (area M1, area 4); pcw: post-conceptual weeks. Bars show mean correlation±SEM. (FIG. 20*b*) Expression levels of selected disease-associated genes across various 3D conditions encapsulating human iN cells (ASD, autism spectrum disorder; ALS, amyotrophic lateral sclerosis; AD, Alzheimer's disease; PD, Parkinson's disease). Color schemes are based on z-score distribution.

(FIG. 21*a*) Schematic showing generation of human astrocytic cells from hESCs by combining transcription factors (NGN1 and NGN2) used for neural induction, a morphogen (cntf, ciliary neurotrophic factor) and fetal bovine serum (fbs). (FIG. 21*b*) Expression of GFAP, S100B, VIM and ALDH1L1 in treated cells at day 5 and day 15. Undifferentiated hESCs were used as negative control. (Expression levels for human primary astrocytes used as positive control can be found in FIG. 23*b*). (n=3 for all conditions and bars show mean±SEM). (n.d. represents not-detected).

(FIG. 23*a*) Immunostaining images of mouse astrocytes and hESC-derived astrocytic cells at day 35 for GFAP, S100β and Vimentin along with DAPI for nuclei staining. Plots show percent of $GFAP^+$, $S100\beta^+$ and $Vimentin^+$ hESC-derived cells at day 35 (n=3). (FIG. 23*b*) Expression of GFAP, S100B, VIM and ALDH1L1 in cells in different conditions of differentiation protocols (involved transcription factors (NGN1 and NGN2) used for neural induction, a morphogen (cntf, ciliary neurotrophic factor) and fetal bovine serum (fbs)) was measured at day 30. Undifferentiated hESCs were used as a negative control and human primary astrocytes were used as positive control (n=3 for all conditions and bars show mean±SEM, and n.d. represents not-detected). (FIG. 23*c*) Expression levels of marker genes for a variety of cell types across different conditions of differentiation protocols at different time points. Undifferentiated hESCs were used as a negative control and human primary astrocytes (huPAst) were used as positive control. Astro: Astrocyte marker genes; RG: Radial Glia marker genes; NE: Neuroepithelial cells marker genes; IPC: Intermediate Progenitor Cells marker genes; ExcN: Excitatory Neurons marker genes; InhbN: Inhibitory Neurons marker genes. Color schemes are based on z-score distribution. (n=3 for all conditions).

(FIG. 24*d*) PCA based on whole-transcriptome data of human astrocytic cells (only huAstC) cultured in Matrigel (7.36 mg/ml) and iN cells cultured (only iN) or co-cultured with either human primary astrocytes (iN–huPAst) or human astrocytic cells (iN–huAstC) in Matrigel (7.36 mg/ml) at 5 weeks. (n=3 for each condition, $10^3$ iN cells were sorted from each replicate of each culture/coculture condition). (FIG. 24*e*) Expression levels of neuronal, radial glia (RG) and astrocyte (Astro) marker genes in conditions shown in FIG. 24D, demonstrating minimal contamination from human astrocytic cells and human primary astrocytes among population of iN cells sorted from their co-cultures (iN–huAstC and iN–huPAst).

(FIG. 25*a*) A t-distributed stochastic embedding (tSNE) plot showing identified clusters by using Louvain clustering for scRNA-seq profiles shown in FIG. 5*f*, with cells colored by cluster membership. (FIG. 25*b*) tSNE plots showing expression levels of cell type marker genes for identified clusters of cell types shown in FIG. 5*g* with cells colored by the expression level of marker genes. CPM: Counts per million. (SNAP25 and SLC17A6, neuron markers; GFAP and S100B, astrocyte markers; PAX6 and HES1, radial glia markers; GAD2, inhibitory neuron marker; COL1A2, neuroepithelial cell marker). (FIG. 25*c*) Heatmap showing average expression of various cell type markers genes (rows) in identified clusters of cell types shown in FIG. 5*g* (columns). (FIG. 25*d*) Heatmap showing average expression of various cell type markers genes (rows) in identified clusters shown in (FIG. 25*a*) (columns). (FIG. 25*e*) Pearson's correlations between the average gene expression in identified clusters shown in (FIG. 25*a*) (rows) and cell types defined by scRNA-seq in the human fetal cortex (Pollen, A. A. et al. Cell 163, 55-67, (2015)) (columns). Int-Neu: Interneurons; IPC: Intermediate Progenitor Cells; RG: Radial Glia cells. (FIG. 25*f*) Pearson's correlations between the average gene expression in identified clusters shown in (FIG. 25*a*) (rows) and cell types (Excitatory Neurons, Inhibitory Neurons, and Astrocytes) defined by DroNC-seq in the adult post-mortem human brain tissues (columns). (FIG. 25*g*) Pearson's correlations between the average gene expression in identified clusters shown in (FIG. 25*a*) (rows) and main clusters and forebrain subclusters defined by scRNA-seq in six-moth-old human brain organoids (Quadrato, G. et al. Nature 545, 48, (2017)) (columns). Forebrain subclusters were derived from forebrain cluster shown in main clusters. IPC: Intermediate Progenitor Cells.

(FIG. 26*a*) Pearson's correlations between the average gene expression in identified clusters shown in FIG. 5*g* (rows) and cell types defined by scRNA-seq in the human fetal cortex (columns). EN: Excitatory Neuron; PFC: Prefrontal Cortex; V1: Primary Visual Cortex; IN: Inhibitory Neuron; CGE: Caudal Ganglionic Eminence; MGE: Medial Ganglionic Eminence; IPC: Intermediate Progenitor Cells; RG: Radial Glia cells. See also Table 32 for descriptions of cell type clusters defined by scRNA-seq in the human fetal cortex. (FIG. 26*b*) Pearson's correlations between the average gene expression in identified clusters shown in FIG. 25*a* (rows) and cell types defined by scRNA-seq in the human fetal cortex (columns). (FIG. 26*c*) Pearson's correlations between main clusters and forebrain subclusters defined by scRNA-seq in six-moth-old human brain organoids (rows) and cell types defined by scRNA-seq in the human fetal cortex (columns). Forebrain subclusters were derived from forebrain cluster shown in main clusters. IPC: Intermediate Progenitor Cells. (FIG. 26*d*) Differential expression analysis between astrocytes and RG cells in the scRNA-seq dataset of the human fetal cortex was performed. The top 9 astrocyte-specific genes and top 9 RG-specific genes were identified based on log fold change. Heatmap showing average expression of top 9 astrocyte-specific genes and top 9 RG-specific genes (rows) in astrocyte and RG clusters defined by scRNA-seq in the human fetal cortex (columns). CPM: Counts per million. (FIG. 26*e*) Heatmap showing average expression of top 9 astrocyte-specific genes and top 9 RG-specific genes (rows) in astrocyte and RG clusters shown in FIG. 5*g* (columns). (FIG. 26*f*) Heatmap showing average expression of top 9 astrocyte-specific genes and top 9 RG-specific, genes (rows) in astrocyte and RG clusters defined by scRNA-seq in six-moth-old human brain organoids (columns).

FIG. 27: Editing efficiencies of gRNAs for three targeted genes. Four gRNAs targeting SOD1 locus (SEQ ID NO:1-4), six gRNAs targeting TARDBP locus (SEQ ID NO:5-10), and three gRNAs targeting TBK1 locus (SEQ ID NO:11-13) were tested for efficacy with AsCpf1 (S542R/K607R) and wild-type AsCpf1 (WT AsCpf1) by transfecting HEK293FT cells. PAM and target sequences for each gRNA are shown. Plots show indel (MLE) percentages of all tested gRNAs for each targeted gene. (n=3 for each condition and bars show mean±SEM).

(FIG. 28*a*) Schematic of AAV vector design for gene editing using AsCpf1 (S542R/K607R). Bottom: gray rectangle, direct repeat; green diamond, spacer for targeted gene. Bottom vector encodes the mCherry-KASH fusion protein for identification of transduced iN cells. (FIG. 28*b*) Graphical representation of the human SOD1 (SEQ ID NO:14 and 15), TARDBP (SEQ ID NO:16 and 17), and TBK1 (SEQ ID NO:18 and 19) loci displaying AsCpf1(S542R/K607R) target locations; targeted genomic locus for genes indicated in blue and PAM sequences marked in magenta (see also FIG. 27). (FIG. 28*c*) Schematic for genome editing in 3D neural tissues. (FIG. 28*d*) Representative mutation patterns detected by sequencing of SOD1 (SEQ ID NO:20-24), TARDBP (SEQ ID NO:25-29), and TBK1 (SEQ ID NO:30-34) loci. (FIG. 28*e*) Indel analysis of Cpf1-mediated editing of SOD1, TARDBP, and TBK1 using AAV vectors in mCherry$^+$ iN cells sorted from 3D human neural tissues (n=2 human neural tissues for targeting guides; bars show mean±SEM). A total of $10^3$ mCherry$^+$ iN cells were sorted for each condition.

DETAILED DESCRIPTION

Tractable Neural Tissue Culture

Figures 1A, 1B, 1C, 1D, 1E:
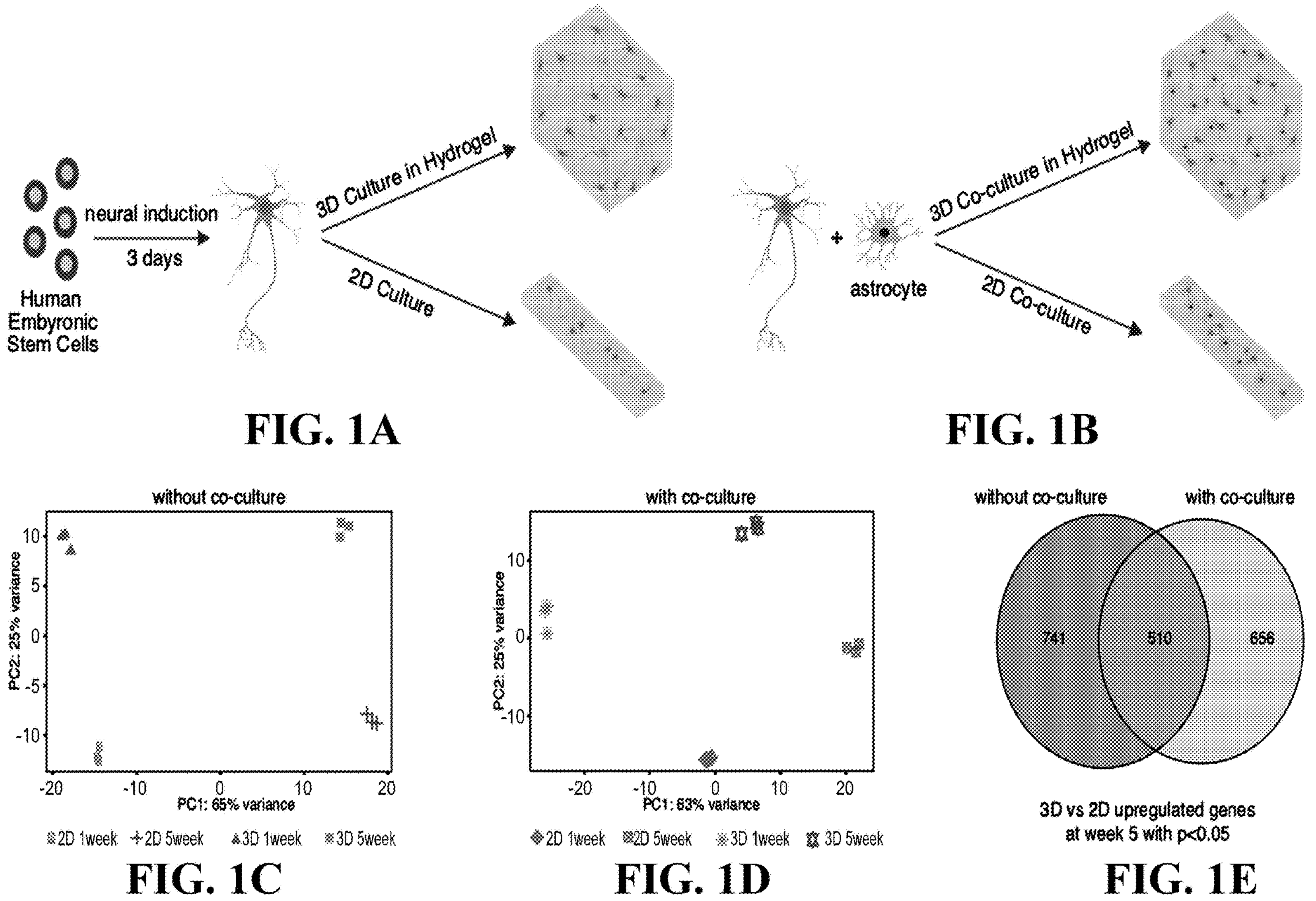

Aspects of this disclosure relate to a tractable neural tissue culture. Without being bound by theory, the tractable neural tissue culture described herein is useful for rapid generation of isogenic 3D human neural tissues. In some aspects, the tractable neural tissue culture comprises, consists of, or consists essentially of neuronal and/or glial cells derived from a stem cell and a three dimensional (3D) matrix comprising a biological supporting material. In some embodiments, the neuronal and/or glial cells are encapsulated within the 3D matrix.

As used herein, the term "tractable" means malleable, conformable, yielding, amenable, or controllable.

In some aspects, the stem cell from which the neuronal cells are derived are embryonic stem cells (ESCs) or induced pluripotent stem cells (iPSCs). In some aspects, the stem cells are from a mammalian species, e.g., human, ovine, bovine, canine, feline, murine, rat, or equine. In preferred aspects, the stem cells are human ESCs (hESCs) or human iPSCs.

Suitable ESCs may be obtained from an embryo through conventional techniques or through use of established cultured ESC lines. Exemplary hESC cell lines include but are not limited to cell lines listed on the National Institutes of Health Embryonic Stem Cell Registry such as CHB-1-6, 8-12 (Children's Hospital Corporation), RUES1-3 (The Rockefeller University), HUES1-28, 42, 44, 45, 48, 49, 53, 62-66, 68-75 (Harvard University), CyT49 (ViaCyte, Inc.), RUES3 (The Rockefeller University), WA01, 07, 09, 13, 14, 13-27 (WiCell Research Institute), UCSF4 (University of California, San Francisco), NYUES1-13 (New York University School of Medicine), UCLA1-6, 8-18, 19n, 20n (University of California, Los Angeles), CT1-4 (University of Connecticut School of Medicine), MA135 (Advanced Cell Technology, Inc.), Endeavour-2 (University of New South Wales), WIBR1-6 and WIN-1-5 (Whitehead Institute for Biomedical Research), Shef 3 and 6 (University of Sheffield), ESI-014, -17, -035, -049, -051, -053 (BioTime, Inc.), CSES2, 4, 7, 15, 17-19, 25 (Cedars-Sinai Medical Center), SA0001 (Cellartis AB), GENEA001, 002, 015, 016, 042, 043, 047, 052, 057, 093, 094, 104 (Genea Biocells), WCMC10, 23, 39 (Weill Cornell Medical College of Cornell University), and HS346, 401, 420 (Karolinska Institute).

In some aspects, the hESCs may have an abnormal karyotype or carry a disease-specific gene (e.g. HUES PGD1 (Harvard University)).

iPSCs are cells derived from non-pluripotent cells such as somatic cells (e.g. fibroblasts, peripheral blood mononucleocytes, and keratinocytes) and multipotent stem and progenitor cells (e.g., CD34+ hematopoietic progenitors, neural progenitor cells, and adipose-derived stem cells) and reprogrammed by the introduction or activation of pluripotency genes. Exemplary reprogramming genes include but are not limited to OCT4, SOX2, KLF4, cMYC, NANOG, LIN28, REX1, Zfp296, DNMT3B, AURKB, PRMT5, SETD7, and Glis1. Techniques for the production of iPSCs are well-known in the art (see, e.g., Yu, J. et al. *Science* 318 (5858): 1917-20 (2007); Takahashi, K. et al. *Cell* 131 (5): 861-72 (2007); Okita, K. et al., *Nature,* 448(7151):313-17 (2007); Mali, N. and Rao, M. S., *Method Mol Biol,* 997:23-33 (2013); Yu, J. et al., *PLoS ONE,* 6(3): e17557 (2011)).

As used herein, the term "neuronal cell" includes glutamatergic neurons, GABAergic neurons, dopaminergic neurons, microglia, oligodendrocytes, motor neurons, and bipolar neurons. Bipolar neurons are specialized sensory neurons that have two extensions—one axon and one dendrite. They transmit special senses such as smell, sight, taste, hearing and vestibular functions. In some embodiments, the neuronal cells are induced neuronal cells (iN). In some embodiments, the concentration of neuronal cells in the tissue culture ranges from about 1 cell/mL to about $10^8$ cells/mL, 1 cell/mL to about $10^7$ cells/mL, 1 cell/mL to about $10^6$ cells/mL, 1 cell/mL to about $10^5$ cells/mL, 1 cell/mL to about $10^4$ cells/mL, 1 cell/mL to about $10^3$ cells/mL, 1 cell/mL to about $10^2$ cells/mL, 1 cell/mL to about 10 cells/mL, about $10^4$ cells/mL to about $10^8$ cells/mL, about $10^4$ cells/mL to about $10^7$ cells/mL, about $10^4$ cells/mL to about $10^6$ cells/mL, about $10^4$ cells/mL to about $10^5$ cells/mL, about $10^5$ cells/mL to about $10^8$ cells/mL, about $10^5$ cells/mL to about $10^7$ cells/mL, about $10^5$ cells/mL to about $10^6$ cells/mL, about $10^6$ cells/mL to about $10^8$ cells/mL, or about $10^6$ cells/mL to about $10^7$ cells/mL. In some embodiments, the concentration of cells is about 1 million cells/mL, about 2 million cells/mL, about 3 million cells/mL, about 4 million cells/mL, about 5 million cells/mL, about 6 million cells/mL, about 7 million cells/mL, about 8 million cells/mL, about 9 million cells/mL, about 10 million cells/mL, about 11 million cells/mL, about 12 million cells/mL, about 13 million cells/mL, about 14 million cells/mL, about 15 million cells/mL, about 16 million cells/mL, about 17 million cells/mL, about 18 million cells/mL, about 19 million cells/mL, about 20 million cells/mL, about 50 million cells/mL, or about 100 million cells/mL. In particular embodiments, the concentration of cells is about 10 million per mL, about 20 million per mL, or about 30 million per mL.

Glutamatergic neurons produce the excitatory neurotransmitter glutamate. Glutamatergic neurons can be identified by their expression of characteristic markers including but not limited to vGluT1, vGluT2, NMDAR1, SNDAR2B, glutaminase, and glutamine synthetase. Methods of deriving glutamatergic neurons from stem cells through culture in the presence of cyclopamine, FGF2, and SMAD signaling inhibitors LDN193189 and SB432542, followed by BDNF have been described (see, e.g., Vazin, T. et al., *Neurobiol Dis.,* 62: 62-72 (2014)).

GABAergic neurons produce the inhibitory neurotransmitter gamma aminobutyric acid (GABA). GABAergic neurons can be identified by their expression of characteristic markers including but not limited to GABA transporter 1 (GAT1), $GABA_B$ receptor 1 and/or 2, GAD65, and GAD67. Methods of deriving GABAergic neurons from pluripotent stem cells through transcription factor reprogramming or directed differentiation have been described (see Yang, N. et al. *Nature Methods,* 14(6): 621-23 (2017); Ma, L. et al. *Cell Stem Cell* 10: 455-64 (2012)). For directed differentiation, hESCS are exposed to valproic acid (VPA) followed by BDNF, GDNF, IGF, and cyclic-AMP to induce differentiation and maturation. For transcription factor reprogramming, expression of Ngn2, Neurod1, or a combination of Ascl1 with Dlx2 in iPS or ESCs can convert these cells to GABAergic neurons.

Dopaminergic neurons produce the neurotransmitter dopamine. Dopaminergic neurons can be identified by their expression of characteristic markers including but not limited to tyrosine hydroxylase (TH), dopamine transporter (DAT), FOXA2, GIRK2, Nurr1, and LMX1B. Methods of deriving dopaminergic neurons from human adipose neural-crest stem cells or mesenchymal stem cells have been described (see, e.g., Yang, S-Y. et al. *Stem Cell Reports,* 8: 728-42 (2017); Trzaska, K. A. et al. *Methods Mol. Biol.* 698: 295-303 (2011)).

In some embodiments, the neuronal cells may be modified to express a CRIPR-Cas protein as described elsewhere herein.

Microglia function as immune effector cells in the central nervous system. Microglial cells fall into three distinct subtypes: amoeboid microglia, ramified microglia, and reactive microglia that respond to injury or pathogen invasion. Microglia can be identified through their expression of characteristic markers including but not limited to CD11b and $CD45^{low}$, Iba1, F4/80, CD68, HLA-DR, transmembrane protein 119 (Tmem 119), and CD40 (see, e.g., Korzhevskii, D. E. and Kirik, O. V. *Neuroscience and Behavioral Physiology* 46(3): 284-90 (2016); Bennet, M. L. et al., *Proc. Nat. Acad. Sci. U.S.A.* 113(12): E1738-40 (2016)). Methods of differentiating induced pluripotent stem cells to microglia-like cells through sequential differentiation have been described (see, e.g., Pandya, H. et al., *Nature Neurosci.,* 20(5): 753-59 (2017)).

iPSCs are differentiated to microglial cells in a first stage comprising a medium with VEGF, hBMP4, SCF, and Activin A, followed by differentiation in a second medium with SCF, hFLT3L, IL-3, IL-6, G-CSF, and BMP4 and co-culture with human astrocytes.

Oligodendrocytes produce myelin, an important protein that insulates the axons of the central nervous system. Oligodendrocytes can be identified through their expression of characteristic markers including but not limited to PDGF receptor alpha, NG2, Olig 1, Olig 2, Olig 3, oligodendrocyte specific protein (OSP), myelin basic protein (MBP), myelin oligodendrocyte glycoprotein (MOG), and/or SOX10. Methods of deriving oligodendrocyte precursors from human embryonic stem cells through 70 days of in vitro culture conducted in stages including neural induction, patterning of neural precursors, oligodendrocyte progenitor proliferation, and differentiation have been described (see Piao, J. et al., *Cell Stem Cell,* 16: 198-210 (2015)). Methods of generating oligodendrocytes from stem cells through forced expression of transcription factors such as SOX10, OLIG2, and NKX6.2 have been described (see, e.g. Ehrlich, M. et al., *Proc. Nat. Acad. Sci. U.S.A.* 14(11):E2243-E2252 (2017)).

Motor neurons are found in the brain (upper motor neurons) and in the brain stem and spinal cord (lower motor neurons). Motor neurons function to innervate muscle fibers and glands.

Motor neurons can be identified through their expression of characteristic markers including but not limited to Islet-1, Islet-2, Olig 2, HB9, and Neurogenin-2. Methods of deriving motor neurons from human pluripotent stem cells utilizing dual SMAD inhibition (dorsomporphin, TGFβ inhibitor SB4315342) and GSK30 inhibitor (2'Z, 3'E)-6-bromoindirubin-3'-osime, with retinoic acid and purmorphamine to activate sonic hedgehog signaling have been described (see Shimoj o, D. et al. *Molecular Brain* 8:79 (2015)).

Bipolar neurons are sensory neurons that are found, for example, in the retina, spinal ganglia, and vestibuocochlear nerve. Bipolar neurons have two extensions, also called processes. Bipolar neurons can be identified through their expression of characteristic markers including but not limited to Car8, Car10, Cntn4, Lhx3, Nfasc, Og9x, Scgn, Trpm1, Bhlhb4, Irx5, Gli5, Lhx4, Cabp5, Prkca, Grm6, and Zf. Methods of deriving bipolar neurons from induced pluripotent human stem cells through overexpression of Neurogenin-1 and Neurogenin-2 have been described (see Busskamp, V. et al. *Mol. Syst. Biol.* 10(11):760 (2014)).

As used herein, the term "glial cell" refers to a cell that surrounds neurons and provides support for and insulation between them. Glial cells are the most abundant cell types in the central nervous system. Types of glial cells include oligodendrocytes, astrocytes, ependymal cells, Schwann cells, microglia, and satellite cells. Oligodendrocytes are neural cells of ectodermal origin, forming part of the adventitial structure (neuroglia) of the central nervous system. They have variable numbers of veil-like or sheet-like processes that wrap around individual axons to form the myelin sheath of the CNS. They can be identified by morphological, phenotypic, or functional criteria as explained later in this disclosure. Astrocytes are specialized glial cells that outnumber neurons by over fivefold. They contiguously tile the entire central nervous system (CNS) and exert many essential complex functions in the healthy CNS. Astrocytes respond to all forms of CNS insults through a process referred to as reactive astrogliosis, which has become a pathological hallmark of CNS structural lesions.

As used herein, the term "distance in expression space" refers to a distance measured using metrics known in the art to describe the difference in gene expression profile between the tractable neural tissue culture of the present invention and a target tissue, for example by Gene Set Enrichment Analysis (GSEA). In some embodiments, the distance is measured by a Euclidean distance, Pearson correlation coefficient, Spearman coefficient, Cosine similarity, Manhattan distance, or a combination thereof, over a gene, a set of genes, or entire transcriptome.

In some embodiments, the expression space is over one or more genes, 10 or more genes, 20 or more genes, 30 or more genes, 40 or more genes, 50 or more genes, 100 or more genes, 500 or more genes, or 1000 or more genes. In some embodiments, the expression space is over a set of genes. In some embodiments, the set of genes defines a cell pathway. In some embodiments, the expression space is over an entire transcriptome. In some embodiments, changes in the distance in expression space are determined from single cell sequencing data from the neural tissue culture, target tissue, or both.

As used herein, "target tissue" refers to a tissue used as a reference for comparison with the tractable neural tissue culture. In some embodiments, the target issue is a healthy neural tissue or a diseased tissue. In some embodiments, the healthy neural tissue represents neural tissues of different regions of a human brain, including human primary visual cortex (V1C), dorsolateral prefrontal cortex (DFC), primary auditory cortex (core), and primary motor cortex (MIC) subregion. In some embodiments, the healthy neural tissue represents neural tissues of different developmental stages of a human brain, for example, 1 week post-conceptual week, 2 weeks post-conceptual week, 3 weeks post-conceptual week, 4 weeks post-conceptual week, 5 weeks post-conceptual week, 6 weeks post-conceptual week, 7 weeks post-conceptual week, 8 weeks post-conceptual week, 9 weeks post-conceptual week, 10 weeks post-conceptual week, 11 weeks post-conceptual week, 12 weeks post-conceptual week, 13 weeks post-conceptual week, 14 weeks post-conceptual week, 15 weeks post-conceptual week, 16 weeks post-conceptual week, 17 weeks post-conceptual week, 18 weeks post-conceptual week, 19 weeks post-conceptual week, 20 weeks post-conceptual week, 21 weeks post-conceptual week, 22 weeks post-conceptual week, 23 weeks post-conceptual week, 24 weeks post-conceptual week, 25 weeks post-conceptual week, 26 weeks post-conceptual week, 27 weeks post-conceptual week, 28 weeks post-conceptual week, 29 weeks post-conceptual week, 30 weeks post-conceptual week; 31 weeks post-conceptual week, 32 weeks post-conceptual week, 33 weeks post-conceptual week, 34 weeks post-conceptual week, 35 weeks post-conceptual week, 36 weeks post-conceptual week, 37 weeks post-conceptual week, 38 weeks post-conceptual week, 39 weeks post-conceptual week, 40 weeks post-conceptual week.

In some embodiments, the diseased tissue is representative of tissues associated with a neurological disease such as Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), or spinal and bulbar muscular atrophy (SBMA). In some embodiments, the diseases tissue is representative of tissues associated with a brain cancer, a neurodegenerative disease, a psychiatric or cognitive disorder, or an autoimmune disease.

As used herein, "statistically significant shift" in gene expression refers to a shift over one or more genes, 10 or more genes, 20 or more genes, 30 or more genes, 40 or more genes, 50 or more genes, 100 or more genes, 500 or more genes, or 1000 or more genes. In some embodiments, the statistically significant shift is least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%. In some embodiments, the statistically significant shift in gene expression distribution is over a set of genes. In some embodiments, the set of genes defines a cell pathway.

In some embodiments, the statistically significant shift may be measured by a Fisher's exact test. Fisher's exact test is a statistical test used to determine if there are nonrandom associations between two categorical variables. It is one of a class of exact tests typically used in the analysis of contingency tables. It is so called because the significance of the deviation from a null hypothesis (e.g. P-value) can be calculated exactly, rather than relying on an approximation that becomes exact in the limit as the sample size grows to infinity, as with many statistical tests. It is usually used when sample sizes are small, however, it is valid for all sample sizes.

In some embodiments, the statistically significant shift may be measured by a Likelihood ratio test. The likelihood ratio test is a statistical test used to compare the goodness of fit of two statistical models—a null model against an alternative model. The test is based on the likelihood ratio, which expresses how many times more likely the data are under one model than the other. The likelihood ratio or logarithm thereof, can then be used to calculate a p-value. It can also be compared to a critical value to decide whether to reject the null model. If one uses the logarithm of the likelihood ratio, the statistic is known as a log-likelihood ratio statistic, and one can approximate the probability distribution of this test statistic using Wilk's theroem, assuming that the null model is true. In the case of distinguishing between two models, each of which has no unknown parameters, use of the likelihood ratio test can be justified by the Neyman-Pearson lemma, which demonstrates that such a test has the highest power among all competitors.

In some embodiments, the statistically significant shift may be measured by a negative binomial model. This model provides a discrete probability distribution of the number of successes in a sequence of independent and identically distributed Bernoulli trials (binomial trial with two possible outcomes, i.e. "success" or "failure") before a specified (non-random) number of failures (denoted r) occurs. For example, if 1 is defined as failure and all non-1s as successes, and we throw a die repeatedly until 1 appears for the third time (r=three failures), then the probability distribution of the number of non-1s that appeared will be a negative binomial distribution. In some embodiments, the statistically significant shift may be measured by a beta binomial model. This is a binomial distribution in which the probability of success at each trial is fixed but randomly drawn from a beta distribution (defined by the interval [0, 1] and parametrized by two positive shape parameters denoted by $\alpha$ and $\beta$) prior to n number of Bernoulli trials. It is frequently used in Bayesian statistics, empirical Bayes methods and classical statistics to capture overdispersion in binomial type distributed data. In some embodiments, the statistically significant shift may be measured by a two-stage poisson model. In some embodiments, the statistically significant shift may be measured by a combination of the aforementioned tests.

As used herein, the term "biological supporting material" refers to a three-dimensional matrix material that supports growth of cells in culture. In some embodiments, the biological supporting material is selected from the group consisting of one or more extracellular matrix proteins, a basement membrane matrix, collagen, laminin, gelatin, proteoglycans, alginate, polyethylene glycol, agarose, chitosan, silk protein-based and other porous scaffolds, and composite hydrogel.

Extracellular matrix proteins include but are not limited to laminin, collagen, vitronectin, fibronectin, entactin, nidogen-2, elastin, perlecan, and tropoelastin. In some embodiments, two or more extracellular matrix proteins and/or protein complexes are combined to form an extracellular matrix composition. For example, the biological supporting material may comprise a mixture of laminin and collagen IV. In some embodiments, the extracellular matrix protein is recombinant. Extracellular matrix proteins and heterogenous compositions of extracellular matrix proteins are available from, for example ThermoFisher Scientific (e.g. Coating Matrix Kit Protein, cat. #R011K).

Collagen is a structural protein that is generally found in connective tissue and the extracellular space of animals. Collagen is classified into several types including but not limited to type I (e.g. COL1A1 (Entrez gene: 1277, UniProt: P02452); COL1A2 (Entrez gene: 1278, UniProt: P08123)), type II (e.g. COL2A1 (Entrez gene: 1280, UniProt: P02458)), type III (e.g. COL3A1 (Entrez gene: 1281, UniProt: P02461)), type IV (basement membrane collagen, e.g. COL4A1 (Entrez gene: 1282, UniProt: P02462), COL4A2 (Entrez gene: 1284, UniProt: P08572), COL4A3 (Entrez gene: 1285, UniProt: Q01955), COL4A4 (Entrez gene: 1286, UniProt: P53420), COL4A5 (Entrez gene: 1287, UniProt: P29400), COL4A6 (Entrez gene: 1288, UniProt: Q14031)), type V (e.g. COL5A1 (Entrez gene: 1289, UniProt: P20908), COL5A2 (Entrez gene: 1290, UniProt: P05997), COL5A3 (Entrez gene: 5059, UniProt: P25940)), type VI (e.g. COL6A1 (Entrez gene: 1291, UniProt: P12109), COL6A2 (Entrez gene: 1292, UniProt: P12110), COL6A3 (Entrez gene: 1293, UniProt: P12111), COL6A5 (Entrez gene: 256076, UniProt: PA8TX70, H0Y935)), type VII (e.g. COL7A1 (Entrez gene: 1294, UniProt: Q02388)), type VIII (e.g. COL8A1 (Entrez gene: 1295, UniProt: P27658), COL8A2 (Entrez gene: 1296, UniProt: P25067, Q4VAQ0)), type IX (e.g. COL9A1 (Entrez gene: 1297, UniProt: P20908), COL9A2 (Entrez gene: 1290, UniProt: P05997), COL9A3 (Entrez gene: 5059, UniProt: P25940)), type X (e.g. COL10A1 (Entrez gene: 1300, UniProt: A03692)), type XI (e.g. COL11A1 (Entrez gene: 1301, UniProt: P12107), COL11A2 (Entrez gene: 1302, UniProt: P13942)), type XII (e.g. COL12A1 (Entrez gene: 1303, UniProt: Q99715)), or type XIII (e.g. COL10A1 (Entrez gene: 1300, UniProt: A03692). In particular embodiments, the collagen is type IV collagen. Collagens are available from, for example, Sigma Aldrich, St. Louis, Missouri, U.S.A. (e.g. CAS #9007-34-5, cat. #: C6745).

Laminins are heterotrimeric proteins formed by combinations of an alpha chain (e.g. LAMA1 (Entrez gene: 284217, UniProt: P25391), LAMA2 (Entrez gene: 3908, UniProt: P24043), LAMA3 (Entrez gene: 3909, UniProt: Q16787), LAMA4 (Entrez gene: 3910, UniProt: Q16363), or LAMA5 (Entrez gene: 3911, UniProt: 015230)), beta chain (e.g. LAMB1 (Entrez gene: 3912, UniProt: P07942), LAMB2 (Entrez gene: 3913, UniProt: P55268), LAMB3 (Entrez gene: 3914, UniProt: Q13751), or LAMB4 (Entrez gene: 22798)), and gamma chain (e.g. LAMC1 (Entrez gene: 22798, UniProt: P25391), LAMC2 (Entrez gene: 284217, UniProt: P25391), or LAMC3 (Entrez gene: 284217, UniProt: P25391)) of laminin. Laminins include but are not limited to the following trimers: laminin 111, laminin 211, laminin 121, laminin 221, laminin 332, laminin 3A32, laminin 3B32, laminin 311, laminin 3A11, laminin 312, laminin 3A21, laminin 411, laminin 421, laminin 511, laminin 521, laminin 213, laminin 423, laminin 522, and laminin 523. Laminin is available from, for example, Sigma Aldrich (e.g. Laminin from Engelbreth-Holm-Swarm murine sarcoma basement membrane, CAS #: 114956-81-9, cat. #: L2020).

Vitronectin is an extracellular matrix glycoprotein encoded by the VTN gene (Entrez gene: 7448, UniProt: P04004). Vitronectin is available from, for example, Sigma Aldrich (e.g. CAS #: 83380-82-9; cat. #: V8379). Fibronectin is an extracellular matrix glycoprotein that is capable of binding integrins. Fibronectin is encoded by the FN1 gene (Entrez gene: 2335, UniProt: P02751) and is available from, for example, Sigma Aldrich (e.g. CAS #86088-83-7; cat. #: F2006). Entactin (also known as Nidogen-1) is a component of the basement membrane and is encoded by the NID-1 gene (Entrez gene: 4811, UniProt: P14543). Entactin is available from, for example, R&D Systems, Minneapolis, Minnesota, U.S.A. (e.g. cat. #: 2570-ND). Nidogen-2 (also known as osteonidogen) is a component of the basement membrane and is encoded by the NID2 gene (Entrez gene: 22795, UniProt: Q14112). Nidogen-2 is available from, for example, R&D Systems (e.g. cat. #: 3385-ND). Elastin is a connective tissue protein encoded by the ELN gene (Entrez gene: 2006, UniProt P15502). Elastin is available from, for example, Sigma Aldrich (e.g. CAS #9007-58-3; cat. #: 324751). Tropoelastin is a highly purified, soluble elastin monomer and is available from, for example, Sigma Aldrich (e.g. cat. #: T0706). Perlecan is a proteoglycan that binds to extracellular matrix and cell surface molecules. Endorepellin protein is a 80 kDa glycoprotein derived from the C-terminal end of perlecan. Perlecan is encoded by the heparin sulfate proteoglycan 2 gene (HSPG2, Entrez gene: 3339, UniProt P98160) and is available from, for example, R&D Systems (e.g. Endorepellin: cat. #: 2364-ER).

Basement membrane matrices are derived from the extracellular matrix that separates the epithelium, endothelium, muscle, or neuronal cells from adjacent stromal tissue (known as the basement membrane). The basement membrane is comprised of a thin, delicate membrane of extracellular matrix proteins and glycosaminoglycans (LeBleu, V. S. et al. Exp Biol Med 232(9):1121-29 (2007)). A solubilized basement membrane matrix can be prepared from the extracellular matrix of Engelbreth-Holm-Swarm (EHS) mouse sarcoma cells (see, e.g. Robinson, L. K. et al. J Biol. Chem. 264(9): 5141-47 (1989). For example, Matrigel is derived from EHS and comprises extracellular matrix proteins such as laminin, collagen IV, growth factors, heparin sulfate proteoglycans, entactin, and nidogen. Matrigel is available in a standard formulation (Corning cat. #356234), high protein concentration formulation (Corning cat. #354248), growth factor reduced formulation comprising a more highly defined basement membrane preparation (Corning cat. #356230), and hESC-qualified formulations that have been pre-screened for compatibility with mTeSR1 medium from Stem Cell Technologies (Corning cat. #354277). The standard protein concentration formulations comprise 8-12 mg/mL. The high protein concentration formulations comprise 18-21 mg/mL. Cultrex BME is also derived from EHS and comprises laminin, collagen IV, entactin, and heparin sulfate proteoglycans. Cultrex BME is available in a reduced growth factor formulation for 3-D culture (Trevigen cat. #3433-001-01), stem cell qualified formulation (Trevigen cat. #3434-001-02), and organoid qualified formulations (e.g., Trevigen cat. #3533-001-02). All Cultrex formulations range from 12-18 mg/mL of protein except the reduced growth factor culture formulation which ranges from 14-16 mg/mL of protein. Gibco Geltrex Matrix is a basement membrane matrix derived from EHS and available in reduced growth factor formulations (ThermoFisher Scientific cat. #A1569601).

Silk protein based porous scaffolds in combination with extracellular matrix proteins have been described (see Tang-Schomer, M. D. et al. Proc. Nat. Acad. Sci. U.S.A. 111(38): 13811-16 (2014)). Silk solution and porous scaffolds can be prepared from *Bombyx mori* cocoons and combined with extracellular matrix proteins such as collagen (e.g. type I collagen gel from rat tail), fibrinogen, and/or thrombin.

Gelatin is a heterogeneous mixture of proteins and protein fragments (e.g. peptides) produced by hydrolysis of collagen. Type A gelatin is derived from acid-cured animal tissue (e.g. skin, tendons, ligaments, and bones) and type B gelatin is derived from lime-cured animal tissue. Gelatin is available from, for example, Sigma Aldrich (e.g. CAS #: 9000-70-8, cat. #: G1393, G9391, G1890).

In some embodiments, the concentration of biological supporting material in the tissue culture ranges from about 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 30 mg/mL, about 4 mg/mL to about 25 mg/mL, about 4 mg/mL to about 20 mg/mL, about 1 mg/mL to about 3 mg/mL, about 1 mg/mL to about 2 mg/mL, about 4 mg/mL to about 20 mg/mL, about 4 mg/mL to about 15 mg/mL, about 4 mg/mL to about 10 mg/mL, about 4 mg/mL to about 9 mg/mL, about 4 mg/mL to about 8 mg/mL, about 4 mg/mL to about 7 mg/mL, about 4 mg/mL to about 6 mg/mL, about 4 mg/mL to about 5 mg/mL, about 7 mg/mL to about 10 mg/mL, about 7 mg/mL to about 15 mg/mL, about 7 mg/mL to about 20 mg/mL, about 8 mg/mL to about 10 mg/mL, or about 0.001 mg/mL to about 1 mg/mL. In particular embodiments, the concentration of basement membrane matrix is about 4.4 mg/mL, about 4.6 mg/mL, about 7.36 mg/mL, about 8.5 mg/mL, or about 10 mg/mL.

In some embodiments, the 3D matrix further comprises alginate and/or crosslinkers, which form a composite hydrogel (CH) with the biological supporting material. Alginate is an anionic polysaccharide with the chemical formula $(C_6H_8O_6)_n$. In some embodiments, the alginate is a salt alginate such as sodium alginate ($NaC_6H_7O_6$, PRONOVA UP VLVG, NovaMatrix), potassium alginate ($KC_6H_7O_6$), or calcium alginate ($C_{12}H_{14}CaO_{12}$). In some embodiments, the concentration of alginate in the tissue culture ranges from about 0.01 mg/mL to about 100 mg/mL, about 1 mg/mL to about 50 mg/mL, 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 50 mg/mL, about 4 mg/mL to about 30 mg/mL, about 4 mg/mL to about 25 mg/mL, about 4 mg/mL to about 20 mg/mL, about 1 mg/mL to about 3 mg/mL, about 1 mg/mL to about 2 mg/mL, about 4 mg/mL to about 20 mg/mL, about 4 mg/mL to about 15 mg/mL, about 4 mg/mL to about 10 mg/mL, about 4 mg/mL to about 9 mg/mL, about 4 mg/mL to about 8 mg/mL, about 4 mg/mL to about 7 mg/mL, about 4 mg/mL to about 6 mg/mL, about 4 mg/mL to about 5 mg/mL, about 7 mg/mL to about 10 mg/mL, about 7 mg/mL to about 15 mg/mL, about 7 mg/mL to about 20 mg/mL, about 8 mg/mL to about 10 mg/mL, or about 0.001 mg/mL to about 1 mg/mL. In particular embodiments, the concentration of alginate is about 5 mg/mL.

Suitable crosslinkers include but are not limited to calcium chloride (CaCl2), zinc sulfate, aluminum chloride, and barium chloride. In some embodiments, the concentration of crosslinker in the tissue culture ranges from about 1 mM to about 100 mM, about 1 mM to about 50 mM, about 1 mM to about 40 mM, about 1 mM to about 30 mM, about 1 mM to about 25 mM, about 1 mM to about 20 mM, about 1 mM to about 15 mM, about 1 mM to about 10 mM, about 1 mM to about 9 mM, about 1 mM to about 8 mM, about 1 mM to about 7 mM, about 1 mM to about 6 mM, about 1 mM to about 5 mM, about 1 mM to about 2 mM, about 3 mM to about 50 mM, about 3 mM to about 30 mM, about 3 mM to about 25 mM, about 3 mM to about 20 mM, about 3 mM to about 15 mM, about 3 mM to about 10 mM, about 3 mM to about 9 mM, about 3 mM to about 8 mM, about 3 mM to about 7 mM, about 3 mM to about 6 mM, about 3 mM to about 5 mM, about 6 mM to about 50 mM, about 6 mM to about 30 mM, about 6 mM to about 25 mM, about 6 mM to about 15 mM, or about 6 mM to about 10 mM. In particular embodiments, the concentration of crosslinker is about 25 mM, about 12.5 mM, about 6.25 mM, or about 3.125 mM.

In some embodiments, the tissue culture further comprises hyaluronic acid. Hyaluronic acid is an unsulfated, anionic glycosaminoglycan abundant in extracellular matrices and having the chemical formula (C14H21NO11)n (e.g. Sigma cat. #N9164). In some embodiments, the concentration of hyaluronic acid in the tissue culture ranges from about 0.001 to about 2 mg/mL, about 0.001 to about 1 mg/mL, about 0.01 mg/mL to about 10 mg/mL, about 0.01 mg/mL to about 5 mg/mL, about 0.01 mg/mL to about 2 mg/mL, about 0.01 mg/mL to about 1 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 50 mg/mL, about 4 mg/mL to about 30 mg/mL, about 4 mg/mL to about 25 mg/mL, about 4 mg/mL to about 20 mg/mL, about 1 mg/mL to about 3 mg/mL, or about 1 mg/mL to about 2 mg/mL.

In some embodiments, the tissue culture further comprises astrocytes (also known as astrocytic cells or astrocytic glial cells). In some embodiments, the neuronal cells are co-cultured with astrocytes at a ratio of 1:1. In some embodiments, the neuronal cells are co-cultured with astrocytes at a ratio of about 1:2, about 1:3, about 1:4, about 1:5, about 1:6, about 1:7, about 1:8, about 1:9, about 1:10, about 1:15, about 1:20, about 1:50, about 1:100, about 100:1, about 50:1, about 20:1, about 15:1, about 10:1, about 9:1, about 8:1, about 7:1, about 6:1, about 5:1, about 4:1, about 3:1, about 2:1, or about 1.5:1 neuronal cells:astrocytes. In some embodiments, the astrocytes are human. Methods for generating astrocytes are described herein. In some embodiments, the concentration of neuronal cells and astrocytes in the tissue culture ranges from about 1 cell/mL to about 108 cells/mL, 1 cell/mL to about 107 cells/mL, 1 cell/mL to about 106 cells/mL, 1 cell/mL to about 105 cells/mL, 1 cell/mL to about 104 cells/mL, 1 cell/mL to about 103 cells/mL, 1 cell/mL to about 102 cells/mL, 1 cell/mL to about 10 cells/mL, about 104 cells/mL to about 108 cells/mL, about 104 cells/mL to about 107 cells/mL, about 104 cells/mL to about 106 cells/mL, about 104 cells/mL to about 105 cells/mL, about 105 cells/mL to about 108 cells/mL, about 105 cells/mL to about 107 cells/mL, about 105 cells/mL to about 106 cells/mL, about 106 cells/mL to about 108 cells/mL, or about 106 cells/mL to about 107 cells/mL. In some embodiments, the concentration of cells is about 1 million cells/mL, about 2 million cells/mL, about 3 million cells/mL, about 4 million cells/mL, about 5 million cells/mL, about 6 million cells/mL, about 7 million cells/mL, about 8 million cells/mL, about 9 million cells/mL, about 10 million cells/mL, about 11 million cells/mL, about 12 million cells/mL, about 13 million cells/mL, about 14 million cells/mL, about 15 million cells/mL, about 16 million cells/mL, about 17 million cells/mL, about 18 million cells/mL, about 19 million cells/mL, about 20 million cells/mL, about 50 million cells/mL, or about 100 million cells/mL. In particular embodiments, the concentration of cells is about 10 million per mL, about 20 million per mL, or about 30 million per mL.

In some embodiments, the 3D matrix further comprises an effective amount of a proliferation inhibitor, which suppresses proliferation of undifferentiated stem cells. In some embodiments, the proliferation inhibitor suppresses proliferation through inhibition of DNA replication and/or induction of G1/S phase cell cycle arrest. Non-limiting examples of proliferation inhibitors include 1-β-D-Arabinofuranosylcytosin (Ara-C), MCT1 Inhibitor (SR13800), GDH1 Inhibitor (R162), RSK Inhibitor (SL0101), Valproic Acid, sodium salt, Histone Deacetylase (HDAC) Inhibitor, Inauhzin, dactinomycin, actinomycin D, TAS-301, VTCN1, Galangin, Gramine, D-Valine, TBCA, sPLA2 inhibitor, 3-hydroxy-2-nitropyridine, FAK Inhibitor 14, Akt1/2 kinase inhibitor, linoleic acid, 2-methoxyestradiol, 4-(Trifluoromethoxy)phenylboronic acid, 4-Methyl-3-nitrophenylboronic acid, HS-72, SKLB1002, mimosine, 1,3-Diphenyl-2-propenone, CTX1, deferoxamine, ciclopirox, mitomycin C, or thymidine. In particular embodiments, the proliferation inhibitor is Ara-C. An effective amount is the amount required to suppress proliferation of undifferentiated stem cells. For embodiments wherein the proliferation inhibitor is Ara-C, an effective amount is from about 10 μM from about 1 μM to about 100 μM, about 1 μM to about 50 μM, about 1 μM to about 40 μM, about 1 μM to about 30 μM, about 1 μM to about 25 μM, about 1 μM to about 20 μM, about 1 μM to about 15 μM, about 1 μM to about 10 μM, about 1 μM to about 9 μM, about 1 μM to about 8 μM, about 1 μM to about 7 μM, about 1 μM to about 6 μM, about 1 μM to about 5 μM, about 1 μM to about 2 μM, about 3 μM to about 50 μM, about 3 μM to about 30 μM, about 3 μM to about 25 μM, about 3 μM to about 20 μM, about 3 μM to about 15 μM, about 3 μM to about 10 μM, about 3 μM to about 9 μM, about 3 μM to about 8 μM, about 3 μM to about 7 μM, about 3 μM to about 6 μM, about 3 μM to about 5 μM, about 6 μM to about 50 μM, about 6 μM to about 30 μM, about 6 μM to about 25 μM, about 6 μM to about 15 μM, or about 6 μM to about 10 μM. In particular embodiments, an effective amount of Ara-C is about 10 μM.

In some embodiments, the neuronal cells express one or more genes involved in neuron and forebrain development, axon guidance, and channel activity, at an increased level compared to the neuronal cells in a tissue culture without hyaluronic acid. In some embodiments, the one or more genes are cyclin-dependent kinase 5 (CDK5), Ras-related C3 botulinum toxin substrate 3 (RAC3), ephrin type-B receptor 1 (EPHB1), superoxide dismutase 1 (SOD1), phosphatase and tensin homolog (PTEN), discs large homolog 4 (DLG4), glutamate receptor subunit 3A (GRIN3A), neurofibromin 1 (NF1), nucleoside diphosphate kinase 1 (NME1), glycogen synthase kinase 3 beta (GSK3B), chromodomain helicase DNA binding protein 5 (CHD5), or a combination of these. In some embodiments, the one or more genes are Brain-derived neurotrophic factor (BDNF), Disks large homolog 2 (DLG2), Ras homolog gene family, member A (RHOA), or Calcium/calmodulin-dependent protein kinase type II delta chain (CAMK2D). Expression of genes and/or detection of gene products can be assayed by any method known in the art including but not limited to immunohistochemistry, immunofluorescence, flow cytometry, polymerase chain reaction (PCR), quantitative PCR, real-time PCR, gene expression array, mRNA sequencing, high-throughput sequencing, Western blot, Northern blot, and ELISA. Exemplary mRNA sequences are provided below:

- BDNF RefSeq (human mRNA): NM_001143805, NM_001143806, NM_001143807, NM_001143808, NM_001143809, NM_001143810, NM_001143811, NM_001143812, NM_001143813, NM_001143814, NM_001143815, NM_001143816, NM_001709, NM_170731, NM_170732, NM_170733, NM_170734, and NM_170735. A nonlimiting example of a BDNF mRNA sequence is NM_001143805.
- DLG2 RefSeq (human mRNA): NM_001142699, NM_001142700, NM_001142702, NM_001206769, NM_001300983, NM_001364, NM_001351274, NM_001351275, and NM_001351276. A nonlimiting example of a DLG2 mRNA sequence is NM_001142699.
- RHOA RefSeq (human mRNA): NM_001313941, NM_001313943, NM_001313944, NM_001313945, NM_001313946, NM_001313947, and NM_001664. A nonlimiting example of a RHOA mRNA sequence is NM_001313941.
- CAMK2D RefSeq (human mRNA): NM_001221, NM_172114, NM_172115, NM_172127, NM_172128, NM_172129, NM_001321566, NM_001321567, NM_001321568, NM_001321569, NM_001321570, NM_001321571, NM_001321572, NM_001321573, NM_001321574, NM_001321575, NM_001321576, NM_001321577, NM_001321578, NM_001321579, NM_001321580, NM_001321581, NM_001321582, NM_001321583, NM_001321584, NM_001321585, NM_001321586, NM_001321587, NM_001321588, NM_001321589, NM_001321590, NM_001321591, and NM_001321592. A nonlimiting example of a CAMK2D mRNA sequence is NM_001221.

In some embodiments, changing the concentration of the crosslinkers in the 3D matrix alters the expression of one or more genes associated with forebrain development, axon guidance, and neuron development biological processes in the neuronal cells. In some embodiments, increasing the concentration of the crosslinkers in the 3D matric decreases the expression of one or more of nuclear factor 1 B-type (NFIB), REGLN, semaphorin 3C (SEMA3C), roundabout homolog 1 (ROBO1), netrin G1 (NTNG1), neuroligin 3 (NLGN3), semaphorin 3E (SEMA3E), LHZ1, or a combination of these, in neuronal cells. In some embodiments, increasing the concentration of the crosslinkers in the 3D matrix decreases the expression of one or more of: c-Jun (JUN), DLG4, BDNF, LIM/homeobox protein Lhx2 (LHX2), Homeobox protein OTX1 (OTX1), Homeobox protein SIX3 (SIX3), RHOA, Semaphorin 7A, GPI membrane anchor (John Milton Hagen blood group) (SEMA7A), POU domain, class 4, transcription factor 1 (POU4F1), Reticulon-4 (RTN4), and Chimerin 1 (CHN1) in the neuronal cells. Detection of changes in expression of genes and/or gene products can be assayed by any method known in the art including but not limited to immunohistochemistry, immunofluorescence, flow cytometry, polymerase chain reaction (PCR), quantitative PCR, real-time PCR, gene expression array, mRNA sequencing, high-throughput sequencing, Western blot, Northern blot, and ELISA. Exemplary mRNA sequences are provided below:

A nonlimiting example of a JUN mRNA sequence is NM_002228.

- LHX2 RefSeq (human mRNA): NM_004789; human Entrez gene: 9355. A nonlimiting example of a LHX2 mRNA sequence is NM_004789.
- OTX1 RefSeq (human mRNA): NM_001199770, NM_014562; human Entrez gene: 5013. A nonlimiting example of a OTX1 mRNA sequence is NM_001199770.
- SIX3 RefSeq (human mRNA): NM_005413; human Entrez gene: 6496. A nonlimiting example of a SIX3 mRNA sequence is NM_005413.
- SEMA7A RefSeq (human mRNA): NM_003612, NM_001146029, NM_001146030; human Entrez gene: 8482. A nonlimiting example of a SEMA7A mRNA sequence is NM_003612.
- POU4F1 RefSeq (human mRNA): NM_006237; human Entrez gene: 5457. A nonlimiting example of a POU4F1 mRNA sequence is NM_006237.
- RTN4 RefSeq (human mRNA): NM_007008, NM_020532, NM_153828, NM_207520, NM_207521, NM_001321859, NM_001321860, NM_001321861, NM_001321862, NM_001321863, NM_001321904; human Entrez gene: 57142. A nonlimiting example of a RTN4 mRNA sequence is NM_007008.
- CHN1 RefSeq (human mRNA): NM_001822; human Entrez gene: 1123. A nonlimiting example of a CHN1 mRNA sequence is NM_001822.

In some embodiments, increasing the concentration of the crosslinkers in the 3D matrix results in a positive correlation of the transcriptome of the neuronal cells to the transcriptome of human primary visual cortex (V1C), dorsolateral prefrontal cortex (DFC), primary auditory cortex (core), or primary motor cortex (MIC) subregion at the fetal developmental stage of 19 post-conceptual weeks (pcw) and/or at 37 pcw.

In some embodiments, the volume of the 3D matrix that encapsulates the neuronal cells is about 5 μL, about 10 μL, about 15 μL, about 20 μL, about 25 μL, about 30 μL, about 35 μL, about 40 μL, about 45 μL, about 50 μL, about 55 μL, about 60 μL, about 65 μL, about 70 μL, about 75 μL, about 80 μL, about 85 μL, about 90 μL, about 95 μL, about 100 μL, about 105 μL, about 110 μL, about 115 μL, about 120 μL, about 125 μL, about 130 μL, about 135 μL, about 140 μL, about 145 μL, about 150 μL, about 155 μL, about 160 μL, about 165 μL, about 170 μL, about 175 L, about 180 μL, about 185 μL, about 190 μL, about 195 μL, about 200 μL, about 205 μL, about 210 μL, about 215 μL, about 220 μL, about 225 μL, about 230 μL, about 235 μL, about 240 μL, about 245 μL, about 250 μL, about 255 μL, about 260 μL, about 265 μL, about 270 μL, about 275 L, about 280 μL, about 285 μL, about 290 μL, about 295 μL, about 300 μL, about 350 μL, about 400 μL, about 450 μL, about 500 μL, about 550 μL, about 600 μL, about 650 μL, about 700 μL, about 750 μL, about 800 μL, about 850 μL, about 900 μL, about 950 μL, about 1 mL, about 2 mL, about 3 mL, about 4 mL, about 5 mL, or about 10 mL. In particular embodiments, the volume of the 3D matrix that encapsulates the neuronal cells is about 50 μL, about 100 μL, about 150 μL, about 200 μL, or about 250 μL.

In some embodiments, increasing the volume of the 3D matrix that encapsulates the neuronal cells increases the expression of one or more genes associated with forebrain development, axon guidance, and/or neuron development biological processes. For example, increasing the encapsulation volume from 50 μL to 200 μL 3D matrix (with or without hyaluronic acid) increases the expression of genes involved in CNS development (e.g. CASP3, ATF5, PPP1R17, DDIT4, NHLH1, NES, CDK6, IGF2BP1, VCAN, CHD1), forebrain development (e.g. IGF2Bp1, CDK6, CASP3, ATF5, CHD7), and neuron development (e.g. ATF5, NEUROD4, NBL1, UNC5B, TNC).

Methods of Generating Tractable Neural Tissue Culture

Further aspects of the disclosure relate to methods for generating a three-dimensional neural tissue culture, comprising, consisting of, or consisting essentially of: culturing pluripotent stem cells on a two-dimensional plate, inducing differentiation of pluripotent stem cells into neuronal cells, and detaching and encapsulating the neuronal cells in a 3D matrix comprising a biological supporting material.

In some aspects, the pluripotent stem cells are embryonic stem cells (ESCs) or induced pluripotent stem cells (iPSCs). In some aspects, the stem cells are from a mammalian species, e.g., human, ovine, bovine, canine, feline, murine, rat, or equine. In preferred aspects, the stem cells are human ESCs (hESCs) or human iPSCs.

In some embodiments, the neuronal cells are selected from the group consisting of glutamatergic neurons, GABAergic neurons, dopaminergic neurons, microglia, oligodendrocytes, motor neurons, and bipolar neurons. In some embodiments, the neuronal cells are induced neuronal cells (iN). In some embodiments, the concentration of neuronal cells in the tissue culture ranges from about 1 cell/mL to about 108 cells/mL, 1 cell/mL to about 107 cells/mL, 1 cell/mL to about 106 cells/mL, 1 cell/mL to about 105 cells/mL, 1 cell/mL to about 104 cells/mL, 1 cell/mL to about 103 cells/mL, 1 cell/mL to about 102 cells/mL, 1 cell/mL to about 10 cells/mL, about 104 cells/mL to about 108 cells/mL, about 104 cells/mL to about 107 cells/mL, about 104 cells/mL to about 106 cells/mL, about 104 cells/mL to about 105 cells/mL, about 105 cells/mL to about 108 cells/mL, about 105 cells/mL to about 107 cells/mL, about 105 cells/mL to about 106 cells/mL, about 106 cells/mL to about 108 cells/mL, or about 106 cells/mL to about 107 cells/mL. In some embodiments, the concentration of cells is about 1 million cells/mL, about 2 million cells/mL, about 3 million cells/mL, about 4 million cells/mL, about 5 million cells/mL, about 6 million cells/mL, about 7 million cells/mL, about 8 million cells/mL, about 9 million cells/mL, about 10 million cells/mL, about 11 million cells/mL, about 12 million cells/mL, about 13 million cells/mL, about 14 million cells/mL, about 15 million cells/mL, about 16 million cells/mL, about 17 million cells/mL, about 18 million cells/mL, about 19 million cells/mL, about 20 million cells/mL, about 50 million cells/mL, or about 100 million cells/mL. In particular embodiments, the concentration of cells is about 10 million per mL, about 20 million per mL, or about 30 million per mL.

In some embodiments, the biological supporting material is configured to decrease the distance in expression space of the neural tissue culture as compared to a target tissue. In some embodiments, the biological supporting material is selected from the group consisting of one or more extracellular matrix proteins, a basement membrane matrix, gelatin, silk protein-based porous scaffolds, alginate, and composite hydrogel.

Extracellular matrix proteins include but are not limited to laminin, collagen, vitronectin, fibronectin, entactin, nidogen-2, elastin, perlecan, and tropoelastin. In some embodiments, two or more extracellular matrix proteins and/or protein complexes are combined to form an extracellular matrix composition. For example, the biological supporting material may comprise a mixture of laminin and collagen IV. In some embodiments, the extracellular matrix protein is recombinant.

A solubilized basement membrane matrix can be prepared from the extracellular matrix of Engelbreth-Holm-Swarm (EHS) mouse sarcoma cells (see, e.g. Robinson, L. K. et al. J Biol. Chem. 264(9): 5141-47 (1989). Non-limiting examples of basement membrane matrices from EHS cells include Matrigel, Cultrex BME, and Geltrex.

In some embodiments, the concentration of biological supporting material in the tissue culture ranges from about 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 30 mg/mL, about 4 mg/mL to about 25 mg/mL, about 4 mg/mL to about 20 mg/mL, about 1 mg/mL to about 3 mg/mL, about 1 mg/mL to about 2 mg/mL, about 4 mg/mL to about 20 mg/mL, about 4 mg/mL to about 15 mg/mL, about 4 mg/mL to about 10 mg/mL, about 4 mg/mL to about 9 mg/mL, about 4 mg/mL to about 8 mg/mL, about 4 mg/mL to about 7 mg/mL, about 4 mg/mL to about 6 mg/mL, about 4 mg/mL to about 5 mg/mL, about 7 mg/mL to about 10 mg/mL, about 7 mg/mL to about 15 mg/mL, about 7 mg/mL to about 20 mg/mL, about 8 mg/mL to about 10 mg/mL, or about 0.001 mg/mL to about 1 mg/mL. In particular embodiments, the concentration of basement membrane matrix is about 4.4 mg/mL, about 4.6 mg/mL, about 7.36 mg/mL, about 8.5 mg/mL, or about 10 mg/mL.

In some embodiments, the 3D matrix further comprises alginate and/or crosslinkers, which form a composite hydrogel (CH) with the biological supporting material. Alginate is an anionic polysaccharide with the chemical formula (C6H8O6)n. In some embodiments, the alginate is a salt alginate such as sodium alginate (NaC6H7O6, PRONOVA UP VLVG, NovaMatrix), potassium alginate (KC6H7O6), or calcium alginate (C12H14CaO12). In some embodiments, the concentration of alginate in the tissue culture ranges from about 0.01 mg/mL to about 100 mg/mL, about 1 mg/mL to about 50 mg/mL, 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 50 mg/mL, about 4 mg/mL to about 30 mg/mL, about 4 mg/mL to about 25 mg/mL, about 4 mg/mL to about 20 mg/mL, about 1 mg/mL to about 3 mg/mL, about 1 mg/mL to about 2 mg/mL, about 4 mg/mL to about 20 mg/mL, about 4 mg/mL to about 15 mg/mL, about 4 mg/mL to about 10 mg/mL, about 4 mg/mL to about 9 mg/mL, about 4 mg/mL to about 8 mg/mL, about 4 mg/mL to about 7 mg/mL, about 4 mg/mL to about 6 mg/mL, about 4 mg/mL to about 5 mg/mL, about 7 mg/mL to about 10 mg/mL, about 7 mg/mL to about 15 mg/mL, about 7 mg/mL to about 20 mg/mL, about 8 mg/mL to about 10 mg/mL, or about 0.001 mg/mL to about 1 mg/mL. In particular embodiments, the concentration of alginate is about 5 mg/mL.

Suitable crosslinkers include but are not limited to calcium chloride (CaCl2), zinc sulfate, aluminum chloride, and barium chloride. In some embodiments, the concentration of crosslinker in the tissue culture ranges from about 1 mM to about 100 mM, about 1 mM to about 50 mM, about 1 mM to about 40 mM, about 1 mM to about 30 mM, about 1 mM to about 25 mM, about 1 mM to about 20 mM, about 1 mM to about 15 mM, about 1 mM to about 10 mM, about 1 mM to about 9 mM, about 1 mM to about 8 mM, about 1 mM to about 7 mM, about 1 mM to about 6 mM, about 1 mM to about 5 mM, about 1 mM to about 2 mM, about 3 mM to about 50 mM, about 3 mM to about 30 mM, about 3 mM to about 25 mM, about 3 mM to about 20 mM, about 3 mM to about 15 mM, about 3 mM to about 10 mM, about 3 mM to about 9 mM, about 3 mM to about 8 mM, about 3 mM to about 7 mM, about 3 mM to about 6 mM, about 3 mM to about 5 mM, about 6 mM to about 50 mM, about 6 mM to about 30 mM, about 6 mM to about 25 mM, about 6 mM to about 15 mM, or about 6 mM to about 10 mM. In particular embodiments, the concentration of crosslinker is about 25 mM, about 12.5 mM, about 6.25 mM, or about 3.125 mM.

In some embodiments, the method further comprises adding hyaluronic acid to the tissue culture. In some embodiments, the concentration of hyaluronic acid in the tissue culture ranges from about 0.001 to about 2 mg/mL, about 0.001 to about 1 mg/mL, about 0.01 mg/mL to about 10 mg/mL, about 0.01 mg/mL to about 5 mg/mL, about 0.01 mg/mL to about 2 mg/mL, about 0.01 mg/mL to about 1 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 50 mg/mL, about 4 mg/mL to about 30 mg/mL, about 4 mg/mL to about 25 mg/mL, about 4 mg/mL to about 20 mg/mL, about 1 mg/mL to about 3 mg/mL, or about 1 mg/mL to about 2 mg/mL.

In some embodiments, the method further comprises co-culturing the cells with astrocytes. In some embodiments, the neuronal cells are co-cultured with astrocytes at a ratio of 1:1 neuronal cell:astrocyte, 1:2, 1:3, 1:4, 1:5, 1:6, 1:7: 1:8, 1:9, 1:10, 1:20, 1:30, 1:50, 1:100, 100:1, 50:1, 30:1, 20:1, 10:1, 9:1, 8:1, 7:1, 6:1, 5:1, 4:1, 3:1, or 2:1. In some embodiments, the astrocytes are mammalian (e.g. human). Methods for generating astrocytes are described herein. In some embodiments, the concentration of neuronal cells and astrocytes in the tissue culture ranges from about 1 cell/mL to about 108 cells/mL, 1 cell/mL to about 107 cells/mL, 1 cell/mL to about 106 cells/mL, 1 cell/mL to about 105 cells/mL, 1 cell/mL to about 104 cells/mL, 1 cell/mL to about 103 cells/mL, 1 cell/mL to about 102 cells/mL, 1 cell/mL to about 10 cells/mL, about 104 cells/mL to about 108 cells/mL, about 104 cells/mL to about 107 cells/mL, about 104 cells/mL to about 106 cells/mL, about 104 cells/mL to about 105 cells/mL, about 105 cells/mL to about 108 cells/mL, about 105 cells/mL to about 107 cells/mL, about 105 cells/mL to about 106 cells/mL, about 106 cells/mL to about 108 cells/mL, or about 106 cells/mL to about 107 cells/mL. In some embodiments, the concentration of cells is about 1 million cells/mL, about 2 million cells/mL, about 3 million cells/mL, about 4 million cells/mL, about 5 million cells/mL, about 6 million cells/mL, about 7 million cells/mL, about 8 million cells/mL, about 9 million cells/mL, about 10 million cells/mL, about 11 million cells/mL, about 12 million cells/mL, about 13 million cells/mL, about 14 million cells/mL, about 15 million cells/mL, about 16 million cells/mL, about 17 million cells/mL, about 18 million cells/mL, about 19 million cells/mL, about 20 million cells/mL, about 50 million cells/mL, or about 100 million cells/mL. In particular embodiments, the concentration of cells is about 10 million per mL, about 20 million per mL, or about 30 million per mL.

In some embodiments, the 3D matrix further comprises an effective amount of a proliferation inhibitor, which suppresses proliferation of undifferentiated stem cells. In some embodiments, the proliferation inhibitor suppresses proliferation through inhibition of DNA replication and/or induction of G1/S phase cell cycle arrest. Non-limiting examples of proliferation inhibitors include 1-β-D-Arabinofuranosylcytosin (Ara-C), MCT1 Inhibitor (SR13800), GDH1 Inhibitor (R162), RSK Inhibitor (SL0101), Valproic Acid, sodium salt, Histone Deacetylase (HDAC) Inhibitor, Inauhzin, dactinomycin, actinomycin D, TAS-301, VTCN1, Galangin, Gramine, D-Valine, TBCA, sPLA2 inhibitor, 3-hydroxy-2-nitropyridine, FAK Inhibitor 14, Akt1/2 kinase inhibitor, linoleic acid, 2-methoxyestradiol, 4-(Trifluoromethoxy)phenylboronic acid, 4-Methyl-3-nitrophenylboronic acid, HS-72, SKLB1002, mimosine, 1,3-Diphenyl-2-propenone, CTX1, deferoxamine, ciclopirox, mitomycin C, or thymidine. In particular embodiments, the proliferation inhibitor is Ara-C. An effective amount is the amount required to suppress proliferation of undifferentiated stem cells. For embodiments wherein the proliferation inhibitor is Ara-C, an effective amount is from about 10 μM from about 1 μM to about 100 μM, about 1 μM to about 50 μM, about 1 μM to about 40 μM, about 1 μM to about 30 μM, about 1 μM to about 25 μM, about 1 μM to about 20 μM, about 1 μM to about 15 μM, about 1 μM to about 10 μM, about 1 μM to about 9 μM, about 1 μM to about 8 μM, about 1 μM to about 7 μM, about 1 μM to about 6 μM, about 1 μM to about 5 μM, about 1 μM to about 2 μM, about 3 μM to about 50 μM, about 3 μM to about 30 μM, about 3 μM to about 25 μM, about 3 μM to about 20 μM, about 3 μM to about 15 μM, about 3 μM to about 10 μM, about 3 μM to about 9 μM, about 3 μM to about 8 μM, about 3 μM to about 7 μM, about 3 μM to about 6 μM, about 3 μM to about 5 μM, about 6 μM to about 50 μM, about 6 μM to about 30 μM, about 6 μM to about 25 μM, about 6 μM to about 15 μM, or about 6 μM to about 10 μM. In particular embodiments, an effective amount of Ara-C is about 10 μM. In some embodiments, the hESCs express one or more transcription factors selected from the group consisting of NGN1, NGN2, Neurod1, ASCl1, Dlx2, SOX10, OLIG2, NKX6.2, ISL1, Lhx3, Phox2a, Brn2, Myt1l, Neurogenin-1, and Neurogenin-2.

In the embodiments wherein the neuronal cells are glutamatergic neurons, the methods may further comprise administration of cyclopamine, FGF2, and SMAD signaling inhibitors LDN193189 and SB432542, optionally followed by BDNF (see, e.g., Vazin, T. et al., Neurobiol Dis., 62: 62-72 (2014)). In the embodiments wherein the neuronal cells are GABAergic neurons, the methods may further comprise administration of valproic acid (VPA) followed by BDNF, GDNF, IGF, and cyclic-AMP to induce differentiation and maturation. Alternatively, the methods may further comprise transcription factor reprogramming, expression of Ngn2, Neurod1, or a combination of Ascl1 with Dlx2. In the embodiments wherein the neuronal cells are microglia, the methods may further comprise administration of VEGF, hBMP4, SCF, and Activin A, followed by differentiation in a second medium with SCF, hFLT3L, IL-3, IL-6, G-CSF, and BMP4 and co-culture with human astrocytes. In the embodiments wherein the neuronal cells are oligodendrocytes, the methods may further comprise induced expression of transcription factors such as SOX10, OLIG2, and NKX6.2 (see, e.g. Ehrlich, M. et al., Proc. Nat. Acad. Sci. U.S.A. 14(11):E2243-E2252 (2017)).

Astrocytic Cells

Astrocytes are star-shaped glial cells that perform a wide variety of functions in the central nervous system. The present disclosure provides novel methods for fast generation of astrocytic cells. Compared to conventional culturing methods, which take about 6 months to grow glial cells to organoids, the present methods generate astrocytic cells in a month, which enables rapid generation of isogenic 3D human neural tissues by controlling the number of neuronal and astrocytic cells from the same pool of hESCs.

Some aspects of the disclosure relate to methods of generating human astrocytic cells, comprising, consisting of, or consisting essentially of: providing a sample of pluripotent stem cells; introducing expression of neurogenin transcription factors NGN1 (NM_006161), NGN2 (NM_024019), and/or morphogen (ciliary neurotrophic factor, CTNF, NM_000614) in the pluripotent stem cells; and culturing the pluripotent stem cells in serum for a sufficient time to allow the pluripotent stem cells to differentiate into astrocytic cells.

NGN1 Entrez gene: 4762, RefSeq (human mRNA): NM_006161. A nonlimiting example of an NGN1 mRNA sequence is NM_006161.

NGN2 Entrez gene: 63973, RefSeq (human mRNA): NM_024019. A nonlimiting example of an NGN2 mRNA sequence is NM_024019.

CTNF Entrez gene: 1270, RefSeq (human mRNA): NM_000614. A nonlimiting example of an NGN1 mRNA sequence is NM_000614.

Astrocytes can be identified by their characteristic expression of one or more markers including but not limited to GFAP, EAAT1/GLAST, EAAT2/GLT-1, glutamine synthetase, S100 beta, ALDH1L1, and VIM. Detection of expression of these markers can be performed by any method known in the art including but not limited to immunohistochemistry, immunofluorescence, flow cytometry, PCR, quantitative PCR, real-time PCR, gene expression array, mRNA sequencing, high-throughput sequencing, Western blot, Northern blot, mass spectrometry, and ELISA.

In some aspects, the pluripotent stem cells are embryonic stem cells (ESCs) or induced pluripotent stem cells (iPSCs). In some aspects, the stem cells are from a mammalian species, e.g., human, ovine, bovine, canine, feline, murine, rat, or equine. In preferred aspects, the stem cells are human ESCs (hESCs) or human iPSCs.

In some embodiments, the concentration of pluripotent stem cells and/or astrocytes in the tissue culture ranges from about 1 cell/mL to about $10^8$ cells/mL, about 1 cell/mL to about $10^7$ cells/mL, 1 cell/mL to about $10^6$ cells/mL, 1 cell/mL to about $10^5$ cells/mL, 1 cell/mL to about $10^4$ cells/mL, 1 cell/mL to about $10^3$ cells/mL, 1 cell/mL to about 102 cells/mL, 1 cell/mL to about 10 cells/mL, about $10^4$ cells/mL to about $10^8$ cells/mL, about $10^4$ cells/mL to about $10^7$ cells/mL, about $10^4$ cells/mL to about $10^6$ cells/mL, about $10^4$ cells/mL to about $10^5$ cells/mL, about $10^5$ cells/mL to about $10^8$ cells/mL, about $10^5$ cells/mL to about $10^7$ cells/mL, about $10^5$ cells/mL to about $10^6$ cells/mL, about $10^6$ cells/mL to about $10^8$ cells/mL, or about $10^6$ cells/mL to about $10^7$ cells/mL. In some embodiments, the concentration of cells is about 1 million cells/mL, about 2 million cells/mL, about 3 million cells/mL, about 4 million cells/mL, about 5 million cells/mL, about 6 million cells/mL, about 7 million cells/mL, about 8 million cells/mL, about 9 million cells/mL, about 10 million cells/mL, about 11 million cells/mL, about 12 million cells/mL, about 13 million cells/mL, about 14 million cells/mL, about 15 million cells/mL, about 16 million cells/mL, about 17 million cells/mL, about 18 million cells/mL, about 19 million cells/mL, about 20 million cells/mL, about 50 million cells/mL, or about 100 million cells/mL. In particular embodiments, the concentration of cells is about 10 million per mL, about 20 million per mL, or about 30 million per mL.

Timing is critical for generating astrocytes. For example, in some embodiments expression of NGN1 and NGN2 transcription factors is induced for 2 days along with drug selection. Next, expression of the transcription factors is terminated and the cells are exposed to different culture conditions comprising one or more of morphogen and fetal bovine serum. Cells are immunostained at day 35 post induction for GFAP, S100 beta, VIM, and ALDH1L1. In some embodiments, cells must be cultured for at least 30 days to derive human astrocytic cells showing expression of astrocyte markers. In some embodiments, a sufficient time to allow the pluripotent stem cells to differentiate into astrocytic cells is about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, or about 50 days. In particular embodiments, sufficient time is between 28-42 days, between 28-35 days, between 30-35 days, between 35-40 days, 35 days, or 30 days.

In some embodiments, the serum is fetal bovine serum (FBS), fetal calf serum, human serum, animal-free growth supplement, goat serum, horse serum, mouse serum, rat serum, or rabbit serum. In some embodiments, the serum is heat inactivated and/or gamma irradiated. In a preferred aspect, the serum is FBS. In some embodiments, the concentration of serum is about 0.1% to about 1%, about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 1% to about 15%, about 1% to about 20%, about 1% to about 30%, about 1% to about 40%, about 1% to about 50%, about 1% to about 100%, about 5% to about 15%, or about 1% to about 20%. In particular embodiments, the concentration of serum is about 1%, about 5%, about 10%, or about 20%.

Introducing expression of genes can be performed by any method known in the art. Non-limiting examples include transduction with a viral vector (e.g. adenovirus, retrovirus, lentivirus), transfection, CRISPR-Cas systems, electroporation, plasmid injection, vesicle-mediated gene transfer, and inducible transgene expression.

Methods for Identifying Therapeutic Agents

The present disclosure also includes assays suitable for high-throughput screening of therapeutic agents for treating a neurological disease. Some aspects of the disclosure relate to methods of identifying a candidate agent for treating a neurological disease, comprising, consisting of, or consisting essentially of: providing a 3D neural tissue culture comprising neuronal cells derived from pluripotent stem cells and a 3D matrix comprising a biological supporting material, contacting the 3D neural tissue culture with a test compound, and detecting the expression and/or activity of one or more genes associated with the neurological disease, wherein an increase or decrease of one or more genes associated with the neurological disease indicates that the agent is effective for treating the neurological disease.

In some embodiments, the neurological disease is Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), spinal and bulbar muscular atrophy (SBMA), a brain cancer, a neurodegenerative disease, a psychiatric or cognitive disorder, or an autoimmune disease, as described herein.

In some embodiments, the candidate agent includes small molecule drugs, peptides, polynucleotides, and antibodies that affect the characteristics of the neuronal cells. Two or more agents can be tested in combination (by exposing to the cells either simultaneously or sequentially), to detect possible interactions between the two agents and/or rescue effects (e.g., by testing a toxin and a potential anti-toxin). Agent(s) and environmental condition(s) can be tested in combination (by treating the cells with an agent either simultaneously or sequentially relative to an environmental condition), to detect possible agent-environment interaction effects.

In some embodiments, the screening assay is selected in a manner appropriate to the cell type and agent and/or environmental factor being studied. For example, changes in cell morphology may be assayed by standard light, or electron microscopy. Alternatively, the effects of treatments by the agent potentially affecting the expression of one or more genes may be assayed by measuring the expression level of the genes. As another example, the effects of treatments or compounds which potentially alter the pH or levels of various ions within cells may be assayed using various dyes which change in color at determined pH values or in the presence of particular ions. The use of such dyes is well known in the art. For cells which have been transformed or transfected with a genetic marker, such as the β-galactosidase, alkaline phosphatase, or luciferase genes, the effects of treatments or compounds may be assessed by assays for expression of that marker. In particular, the marker may be chosen so as to cause spectrophotometrically assayable changes associated with its expression.

In some embodiments, the present disclosure provides a method for screening therapeutic agents for potential cytotoxicity. Cytotoxicity can be determined by the effect on cell viability, morphology, and leakage of enzymes into the culture medium. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT In some embodiments, a colorimetric assay can be performed to quantitatively measure LDH released into the media from cells as a biomarker for cellular cytotoxicity and cytolysis (e.g. ThermoFisher Scientific cat. #88953). For these embodiments, culture mediums can be collected without disassociated 3D tissues. These collections can occur at different timepoints and/or regular intervals (e.g. every 24 hours) to measure lactate dehydrogenase (LDH) released from the tissue as a result of gene perturbation.

In some embodiments, the present disclosure provides method for determining whether the therapeutic agent(s) affect neuronal cell function without causing toxicity. In certain embodiments, the present disclosure includes a method for assessing an agent that alters biological activity of neuronal cells, comprising contacting a 3D neural tissue culture as described herein with an agent, and assaying for an alteration in biological activity of neuronal cells relative to a control 3D tissue neural culture not exposed to the agent, wherein detection of the alteration identifies the agent as altering biological activity of neuronal cells. In certain embodiments, the biological activity of the neuronal cells is selected from proliferation, survival, differentiation, toxicity, ion channel activity, neuronal excitability, or combinations thereof.

In some embodiments, the disclosure provides a method for assessing the metabolism of a therapeutic agent by neuronal cells, comprising exposing the 3D neural tissue culture of the invention to a candidate agent, and determining the effect of the neuronal cells on the agent. For example, the effect may be measured by detecting, identifying, and/or quantifying metabolites of the agent.

In the embodiments wherein the neurological disease is FTD, the one or more genes are selected from the group of superoxide dismutase 1 (SOD1, Entrez gene: 6647), TAR DNA-binding protein 43 (TARDBP, Entrez gene: 23435), and Serine/threonine-protein kinase TBK1 (TBK1, Entrez gene: 29110). In the embodiments wherein the neurological disease is ASD, the one or more genes are selected from the group of clusterin (CLU, Entrez gene: 1191), Probable E3 ubiquitin-protein ligase TRIP12 (TRIP12, Entrez gene: 9320), Ubiquitin-protein ligase E3A (UBE3A, Entrez gene: 7337), Calcium channel, voltage-dependent, L type, alpha 1C subunit (CACNA1C, Entrez gene: 775), Chromodomain-helicase-DNA-binding protein 8 (CHD8, Entrez gene: 57680), SET domain containing 5 (SETD5, Entrez gene: 55209), Phosphatase and tensin homolog (PTEN, Entrez gene: 5728), sodium channel, voltage-gated, type II, alpha subunit (SCN2A, Entrez gene: 6326), methyl CpG binding protein 2 (Rett syndrome) (MECP2, Entrez gene: 4204), Probable global transcription activator SNF2L2 (SMARCA2, Entrez gene: 6595), and chromosome 12 open reading frame 57 (C12orf57, Entrez gene: 113246). In the embodiments wherein the neurological disease is ALS, the one or more genes are selected from the group of Zinc Finger SWIM-Type Containing 7 (ZSWIM7, Entrez gene: 125150), SOD1, Netrin-G1 (NTNG1, Entrez gene: 22854), Lipoma HMGIC fusion partner (LHFP, Entrez gene: 10186), chromosome 9 open reading frame 72 (C9orf72, Entrez gene: 203228), TARDBP, TBK1, and ciliary neurotrophic factor (CNTF, Entrez gene: 1270). In the embodiments wherein the neurological disease is AD, the one or more genes are selected from the group of CLU, solute carrier family 24 member 4 (SLC24A4, Entrez gene 123041), Parkinson disease protein 7 (PARK7, Entrez gene: 11315), Myc box-dependent-interacting protein 1 (BIN1, Entrez gene: 274), Phosphatidylinositol binding clathrin assembly protein (PICALM, Entrez gene: 8301), Fermitin family homolog 2 (FERMT2, Entrez gene: 10979), CUG triplet repeat, RNA binding protein 1 (CELF1, Entrez gene: 10658), and ATP-binding cassette sub-family A member 7 (ABCA7, Entrez gene: 10347). In the embodiments wherein the neurological disease is PD, the one or more genes are selected from the group of alpha-synuclein (SNCA, Entrez gene: 6622), STE20/SPS1-related proline-alanine-rich protein kinase (STK39, 27347), Disks large homolog 2 (DLG2, Entrez gene: 1740), ASH1L (Entrez gene: 55870), Branched chain ketoacid dehydrogenase kinase (BCKDK, Entrez gene: 10295), Tau protein (MAPT, Entrez gene: 4137), Transmembrane protein 229b (TMEM229B, Entrez gene: 161145), and Leucine-rich repeat kinase 2 (LRRK2, Entrez gene: 120892).

Detection of changes in expression of genes and/or gene products can be assayed by any method known in the art including but not limited to immunohistochemistry, immunofluorescence, flow cytometry, polymerase chain reaction (PCR), quantitative PCR, real-time PCR, gene expression array, mRNA sequencing, high-throughput sequencing, Western blot, Northern blot, and ELISA.

SNCA RefSeq (mRNA): NM_000345, NM_001146054, NM_001146055, NM_007308. A nonlimiting example of SNCA mRNA is NM_000345

STK39 RefSeq (mRNA): NM_013233. A nonlimiting example of STK39 mRNA is NM_013233.

DLG2 RefSeq (mRNA): NM_001142699, NM_001142700, NM_001142702, NM_001206769, NM_001300983, NM_001364, NM_001351274, NM_001351275, NM_001351276. A nonlimiting example of DLG2 mRNA is NM_001142699.

ASH1L RefSeq (mRNA): NM_018489. A nonlimiting example of ASH1L mRNA is NM_018489.

BCKDK RefSeq (mRNA): NM_005881, NM_001122957, NM_001271926. A nonlimiting example of BCKDK mRNA is NM_005881.

MAPT RefSeq (mRNA): NM_001123066, NM_001123067, NM_001203251, NM_001203252, NM_005910. A nonlimiting example of MAPT mRNA is NM_001123066.

TMEM229B RefSeq (mRNA): NM_182526. A nonlimiting example of TMEM229B mRNA is NM_182526.

NTNG1 RefSeq (mRNA): NM_001113226, NM_001113228, NM_001312688, NM_014917, NM_001330665. A nonlimiting example of NTNG1 mRNA is NM_001113226.

LHFP RefSeq (mRNA): NM_005780. A nonlimiting example of LHFP mRNA is NM_005780.

C9orf72 RefSeq (mRNA): NM_005780, NM_145005, NM_001256054, NM_018325. A nonlimiting example of C9orf72 mRNA is NM_005780.

CNTF RefSeq (mRNA): NM_000614. A nonlimiting example of CNTF mRNA is NM_000614.

SLC24A4 RefSeq (mRNA): NM_153646, NM_153647, NM_153648. A nonlimiting example of SLC24A4 mRNA is NM_153646.

PARK7 RefSeq (mRNA): NM_001123377, NM_007262. A nonlimiting example of PARK7 mRNA is NM_001123377.

BIN1 RefSeq (mRNA): NM_004305, NM_139343, NM_139344, NM_139345, NM_139346. A nonlimiting example of BIN1 mRNA is NM_004305.

PICALM RefSeq (mRNA): NM_001008660, NM_001206946, NM_001206947, NM_007166. A nonlimiting example of PICALM mRNA is NM_001008660.

FERMT2 RefSeq (mRNA): NM_001134999, NM_001135000, NM_006832. A nonlimiting example of FERMT2 mRNA is NM_001134999.

CELF1 RefSeq (mRNA): NM_001025596, NM_001172639, NM_001172640, NM_006560, NM_198700, NM_001330272. A nonlimiting example of CELF1 mRNA is NM_001025596.

ABCA7 RefSeq (mRNA): NM_019112, NM_033308. A nonlimiting example of ABCA7 mRNA is NM_019112.

ZSWIM7 RefSeq (mRNA): NM_001042697, NM_001042698. A nonlimiting example of ZSWIM7 mRNA is NM_001042697.

TBK1 RefSeq (mRNA): NM_013254. A nonlimiting example of TBK mRNA is NM_013254.

CLU RefSeq (mRNA): NM_001831. A nonlimiting example of CLU mRNA is NM_001831.

TRIP12 RefSeq (mRNA): NM_001284214, NM_001284215, NM_001284216, NM_004238. A nonlimiting example of TRIP12 mRNA is NM_001284214.

UBE3A RefSeq (mRNA): NM_000462, NM_130838, NM_130839. A nonlimiting example of UBE3A mRNA is NM_000462.

CACNA1C RefSeq (mRNA): NM_000719, NM_001129827, NM_001129829, NM_001129830, NM_001129831. A nonlimiting example of CACNA1C mRNA is NM_000719.

CHD8 RefSeq (mRNA): NM_020920, NM_001170629. A nonlimiting example of CHD8 mRNA is NM_020920.

SETD5 RefSeq (mRNA): NM_001080517, NM_001292043, NM_018187, NM_001349451. A nonlimiting example of SETD5 mRNA is NM_001080517.

PTEN RefSeq (mRNA): NM_000314, NM_001304717, NM_001304718. A nonlimiting example of PTEN mRNA is NM_000314.

SCN2A RefSeq (mRNA): NM_001040142, NM_001040143, NM_021007. A nonlimiting example of SCN2A mRNA is NM_001040142.

MECP2 RefSeq (mRNA): NM_001110792, NM_004992, NM_001316337. A nonlimiting example of MECP2 mRNA is NM_001110792

SMARCA2 RefSeq (mRNA): NM_139045, NM_001289396, NM_001289397, NM_001289398, NM_001289399, NM_001289400, NM_003070. A nonlimiting example of SMARCA2 mRNA is NM_139045.

C12orf57 RefSeq (mRNA): NM_001301834, NM_001301836, NM_001301837, NM_001301838, NM_138425. A nonlimiting example of C12orf57 mRNA is NM_001301834.1.

SOD1 RefSeq (mRNA): NM_000454. A nonlimiting example of SOD1 mRNA is NM_000454.

TARDBP RefSeq (mRNA): NM_007375. A nonlimiting example of TARDBP mRNA is NM_007375.

Kits

Some aspects of the disclosure relate to kits for screening a candidate agent for treating a neurological disease, comprising: a 3D neural tissue culture comprising neuronal cells derived from pluripotent stem cells and a 3D matrix comprising a biological supporting material, wherein one or more genes associated with the neurological disease in the neuronal cells have been disrupted.

In some embodiments, the neurological disease is Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), or spinal and bulbar muscular atrophy (SBMA), as described herein.

In some embodiments, the neurological disease may be FTD, and the one or more genes associated with the neurological disease may be SOD1, TARDBP, and TBK1, as described herein.

In some embodiments, the neurological disease may be ASD, and the one or more genes associated with the neurological disease may be CLU3, TRIP12, UBE3A, CACNA1C, CHD8, SETD5, PTEN, SCN2A, MECP2, SMARCA2, and C12orf57, as described herein.

In some embodiments, the neurological disease may be ALS, and the one or more genes associated with the neurological disease may be ZSWIM7, SOD1, NTNG1, LHFP, C9orf72, TARDBP, TBK1, and CNTF, as described herein.

In some embodiments, the neurological disease may be AD, and the one or more genes associated with the neurological disease may be CLU, SLC24A4, PARK7, BIN1, PICALM, FERMT2, CELF1, and ABCA7, as described herein.

In some embodiments, the neurological disease may be PD, and the one or more genes associated with the neurological disease may be SNCA, STK39, DLG2, ASH1L, BCKDK, MAPT, TMEM229B, and LRRK2, as described herein.

Cell Line Models

Some aspects of the disclosure relate to methods of constructing a cell line model for a neurological disease, comprising, consisting of, or consisting essentially of: providing a 3D neural tissue culture comprising neuronal cells derived from hESCs and a 3D matrix comprising a biological supporting material, wherein the neuronal cells have been modified to express a CRISPR-Cas protein; and modifying the expression of one or more genes associated with the neurological disease in the neuronal cells by a CRISPR-Cas system to obtain a cell line model for the neurological disease.

In some embodiments, the one or more genes associated with the neurological disease are selected from the group consisting of CLU3, TRIP12, UBE3A, CACNA1C, ZSWIM7, SOD1, NTNG1, CLU, SLC24A, SNCA, STK39, and DLG2.

In some embodiments, the neuronal cells are selected from the group consisting of glutamatergic neurons, GABAergic neurons, dopaminergic neurons, microglia, oligodendrocytes, motor neurons, and bipolar neurons. In some embodiments, the neuronal cells are induced neuronal cells (iN). In some embodiments, the concentration of neuronal cells in the tissue culture ranges from about 1 cell/mL to about 108 cells/mL, 1 cell/mL to about 107 cells/mL, 1 cell/mL to about 106 cells/mL, 1 cell/mL to about 105 cells/mL, 1 cell/mL to about 104 cells/mL, 1 cell/mL to about 103 cells/mL, 1 cell/mL to about 102 cells/mL, 1 cell/mL to about 10 cells/mL, about 104 cells/mL to about 108 cells/mL, about 104 cells/mL to about 107 cells/mL, about 104 cells/mL to about 106 cells/mL, about 104 cells/mL to about 105 cells/mL, about 105 cells/mL to about 108 cells/mL, about 105 cells/mL to about 107 cells/mL, about 105 cells/mL to about 106 cells/mL, about 106 cells/mL to about 108 cells/mL, or about 106 cells/mL to about 107 cells/mL. In some embodiments, the concentration of cells is about 1 million cells/mL, about 2 million cells/mL, about 3 million cells/mL, about 4 million cells/mL, about 5 million cells/mL, about 6 million cells/mL, about 7 million cells/mL, about 8 million cells/mL, about 9 million cells/mL, about 10 million cells/mL, about 11 million cells/mL, about 12 million cells/mL, about 13 million cells/mL, about 14 million cells/mL, about 15 million cells/mL, about 16 million cells/mL, about 17 million cells/mL, about 18 million cells/mL, about 19 million cells/mL, about 20 million cells/mL, about 50 million cells/mL, or about 100 million cells/mL. In particular embodiments, the concentration of cells is about 10 million per mL, about 20 million per mL, or about 30 million per mL.

In some embodiments, the biological supporting material is selected from the group consisting of one or more extracellular matrix proteins, a basement membrane matrix, gelatin, silk protein-based porous scaffolds, alginate, and composite hydrogel.

Extracellular matrix proteins include but are not limited to laminin, collagen, vitronectin, fibronectin, entactin, nidogen-2, elastin, perlecan, and tropoelastin. In some embodiments, two or more extracellular matrix proteins and/or protein complexes are combined to form an extracellular matrix composition. For example, the biological supporting material may comprise a mixture of laminin and collagen IV. In some embodiments, the extracellular matrix protein is recombinant.

Basement membrane matrices are derived from the extracellular matrix that separates the epithelium, endothelium, muscle, or neuronal cells from adjacent stromal tissue (known as the basement membrane). The basement membrane is comprised of a thin, delicate membrane of extracellular matrix proteins and glycosaminoglycans (LeBleu, V. S. et al. Exp Biol Med 232(9):1121-29 (2007)). A solubilized basement membrane matrix can be prepared from the extracellular matrix of Engelbreth-Holm-Swarm (EHS) mouse sarcoma cells (see, e.g. Robinson, L. K. et al. J Biol. Chem. 264(9): 5141-47 (1989). For example, Matrigel is derived from EHS and comprises extracellular matrix proteins such as laminin, collagen IV, growth factors, heparin sulfate proteoglycans, entactin, and nidogen. Matrigel is available in a standard formulation (Corning cat. #356234), high protein concentration formulation (Corning cat. #354248), growth factor reduced formulation comprising a more highly defined basement membrane preparation (Corning cat. #356230), and hESC-qualified formulations that have been pre-screened for compatibility with mTeSR1 medium from Stem Cell Technologies (Corning cat. #354277). The standard protein concentration formulations comprise 8-12 mg/mL. The high protein concentration formulations comprise 18-21 mg/mL. Cultrex BME is also derived from EHS and comprises laminin, collagen IV, entactin, and heparin sulfate proteoglycans. Cultrex BME is available in a reduced growth factor formulation for 3-D culture (Trevigen cat. #3433-001-01), stem cell qualified formulation (Trevigen cat. #3434-001-02), and organoid qualified formulations (e.g., Trevigen cat. #3533-001-02). All Cultrex formulations range from 12-18 mg/mL of protein except the reduced growth factor culture formulation which ranges from 14-16 mg/mL of protein. Gibco Geltrex Matrix is a basement membrane matrix derived from EHS and available in reduced growth factor formulations (ThermoFisher Scientific cat. #A1569601).

In some embodiments, the concentration of biological supporting material in the tissue culture ranges from about 1 mg/mL to about 30 mg/mL, about 1 mg/mL to about 25 mg/mL, about 1 mg/mL to about 20 mg/mL, about 1 mg/mL to about 15 mg/mL, about 1 mg/mL to about 10 mg/mL, about 1 mg/mL to about 9 mg/mL, about 1 mg/mL to about 8 mg/mL, about 1 mg/mL to about 7 mg/mL, about 1 mg/mL to about 6 mg/mL, about 1 mg/mL to about 5 mg/mL, about 4 mg/mL to about 30 mg/mL, about 4 mg/mL to about 25 mg/mL, about 4 mg/mL to about 20 mg/mL, about 1 mg/mL to about 3 mg/mL, about 1 mg/mL to about 2 mg/mL, about 4 mg/mL to about 20 mg/mL, about 4 mg/mL to about 15 mg/mL, about 4 mg/mL to about 10 mg/mL, about 4 mg/mL to about 9 mg/mL, about 4 mg/mL to about 8 mg/mL, about 4 mg/mL to about 7 mg/mL, about 4 mg/mL to about 6 mg/mL, about 4 mg/mL to about 5 mg/mL, about 7 mg/mL to about 10 mg/mL, about 7 mg/mL to about 15 mg/mL, about 7 mg/mL to about 20 mg/mL, about 8 mg/mL to about 10 mg/mL, or about 0.001 mg/mL to about 1 mg/mL. In particular embodiments, the concentration of basement membrane matrix is about 4.4 mg/mL, about 4.6 mg/mL, about 7.36 mg/mL, about 8.5 mg/mL, or about 10 mg/mL.

In some embodiments, the method further comprises mutating an endogenous gene by a CRISPR-Cas system. In some embodiments, the method further comprises transcriptionally activating expression of an endogenous gene by a CRISPR-Cas system. In some embodiments, the method further comprises transcriptionally repressing expression of an endogenous gene by a CRISPR-Cas system. In some embodiments, the method further comprises introducing an exogenous gene by a CRISPR-Cas system.

Further aspects of the disclosure relate to a cell line model for a neurological disease obtained by any one of the methods of constructing a cell line model described herein.

In other aspects the cell line model may be constructed by (a) providing a tractable three-dimensional neural tissue culture as described herein; (b) identifying differences in one or more cell types and/or cell states between the three-dimensional neural tissue culture and an in vivo system; and (c) modulating the density/stiffness of the biological supporting material of the matrix to decrease the distance in expression space between the neural tissue culture and an in vivo system. In some embodiments, identifying differences in one or more cell types and/or cell states comprises comparison of differentially expressed genes.

In some embodiments, the neurological disease is Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), or spinal and bulbar muscular atrophy (SBMA).

In certain embodiments, the gene signatures described herein are screened by perturbation of target genes within said signatures. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; and International publication serial number WO/2017/075294). The present invention is compatible with perturb-seq, such that signature genes may be perturbed and the perturbation may be identified and assigned to the proteomic and gene expression readouts of single cells. In certain embodiments, signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a cancer. Thus, in certain embodiments, perturb-seq is used to discover novel drug targets to allow treatment of specific cancer patients having the gene signature of the present invention.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10× genomics). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/naturel4136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimizing deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (~10 sgRNAs/gene) may also be used in a mouse that expresses a Cas9 protein (see, e.g., WO2014204727A1).

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

CRISPR Development and Use

In another aspect, the present disclosure provides methods of gene targeting and/or genome editing of one or more genes in the neuronal cells by any method known in the art including but not limited to CRISPR-Cas mediated gene disruption. Such methods are useful, e.g., in the context of decreasing protein expression in neuronal cells. In some embodiments, genes are targeting and/or edited using DNA binding proteins. In the embodiments wherein the neurological disease is FTD, the one or more genes are selected from the group of SOD1, TARDBP, and TBK1. In the embodiments wherein the neurological disease is ASD, the one or more genes are selected from the group of CLU3, TRIP12, UBE3A, CACNA1C, CHD8, SETD5, PTEN, SCN2A, MECP2, SMARCA2, and C12orf57. In the embodiments wherein the neurological disease is ALS, the one or more genes are selected from the group of ZSWIM7, SOD1, NTNG1, LHFP, C9orf72, TARDBP, TBK1, and CNTF. In the embodiments wherein the neurological disease is AD, the one or more genes are selected from the group of CLU, SLC24A4, PARK7, BIN1, PICALM, FERMT2, CELF1, and ABCA7. In the embodiments wherein the neurological disease is AD, the one or more genes are selected from the group of CLU, SLC24A4, PARK7, BIN1, PICALM, FERMT2, CELF1, and ABCA7. In the embodiments wherein the neurological disease is PD, the one or more genes are selected from the group of SNCA, STK39, DLG2, ASH1L, BCKDK, MAPT, TMEM229B, and LRRK2.

In certain embodiments, the DNA binding protein is a (endo)nuclease or a variant thereof having altered or modified activity (i.e. a modified nuclease, as described herein elsewhere). In certain embodiments, said nuclease is a targeted or site-specific or homing nuclease or a variant thereof having altered or modified activity. In certain embodiments, said nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease. In certain embodiments, said (modified) nuclease or targeted/site-specific/homing nuclease is, comprises, consists essentially of, or consists of a (modified) RNA-guided nuclease. As used herein, the term "Cas" generally refers to a (modified) effector protein of the CRISPR/Cas system or complex, and can be without limitation a (modified) Cas9, or other enzymes such as Cpf1, C2c1, C2c2, or C2c3. The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

As used herein, the term "targeting" of a selected nucleic acid sequence means that a nuclease or nuclease complex is acting in a nucleotide sequence specific manner. For instance, in the context of the CRISPR/Cas system, the guide RNA is capable of hybridizing with a selected nucleic acid sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

In certain embodiments, the DNA binding protein is a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification is effected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9CRISPR/Cas-expressing eukaryotic cells, Cas-9 CRISPR/Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), WO2015/058052 (PCT/US2014/061077), WO2015070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO/2016/04925 (PCT/US2015/051830), WO/2016/094867 (PCT/US2015/065385), WO/2016/094872 (PCT/US2015/065393), WO/2016/094874 (PCT/US2015/065396), WO/2016/106244 (PCT/US2015/067177)

Reference is further made to Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013); RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013); DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi: 10.1038/nbt.2647 (2013); Genome engineering using the CRISPR-Cas9 system. Ran, F A., Hsu, P D., Wright, J., Agarwala, V., Scott, D A., Zhang, F. Nature Protocols November; 8(11):2281-308. (2013); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print]; Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27. (2014). 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) Apr. 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12): 1262-7 (2014) published online 3 Sep. 2014; doi:10.1038/nbt.3026, and In vivo interrogation of gene function in the mammalian brain using CRISPR-Cas9, Swiech et al, Nature Biotechnology 33, 102-106 (2015) published online 19 Oct. 2014; doi:10.1038/nbt.3055, Cpf1 Is a Single RNA-Guided Endonuclease of a Class 2 CRISPR-Cas System, Zetsche et al., Cell 163, 1-13 (2015); Discovery and Functional Characterization of Diverse Class 2 CRISPR-Cas Systems, Shmakov et al., Mol Cell 60(3): 385-397 (2015); Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Preferred DNA binding proteins are CRISPR/Cas enzymes or variants thereof. In certain embodiments, the CRISPR/Cas protein is a class 2 CRISPR/Cas protein. In certain embodiments, said CRISPR/Cas protein is a type II, type V, or type VI CRISPR/Cas protein. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using said short RNA guide.

In general, the CRISPR/Cas or CRISPR system is as used herein foregoing documents refers collectively to elements involved in the expression of or directing the activity of CRISPR-associated ("Cas") proteins or genes, including sequences encoding a Cas protein and a guide RNA. In this context of the guide RNA this may include one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

In certain embodiments, the gRNA comprises a guide sequence fused to a tracr mate sequence (or direct repeat), and a tracr sequence In particular embodiments, the guide sequence fused to the tracr mate and the tracr sequence are provided or expressed as discrete RNA sequences. In preferred embodiments, the gRNA is a chimeric guide RNA or single guide RNA (sgRNA), comprising a guide sequence fused to the tracr mate which is itself linked to the tracr sequence. In particular embodiments, the CRISPR/Cas system or complex as described herein does not comprise and/or does not rely on the presence of a tracr sequence (e.g. if the Cas protein is Cpf1).

As used herein, the term "guide sequence" in the context of a CRISPR/Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay.

In certain embodiments, the target sequence should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/naturel4592. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. The skilled person will understand that other Cas proteins may be modified analogously.

In some embodiments, the nucleic acid-targeting effector protein may be mutated with respect to a corresponding wild-type enzyme such that the mutated nucleic acid-targeting effector protein lacks the ability to cleave one or both DNA strands of a target polynucleotide containing a target sequence. As a further example, two or more catalytic domains of a Cas protein (e.g. RuvC I, RuvC II, and RuvC III or the HNH domain of a Cas9 protein, or HEPN domain of Cas13) may be mutated to produce a mutated Cas protein which cleaves only one DNA strand of a target sequence.

In particular embodiments, the nucleic acid-targeting effector protein may be mutated with respect to a corresponding wild-type enzyme such that the mutated nucleic acid-targeting effector protein lacks substantially all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

As used herein, the term "modified" Cas generally refers to a Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

In certain embodiments, the nuclease, and in particular the Cas proteins of prokaryotic origin, may be codon optimized for expression into a particular host (cell). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid. Codon optimization may be for expression into any desired host (cell), including mammalian, plant, algae, or yeast.

With particular reference to the CRISPR/Cas system as described herein, besides the Cas protein, in addition or in the alternative, the gRNA and/or tracr (where applicable) and/or tracr mate (or direct repeat) may be modified. Suitable modifications include, without limitation dead guides, escorted guides, protected guides, or guides provided with aptamers, suitable for ligating to, binding or recruiting functional domains (see e.g. also elsewhere herein the reference to synergistic activator mediators (SAM)). Mention is also made of WO/2016/049258 (FUNCTIONAL SCREENING WITH OPTIMIZED FUNCTIONAL CRISPR-CAS SYSTEMS (SAM)), WO/2016/094867 (PROTECTED GUIDE RNAS (PGRNAS); WO/2016/094872 (DEAD GUIDES FOR CRISPR TRANSCRIPTION FACTORS); WO/2016/094874 (ESCORTED AND FUNCTIONALIZED GUIDES FOR CRISPR-CAS SYSTEMS); all incorporated herein by reference. In certain embodiments, the tracr sequence (where appropriate) and/or tracr mate sequence (direct repeat), may comprise one or more protein-interacting RNA aptamers. The one or more aptamers may be located in the tetraloop and/or stemloop 2 of the tracr sequence. The one or more aptamers may be capable of binding MS2 bacteriophage coat protein. In certain embodiments, the gRNA (or trace or tracr mate) is modified by truncations, and/or incorporation of one or more mismatches vis-à-vis the intended target sequence or sequence to hybridize with.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

CRISPR-Cas9

In certain embodiments, the CRISPR enzyme is Type-II or Type-V CRISPR-Cas proteins. This is exemplified herein with Cas9, C2c1 and C2c3, whereby a number of orthologs or homologs have been identified. It will be apparent to the skilled person that further orthologs or homologs can be identified and that any of the functionalities described herein may be engineered into other orthologs, including chimeric enzymes comprising fragments from multiple orthologs.

Orthologs of Cas9

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related.

The Cas9 gene is found in several diverse bacterial genomes, typically in the same locus with casl, cas2, and cas4 genes and a CRISPR cassette. Furthermore, the Cas9 protein contains a readily identifiable C-terminal region that is homologous to the transposon ORF-B and includes an active RuvC-like nuclease, an arginine-rich region.

In particular embodiments, the effector protein is a Cas9 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium*, or *Corynebacter,*

In particular embodiments, the effector protein is a Cas9 effector protein from an organism from a genus comprising *Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes,*

*Helcococcus, Letospira, Desulfovibrio, Desulfonatronum, Opitutaceae, Tuberibacillus, Bacillus, Brevibacilus, Methylobacterium* or *Acidaminococcus.*

In further particular embodiments, the Cas9 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii.* In particular embodiments, the effector protein is a Cas9 effector protein from an organism from *Streptococcus pyogenes, Staphylococcus aureus*, or *Streptococcus thermophilus* Cas9.

The effector protein may comprise a chimeric effector protein comprising a first fragment from a first effector protein (e.g., a Cas9) ortholog and a second fragment from a second effector (e.g., a Cas9) protein ortholog, and wherein the first and second effector protein orthologs are different. At least one of the first and second effector protein (e.g., a Cas9) orthologs may comprise an effector protein (e.g., a Cas9) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium* or *Acidaminococcus*; e.g., a chimeric effector protein comprising a first fragment and a second fragment wherein each of the first and second fragments is selected from a Cas9 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium* or *Acidaminococcus* wherein the first and second fragments are not from the same bacteria; for instance a chimeric effector protein comprising a first fragment and a second fragment wherein each of the first and second fragments is selected from a Cas9 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*, wherein the first and second fragments are not from the same bacteria.

In a more preferred embodiment, the Cas9 is derived from a bacterial species selected from *Streptococcus pyogenes, Staphylococcus aureus*, or *Streptococcus thermophilus* Cas9. In certain embodiments, the Cas9p is derived from a bacterial species selected from *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*. In certain embodiments, the Cas9p is derived from a bacterial species selected from *Acidaminococcus* sp. BV3L6, Lachnospiraceae bacterium MA2020. In certain embodiments, the effector protein is derived from a subspecies of *Francisella tularensis* 1, including but not limited to *Francisella tularensis* subsp. *Novicida.*

In particular embodiments, the homologue or orthologue of Cas9 as referred to herein has a sequence homology or identity of at least 80%, more preferably at least 85%, even more preferably at least 90%, such as for instance at least 95% with Cas9. In further embodiments, the homologue or orthologue of Cas9 as referred to herein has a sequence identity of at least 80%, more preferably at least 85%, even more preferably at least 90%, such as for instance at least 95% with the wild type Cas9. Where the Cas9 has one or more mutations (mutated), the homologue or orthologue of said Cas9 as referred to herein has a sequence identity of at least 80%, more preferably at least 85%, even more preferably at least 90%, such as for instance at least 95% with the mutated Cas9.

In an embodiment, the Cas9 protein may be an ortholog of an organism of a genus which includes, but is not limited to *Streptococcus* sp. or *Staphilococcus* sp.; in particular embodiments, Cas9 protein may be an ortholog of an organism of a species which includes, but is not limited to *Streptococcus pyogenes, Staphylococcus aureus*, or *Streptococcus thermophilus* Cas9. In particular embodiments, the homologue or orthologue of Cas9p as referred to herein has a sequence homology or identity of at least 80%, more preferably at least 85%, even more preferably at least 90%, such as for instance at least 95% with one or more of the Cas9 sequences disclosed herein. In further embodiments, the homologue or orthologue of Cas9 as referred to herein has a sequence identity of at least 80%, more preferably at least 85%, even more preferably at least 90%, such as for instance at least 95% with the wild type SpCas9, SaCas9 or StCas9.

In particular embodiments, the Cas9 protein of the invention has a sequence homology or identity of at least 60%, more particularly at least 70, such as at least 80%, more preferably at least 85%, even more preferably at least 90%, such as for instance at least 95% with SpCas9, SaCas9 or StCas9. In further embodiments, the Cas9 protein as referred to herein has a sequence identity of at least 60%, such as at least 70%, more particularly at least 80%, more preferably at least 85%, even more preferably at least 90%, such as for instance at least 95% with the wild type SpCas9, SaCas9 or StCas9. The skilled person will understand that this includes truncated forms of the Cas9 protein whereby the sequence identity is determined over the length of the truncated form.

C2c1 and C2c3 Effector Protein

In some embodiments, the Type-V CRIPSR protein is a C2c1 or C2c3 protein from a genus selected from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium,*

*Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium* or *Acidaminococcus.*

In certain embodiments, the C2c1 protein, may originate from, may be isolated from or may be derived from a bacterial species belonging to the taxa Bacilli, Verrucomicrobia, alpha-proteobacteria or delta-proteobacteria. In certain embodiments, the C2c1 protein, may originate from, may be isolated from or may be derived from a bacterial species belonging to a genus selected from the group consisting of *Alicyclobacillus, Desulfovibrio, Desulfonatronum, Opitutaceae, Tuberibacillus, Bacillus, Brevibacillus, Desulfatirhabdium, Citrobacter*, and *Methylobacterium*. In certain embodiments, the C2c1 protein, may originate, may be isolated or may be derived from a bacterial species selected from the group consisting of *Alicyclobacillus acidoterrestris* (e.g., ATCC 49025), *Alicyclobacillus contaminans* (e.g., DSM 17975), *Desulfovibrio inopinatus* (e.g., DSM 10711), *Desulfonatronum thiodismutans* (e.g., strain MLF-1), Opitutaceae bacterium TAV5, *Tuberibacillus calidus* (e.g., DSM 17572), *Bacillus thermoamylovorans* (e.g., strain B4166), *Brevibacillus* sp. CF112, *Bacillus* sp. NSP2.1, *Desulfatirhabdium butyrativorans* (e.g., DSM 18734), *Alicyclobacillus herbarius* (e.g., DSM 13609), *Citrobacter freundii* (e.g., ATCC 8090), *Brevibacillus agri* (e.g., BAB-2500), *Methylobacterium nodulans* (e.g., ORS 2060).

In certain embodiments, the C2c3 protein, may originate, may be isolated or may be derived from a bacterial metagenome. Additional C2c1 and C2c3 proteins and orthologues are described in WO 2016/205749, which is described herein by reference in its entirety.

In certain embodiments, the C2c1 protein, and preferably the C-terminal portion of said C2c1 protein, comprises the three catalytic motifs of the RuvC-like nuclease (i.e., RuvCI, RuvCII and RuvCIII). In certain embodiments, said C2c1 protein, and preferably the C-terminal portion, may further comprise a region corresponding to the bridge helix (also known as arginine-rich cluster) that in Cas9 protein is involved in crRNA-binding. In certain embodiments, said C2c1 protein, and preferably the C-terminal portion, may further comprise a Zn finger region, which may be inactive (i.e., which does not bind zinc, e.g., in which the Zn-binding cysteine residue(s) are missing). In certain embodiments, said C2c1 protein, and preferably the C-terminal portion, may comprise the three catalytic motifs of the RuvC-like nuclease (i.e., RuvCI, RuvCII and RuvCIII), the region corresponding to the bridge helix, and the Zn finger region, preferably in the following order, from N to C terminus: RuvCI-bridge helix-RuvCII-Zinc finger-RuvCIII. In certain embodiments, the C2c1 protein is engineered and can comprise one or more mutations that reduce or eliminate a nuclease activity. In some embodiments, only the RuvC domain is inactivated, and in other embodiments, another putative nuclease domain is inactivated, wherein the effector protein complex functions as a nickase and cleaves only one DNA strand.

In certain embodiments, the C2c3 protein, and preferably the C-terminal portion of said C2c3 protein, comprises the three catalytic motifs of the RuvC-like nuclease (i.e., RuvCI, RuvCII and RuvCIII). In certain embodiments, said C2c3 protein, and preferably the C-terminal portion, may further comprise a region corresponding to the bridge helix (also known as arginine-rich cluster) that in Cas9 protein is involved in crRNA-binding. In certain embodiments, said C2c3 protein, and preferably the C-terminal portion, may further comprise a Zn finger region. Preferably, the Zn-binding cysteine residue(s) may be conserved in C2c3p. In certain embodiments, said C2c3 protein, and preferably the C-terminal portion, may comprise the three catalytic motifs of the RuvC-like nuclease (i.e., RuvCI, RuvCII and RuvCIII), the region corresponding to the bridge helix, and the Zn finger region, preferably in the following order, from N to C terminus: RuvCI-bridge helix-RuvCII-Zinc finger-RuvCIII. In certain embodiments, the C2c3 protein is engineered and can comprise one or more mutations that reduce or eliminate a nuclease activity. In some embodiments, only the RuvC domain is inactivated, and in other embodiments, another putative nuclease domain is inactivated, wherein the effector protein complex functions as a nickase and cleaves only one DNA strand.

The inactivated C2c1/C2c3 or C2c1/C2c3 nickase thereof may have associated (e.g., via fusion protein) one or more functional domains, including for example, an adenosine deaminase or catalytic domain thereof. In some cases it is advantageous that additionally at least one heterologous NLS is provided. In some instances, it is advantageous to position the NLS at the N terminus. In general, the positioning of the one or more functional domain on the inactivated C2c1/C2c3 enzyme or C2c1/C2c3 nickase is one which allows for correct spatial orientation for the functional domain to affect the target with the attributed functional effect. For example, when the functional domain is an adenosine deaminase catalytic domain thereof, the adenosine deaminase catalytic domain is placed in a spatial orientation which allows it to contact and deaminate a target adenine. This may include positions other than the N-/C-terminus of C2c1/C2c3. In some embodiments, the adenosine deaminase protein or catalytic domain thereof is inserted into an internal loop of C2c1/C2c3.

In some embodiments, the Type-V CRIPSR protein is an inactive *Alicyclobacillus acidoterrestris* C2c1 comprising one or more mutations selected from D570A, E848A, or D977A.

CRISPR-Cas 13

In certain embodiments, the CRISPR enzyme is Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayyeh et al. 2016, Science, 5; 353(6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Casl. In further embodiments, the CRISPR array is used as a seed to identify new effector proteins.

Preassembled recombinant CRISPR-Cas13 complexes comprising Cas13 and crRNA may be transfected, for example by electroporation, resulting in high mutation rates and absence of detectable off-target mutations. Hur, J. K. et al, Targeted mutagenesis in mice by electroporation of Cas13 ribonucleoproteins, Nat Biotechnol. 2016 Jun. 6. doi:

10.1038/nbt.3596. Genome-wide analyses shows that Cas13 is highly specific. By one measure, in vitro cleavage sites determined for Cas13 in human HEK293T cells were significantly fewer that for SpCas9. Kim, D. et al., Genome-wide analysis reveals specificities of Cas13 endonucleases in human cells, Nat Biotechnol. 2016 Jun. 6. doi: 10.1038/nbt.3609. An efficient multiplexed system employing Cas13 has been demonstrated in *Drosophila* employing gRNAs processed from an array containing inventing tRNAs. Port, F. et al, Expansion of the CRISPR toolbox in an animal with tRNA-flanked Cas9 and Cas13 gRNAs. doi: http://dx-.doi.org/10.1101/046417.

A number of orthologs or homologs of Cas13 have been identified. It will be apparent to the skilled person that further orthologs or homologs can be identified and that any of the functionalities described herein may be engineered into other orthologs, including chimeric enzymes comprising fragments from multiple orthologs.

In one aspect the identifying all predicted protein coding genes is carried out by comparing the identified genes with Cas protein-specific profiles and annotating them according to NCBI Conserved Domain Database (CDD) which is a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM). In a further aspect, CRISPR arrays were predicted using a PILER-CR program which is a public domain software for finding CRISPR repeats as described in "PILER-CR: fast and accurate identification of CRISPR repeats", Edgar, R. C., BMC Bioinformatics, January 20; 8:18(2007), herein incorporated by reference.

In a further aspect, the case by case analysis is performed using PSI-BLAST (Position-Specific Iterative Basic Local Alignment Search Tool). PSI-BLAST derives a position-specific scoring matrix (PSSM) or profile from the multiple sequence alignment of sequences detected above a given score threshold using protein-protein BLAST. This PSSM is used to further search the database for new matches, and is updated for subsequent iterations with these newly detected sequences. Thus, PSI-BLAST provides a means of detecting distant relationships between proteins.

In another aspect, the case by case analysis is performed using HHpred, a method for sequence database searching and structure prediction that is as easy to use as BLAST or PSI-BLAST and that is at the same time much more sensitive in finding remote homologs. In fact, HHpred's sensitivity is competitive with the most powerful servers for structure prediction currently available. HHpred is the first server that is based on the pairwise comparison of profile hidden Markov models (HMMs). Whereas most conventional sequence search methods search sequence databases such as UniProt or the NR, HHpred searches alignment databases, like Pfam or SMART. This greatly simplifies the list of hits to a number of sequence families instead of a clutter of single sequences. All major publicly available profile and alignment databases are available through HHpred. HHpred accepts a single query sequence or a multiple alignment as input. Within only a few minutes it returns the search results in an easy-to-read format similar to that of PSI-BLAST. Search options include local or global alignment and scoring secondary structure similarity. HHpred can produce pairwise query-template sequence alignments, merged query-template multiple alignments (e.g. for transitive searches), as well as 3D structural models calculated by the MODELLER software from HHpred alignments.

Orthologs of Cas13

The Cas13 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cas13 protein contains a readily identifiable C-terminal region that is homologous to the transposon ORF-B and includes an active RuvC-like nuclease, an arginine-rich region, and a Zn finger (absent in Cas9). However, unlike Cas9, Cas13 is also present in several genomes without a CRISPR-Cas context and its relatively high similarity with ORF-B suggests that it might be a transposon component. It was suggested that if this was a genuine CRISPR-Cas system and Cas13 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cas13 is denoted to be in subtype V-A to distinguish it from C2c1p which does not have an identical domain structure and is hence denoted to be in subtype V-B.

The present invention encompasses the use of a Cas13 effector protein, derived from a Cas13 locus denoted as subtype V-A. Herein such effector proteins are also referred to as "Cas13p", e.g., a Cas13 protein (and such effector protein or Cas13 protein or protein derived from a Cas13 locus is also called "CRISPR-Cas protein").

In particular embodiments, the effector protein is a Cas13 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacilus, Methylobacterium, Butyvibrio, Perigrinibacterium, Pareubacterium, Moraxella, Thiomicrospira* or *Acidaminococcus*. In particular embodiments, the Cas13 effector protein is selected from an organism from a genus selected from *Eubacterium, Lachnospiraceae, Leptotrichia, Francisella, Methanomethyophilus, Porphyromonas, Prevotella, Leptospira, Butyvibrio, Perigrinibacterium, Pareubacterium, Moraxella, Thiomicrospira* or *Acidaminococcus.*

In further particular embodiments, the Cas13 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii, L inadai, F. tularensis* 1, *P. albensis, L. bacterium, B. proteoclasticus, P. bacterium, P. creviricanis, P. disiens* and *P. macacae.*

The effector protein may comprise a chimeric effector protein comprising a first fragment from a first effector protein (e.g., a Cas13) ortholog and a second fragment from a second effector (e.g., a Cas13) protein ortholog, and wherein the first and second effector protein orthologs are different. At least one of the first and second effector protein (e.g., a Cas13) orthologs may comprise an effector protein (e.g., a Cas13) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Butyvibrio, Perigrinibacterium, Pareubacterium, Moraxella, Thiomicrospira* or *Acidaminococcus*; e.g., a chimeric effector protein comprising a first fragment and a second fragment wherein each of the first and second fragments is selected from a Cas13 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Butyvibrio, Perigrinibacterium, Pareubacterium, Moraxella, Thiomicrospira* or *Acidaminococcus* wherein the first and second fragments are not from the same bacteria; for instance a chimeric effector protein comprising a first fragment and a second fragment wherein each of the first and second fragments is selected from a Cas13 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*, wherein the first and second fragments are not from the same bacteria.

In a more preferred embodiment, the Cas13p is derived from a bacterial species selected from *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Moraxella bovoculi AAX*08_00205, *Moraxella bovoculi AAX*11_00205, *Butyrivibrio* sp. NC3005, *Thiomicrospira* sp. XS5, *Leptospira inadai*, Lachnospiraceae bacterium ND2006, *Porphyromonas crevioricanis* 3, *Prevotella disiens* and *Porphyromonas macacae*. In certain embodiments, the Cas13p is derived from a bacterial species selected from *Acidaminococcus* sp. BV3L6, Lachnospiraceae bacterium MA2020. In certain embodiments, the effector protein is derived from a subspecies of *Francisella tularensis* 1, including but not limited to *Francisella tularensis* subsp. *Novicida*. In certain preferred embodiments, the Cas13p is derived from a bacterial species selected from *Acidaminococcus* sp. BV3L6, Lachnospiraceae bacterium ND2006, Lachnospiraceae bacterium MA2020, *Moraxella bovoculi AAX*08_00205, *Moraxella bovoculi* AAX11_00205, *Butyrivibrio* sp. NC3005, or *Thiomicrospira* sp. XS5.

In particular embodiments, the homologue or orthologue of Cas13 as referred to herein has a sequence homology or identity of at least 80%, more preferably at least 85%, even more preferably at least 90%, such as for instance at least 95% with the example Cas13 proteins disclosed herein. In further embodiments, the homologue or orthologue of Cas13 as referred to herein has a sequence identity of at least 80%, more preferably at least 85%, even more preferably at least 90%, such as for instance at least 95% with the wild type Cas13. Where the Cas13 has one or more mutations (mutated), the homologue or orthologue of said Cas13 as referred to herein has a sequence identity of at least 80%, more preferably at least 85%, even more preferably at least 90%, such as for instance at least 95% with the mutated Cas13.

In an embodiment, the Cas13 protein may be an ortholog of an organism of a genus which includes, but is not limited to *Acidaminococcus* sp, Lachnospiraceae bacterium or *Moraxella bovoculi*; in particular embodiments, the type V Cas protein may be an ortholog of an organism of a species which includes, but is not limited to *Acidaminococcus* sp. BV3L6; Lachnospiraceae bacterium ND2006 (LbCas13) or *Moraxella bovoculi* 237. In particular embodiments, the homologue or orthologue of Cas13 as referred to herein has a sequence homology or identity of at least 80%, more preferably at least 85%, even more preferably at least 90%, such as for instance at least 95% with one or more of the Cas13 sequences disclosed herein. In further embodiments, the homologue or orthologue of Cas13 as referred to herein has a sequence identity of at least 80%, more preferably at least 85%, even more preferably at least 90%, such as for instance at least 95% with the wild type FnCas13, AsCas13 or LbCas13.

In particular embodiments, the Cas13 protein of the invention has a sequence homology or identity of at least 60%, more particularly at least 70, such as at least 80%, more preferably at least 85%, even more preferably at least 90%, such as for instance at least 95% with FnCas13, AsCas13 or LbCas13. In further embodiments, the Cas13 protein as referred to herein has a sequence identity of at least 60%, such as at least 70%, more particularly at least 80%, more preferably at least 85%, even more preferably at least 90%, such as for instance at least 95% with the wild type AsCas13 or LbCas13. In particular embodiments, the Cas13 protein of the present invention has less than 60% sequence identity with FnCas13. The skilled person will understand that this includes truncated forms of the Cas13 protein whereby the sequence identity is determined over the length of the truncated form. In particular embodiments, the Cas13 enzyme is not FnCas13.

Modified Cas13 Enzymes

In particular embodiments, it is of interest to make use of an engineered Cas13 protein as defined herein, such as Cas13, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cas13 protein, and wherein the CRISPR complex comprising the modified protein has altered activity as compared to the complex comprising the unmodified Cas13 protein. It is to be understood that when referring herein to CRISPR "protein", the Cas13 protein preferably is a modified CRISPR-Cas protein (e.g. having increased or decreased (or no) enzymatic activity, such as without limitation including Cas13. The term "CRISPR protein" may be used interchangeably with "CRISPR-Cas protein", irrespective of whether the CRISPR protein has altered, such as increased or decreased (or no) enzymatic activity, compared to the wild type CRISPR protein.

Computational analysis of the primary structure of Cas13 nucleases reveals three distinct regions. First a C-terminal RuvC like domain, which is the only functional characterized domain. Second a N-terminal alpha-helical region and thirst a mixed alpha and beta region, located between the RuvC like domain and the alpha-helical region.

Several small stretches of unstructured regions are predicted within the Cas13 primary structure. Unstructured regions, which are exposed to the solvent and not conserved within different Cas13 orthologs, are preferred sides for splits and insertions of small protein sequences. In addition, these sides can be used to generate chimeric proteins between Cas13 orthologs.

Based on the above information, mutants can be generated which lead to inactivation of the enzyme or which modify the double strand nuclease to nickase activity. In alternative embodiments, this information is used to develop enzymes with reduced off-target effects (described elsewhere herein).

Deactivated/Inactivated Cas13 Protein

Where the Cas13 protein has nuclease activity, the Cas13 protein may be modified to have diminished nuclease activity e.g., nuclease inactivation of at least 70%, at least 80%, at least 90%, at least 95%, at least 97%, or 100% as compared with the wild type enzyme; or to put in another way, a Cas13 enzyme having advantageously about 0% of the nuclease activity of the non-mutated or wild type Cas13 enzyme or CRISPR-Cas protein, or no more than about 3% or about 5% or about 10% of the nuclease activity of the non-mutated or wild type Cas13 enzyme, e.g. of the non-mutated or wild type *Francisella novicida* U112 (FnCas13), *Acidaminococcus* sp. BV3L6 (AsCas13), Lachnospiraceae bacterium ND2006 (LbCas13) or *Moraxella bovoculi* 237 (MbCas13 Cas13 enzyme or CRISPR-Cas protein. This is possible by introducing mutations into the nuclease domains of the Cas13 and orthologs thereof.

In preferred embodiments of the present invention at least one Cas13 protein is used which is a Cas13 nickase. More particularly, a Cas13 nickase is used which does not cleave the target strand but is capable of cleaving only the strand which is complementary to the target strand, i.e. the non-target DNA strand also referred to herein as the strand which is not complementary to the guide sequence. More particularly the Cas13 nickase is a Cas13 protein which comprises a mutation in the arginine at position 1226A in the Nuc domain of Cas13 from *Acidaminococcus* sp., or a corresponding position in a Cas13 ortholog. In further particular embodiments, the enzyme comprises an arginine-to-alanine substitution or an R1226A mutation. It will be understood by the skilled person that where the enzyme is not AsCas13, a mutation may be made at a residue in a corresponding position. In particular embodiments, the Cas13 is FnCas13 and the mutation is at the arginine at position R1218. In particular embodiments, the Cas13 is LbCas13 and the mutation is at the arginine at position R1138. In particular embodiments, the Cas13 is MbCas13 and the mutation is at the arginine at position R1293.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain.

The inactivated Cas13 or Cas13 nickase may have associated (e.g., via fusion protein) one or more functional domains, including for example, an adenosine deaminase or catalytic domain thereof. In some cases it is advantageous that additionally at least one heterologous NLS is provided. In some instances, it is advantageous to position the NLS at the N terminus. In general, the positioning of the one or more functional domain on the inactivated Cas13 or Cas13 nickase is one which allows for correct spatial orientation for the functional domain to affect the target with the attributed functional effect. For example, when the functional domain is an adenosine deaminase catalytic domain thereof, the adenosine deaminase catalytic domain is placed in a spatial orientation which allows it to contact and deaminate a target adenine. This may include positions other than the N-/C-terminus of Cas13. In some embodiments, the adenosine deaminase protein or catalytic domain thereof is inserted into an internal loop of Cas13.

CRISPR-Cpf1

In certain embodiments, the CRISPR enzyme is Cpf1 a type II nuclease that does not make use of tracrRNA. Orthologs of Cpf1 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Preassembled recombinant CRISPR-Cpf1 complexes comprising Cpf1 and crRNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun. 6. doi: 10.1038/nbt.3596. Genome-wide analyses shows that Cpf1 is highly specific. By one measure, in vitro cleavage sites determined for Cpf1 in human HEK293T cells were significantly fewer that for SpCas9. Kim, D. et al., Genome-wide analysis reveals specificities of Cpf1 endonucleases in human cells, Nat Biotechnol. 2016 Jun. 6. doi: 10.1038/nbt.3609. An efficient multiplexed system employing Cpf1 has been demonstrated in *Drosophila* employing gRNAs processed from an array containing inventing tRNAs. Port, F. et al, Expansion of the CRISPR toolbox in an animal with tRNA-flanked Cas9 and Cpf1 gRNAs. doi: http://dx.doi.org/10.1101/046417.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

The application describes methods using Type-V CRISPR-Cas proteins. This is exemplified herein with Cpf1, whereby a number of orthologs or homologs have been identified. It will be apparent to the skilled person that further orthologs or homologs can be identified and that any of the functionalities described herein may be engineered into other orthologs, including chimeric enzymes comprising fragments from multiple orthologs.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is devoted to be in subtype V-A to distinguish it from C2c1p which does not have an identical domain structure and is hence denoted to be in subtype V-B.

The present invention encompasses the use of a Cpf1 effector protein, derived from a Cpf1 locus denoted as subtype V-A. Herein such effector proteins are also referred to as "Cpf1p", e.g., a Cpf1 protein (and such effector protein or Cpf1 protein or protein derived from a Cpf1 locus is also called "CRISPR-Cas protein").

In particular embodiments, the effector protein is a Cpf1 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacilus, Methylobacterium, Butyvibrio, Perigrinibacterium, Pareubacterium, Moraxella, Thiomicrospira* or *Acidaminococcus*. In particular embodiments, the Cpf1 effector protein is selected from an organism from a genus selected from *Eubacterium, Lachnospiraceae, Leptotrichia, Francisella, Methanomethyophilus, Porphyromonas, Prevotella, Leptospira, Butyvibrio, Perigrinibacterium, Pareubacterium, Moraxella, Thiomicrospira* or *Acidaminococcus.*

In further particular embodiments, the Cpf1 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii, L inadai, F. tularensis* 1, *P. albensis, L. bacterium, B. proteoclasticus, P. bacterium, P. crevioricanis, P. disiens* and *P. macacae.*

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different. At least one of the first and second effector protein (e.g., a Cpf1) orthologs may comprise an effector protein (e.g., a Cpf1) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Butyvibrio, Perigrinibacterium, Pareubacterium, Moraxella, Thiomicrospira* or *Acidaminococcus*; e.g., a chimeric effector protein comprising a first fragment and a second fragment wherein each of the first and second fragments is selected from a Cpf1 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Butyvibrio, Perigrinibacterium, Pareubacterium, Moraxella, Thiomicrospira* or *Acidaminococcus* wherein the first and second fragments are not from the same bacteria; for instance a chimeric effector protein comprising a first fragment and a second fragment wherein each of the first and second fragments is selected from a Cpf1 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae*, wherein the first and second fragments are not from the same bacteria.

In a more preferred embodiment, the Cpf1p is derived from a bacterial species selected from *Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus Methanoplasma termitum, Eubacterium eligens, Moraxella bovoculi* 237, *Moraxella bovoculi* AAX08_00205, *Moraxella bovoculi* AAX11_00205, *Butyrivibrio* sp. NC3005, *Thiomicrospira* sp. XS5, *Leptospira inadai*, Lachnospiraceae bacterium ND2006, *Porphyromonas* crevioricanis 3, *Prevotella disiens* and *Porphyromonas macacae*. In certain embodiments, the Cpf1p is derived from a bacterial species selected from *Acidaminococcus* sp. BV3L6, Lachnospiraceae bacterium MA2020. In certain embodiments, the effector protein is derived from a subspecies of *Francisella tularensis* 1, including but not limited to *Francisella tularensis* subsp. *Novicida*. In certain preferred embodiments, the Cpf1p is derived from a bacterial species selected from *Acidaminococcus* sp. BV3L6, Lachnospiraceae bacterium ND2006, Lachnospiraceae bacterium MA2020, *Moraxella bovoculi* AAX08_00205, *Moraxella bovoculi* AAX11_00205, *Butyrivibrio* sp. NC3005, or Thiomicrospira sp. XS5.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to *Acidaminococcus* sp, Lachnospiraceae bacterium or *Moraxella bovoculi*; in particular embodiments, the type V Cas protein may be an ortholog of an organism of a species which includes, but is not limited to *Acidaminococcus* sp. BV3L6; Lachnospiraceae bacterium ND2006 (LbCpf1) or *Moraxella bovoculi* 237. In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1.

In particular embodiments, the Cpf1 protein of the invention has a sequence homology or identity of at least 60%, more particularly at least 70, such as at least 80%, more preferably at least 85%, even more preferably at least 90%, such as for instance at least 95% with FnCpf1, AsCpf1 or LbCpf1. In further embodiments, the Cpf1 protein as referred to herein has a sequence identity of at least 60%, such as at least 70%, more particularly at least 80%, more preferably at least 85%, even more preferably at least 90%, such as for instance at least 95% with the wild type AsCpf1 or LbCpf1. In particular embodiments, the Cpf1 protein of the present invention has less than 60% sequence identity with FnCpf1. The skilled person will understand that this includes truncated forms of the Cpf1 protein whereby the sequence identity is determined over the length of the truncated form. In particular embodiments, the Cpf1 enzyme is not FnCpf1.

Modified Cpf1 Enzymes

In particular embodiments, it is of interest to make use of an engineered Cpf1 protein as defined herein, such as Cpf1, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cpf1 protein, and wherein the CRISPR complex comprising the modified protein has altered activity as compared to the complex comprising the unmodified Cpf1 protein. It is to be understood that when referring herein to CRISPR "protein", the Cpf1 protein preferably is a modified CRISPR-Cas protein (e.g. having increased or decreased (or no) enzymatic activity, such as without limitation including Cpf1. The term "CRISPR protein" may be used interchangeably with "CRISPR-Cas protein", irrespective of whether the CRISPR protein has altered, such as increased or decreased (or no) enzymatic activity, compared to the wild type CRISPR protein.

Computational analysis of the primary structure of Cpf1 nucleases reveals three distinct regions. First a C-terminal RuvC like domain, which is the only functional characterized domain. Second a N-terminal alpha-helical region and thirst a mixed alpha and beta region, located between the RuvC like domain and the alpha-helical region.

Several small stretches of unstructured regions are predicted within the Cpf1 primary structure. Unstructured regions, which are exposed to the solvent and not conserved within different Cpf1 orthologs, are preferred sides for splits and insertions of small protein sequences. In addition, these sides can be used to generate chimeric proteins between Cpf1 orthologs.

Based on the above information, mutants can be generated which lead to inactivation of the enzyme or which modify the double strand nuclease to nickase activity. In alternative embodiments, this information is used to develop enzymes with reduced off-target effects (described elsewhere herein).

Determination of PAM

Determination of PAM can be ensured as follows. This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In further detail, the assay is as follows for a DNA target. Two *E. coli* strains are used in this assay. One carries a plasmid that encodes the endogenous effector protein locus from the bacterial strain. The other strain carries an empty plasmid (e.g. pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has a 8 random bp 5' of the proto-spacer (e.g. total of 65536 different PAM sequences=complexity). The other library has 7 random bp 3' of the proto-spacer (e.g. total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12 h after transformation, all colonies formed by the test and control strains where harvested and plasmid DNA was isolated. Plasmid DNA was used as template for PCR amplification and subsequent deep sequencing. Representation of all PAMs in the untransfomed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

With respect to the C2c1 protein, it may recognize a 5' PAM. In certain embodiments, the C2c1 protein may recognize a 5' PAM which is 5' TTN or 5' ATTN, where N is A, C, G or T. In certain preferred embodiments, the Type-V CRIPSR protein may be *Alicyclobacillus acidoterrestris* C2c1, more preferably *Alicyclobacillus acidoterrestris* ATCC 49025 C2c1, and the 5' PAM is 5' TTN, where N is A, C, G or T, more preferably where N is A, G or T. In other preferred embodiments, the Type-V CRIPSR protein is *Bacillus thermoamylovorans* C2c1, more preferably *Bacillus thermoamylovorans* strain B4166 C2c1, and the 5' PAM is 5' ATTN, where NisA, C, GorT.

Codon Optimized Nucleic Acid Sequences

Where the effector protein is to be administered as a nucleic acid, the application envisages the use of codon-optimized Cas9, C2c1 or C2c3 sequences (and optionally protein sequences). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cas9, C2c1 or C2c3) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gowri, Plant Physiol. 1990 January; 92(1): 1-11; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59.

In certain of the above-described Cpf1 enzymes, the enzyme is modified by mutation of one or more residues (in the RuvC domain) including but not limited to positions R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, R1220, R1226, R1242, and/or R1252 with reference to amino acid position numbering of AsCpf1 (*Acidaminococcus* sp. BV3L6). In certain embodiments, the Cpf1 enzymes comprising said one or more mutations have modified, more preferably increased specificity for the target.

In certain of the above-described non-naturally-occurring CRISPR-Cas proteins, the enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (*Acidaminococcus* sp. BV3L6). In certain embodiments, the Cpf1 enzymes comprising said one or more mutations have modified, more preferably increased specificity for the target.

In certain of the Cpf1 enzymes, the enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (*Acidaminococcus* sp. BV3L6). In certain embodiments, the Cpf1 enzymes comprising said one or more mutations have modified, more preferably increased specificity for the target.

In certain embodiments, the Cpf1 enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (Lachnospiraceae bacterium ND2006). In certain embodiments, the Cpf1 enzymes comprising said one or more mutations have modified, more preferably increased specificity for the target.

In certain embodiments, the Cpf1 enzyme is modified by mutation of one or more residues including but not limited positions K15, R18, K26, Q34, R43, K48, K51, R56, R84, K85, K87, N93, R103, N104, T118, K123, K134, R176, K177, R192, K200, K226, K273, K275, T291, R301, K307, K369, S404, V409, K414, K436, K438, K468, D482, K516, R518, K524, K530, K532, K548, K559, K570, R574, K592, D596, K603, K607, K613, C647, R681, K686, H720, K739, K748, K757, T766, K780, R790, P791, K796, K809, K815, T816, K860, R862, R863, K868, K897, R909, R912, T923, R947, K949, R951, R955, K965, K968, K1000, R1003, K1009, K1017, K1022, K1029, A1053, K1072, K1086, F1103, S1209, R1226, R1252, K1273, K1282, and/or K1288 with reference to amino acid position numbering of AsCpf1 (*Acidaminococcus* sp. BV3L6). In certain embodiments, the Cpf1 enzymes comprising said one or more mutations have modified, more preferably increased specificity for the target.

In certain embodiments, the enzyme is modified by mutation of one or more residues including but not limited positions K15, R18, K26, R34, R43, K48, K51, K56, K87, K88, D90, K96, K106, K107, K120, Q125, K143, R186, K187, R202, K210, K235, K296, K298, K314, K320, K326, K397, K444, K449, E454, A483, E491, K527, K541, K581, R583, K589, K595, K597, K613, K624, K635, K639, K656, K660, K667, K671, K677, K719, K725, K730, K763, K782, K791, R800, K809, K823, R833, K834, K839, K852, K858, K859, K869, K871, R872, K877, K905, R918, R921, K932, 1960, K962, R964, R968, K978, K981, K1013, R1016, K1021, K1029, K1034, K1041, K1065, K1084, and/or K1098 with reference to amino acid position numbering of FnCpf1 (*Francisella novicida* U112). In certain embodiments, the Cpf1 enzymes comprising said one or more mutations have modified, more preferably increased specificity for the target.

In certain embodiments, the enzyme is modified by mutation of one or more residues including but not limited positions K15, R18, K26, K34, R43, K48, K51, R56, K83, K84, R86, K92, R102, K103, K116, K121, R158, E159, R174, R182, K206, K251, K253, K269, K271, K278, P342, K380, R385, K390, K415, K421, K457, K471, A506, R508, K514, K520, K522, K538, Y548, K560, K564, K580, K584, K591, K595, K601, K634, K640, R645, K679, K689, K707, T716, K725, R737, R747, R748, K753, K768, K774, K775, K785, K787, R788, Q793, K821, R833, R836, K847, K879, K881, R883, R887, K897, K900, K932, R935, K940, K948, K953, K960, K984, K1003, K1017, R1033, K1121, R1138, R1165, K1190, K1199, and/or K1208 with reference to amino acid position numbering of LbCpf1 (Lachnospiraceae bacterium ND2006). In certain embodiments, the Cpf1 enzymes comprising said one or more mutations have modified, more preferably increased specificity for the target.

In certain embodiments, the enzyme is modified by mutation of one or more residues including but not limited positions K14, R17, R25, K33, M42, Q47, K50, D55, K85, N86, K88, K94, R104, K105, K118, K123, K131, R174, K175, R190, R198, I221, K267, Q269, K285, K291, K297, K357, K403, K409, K414, K448, K460, K501, K515, K550, R552, K558, K564, K566, K582, K593, K604, K608, K623, K627, K633, K637, E643, K780, Y787, K792, K830, Q846, K858, K867, K876, K890, R900, K901, M906, K921, K927, K928, K937, K939, R940, K945, Q975, R987, R990, K1001, R1034, 11036, R1038, R1042, K1052, K1055, K1087, R1090, K1095, N1103, K1108, K1115, K1139, K1158, R1172, K1188, K1276, R1293, A1319, K1340, K1349, and/or K1356 with reference to amino acid position numbering of MbCpf1 (*Moraxella bovoculi* 237). In certain embodiments, the Cpf1 enzymes comprising said one or more mutations have modified, more preferably increased specificity for the target.

In one embodiment, the Cpf1 protein is modified with a mutation at S1228 (e.g., S1228A) with reference to amino acid position numbering of AsCpf1. See Yamano et al., Cell 165:949-962 (2016), which is incorporated herein by reference in its entirety.

In certain embodiments, the Cpf1 protein has been modified to recognize a non-natural PAM, such as recognizing a PAM having a sequence or comprising a sequence YCN, YCV, AYV, TYV, RYN, RCN, TGYV, NTTN, TTN, TRTN, TYTV, TYCT, TYCN, TRTN, NTTN, TACT, TYCC, TRTC, TATV, NTTV, TTV, TSTG, TVTS, TYYS, TCYS, TBYS, TCYS, TNYS, TYYS, TNTN, TSTG, TTCC, TCCC, TATC, TGTG, TCTG, TYCV, or TCTC. In particular embodiments, said mutated Cpf1 comprises one or more mutated amino acid residue at position 11, 12, 13, 14, 15, 16, 17, 34, 36, 39, 40, 43, 46, 47, 50, 54, 57, 58, 111, 126, 127, 128, 129, 130, 131, 132, 133, 134, 135, 136, 157, 158, 159, 160, 161, 162, 163, 164, 165, 166, 167, 168, 169, 170, 171, 172, 173, 174, 175, 176, 177, 178, 532, 533, 534, 535, 536, 537, 538, 539, 540, 541, 542, 543, 544, 545, 546, 547, 548, 549, 550, 551, 552, 553, 554, 555, 556, 565, 566, 567, 568, 569, 570, 571, 572, 573, 574, 575, 592, 593, 594, 595, 596, 597, 598, 599, 600, 601, 602, 603, 604, 605, 606, 607, 608, 609, 610, 611, 612, 613, 614, 615, 616, 617, 618, 619, 620, 626, 627, 628, 629, 630, 631, 632, 633, 634, 635, 636, 637, 638, 642, 643, 644, 645, 646, 647, 648, 649, 651, 652, 653, 654, 655, 656, 676, 679, 680, 682, 683, 684, 685, 686, 687, 688, 689, 690, 691, 692, 693, 707, 711, 714, 715, 716, 717, 718, 719, 720, 721, 722, 739, 765, 768, 769, 773, 777, 778, 779, 780, 781, 782, 783, 784, 785, 786, 871, 872, 873, 874, 875, 876, 877, 878, 879, 880, 881, 882, 883, 884, or 1048 of AsCpf1 or a position corresponding thereto in a Cpf1 ortholog; preferably, one or more mutated amino acid residue at position 130, 131, 132, 133, 134, 135, 136, 162, 163, 164, 165, 166, 167, 168, 169, 170, 171, 172, 173, 174, 175, 176, 177, 536, 537, 538, 539, 540, 541, 542, 543, 544, 545, 546, 547, 548, 549, 550, 551, 552, 570, 571, 572, 573, 595, 596, 597, 598, 599, 600, 601, 602, 603, 604, 605, 606, 607, 608, 609, 610, 611, 612, 613, 614, 615, 630, 631, 632, 646, 647, 648, 649, 650, 651, 652, 653, 683, 684, 685, 686, 687, 688, 689, or 690.

In certain embodiments, the Cpf1 protein is modified to have increased activity, i.e. wider PAM specificity. In particular embodiments, the Cpf1 protein is modified by mutation of one or more residues including but not limited positions 539, 542, 547, 548, 550, 551, 552, 167, 604, and/or 607 of AsCpf1, or the corresponding position of an AsCpf1 orthologue, homologue, or variant, preferably mutated amino acid residues at positions 542 or 542 and 607, wherein said mutations preferably are 542R and 607R, such as S542R and K607R; or preferably mutated amino acid residues at positions 542 and 548 (and optionally 552), wherein said mutations preferably are 542R and 548V (and optionally 552R), such as S542R and K548V (and optionally N552R); or at position 532, 538, 542, and/or 595 of LbCpf1, or the corresponding position of an AsCpf1 orthologue, homologue, or variant, preferably mutated amino acid residues at positions 532 or 532 and 595, wherein said mutations preferably are 532R and 595R, such as G532R and K595R; or preferably mutated amino acid residues at positions 532 and 538 (and optionally 542), wherein said mutations preferably are 532R and 538V (and optionally 542R), such as G532R and K538V (and optionally Y542R), most preferably wherein said mutations are S542R and K607R, S542R and K548V, or S542R, K548V and N552R of AsCpf1.

Deactivated/Inactivated Cpf1 Protein

Where the Cpf1 protein has nuclease activity, the Cpf1 protein may be modified to have diminished nuclease activity e.g., nuclease inactivation of at least 70%, at least 80%, at least 90%, at least 95%, at least 97%, or 100% as compared with the wild type enzyme; or to put in another way, a Cpf1 enzyme having advantageously about 0% of the nuclease activity of the non-mutated or wild type Cpf1 enzyme or CRISPR-Cas protein, or no more than about 3% or about 5% or about 10% of the nuclease activity of the non-mutated or wild type Cpf1 enzyme, e.g. of the non-mutated or wild type *Francisella novicida* U112 (FnCpf1), *Acidaminococcus* sp. BV3L6 (AsCpf1), Lachnospiraceae bacterium ND2006 (LbCpf1) or *Moraxella bovoculi* 237 (MbCpf1 Cpf1 enzyme or CRISPR-Cas protein. This is possible by introducing mutations into the nuclease domains of the Cpf1 and orthologs thereof.

In preferred embodiments of the present invention at least one Cpf1 protein is used which is a Cpf1 nickase. More particularly, a Cpf1 nickase is used which does not cleave the target strand but is capable of cleaving only the strand which is complementary to the target strand, i.e. the non-target DNA strand also referred to herein as the strand which is not complementary to the guide sequence. More particularly the Cpf1 nickase is a Cpf1 protein which comprises a mutation in the arginine at position 1226A in the Nuc domain of Cpf1 from *Acidaminococcus* sp., or a corresponding position in a Cpf1 ortholog. In further particular embodiments, the enzyme comprises an arginine-to-alanine substitution or an R1226A mutation. It will be understood by the skilled person that where the enzyme is not AsCpf1, a mutation may be made at a residue in a corresponding position. In particular embodiments, the Cpf1 is FnCpf1 and the mutation is at the arginine at position R1218. In particular embodiments, the Cpf1 is LbCpf1 and the mutation is at the arginine at position R1138. In particular embodiments, the Cpf1 is MbCpf1 and the mutation is at the arginine at position R1293.

In certain embodiments, use is made additionally or alternatively of a CRISPR-Cas protein which is engineered and can comprise one or more mutations that reduce or eliminate a nuclease activity. The amino acid positions in the FnCpf1p RuvC domain include but are not limited to D917A, E1006A, E1028A, D1227A, D1255A, N1257A, D917A, E1006A, E1028A, D1227A, D1255A and N1257A. Applicants have also identified a putative second nuclease domain which is most similar to PD-(D/E)XK nuclease superfamily and HincII endonuclease like. The point mutations to be generated in this putative nuclease domain to substantially reduce nuclease activity include but are not limited to N580A, N584A, T587A, W609A, D610A, K613A, E614A, D616A, K624A, D625A, K627A and Y629A. In a preferred embodiment, the mutation in the FnCpf1p RuvC domain is D917A or E1006A, wherein the D917A or E1006A mutation completely inactivates the DNA cleavage activity of the FnCpf1 effector protein. In another embodiment, the mutation in the FnCpf1p RuvC domain is D1255A, wherein the mutated FnCpf1 effector protein has significantly reduced nucleolytic activity.

More particularly, the inactivated Cpf1 enzymes include enzymes mutated in amino acid positions As908, As993, As1263 of AsCpf1 or corresponding positions in Cpf1 orthologs. Additionally, the inactivated Cpf1 enzymes include enzymes mutated in amino acid position Lb832, 925, 947 or 1180 of LbCpf1 or corresponding positions in Cpf1 orthologs. More particularly, the inactivated Cpf1 enzymes include enzymes comprising one or more of mutations AsD908A, AsE993A, AsD1263A of AsCpf1 or corresponding mutations in Cpf1 orthologs. Additionally, the inactivated Cpf1 enzymes include enzymes comprising one or more of mutations LbD832A, E925A, D947A or D1180A of LbCpf1 or corresponding mutations in Cpf1 orthologs.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain.

The inactivated Cpf1 or Cpf1 nickase may have associated (e.g., via fusion protein) one or more functional domains, including for example, an adenosine deaminase or catalytic domain thereof. In some cases it is advantageous that additionally at least one heterologous NLS is provided. In some instances, it is advantageous to position the NLS at the N terminus. In general, the positioning of the one or more functional domain on the inactivated Cpf1 or Cpf1 nickase is one which allows for correct spatial orientation for the functional domain to affect the target with the attributed functional effect. For example, when the functional domain is an adenosine deaminase catalytic domain thereof, the adenosine deaminase catalytic domain is placed in a spatial orientation which allows it to contact and deaminate a target adenine. This may include positions other than the N-/C-terminus of Cpf1. In some embodiments, the adenosine deaminase protein or catalytic domain thereof is inserted into an internal loop of Cpf1.

The following PAMs have been identified for certain wild-type Cpf1 orthologues: the *Acidaminococcus* sp. BV3L6 Cpf1 (AsCpf1), Lachnospiraceae bacterium ND2006 Cpf1 (LbCpf1) and *Prevotella albensis* (PaCpf1) can cleave target sites preceded by a TTTV PAM, where V is A/C or G, FnCpf1p, can cleave sites preceded by TTN, where N is A/C/G or T. The *Moraxella bovoculi* AAX08_00205, *Moraxella bovoculi* AAX11_00205, *Butyrivibrio* sp. NC3005, Thiomicrospira sp. XS5, or Lachnospiraceae bacterium MA2020 PAM is 5' TTN, where N is A/C/G or T. The natural PAM sequence is TTTV or BTTV, wherein B is T/C or G and V is A/C or G and the effector protein is *Moraxella lacunata* Cpf1.

Where the effector protein is to be administered as a nucleic acid, the application envisages the use of codon-optimized CRISPR-Cas type V protein, and more particularly Cpf1-encoding nucleic acid sequences (and optionally protein sequences). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/

US2013/074667) as an example of a codon optimized sequence (from knowledge in the art and this disclosure, codon optimizing coding nucleic acid molecule(s), especially as to effector protein (e.g., Cpf1) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gowri, Plant Physiol. 1990 January; 92(1): 1-11; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59.

Delivery

In some embodiments, the components of the AD-functionalized CRISPR-Cas system may be delivered in various form, such as combinations of DNA/RNA or RNA/RNA or protein RNA. For example, the C2c1, C2c3, Cas9, Cpf1, or Cas13 protein may be delivered as a DNA-coding polynucleotide or an RNA-coding polynucleotide or as a protein. The guide may be delivered may be delivered as a DNA-coding polynucleotide or an RNA. All possible combinations are envisioned, including mixed forms of delivery.

In some aspects, the invention provides methods comprising delivering one or more polynucleotides, such as or one or more vectors as described herein, one or more transcripts thereof, and/or one or proteins transcribed therefrom, to a host cell.

Methods for Identifying Disease-Relevant Genes

Some aspects of the disclosure relate to methods for identifying a gene associated with a neurological disease comprising, consisting of, or consisting essentially of: introducing one or more guide RNAs into a 3D neural tissue culture comprising neuronal cells derived from hESCs and a 3D matrix comprising a biological supporting material, wherein the neuronal cells have been modified to express a CRISPR-Cas protein, wherein the neuronal cells either are expressing a CRISPR-Cas9 protein or have had the CRISPR-Cas9 protein or a nucleic acid encoding the CRISPR-Cas9 protein introduced simultaneously or sequentially with guide RNAs, wherein the guide RNAs target one or more endogenous genes; and assaying for a phenotype indicative of a neurological disease in the modified neuronal cells to identify a gene associated with the neurological disease.

Nonlimiting examples of neurological diseases that can be modeled in vitro with stem-cell derived neuronal cells include Alzheimer's disease, Parkinson's disease, Huntington's disease, spinal muscular atrophy, amyotrophic lateral sclerosis, duchenne muscular dystrophy, schizophrenia and autism spectrum disorders, which include Timothy syndrome, Fragile X syndrome, Angelman syndrome, Prader-Willi syndrome, Phelan-McDermid, Rett syndrome, and Nonsyndromic Autism (see, e.g. Russo, F. B. et al. World J Transplant 5(4): 209-21 (2015)).

Methods for Identifying Genes Associated with Neuronal Cell Phenotypes

Some aspects of the disclosure relate to methods for identifying a gene associated with a phenotype of neuronal cells, comprising, consisting of, or consisting essentially of: introducing a library of guide RNAs into a 3D neural tissue culture comprising neuronal cells derived from hESCs and a 3D matrix comprising a biological supporting material, wherein the neuronal cells have been modified to express a CRISPR-Cas protein, wherein the neuronal cells either are expressing a CRISPR-Cas9 protein or have had the CRISPR-Cas9 protein or a nucleic acid encoding the CRISPR-Cas9 protein introduced simultaneously or sequentially with guide RNAs, wherein the guide RNAs target a plurality of endogenous genes; selecting the neuronal cells based on a pre-determined phenotype; and sequencing guide RNAs present in the selected neuronal cells, wherein the enrichment or depletion of guide RNAs are quantified and/or ranked to identify a gene associated with the pre-determined phenotype. Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA. In particular embodiments, the vector comprises two or more guide RNAs. Said two or more guide RNAs may target a different target (so as to ensure multiplex targeting) or the same target, in which case the different guide RNAs will target different sequences within the same target sequence. Where provided in a vector the different guide RNAs may be under common control of the same promotor, or may be each be under control of the same or different promoters.

In certain embodiments, the genes associated with a neurological disease and/or with a phenotype of neuronal cells described herein are screened by perturbation of target genes within the neuronal cells. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; and Adamson et al., "A Multiplexed Single-Cell CRISPR Screening Platform Enables Systematic Dissection of the Unfolded Protein Response" 2016, Cell 167, 1867-1882). The present invention is compatible with perturb-seq, such that signature genes may be perturbed and the perturbation may be identified and assigned to the proteomic and gene expression readouts of single cells. In certain embodiments, signature genes may be perturbed in single cells and gene expression analyzed. Not being bound by a theory, networks of genes that are disrupted due to perturbation of a signature gene may be determined. Understanding the network of genes effected by a perturbation may allow for a gene to be linked to a specific pathway that may be targeted to modulate the signature and treat a neurological disease. Thus, in certain embodiments, perturb-seq is used to discover novel drug targets to allow treatment of specific neurological disease.

The perturbation methods and tools allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. Not being bound by a theory, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10× genomics). In certain embodiments, unique barcodes are used to perform Perturb-seq. In certain embodiments, a guide RNA is detected by RNA-seq using a transcript expressed from a vector encoding the guide RNA. The transcript may include a unique barcode specific to the guide RNA. Not being bound by a theory, a guide RNA and guide RNA barcode is expressed from the same vector and the barcode may be detected by RNA-seq. Not being bound by a theory, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, or preferably the binding events or the number of transcripts captured. Not being bound by a theory, the data is more significant if the signal observed is derived from more than one protein binding event or transcript. In preferred embodiments, Perturb-seq is performed using a guide RNA barcode expressed as a polyadenylated transcript, a cell barcode, and a UMI.

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi: 10.1038/naturel4136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353(6305); Yang et al., 2016, Engineering and optimizing deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by theory, Cpf1 does not require Tracr RNA and is a smaller enzyme, thus allowing higher combinatorial perturbations to be tested.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (~10 sgRNAs/gene) may also be used in a mouse that expresses a Cas9 protein (see, e.g., WO2014204727A1).

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus, adenovirus, or adeno associated virus (AAV).

In certain embodiments, whole genome screens can be used for understanding the phenotypic readout of perturbing potential target genes. In preferred embodiments, perturbations target expressed genes as defined by a gene signature using a focused sgRNA library. Libraries may be focused on expressed genes in specific networks or pathways. In other preferred embodiments, regulatory drivers are perturbed. In certain embodiments, Applicants perform systematic perturbation of key genes in neuronal cells in a high-throughput fashion. Applicants can use gene expression profiling data to define the target of interest and perform follow-up single-cell and population RNA-seq analysis. Not being bound by a theory, this approach will accelerate the development of therapeutics for human neurological disease as described herein.

Methods for Array Based Screening

The tissue cultures according to any of the embodiments described herein are suitable for array based gene screening in combination with one or more of electrophysiological measurements, calcium imaging for activity, and fluorescent/bioluminescent imaging for phenotype.

Fluorescent and/or bioluminescent staining may be performed by methods known in the art. In some embodiments, cells are fixed (e.g. with paraformaldehyde or ethanol) and, if applicable, frozen to enable slicing with a cryostat (e.g. Leica CM1950). In some embodiments, sections of cell encapsulating hydrogels are cut at 10-30 μm thickness and washed with DPBS to remove freezing medium before immunostaining. In some embodiments, samples are blocked with a blocking reagent (e.g. serum) and then incubated with primary antibodies. In some embodiments, samples are mounted (e.g. using Prolong Diamond Antifade Mountant with DAPI (Thermo-Fisher Scientific)) and imaged using a fluorescent microscope (e.g. Zeiss AX10, Zeiss LSM710). Non-limiting examples of primary antibodies suitable for immunostaining include: mouse anti-Map2 (M4403, Sigma, 1:300-500); rabbit anti-Pax6 (901301, BioLegend, 1:300); chicken anti-GFAP (ab4674, Abcam, 1:500); mouse anti-S10013 (ab11178, Abcam, 1:500); rabbit anti-Vimentin (5741, Cell Signaling, 1:100).

For electrophysiological measurements, whole cell voltage-clamp and current-clamp recordings may be performed. In some embodiments, 3D cultures/co-cultures are infected with AAV U6-hSyn1-mCherry-KASH-hGH vectors encoding non-targeting sgRNA 6 days after forming the tissues to identify iN cells in 3D cultures. Recordings are performed in room temperature using K-Gluconate based intracellular solution (in mM: 131 K-Gluconate, 17.5 KCl, 9 NaCl, 10 HEPES, 1.1 EGTA, 1 MgCl2, 2 Mg-ATP and 0.2 Na-GTP) and artificial cerebrospinal fluid (in mM: 119 NaCl, 2.3 KCl, 1 NaH2PO4, 11 Glucose, 26.2 $NaHCO_3$, 1.3 MgCl2, 2.5 CaCl2) as the external solution. Data is recorded using, for example pClamp 10 (Molecular Devices). Spontaneous synaptic currents are recorded with the voltage clamped at about −70 mV. In some embodiments, membrane capacitance and resistance are measured using a pClamp membrane test. In some embodiments, the resting membrane potential is recorded under a current clamp configuration. In some embodiments, current voltage relationships of the neurons are recorded under a current clamp configuration, where changes in voltage and subsequent action potentials are recorded after injecting hyperpolarizing and depolarizing currents (−200 pA to +200 pA, 50 pA steps). In some embodiments, recordings are performed using a patch pipette with a resistance ranging from 3-5 mΩ.

In some aspects, culture mediums can be collected without disassociated 3D tissues. These collections can occur at different timepoints and/or regular intervals (e.g. every 24 hours) to measure lactate dehydrogenase (LDH) released from the tissue as a result of gene perturbation. In some embodiments, a colorimetric assay can be performed to quantitatively measure LDH released into the media from cells as a biomarker for cellular cytotoxicity and cytolysis (e.g. ThermoFisher Scientific cat. #88953). The high-throughput array provides population level data relating to gene perturbations on neuronal and/or astrocytic cells in a disease context.

In some aspects, gRNA vectors for gene perturbations of neuronal and/or astrocytic cells are fluorescently labeled (e.g. mCherry-KASH under the control of the hSyn1 promoter) to independently label one or both cell types. After gene perturbations, 3D tissues can be dissociated, and the cells can be sorted by flow cytometry cell sorting and placed into wells. In some embodiments, a fluorimetric apoptosis assay is performed to detect caspases in microplates and determine a specific stage of apoptosis (e.g. Roche cat. #CASPASSY-RO). This approach provides cell-specific data in both array based and pooled screening of genes.

EXAMPLES

The invention is further described in the following examples, which do not limit the scope of the invention described in the claims.

Materials and Methods

Human embryonic stem cell culture. Human Embryonic Stem Cell (hESC) line (HUES66) was obtained from the Harvard Stem Cell Institute. Stem cells were cultured in 10 cm tissue culture dishes coated with 5 ml of geltrex (Thermo-Fisher Scientific) diluted in DMEM (Thermo-Fisher Scientific) with 1:100 ratio for 30 min at 37° C. Stem cell culture medium contained mTeSR (Stemcell Technologies) with provided supplement and normocin (InvivoGen). Stem cells were passaged by detaching with accutase (Stemcell Technologies) diluted in DPBS (Thermo-Fisher Scientific) at 1:3. After each splitting of stem cells, 10 μM Rho-associated kinase (ROCK) inhibitor (EMD Millipore) was added in medium of re-plated cells. Stem cell culture medium was replaced daily.

Generation of iN cells from hESCs. To produce iN cells, hESCs were infected with lentiviral vectors. These vectors provided constitutive expression of rtTA3 driven by human EF 1α promoter, and doxycycline inducible expression of human NGN1 and NGN2 driven by TRE promoter. The Puromycin resistant gene was linked with NGN1 and NGN2 by a P2A linker to enable selection. Lentiviral infected hESCs were plated at ~15×10$^3$ cells/cm$^2$ in 15 cm tissue culture dishes pre-coated with 10 ml of Growth Factor Reduced (GFR) Matrigel (Corning) (at 8.5 mg/ml-10 mg/ml concentration) diluted in DMEM at 1:100 for 30 min at 37° C. Day 0 medium of plated stem cells contained stem cell culture medium and 2 μg/ml doxycycline (Sigma) to initiate expression of NGN1/2. Whole medium at Day 1 was replaced by a medium containing 3 volumes of stem cell culture medium and 1 volume of neural culture medium along with 2 μg/ml doxycycline and 1 μg/ml puromycin. Neural culture medium was prepared by mixing 500 ml of neurobasal medium (Thermo-Fisher Scientific), 10 ml of B27 supplement (Thermo-Fisher Scientific), 5 ml of penicillin-streptomycin (Thermo-Fisher Scientific), and 5 ml of Glutamax (Thermo-Fisher Scientific). On Day 2, whole medium replaced by a medium made of 1:1 mixture of stem cell culture medium and neural culture medium, and 2 μg/ml doxycycline and 2 μg/ml puromycin were added into culture medium. On Day 3, iN cells were ready for detachment and further culture on 2D or in 3D conditions.

Primary mouse glia culture. Mouse glial cells were isolated from cortex of newborn C57 mice in procedures carried out in accordance with Animal Care and Use regulations at the Broad Institute with protocol (0008-06-14) approved by the Broad Institute's Institutional Animal Care and Use Committee (IACUC). Cortices of newborn mice were dissected and digested by using papain for 30 min and applying agitation. Dissociated cells were plated in tissue culture dishes in DMEM supplemented with 10% FBS. Glial cells were passaged by trypsinizing and replating at lower density more than eight times to remove potential low amounts of mouse neurons in culture before their use in 2D and 3D co-cultures with iN cells.

2D cultures and co-cultures of iN cells. For 2D cultures of iN cells, 5 glass coverslips (Corning-Biocoat) were inserted per well of a 6-well plate. Then, each well with coverslips was coated with 1.5 ml of GFR Matrigel diluted in DMEM at 1:100 for 30 min at 37° C. The coating solution was aspirated from each well before cell seeding. iN cells generated within 3 days as described were detached from culture plates with accutase diluted in DPBS at 1:3. iN cells were seeded on each pre-coated well with coverslips at 50×10$^3$ cells/cm$^2$ in 3 ml medium made of 1:3 mixture of stem cell culture medium and neural culture medium (hereafter 1:3 culture medium) with 2 μg/ml doxycycline. One day later, whole medium of each well was replaced with 3 ml neural culture medium with 2 μg/ml doxycycline. On the second day of seeding, 1 ml neural culture medium with doxycycline and 1-P3-D-Arabinofuranosylcytosine (Ara-C) was added in each well, keeping the final concentration of doxycycline in each well at 2 μg/ml and final concentration of Ara-C in each well at 0.5-1 μM. One third of the whole culture medium in each well was replaced every 3-4 days. For 2D co-cultures of iN cells with mouse glia, 6-well plates with coverslips were prepared as described above. Mouse astrocytes were detached from culture plates by using trypsin. iN cells and mouse glia were mixed 1:1 and seeded on each pre-coated well with coverslips at 100×10$^3$ cells/cm$^2$ in 3 ml 1:3 culture medium with 2 μg/ml doxycycline. For the rest of the culture, the protocol was as described above, except the final concentration of Ara-C in each well was at 2-5 μM, which was added with the neural culture medium in each well on the second day of seeding.

3D cultures and co-cultures of iN cells. Three-dimensional cultures and co-cultures of iN cells were performed by encapsulating them within hydrogels. These hydrogels were made of pure GFR Matrigel or GFR Matrigel and hyaluronic acid (HA) or GFR Matrigel and alginate or GFR Matrigel, alginate and HA. Before encapsulation experiments, the following preparations were done: GFR Matrigel was kept on ice, sodium alginate (PRONOVA UP VLVG, NovaMatrix) was first reconstituted at 4% (40 mg/ml) in a medium made of 1:3 mixture of mTeSR and neurobasal medium (without supplements) with 150 mM sodium chloride (NaCl) (Sigma) and this solution was then incubated for 6 hours at 37° C. for further dissolution of alginate. This alginate stock solution was passed through a 0.22 jam filter (EMD Millipore) and kept on ice. Calcium chloride ($CaCl_2$) solution (1M in water, Sigma) was diluted in a medium made of 1:3 mixture of mTeSR and neurobasal medium (without supplements) at concentrations of 25 mM, 12.5 mM, 6.25 mM and 3.125 mM. These $CaCl_2$ solutions were individually passed through 0.22 jam filters and kept on ice. HA sodium salt (Sigma, #53747) was dissolved at 1% (10 mg/ml) concentration under sterile conditions in a medium made of 1:3 mixture of mTeSR and neurobasal medium (without supplements) and then incubated for 6 hours at 37° C. for further dissolution of HA and frequently vortexed. This HA stock solution was kept on ice. A sheet of Parafilm and a microcentrifuge tube rack were sprayed with 70% Ethanol and kept in a biohood under UV light for 30 min. Parafilm dimples were formed by placing a sheet of Parafilm on the microcentrifuge tube rack and pressing gently on Parafilm. Serum-free DMEM was kept on ice.

Three-dimensional cultures of iN cells were performed by encapsulating them within 200 μl hydrogels of Matrigel at 10×10$^6$ cells/ml. iN cells generated within 3 days were detached as previously described and filtered through a 40 m cell strainer (Corning), and pelleted at desired amount. The final concentration of encapsulating Matrigel was either 4.6 mg/ml or 7.36 mg/ml. As the Matrigel stock concentration varied from batch to batch (8.5 mg/ml-10 mg/ml), different amounts of 1:3 culture medium were used to adjust the final concentration of Matrigel in hydrogels and kept on ice until used. A desired amount of Matrigel stock was placed in a 1.5 ml centrifuge tube and kept on ice. A pipette tip was chilled by pipetting cold serum-free DMEM. This pipette tip was then used to resuspend iN cell pellet in pre-chilled 1:3 culture medium. These resuspended iN cells were then mixed with the Matrigel in the 1.5 ml centrifuge tube. The final concentration of iN cells in this cell-gel solution was 10×10$^6$ cells/ml and the final concentration of Matrigel in this solution was either 4.6 mg/ml or 7.36 mg/ml. The cell-gel solution was vortexed for 10 s and then kept on ice while chilling a pipette tip by pipetting cold serum-free DMEM. This pipette tip was then used to place 200 μl droplets of cell-gel solution one by one on Parafilm dimples. These droplets were then placed at 37° C. for 1 hour to allow gelling of Matrigel. Each droplet was subsequently placed in one well of a 6-well plate by gently pipetting from Parafilm with 1 ml of 1:3 culture medium with 6 μg/ml doxycycline. After placing all droplets, 2 ml of same culture medium was added to each well. At day-1, whole medium of each well was substituted with 3 ml neural culture medium containing 6 μg/ml doxycycline. On the second day of encapsulation, 1 ml neural culture medium with doxycycline and Ara-C was added in each well by keeping final concentration of doxycycline in each well at 6 μg/ml and final concentration of Ara-C in each well at 0.5-1 μM. One third of the whole culture medium in each well was renewed every 3-4 days.

3D co-cultures of iN cells with mouse astrocytes were carried out by encapsulating them within 200 μl hydrogels made of either Matrigel (either 4.6 mg/ml or 7.36 mg/ml) or Matrigel and HA (7.36 mg/ml Matrigel and 1 mg/ml or 1.5 mg/ml final HA concentration) or composite hydrogels (CH) (4.6 mg/ml Matrigel and 0.5% final concentration of Alginate, with and without HA). iN cells were prepared as described above. Mouse astrocytes were detached by trypsinizing and filtered through a 40 m cell strainer, and pelleted at desired amount. All hydrogels contained 1:1 mixture of iN cells and mouse astrocytes. For pure Matrigel hydrogels, the cell concentration was either $20\times10^6$ cells/ml or $30\times10^6$ cells/ml. For hydrogels of Matrigel and HA, the cell concentration was $30\times10^6$ cells/ml Different amounts of 1:3 culture medium were used to adjust the final concentration of Matrigel and HA in hydrogels and kept on ice until use. Tissues were prepared as above with the following additions: For hydrogels of Matrigel and HA, a desired volume from 1% HA stock was pipetted in Matrigel in the tube to a final concentration of HA at either 1 mg/ml or 1.5 mg/ml. Cell suspensions were then mixed either with pure Matrigel or with mixture of Matrigel and HA in the centrifuge tube. For CH, the cell concentration within hydrogels was either $20\times10^6$ cells/ml or $30\times10^6$ cells/ml. For CH containing HA, the cell concentration was $30\times10^6$ cells/ml. Calcium chloride was used to crosslink Alginate in CH. Each 200 μl CH was made by mixing 150 μl cell-gel solution with 50 μl calcium chloride solution on a Parafilm dimple. Cell-gel solution was prepared accordingly so that in each 200 μl CH the final concentration of Matrigel was 4.6 mg/ml and that of Alginate was 0.5%. For each 200 μl CH containing HA, the final HA concentration was either 1 mg/ml or 1.5 mg/ml. To prepare gel solutions, a desired volume of Matrigel was placed within a centrifuge tube with a pre-chilled pipette tip and then the desired volume of 4% Alginate was mixed with Matrigel in the centrifuge tube with a pre-chilled pipette tip, vortexed for 10 s, and kept on ice. For CHs containing HA, a desired volume of 10 mg/ml HA was mixed with Matrigel and Alginate solution, vortexed for 10 s, and kept on ice. A volume of 1:3 culture medium required to adjust the concentration of components in gel solution was used to resuspend 1:1 mixture of iN cells and mouse astrocytes. These resuspended cells were then mixed with gel solutions and vortexed for 10 s. Each 200 μl droplet of CH was made by first placing 50 μl calcium chloride solution (at concentrations of 25 mM, 12.5 mM, 6.25 mM, and 3.125 mM) on a Parafilm dimple and then rapidly mixing 150 μl cell-gel solution with this calcium chloride solution on a Parafilm dimple with a pre-chilled pipette tip without generating bubbles. 50 μl droplets of CHs were generated in the same manner by adjusting volumes. To allow Matrigel gelling, all droplets were then placed at 37° C. for 1 hour. After forming hydrogels, the same protocol as previously described was followed for the remaining of the experiment, except the final concentration of Ara-C in each well was at 2-5 μM, which was added with the neural culture medium in each well on the second day of encapsulation.

3D and 2D cultures of iN cells with two different batches of Matrigel. For 2D cultures of iN cells, independent wells of 6-well plate with coverslips were coated with two different batches of Matrigel and iN cells were seeded on each pre-coated well with coverslips at $50\times10^3$ cells/cm$^2$. Three-dimensional cultures of iN cells were performed by encapsulating them within independent 200 μl hydrogels of 4.6 mg/ml Matrigel from two different batches at $10\times10^6$ cells/ml. Protocols for 3D and 2D cultures of iN cells described above were followed afterwards.

Rheolological measurements. Hydrogels at 100 μl volume without cells were formed as described above. Mechanical properties of the hydrogels were characterized using TA Instruments AR 2000 rheometer fitted with a Peltier stage set to 37° C. Oscillatory frequency sweep measurements were conducted at a 0.5% strain amplitude. All measurements were performed using a 8 mm 40 cone and 200 m gap size for triplicate hydrogels, and analyzed using TA instruments TRIOS software.

Derivation of human astrocytic cells. Each well of 6-well plates was coated with 1.5 ml of Growth Factor Reduced Matrigel diluted in DMEM with 1:100 ratio for 30 min at 37° C. Lentivirus infected hESCs containing inducible expression of NGN2 and NGN1 were plated at $\sim15\times10^3$ cells/cm$^2$ in pre-coated wells. Expansion medium was prepared by mixing 500 ml of DMEM, 10 ml of N2 supplement (Thermo-Fisher Scientific), 5 ml of penicillin-streptomycin, and 5 ml of Glutamax. Day 0 medium of plated stem cells contained stem cell culture medium (as previously described), 2 μg/ml doxycycline to initiate expression of NGN2 and NGN1, and 10 μM ROCK inhibitor. At day 1, whole medium was replaced by a medium containing 3 volumes of stem cell culture medium and 1 volume of expansion medium along with 2 μg/ml doxycycline and 2 μg/ml puromycin. At day 2, for the sample termed "unconditioned" (Supplementary FIG. 16*a*), whole medium was replaced by expansion medium, and for the sample termed "morphogen", whole medium was replaced by expansion medium with 15 ng/ml cntf. At day 4, half of the medium in each well for both conditions was renewed with their corresponding culture medium. At day 5, for "unconditioned", one third of the whole culture medium was replaced with expansion medium, for "morphogen", one third of the whole culture medium was replaced with expansion medium with 15 ng/ml cntf, and for the sample termed "morphogen+fbs", one third of the whole culture medium was replaced with expansion medium with 1% fbs and 15 ng/ml cntf One third of the whole culture medium of all conditions was replaced with their corresponding medium every 4-5 days.

At day 20, cells in all conditions were passaged and seeded back in wells pre-coated as described before. "Morphogen+fbs" cells were expanded for further use in generating 3D human neural tissues by co-culturing them with iN cells in a matrix. "Morphogen+fbs" cells at day 35 were used for immunostainings.

For control experiments, lentivirus infected hESCs were seeded as previously described and treated by using the "morphogen" protocol for 30 days without including doxycycline and puromycin application. In addition, lentivirus infected hESCs were cultured in stem cell culture medium without any differentiation protocol and used as a control. Human primary astrocytes (ScienCell) were cultured in expansion medium with 2% fbs and used as a control. For RT-qPCR experiments for astrocytic cells, the protocol for all conditions was continued without passaging cells, except human primary astrocytes, which were in passage 3. For RNA-seq experiments for astrocytic cells, the protocol for all conditions was continued without passaging cells, except for "morphogen+fbs" condition, samples at day 67 were in passage 3 and samples at day 114 were in passage 6, and human primary astrocytes were in passage 3. RNA lysis buffer (Zymo Research) was used to lyse cells in each well for all conditions.

3D co-cultures of iN cells with human astrocytic cells and with human primary astrocytes. Astrocytic cells derived following the protocol termed "morphogen+fbs" cultured until day 52 (passage 5) and day 61 (passage 7) were detached from culture plates with accutase and pooled for 3D cultures and co-cultures with iN cells. For 3D co-cultures of iN cells with human astrocytic cells, a 1:1 mixture at a final cell concentration of $20\times10^6$ cells/ml were encapsulated in 100 μl hydrogels (7.36 mg/ml Matrigel). 3D co-cultures of iN cells with human primary astrocytes (passage 5) were carried out by encapsulating their 1:1 mixture (at a final cell concentration of $20\times10^6$ cells/ml) within 100 μl hydrogels (7.36 mg/ml Matrigel). 3D culture of iN cells alone and 3D culture of human astrocytic cells alone were performed by encapsulating them (at a final cell concentration of $10\times10^6$ cells/ml) within independent 100 μl hydrogels (7.36 mg/ml Matrigel). After encapsulations, culture protocols as described above were followed, with the following changes: the culture mediums did not contain doxycycline and the final concentration of Ara-C in each culture well was 1 μM. 6 days after forming 3D cultures and co-cultures, 3D cultures and co-cultures of iN cells were infected with AAV U6-hSyn1-mCherry-KASH-hGH vectors encoding non-targeting sgRNA to enable fluorescent-activated cell sorting (FACS) of iN cells. At week 5 of culture, 3D cultures and co-cultures of iN cells were disassociated by first individually immersing 3D tissues in accutase, incubating at 37° C. for ~8 min, and then the 3D matrix was disrupted by pipetting in accutase. Each disassociated tissue was resuspended in neural culture medium and centrifuged at 200 g for 5 min. Each pellet was then resuspended in DPBS and passed through a 30 μm filter (Sysmex) to remove potential cell clumps and hydrogel residues before cell sorting. Cell suspensions were sorted using a Beckman Coulter MoFlo Astrios EQ cell sorter (Broad Institute Flow Cytometry Core). Each 3D culture/co-culture had triplicates and a population of $1\times10^3$ $mCherry^+$ iN cells was collected from each disassociated 3D tissue into DNA/RNA Shield (Zymo Research). 3D cultures of human astrocytic cells were individually immersed in DNA/RNA Shield without cell sorting.

RNA isolation. For 2D cultures of iN cells and their 2D co-cultures with mouse astrocytes and for 2D cultures of only mouse astrocytes, 2D cultured hESCs, day-3 iN cells, 300 μl of RNA lysis buffer (Zymo Research) was used to lyse cells in each well of a 6-well plate. Each lysate was then transferred to a 1.5 ml centrifuge tube. For 3D cultures of iN cells and their 3D co-cultures with mouse astrocytes, each hydrogel was transferred with an RNase-free spatula (Corning) from a culture well to a 1.5 ml centrifuge tube and immersed in 300 μl of RNA lysis buffer. All centrifuge tubes were placed on dry ice for rapid freezing and then stored at −80° C. Total RNA isolation was performed using a Zymo RNA QuickPrep Mini kit (Zymo Research) following the manufacturer's protocol with the following modifications. 3D culture hydrogels were homogenized using a hand-held pestle (Fisher Scientific) in a 1.5 ml Eppendorf tube containing 300 μl lysis buffer with a few strikes to break down the large pieces. Lysates were transferred to a ZR Bashing-Bead Lysis Tube (Zymo Research) and bead bashed on a D2400 Homogenizer (BenchMarker) for 45 seconds at full speed 7. After 1 minute of centrifugation at 14,000 g, supernatant was recovered and used for the standard RNA isolation procedure. For CH 3D cultures, another purification step was performed on the eluted RNA samples using 1.8× volumes of RNAClean SPRI beads (Agencourt). For conditions involved in derivation of astrocytic cells, conditions in 3D cultures/co-cultures of iN cells with human astrocytic cells and with human primary astrocytes, and 3D cultures of human astrocytic cells, a Zymo RNA QuickPrep Mini kit (Zymo Research) was used to isolate the total RNA by following the manufacturer's recommended protocol.

RNA-Seq. RNA-Seq libraries were prepared following the Smart-seq2 protocol[55] with the following modifications: 1 ng of total RNA was used in place of a single cell lysate. For 2D and 3D cultures of iN cells, and 3D co-cultures of iN cells with mouse astrocytes, 2D cultured hESCs, day-3 iN cells, 12 cycles of PCR were used to amplify the cDNA, and 0.25 ng amplified cDNA was used in each NexteraXT (Illumina) reaction. For 2D co-cultures of iN cells with mouse astrocytes, 2D cultures of mouse astrocytes, samples in astrocytic cell differentiation protocols, iN cells 3D co-cultured with differentiated astrocytic cells and with human primary astrocytes, and iN cells 3D cultured without any astrocytic cells, 12 cycles of PCR were used to amplify the cDNA, and 0.075 ng amplified cDNA was used in each NexteraXT (Illumina) reaction. For samples in matrigel batch test, 15 cycles of PCR were used to amplify the cDNA, and 0.075 ng amplified cDNA was used in each NexteraXT (Illumina) reaction. Pooled libraries were sequenced on a NextSeq 500 instrument (Illumina) with 50 bases for read1 and 25 bases for read2.

Transcriptome analyses. RSEM v1.3[56] was run on fastq files of cultures of iN cells and their co-cultures with mouse astrocytes using a joint human (hg19 annotation from UCSC) and mouse (mm10 annotation from UCSC) transcriptome and STAR v2.5.2[57], with the options—star—star-gzipped-read-file—paired-end. The count data output by RSEM was used to quantify the percentage mouse reads vs percentage human reads. The STAR bams output by RSEM were used to filter the original fastq files with seqtk (https://github.com/lh3/seqtk). In particular, all reads that mapped to the mouse transcriptome were removed, as were all unmapped reads. These filtered fastq files were run through RSEM with default parameters using human hg19 UCSC genome to estimate gene expression values, which were then used to create an un-normalized count matrix. This count matrix was used for further analysis involving co-culture conditions of iN cells with mouse astrocytes. For data analysis between culture conditions of iN cells without mouse astrocytes, RSEM with default parameters was run on fastq files of cultures of iN cells using human hg19 UCSC genome to estimate gene expression values, used to form an un-normalized count matrix. Similarly, RSEM with default parameters was run on sequencing reads of conditions involved in derivation of astrocytic cells using human hg19 UCSC genome to estimate gene expression values, which was then used to generate an un-normalized count matrix.

Further bulk RNA-seq data analysis was performed using DESeq2 package[58] and R v3.2. Following DESeq2 protocols[58], significant genes in differential expression analysis were identified by using the False Discovery Rate (FDR) adjusted p-value cutoff of 0.05 for all analyses in this study. Principal component analysis (PCA) was carried out using DESeq2 package and R. Database for Annotation, Visualization and Integrated Discovery v6.7 and v6.8 and the Molecular Signatures Database (MSigDB) were used to reveal enriched biological processes for differentially expressed genes (either upregulated or downregulated in one condition). Gene Set Enrichment Analysis (GSEA) was performed using GSEA software[59] v2.2.3 using default parameters to find enriched biological processes in Gene Ontology (GO) and enriched Kyoto Encyclopedia of Genes and Genomes (KEGG) pathways in compared conditions. The k-means function in R was used to cluster groups of genes. Groups were generated by first performing differential expression analysis between a reference condition and other conditions and then filtering resulting differentially expressed genes by setting $\log_2$ (fold change) and p-value cut-offs.

To compare the transcriptomes of 3D cultures of iN cells to the human brain developmental transcriptome, gene-level expression values were obtained from the BrainSpan database (http://www.brainspan.org/static/download.html). To our knowledge, raw data for the BrainSpan transcriptome profiling dataset, in the form of fastq or BAM files are not available for download. Therefore, in an effort to minimize technical differences between the experimental and reference datasets, RNA-seq data of 3D cultures of iN cells was reprocessed to more closely match that of BrainSpan following the alignment and gene quantification protocol described. Briefly, filtered fastq files of RNA-seq samples were realigned with Tophat v.2.0.14, using Bowtie v.0.12.9 and samtools v.0.1.9. To further match the BrainSpan dataset, the data were processed using Gencode v10. RSEQtools, which was utilized by the BrainSpan group, to obtain gene-level expression values. This included converting the reprocessed BAM files into MRF files, and using the mrfQuantifier function to obtain the final gene expression matrix. The BrainSpan region expression matrix between developmental stages of 8 post-conceptual week (pcw) and 1 year old was filtered to maximize the proportion of genes with high expression (RPKM>5) and variance (>1). Pearson correlations based on these 11,972 genes were obtained for each 3D culture condition of iN cells and developmental brain region-time point pair. All plots represent the mean correlation (±SEM) of 3 replicates of 3D culture conditions of iN cells with a specific developmental brain region and time point.

For profiling expression levels of disease-associated genes in iN cells cultured in 3D conditions, ASD-associated genes were obtained from https://gene.sfari.org/autdb/GSGeneList.do?c=S, ALS-associated genes were obtained from ALS Online Database (ALSoD)[60] (http://alsod.iop.kcl.ac.uk/misc/dataDownload.aspx #C1) and ALS Gene Database[61] (http://www.alsgene.org/top_results), AD-associated genes were obtained from a published study[62], and PD-associated genes were obtained from PD Gene Database[63] (http://www.pdgene.org/top_results). To determine which genes are driving the increased correlation in expression with BrainSpan data in iN cells co-cultured in CH 4× crosslinker compared to iN cells co-cultured in Matrigel, for each gene we calculated both the squared log fold change between iN cells co-cultured in Matrigel and BrainSpan data and the squared log fold change between iN cells co-cultured in CH 4× crosslinker and BrainSpan data (using RPKM normalized data), and took the difference between the two values to get our final score.

Single-cell RNA-Seq. 3D co-cultures of iN cells with mouse astrocytes and with human astrocytic cells were generated in 200 μl CHs made by using 12.5 mM calcium chloride solution. A 1:1 mixture of iN cells and mouse astrocytes was encapsulated (at a final cell concentration of $30\times10^6$ cells/ml) in corresponding CHs and cultured as described above. Astrocytic cells derived following the protocol termed “morphogen+fbs” cultured until day 83 in passage 5 and in passage 6 were detached from culture plates with accutase and pooled. A 1:1 mixture of iN cells and astrocytic cells was encapsulated (at a final cell concentration of $30\times10^6$ cells/ml) in corresponding CHs and cultured as described above, with the following change: the culture mediums did not contain doxycycline. At week 5 of culture, cell disassociation from 3D tissues was performed utilizing a previously described protocol[16] with the following modifications. Briefly, each 3D tissue was cut into small pieces with a blade and immersed in 1 ml of 20:1 mix of papain solution (PAP2, Worthington) and DNase solution (D2, Worthington) in a 15 ml tube, which was then incubated at 37° C. for 20 min and shaken by hand every 5 min. After 20 min, pieces of 3D tissues in this solution were pipetted for further dissociation, and then incubated at 37° C. for 10 min. 1 ml Earle’s balanced salt solution (EBSS, Worthington) was mixed with the solution of dissociated tissue. The cloudy cell suspension from this mix was transferred to a new 15 ml tube and mixed with 1.9 ml inhibitor solution (OI.BSA, Worthington). This final solution was then centrifuged at 300 g for 5 min. Cell pellets from three biological replicates of each 3D co-culture condition (iN cells with mouse astrocytes and iN cells with human astrocytic cells) were pooled by resuspending cell pellets in ice-cold DPBS with 0.2% BSA (Sigma), which was then passed through a 30 m filter (Sysmex). Cell suspensions for each condition, 3D co-cultures of iN cells with mouse astrocytes and 3D co-cultures of iN cells with human astrocytic cells, were loaded onto the 10× Chromium Instrument (10× Genomics) through two independent channels to generate single-cell GEMs (Gel bead in EMulsion). Single-cell RNA-Seq libraries were constructed using 10× Chromium 3[Symbol] Solution (10× Genomics) following the manufacturer’s protocol and sequenced on a NextSeq 500 instrument (Illumina) with 26 bases for read1 and 57 bases for read2.

Single-cell data analysis. Cellranger[54] was used to map fastq files to the joint hg19 and mm10 transcriptome, with the option—force-cells=10,000. The cell by gene (hg19 genes only, mm10 genes were explored separately for QC purposes) count matrix was loaded into R using Seurat v1.3[64]. The data was normalized to be log counts per million, and we removed all cells expressing less than 1000 human genes or more than 300 mouse genes. MeanVarPlot was used to find variable genes (with x.low.cutoff=1). The number of genes and percent mitochondrial RNA were regressed out with the RegressOut function, and PCA was performed using PCAFast. Rtsne was applied to the PCA matrix using the top 13 PCs. Clustering was performed as previously described[65], using the top 13 PCs and a 100 shared nearest neighbor graph. Cell types of clusters were identified using known marker genes. Note that the clusters identified as neurons express many IPC markers at high levels, but comparison with outside datasets[38,39] (see below) suggests these clusters are more similar to neurons than IPCs (see Results).

We loaded numerous outside single cell datasets of human fetal cortex[38,39] and a single-nuclei dataset of adult post-mortem human brain tissue[40], and a single cell dataset of six-month-old human brain organoids[16] into R with Seurat. All data were normalized to be log counts per million, and we removed all cells with less than 500 genes. MeanVarPlot was used to find variable genes (with x.low.cutoff==:1). For each dataset, we used the clustering available from their respective papers, and identified cell types based on marker genes. In addition, we extracted the forebrain cluster from the six-month-old human brain organoid[16] dataset, and sub-clustered it using the same pipeline as was used for our single-cell dataset, except we did not regress out percent mitochondria, and used 12 PCs and 50 shared nearest neighbors for clustering.

Correlation heatmaps comparing clusters in our single-cell dataset to clusters in published single-cell[16,38,39] and single-nuclei[40] datasets were generated as follows: for each dataset, the Seurat function AverageCluster was used to generate the average expression profiles of clusters in that dataset. Variable genes from the published single-cell[16,38,39] or single-nuclei[40] dataset were identified by MeanVarPlot and then used to calculate the correlation between these average transcript profiles. For comparison between bulk RNA-Seq of conditions involved in our astrocyte differentiation protocol and single cell and single-nuclei datasets of the human brain, a similar procedure as above was used to calculate the average expression of each cell type in the single cell or single-nuclei data. These average profiles were then compared to the expression profiles from the bulk data (measured in log TPM) using Pearson correlation.

TABLE 1

Taqman qPCR probes used to measure relative RNA expression levels of a number of genes.

| Gene Name | Probe ID |
|---|---|
| CXCR4 | Hs00607978_s1 |
| EPHA3 | Hs00739092_m1 |
| SEMA3C | Hs00989373_m1 |
| UNC5C | Hs00186620_m1 |
| NRG1 | Hs01101538_m1 |
| NTNG1 | Hs01552822_m1 |
| GPX3 | Hs01078668_m1 |
| SST | Hs00356144_m1 |
| DAP | Hs01079452_m1 |
| GFAP | Hs00909233_m1 |
| S100B | Hs00902901_m1 |
| VIM | Hs00958111_m1 |
| ALDH1L1 | Hs00201836_m1 |

Immunostaining and imaging. For immunofluorescent staining of iN cells cultured on 2D for 2 weeks, cells on coverslips in 6-well plates were fixed with 4% PFA for 20 min at room temperature (RT) and then washed 3 times with DPBS. Coverslips containing fixed cells were individually transferred to each well of a 24-well plate for immunostaining procedure. For immunofluorescent staining of iN cells 3D cultured in 200 μl 4.6 mg/ml Matrigel for 30 days without use of Ara-C, cell encapsulating hydrogels were fixed with 4% PFA for 1 h at RT and 2 h at 4° C. and then washed 3 times with DPBS at RT. These hydrogels were then frozen in freezing medium (Tissue-Tek O.C.T. Compound) and maintained at −80° C. overnight. Sections of cell encapsulating hydrogels were cut at 20 m using a cryostat (Leica CM1950) and washed with DPBS to remove freezing medium before immunostaining. For immunofluorescent staining of astrocytic cells generated using "morphogen+fbs" condition, at day 35 cells were fixed on coverslips as previously described and transferred to the 24-well plate for immunostaining. Mouse astrocytes were fixed in the same manner for immunostaining. Samples were blocked with 5% normal goat serum (Sigma) and 0.15% Triton X-100 (Sigma) in DPBS for 1 h at RT. Samples were then incubated with primary antibodies in 2.5% NGS and 0.1% Triton X-100 in DPBS overnight at 4° C. Following the washing step 3 times with 0.1% Triton X-100 in DPBS, samples were incubated with secondary antibodies in 2.5% NGS and 0.1% Triton X-100 in DPBS for 1 h at RT. After washing 3 times with 0.1% Triton X-100 in DPBS, samples were mounted using Prolong Diamond Antifade Mountant with DAPI (Thermo-Fisher Scientific) and imaged using a fluorescent microscope (Zeiss AX10). Quantification of astrocytic cells was performed using ImageJ software. Stem cells encapsulated in 200 μl 4.6 mg/ml Matrigel were stained with calcein (Thermo-Fisher Scientific) after 5 days of neural induction and imaged using a fluorescent microscope (Zeiss AX10). Day 2 phase images of iN cells encapsulated in Matrigel without Ara-C and phase images at different time points of cells exposed to astrocytic cell generation protocols were taken using the same microscope.

For immunofluorescent staining of iN cells 3D cultured in 200 μl 4.6 mg/ml Matrigel for 2 weeks with Ara-C, cell-laden hydrogels were fixed with 4% PFA for 1 h at RT and 2 h at 4° C. and then washed 3 times with DPBS at RT. Samples were immersed in blocking solution of 5% normal goat serum (Sigma) and 0.15% Triton X-100 (Sigma) in DPBS and placed on a shaker overnight at 4° C. Samples were then immersed in a solution with a primary antibody in 2.5% NGS and 0.1% Triton X-100 in DPBS and placed on a shaker for 24 h at 4° C. Samples were washed 2 times with 0.1% Triton X-100 in DPBS and each wash was performed for 3 h on a shaker at RT. Samples were immersed in a solution with a secondary antibody in 2.5% NGS and 0.1% Triton X-100 in DPBS and placed on a shaker for 18 h at RT. Samples were then washed as before. Immunostained cell-laden hydrogels were mounted using Prolong Diamond Antifade Mountant with DAPI on microscope slides by gently pressing them with coverslips and imaged using a confocal microscope (Zeiss LSM 710).

The following primary antibodies were used in this study: mouse anti-Map2 (M4403, Sigma, 1:300-500); rabbit anti-Pax6 (901301, BioLegend, 1:300); chicken anti-GFAP (ab4674, Abcam, 1:500); mouse anti-S100β (ab11178, Abcam, 1:500); rabbit anti-Vimentin (5741, Cell Signaling, 1:100). Secondary antibodies used in this study are: Alexa Fluor 488, 568 and/or 647 (Life Technologies, 1:500-1:1,000).

Electrophysiological measurements. Whole cell voltage-clamp and current-clamp recordings were performed for 3D cultures/co-cultures and 2D co-cultures of iN cells. 3D cultures/co-cultures and 2D co-cultures were infected with AAV U6-hSyn1-mCherry-KASH-hGH vectors encoding non-targeting sgRNA 6 days after forming the tissues to identify iN cells in 3D cultures during electrophysiological experiments. Recordings were performed in room temperature using K-Gluconate based intracellular solution (in mM: 131 K-Gluconate, 17.5 KCl, 9 NaCl, 10 HEPES, 1.1 EGTA, 1 $MgCl_2$, 2 Mg-ATP and 0.2 Na-GTP) and artificial cerebrospinal fluid (in mM: 119 NaCl, 2.3 KCl, 1 $NaH_2PO_4$, 11 Glucose, 26.2 $NaHCO_3$, 1.3 $MgCl_2$, 2.5 $CaCl_2$) as the external solution. Data were recorded using pClamp 10 (Molecular Devices). Spontaneous synaptic currents were recorded with the voltage clamped at −70 mV. Membrane capacitance and resistance were measured online using the built-in pClamp membrane test. The resting membrane potential was recorded under current clamp configuration. Current voltage relationships of the neurons were also recorded under current clamp configuration, where changes in voltage and subsequent action potentials were recorded after injecting hyperpolarizing and depolarizing currents (−200 pA to +200 pA, 50 pA steps). All recordings were performed using a patch pipette with a resistance ranging from 3-5 mΩ.

Genome editing. Guides for Cpf1-mediated genome editing were analyzed for efficacy in human embryonic kidney 293FT (HEK293FT) cells. Each crRNA guide was cloned into a separate U6-driven crRNA expression plasmid (U6-crRNA-CMV-mCherry). An expression vector for the AsCpf S542R/K607R PAM variant (pcDNA3.1-CMV-AsCpf1 (TYCV)-NLS-3xHA) was used as described previously (Gao, L. Y. et al. Nature Biotechnology 35, 789-792 (2017)). HEK293FT cells were maintained in Dulbecco's modified Eagle's medium supplemented with 10% FBS (Gibco) at 37° C. with 5% $CO_2$ incubation. Cells were seeded one day prior to transfection in 96-well plates (Corning) at a density of approximately $2.4\times10^4$ cells per well and transfected at 90-100% confluency using Lipofectamine 2000 (Invitrogen), according to the manufacturer's recommended protocol. A total of 100 ng Cpf1 plasmid and 50 ng crRNA expression plasmid were delivered per well. Cells were harvested using Quick Extract DNA extraction solution (Epicentre) according to the manufacturer's recommended protocol. Indel frequencies were quantified by deep sequencing as described previously (Gao, L. Y. et al. Nature Biotechnology 35, 789-792 (2017)).

For delivery, the AAV hSyn1-HA-NLS-AsCpf1(TYCV)-spA vector was generated by PCR amplifying the AsCpf1 (TYCV) encoding sequence, and cloning of the resulting PCR template into AAV backbone (Zetsche, B. et al. Nat Biotechnol, doi: 10.1038/nbt.3737 (2016)) containing HA-NLS and a short poly A signal, under control of the human Synapsin 1 promoter (hSyn1). For the generation of AAV U6-hSyn1-mCherry-KASH-hGH vectors encoding sgRNAs targeting SOD1, TBK1, and TARDBP (plus a non-targeting control sgRNA), oligonucleotides (Integrated DNA Technologies) containing sgRNA sequences were annealed and cloned into AAV U6-DR(Sap1)-hSyn1-mCherry-KASH-hGH scaffold construct. All constructs were verified by Sanger sequencing.

High-titer AAV1/2 virions encoding AAV hSyn1-HA-NLS-AsCpf1(TYCV)-spA and AAV U6-hSyn1-mCherry-KASH-hGH vectors encoding sgRNAs targeting SOD1, TBK1, and TARDBP (plus a non-targeting control sgRNA) were produced as described previously (Zetsche, B. et al. Nat Biotechnol, doi: 10.1038/nbt.3737 (2016)). Briefly, HEK293T cells were transfected with AAV1 and AAV2 serotype plasmids in equal ratios, transgene plasmid and pDF6 helper plasmid using polyethyleneimine. 72 h after transfection, cells were harvested and high-titer AAV1/2 virus was purified by iodixanol gradient ultracentrifugation. The titer of AAV vectors was determined by real-time quantitative PCR (qPCR) using probe and primers specific for the hSyn1 promoter sequence (Integrated DNA Technologies).

Genome editing was performed in 3D human neural tissues formed by co-culturing 1:1 mixture of human iN cells and human astrocytic cells at a final cell concentration of $20\times10^6$ cells/ml in 100 μl 3D hydrogels (7.36 mg/ml Matrigel), and the culture mediums did not contain doxycycline, as described above. Astrocytic cells formed by following the protocol termed "morphogen+fbs" were cultured until day 70 (passage 3) and detached from culture plates with accutase for co-culturing with iN cells. 6 days after forming 3D human neural tissues, AAV infection was carried out using concentrated AAV constructs containing Cpf1 or targeting/non-targeting gRNAs. Each hydrogel encapsulated a total $2\times10^6$ cells and was in 3 ml of neural culture medium. A 1:1 mixture of AAVs containing Cpf1 and AAVs containing targeting/non-targeting gRNA was mixed with 3 ml culture medium of each 3D tissue by having $40\times10^3$ viral copies of each vector per cell. Each condition of targeting and non-targeting gRNA had two replicate tissues. After mixing AAV mixtures with culture mediums, 6-well plates containing 3D tissues were gently shaken for 1 min and then transferred to an incubator at 37° C. with 5% $CO_2$ atmosphere. For 5 days following AAV infection, the culture medium of 3D tissues was not changed. After that, one third of the whole culture medium was renewed with neural culture medium. 24 days after AAV infection, cells in 3D tissues were disassociated by following the protocol described above (see methods for 3D co-cultures of iN cells with human astrocytic cells and with human primary astrocytes). A population of $1\times10^3$ mCherry$^+$ iN cells was collected by FACS for each disassociated 3D tissue in a well of 96-well plate containing 5 μl of QuickExtract DNA extraction buffer (Epicentre). The 96-well plate was then spun down at 2,000 g for 1 min.

Cells suspended in QuickExtract DNA solution were incubated at 65° C. for 15 min, 68° C. for 15 min, and 98° C. for 10 min. Genomic DNA was PCR-amplified with Herculase II fusion polymerase over 28 cycles using locus-specific primers. An additional round of PCR was then performed to attach Illumina handles to amplicons for deep sequencing. NGS was performed and indel frequencies were quantified as described previously (Gao, L. Y. et al. Nature Biotechnology 35, 789-792 (2017)). For the targeting gRNA, one guide per locus was used. DNA from two biological replicates was used for NGS analysis. For the non-targeting control, DNA from two biological replicates was pooled for NGS analysis.

Example 1. Development of 3D Neural Tissues from hESCs

To generate a system that can serve as a proxy for studying the genetics of the human brain, we compared a number of different conditions used for generating 3D neural tissues from induced neuronal (iN) cells from hESCs and develop a method for rapid generation of 3D co-cultures of iN and astrocytic cells derived from the same population of hESCs. iN cells can be efficiently produced directly from hESCs using ectopic expression of transcription factors[18-22] and have been used to model neurological diseases by culturing them on 2D surfaces[23,24]. This approach has also been used to produce 3D neural tissues on an electrospun scaffold for transplantation[25]. We extended these approaches to create a 3D culture of iN cells within Matrigel, a basement membrane matrix that includes components that closely reflect brain ECM 6,26. We optimized these tissues by exploring the effects of the addition of hyaluronic acid (HA) as well as the formation of a composite hydrogel of Matrigel and alginate with varying crosslinking density and volume. We compared the transcriptome of these iNs to a panel of human brain transcriptomic data and showed that the gene expression of iN cells can be tuned to correlate with specific developmental time points and brain regions by modulating the composition of the 3D matrix. Single-cell sequencing of cells co-cultured in 3D tissues confirmed their transcriptomic correlations to cell types found in the human brain. Finally, we used gene editing tools to create gene knock-outs in our 3D tissues of genes implicated in neurodegenerative diseases, demonstrating the feasibility of combining these technologies.

Figures 6A, 6B:
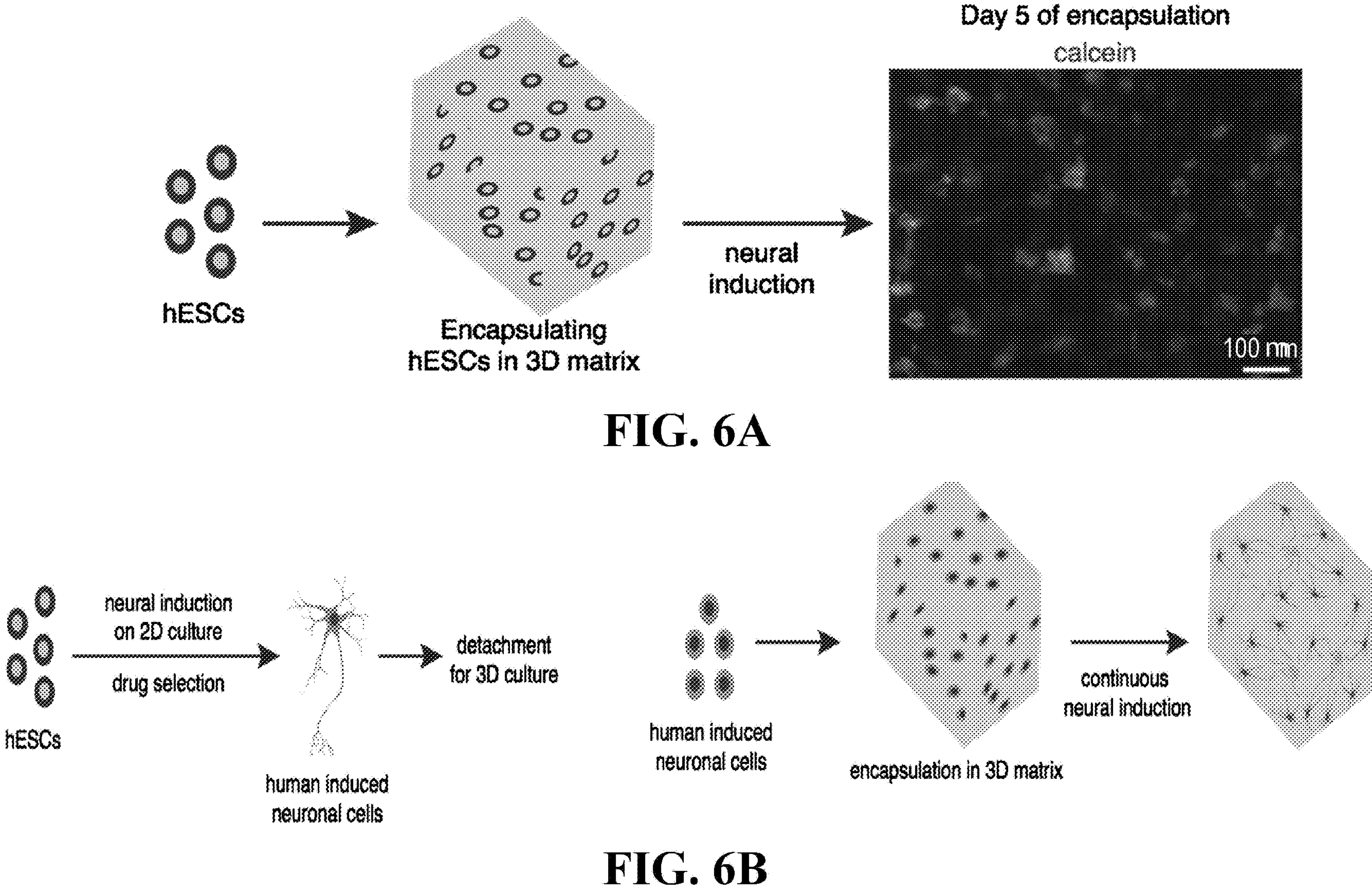
FIGS. 6A-6E: Method for generating pure 3D human neural tissue.
Figures 6C, 6D, 6E:
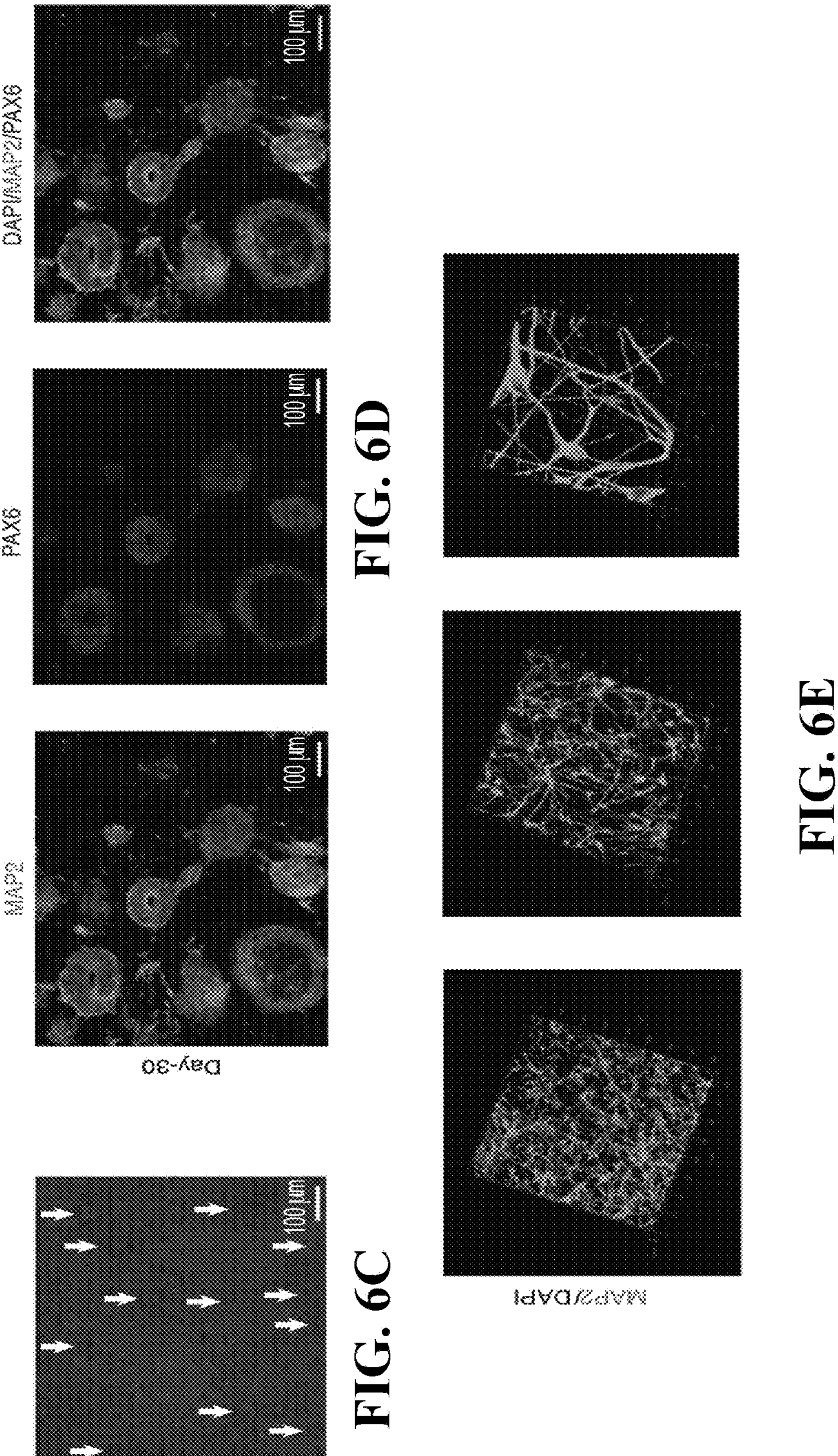

To create a robust, genetically tractable 3D neural tissue system, we used a transcriptional activation approach to differentiate iN cells from hESCs and encapsulate them in a Matrigel matrix (FIG. 1_a_). We initially tested whether encapsulated hESCs transduced with NGN1 and NGN2 overexpression constructs could be directly differentiated in a Matrigel 3D matrix, but this approach resulted in aggregation of encapsulated cells within 5 days (FIG. 6*a*), preventing efficient differentiation. To circumvent aggregation, hESCs were first seeded on 2D plates and then induced to form neuronal cells, which were subsequently detached and then encapsulated in Matrigel (FIG. 6*b*). Although this led to less aggregation, over time, aggregates continued to form, with spheroids present at day-30 (FIGS. 6C, 6D). Further improvements were made by increasing selection for NGN1/2 constructs and introducing a proliferation inhibitor, 1-3-D-Arabinofuranosylcytosine (Ara-C), to suppress proliferation of undifferentiated stem cells. This resulted in 3D pure human neural tissues without cell aggregates (FIG. 6*e*). For comparison, we also generated 2D cultures of iN cells (FIG. 1*a*) using the methods described herein.

Example 2. Characterization of 3D Cultures

Figure 7A:
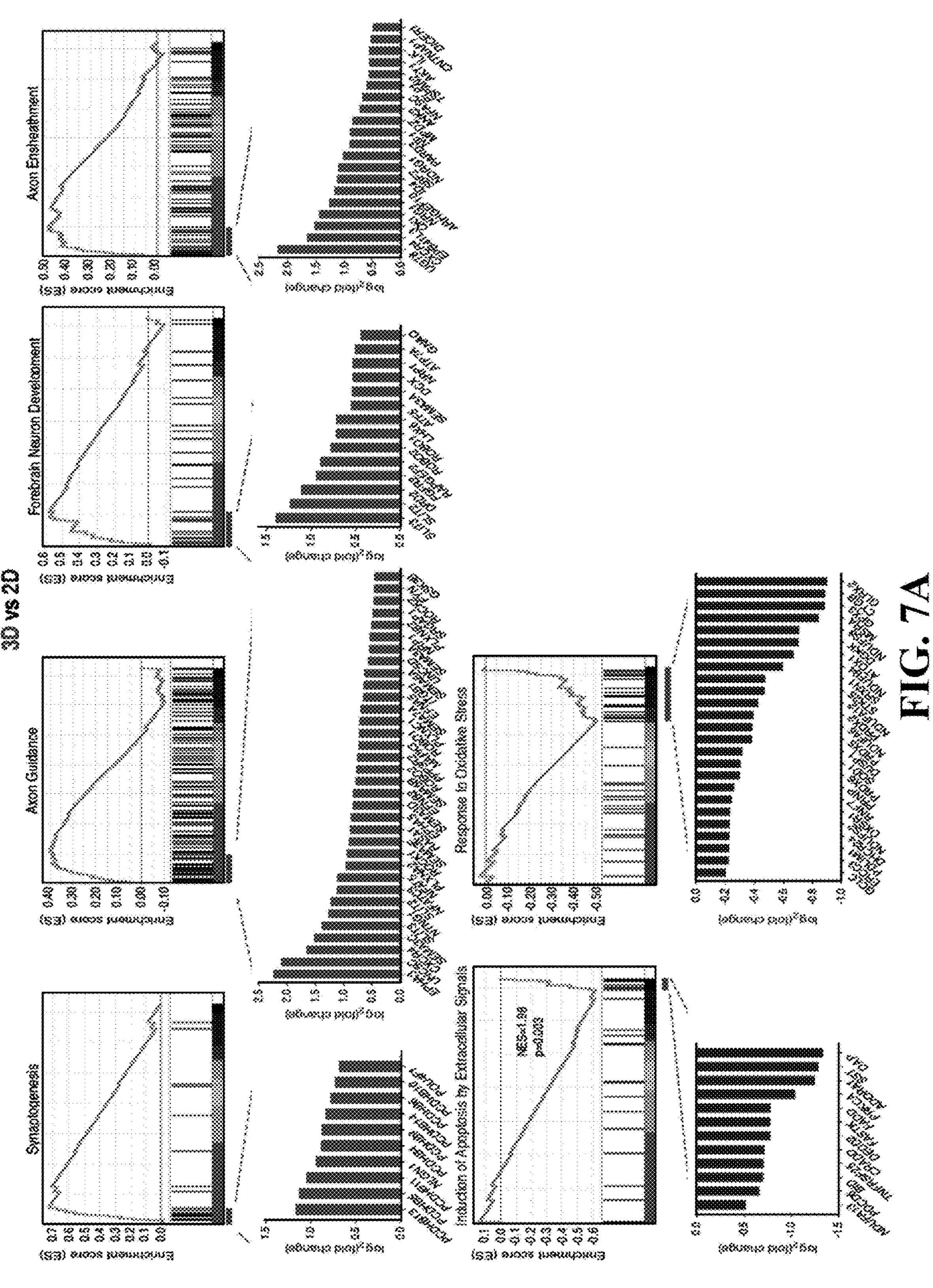
FIGS. 7A-7B: Analysis of 3D cultured iN cells.
Figure 7B:
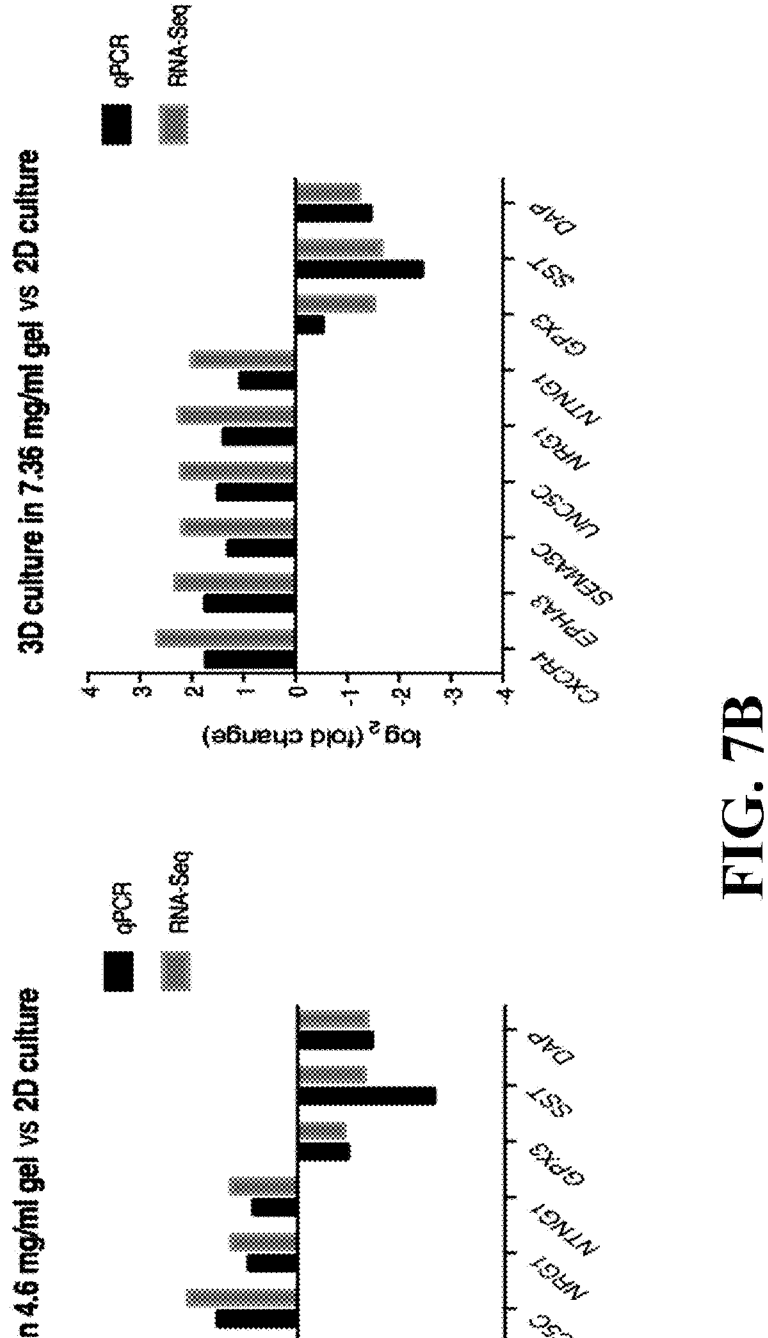
Figures 8A, 8B:
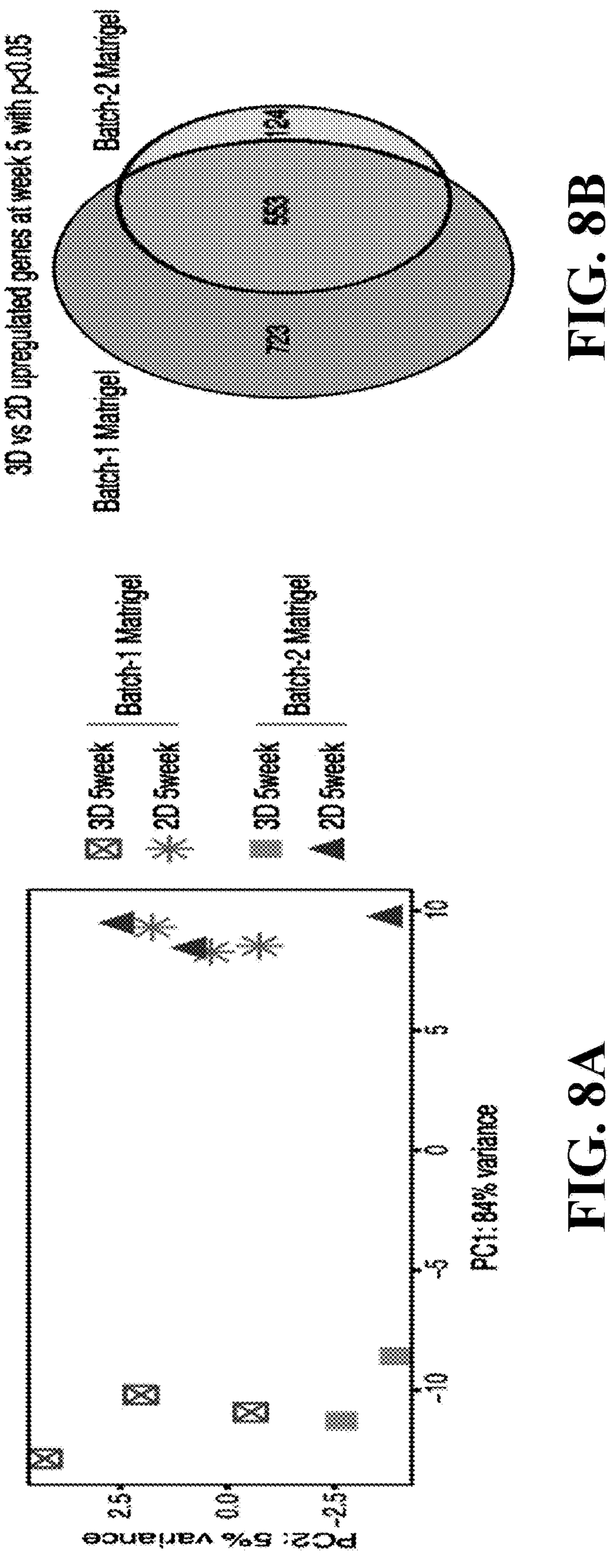
FIGS. 8A-8E: Analysis of the effect of batch and concentration of Matrigel on the gene expression profiles of 3D cultured iN cells.
Figure 8C:
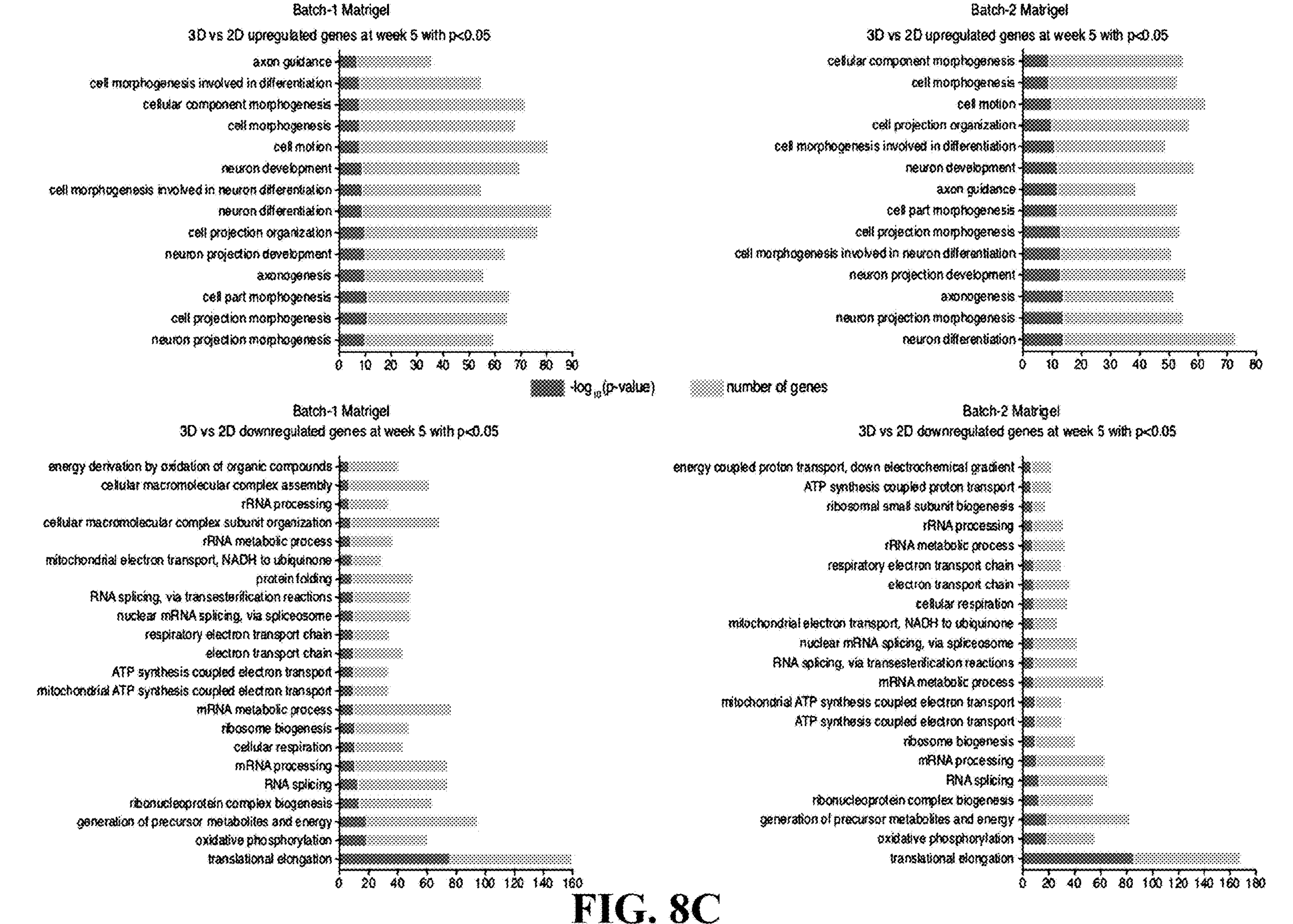
Figures 8D, 8E:
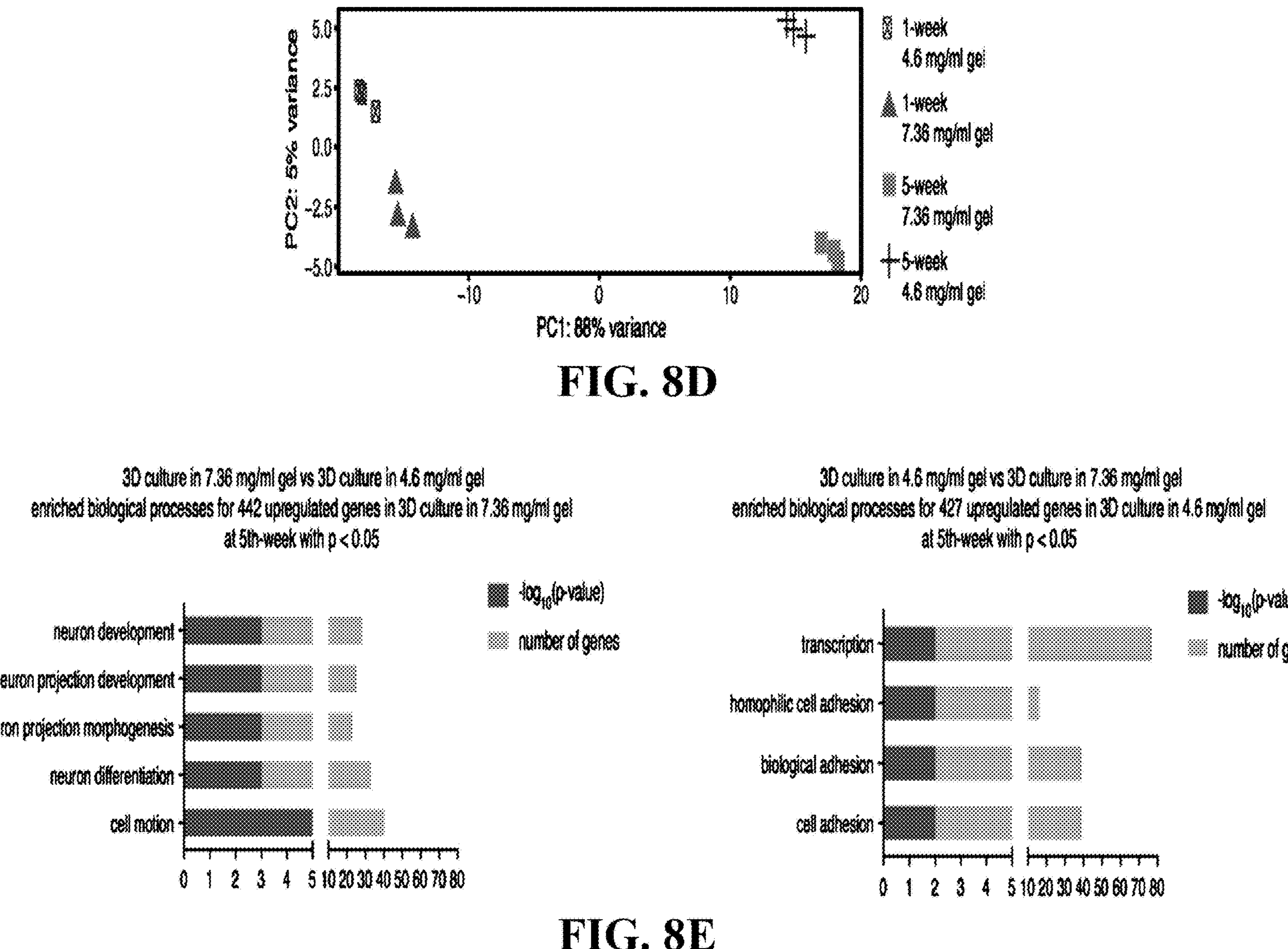
Figures 9A, 9B:
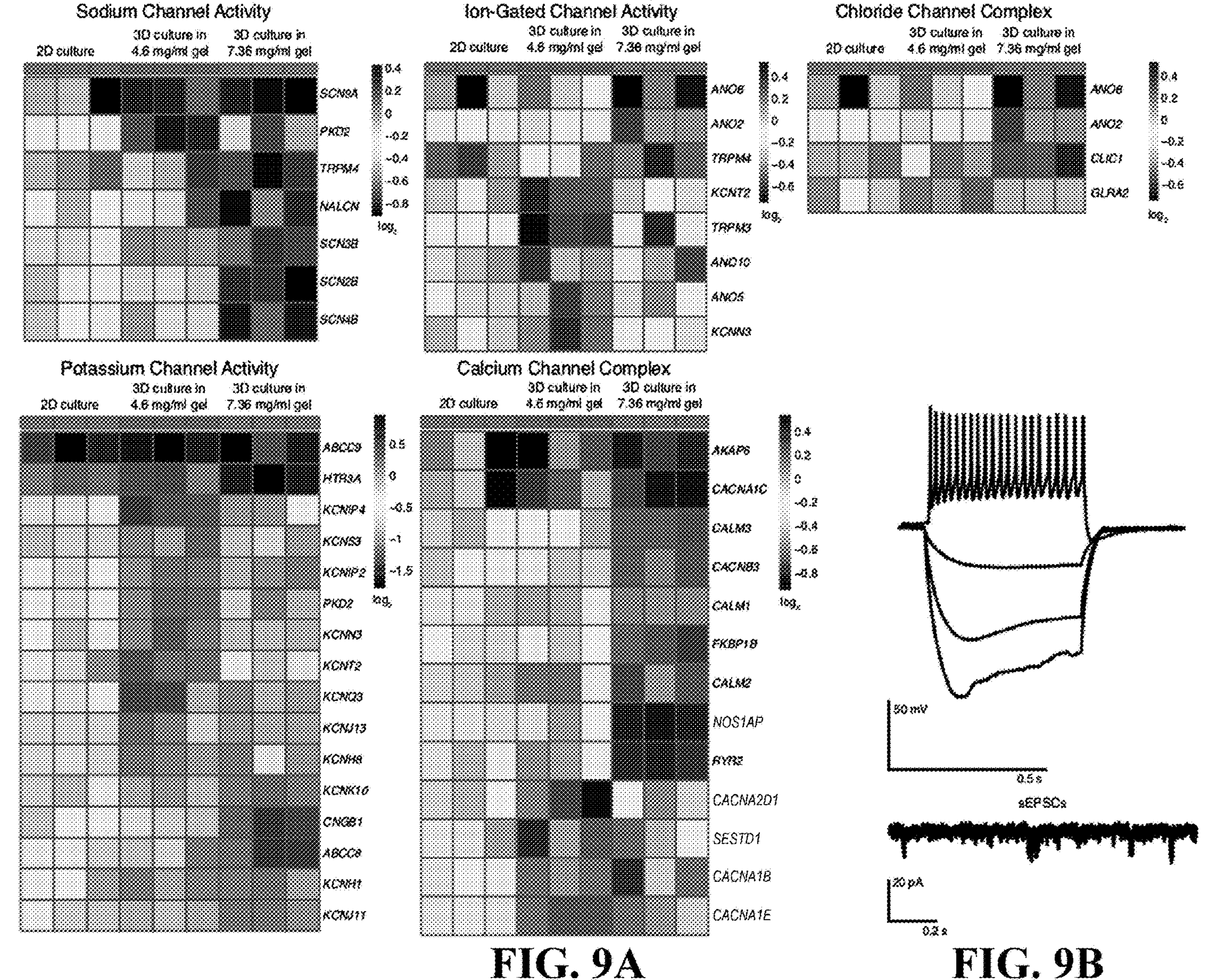
FIGS. 9A-9C: Long-term culture of iN cells in 3D hydrogels promotes expression of some genes associated with channels and healthy electrophysiological properties relative to iN cells on 2D cultures.
Figure 9C:
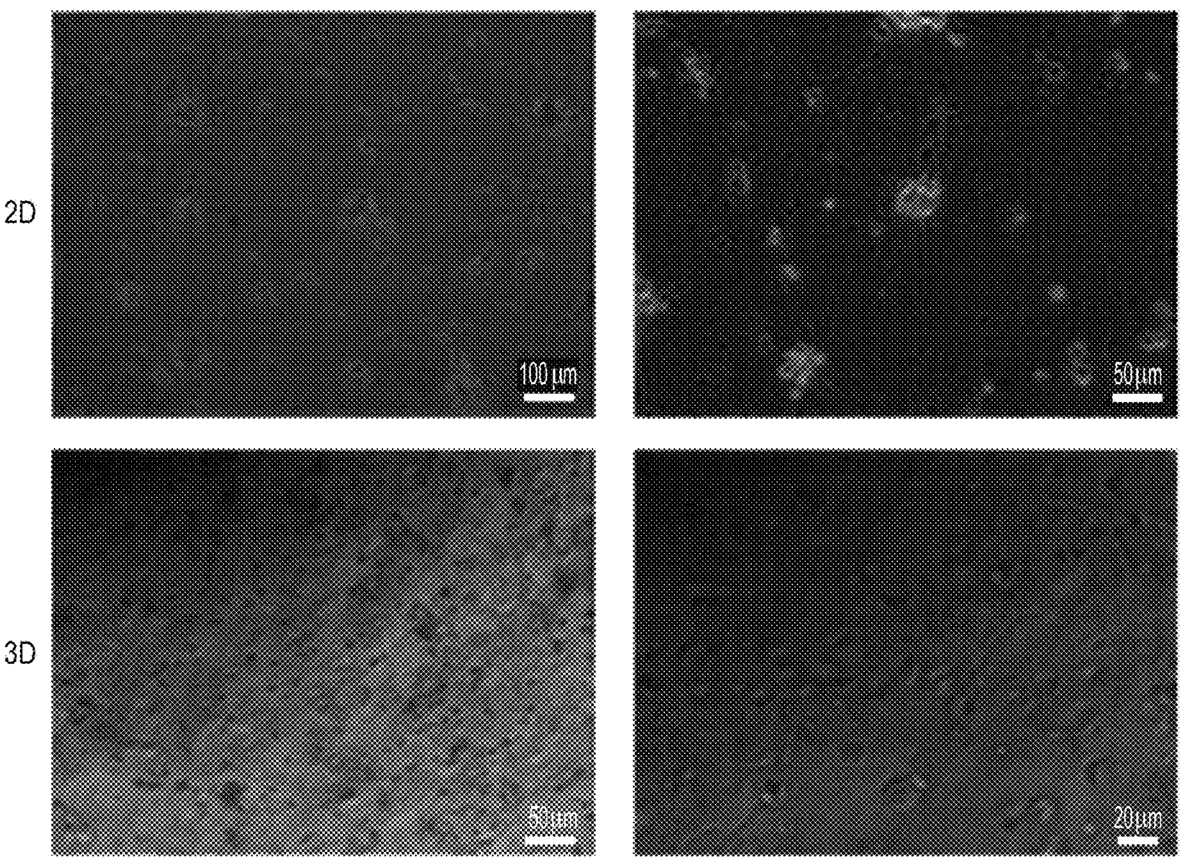
Figure 10B:
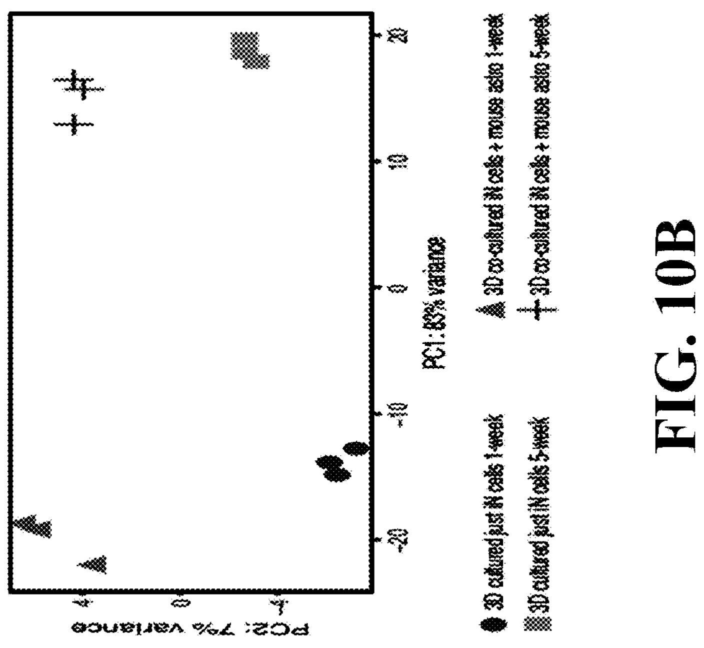
FIGS. 10A-10C: Filtering mouse reads from RNA-seq data involving co-cultures of human iN cells with mouse astrocytes and analysis of the effect of 3D co-culture of human iN cells with mouse astrocytes on gene expression profile of human iN cells.
Figure 10A:
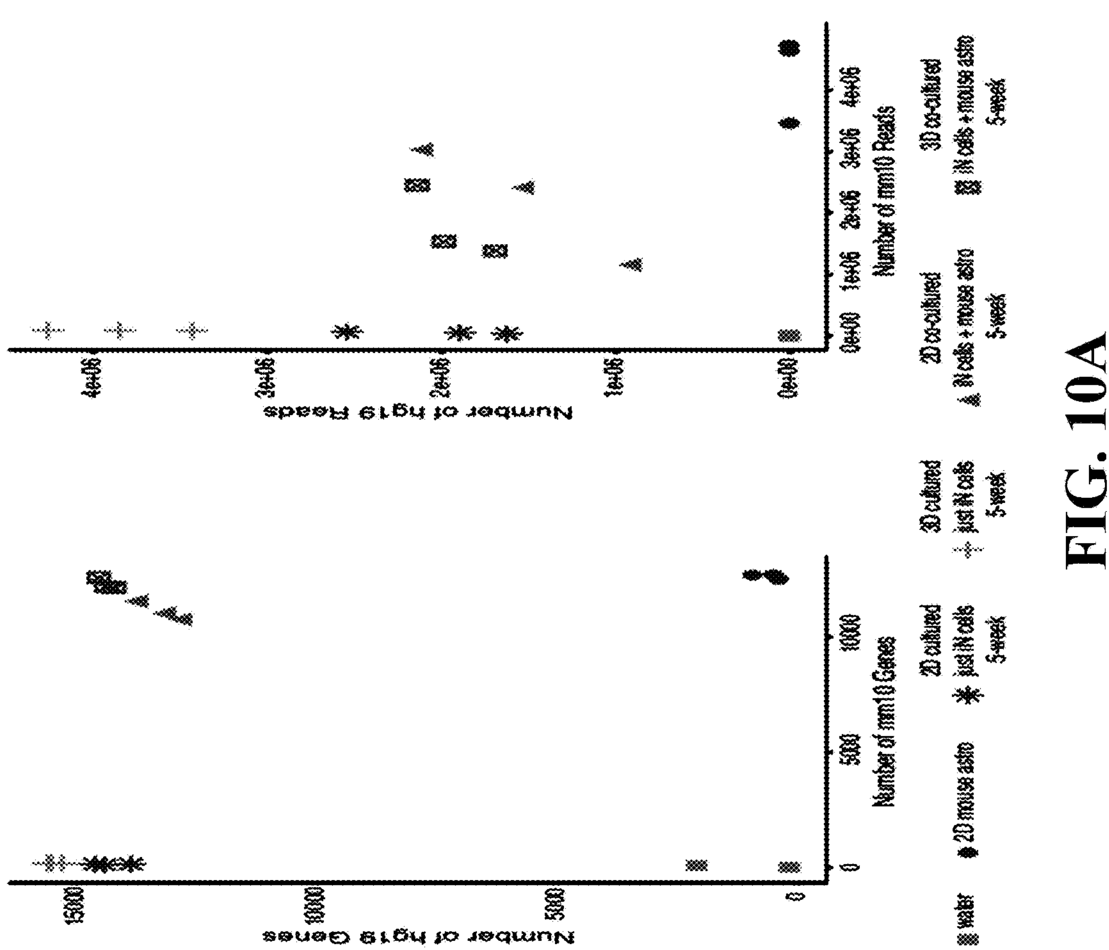
Figure 10C:
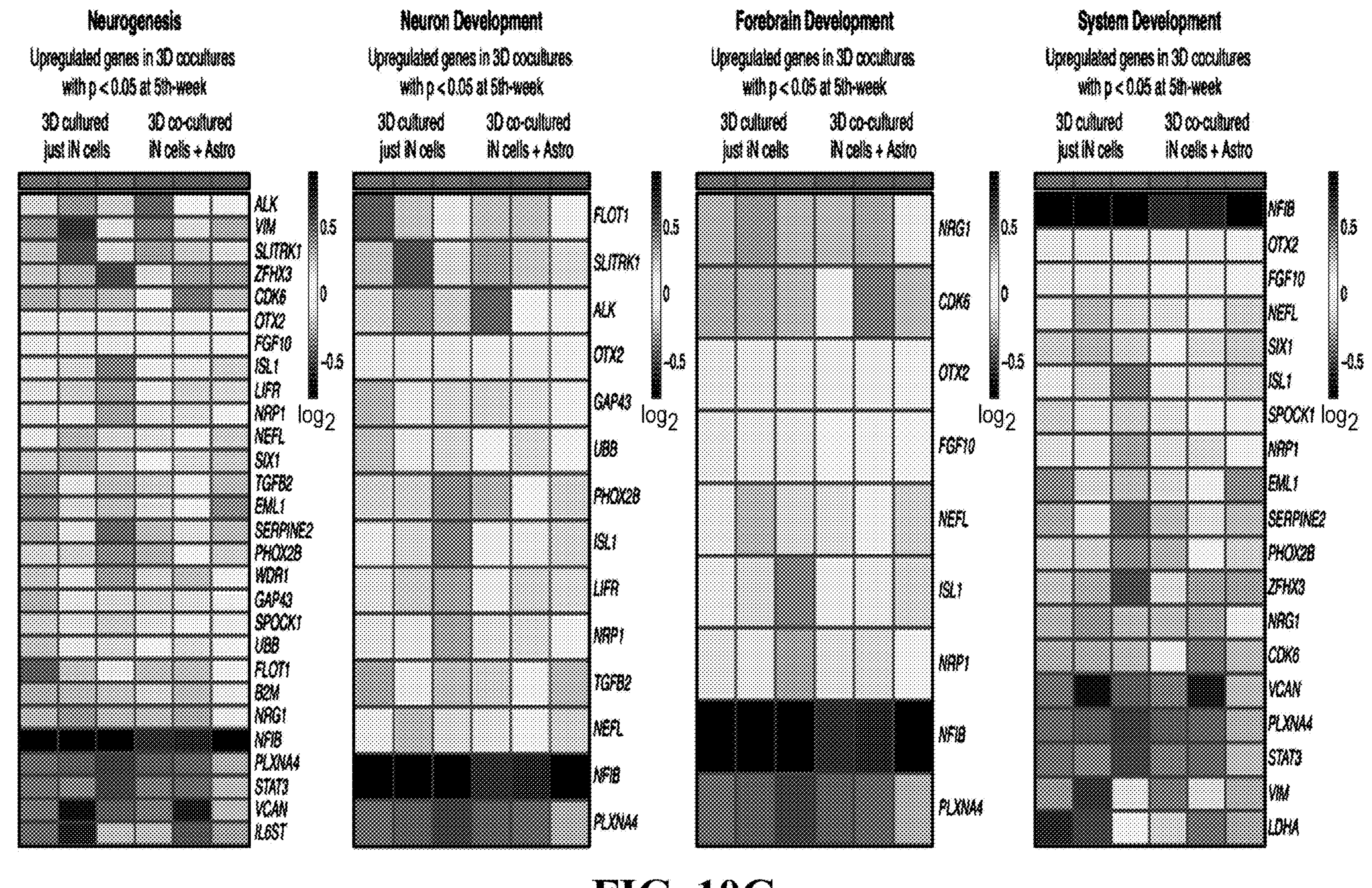
Figures 11A, 11B, 11C:
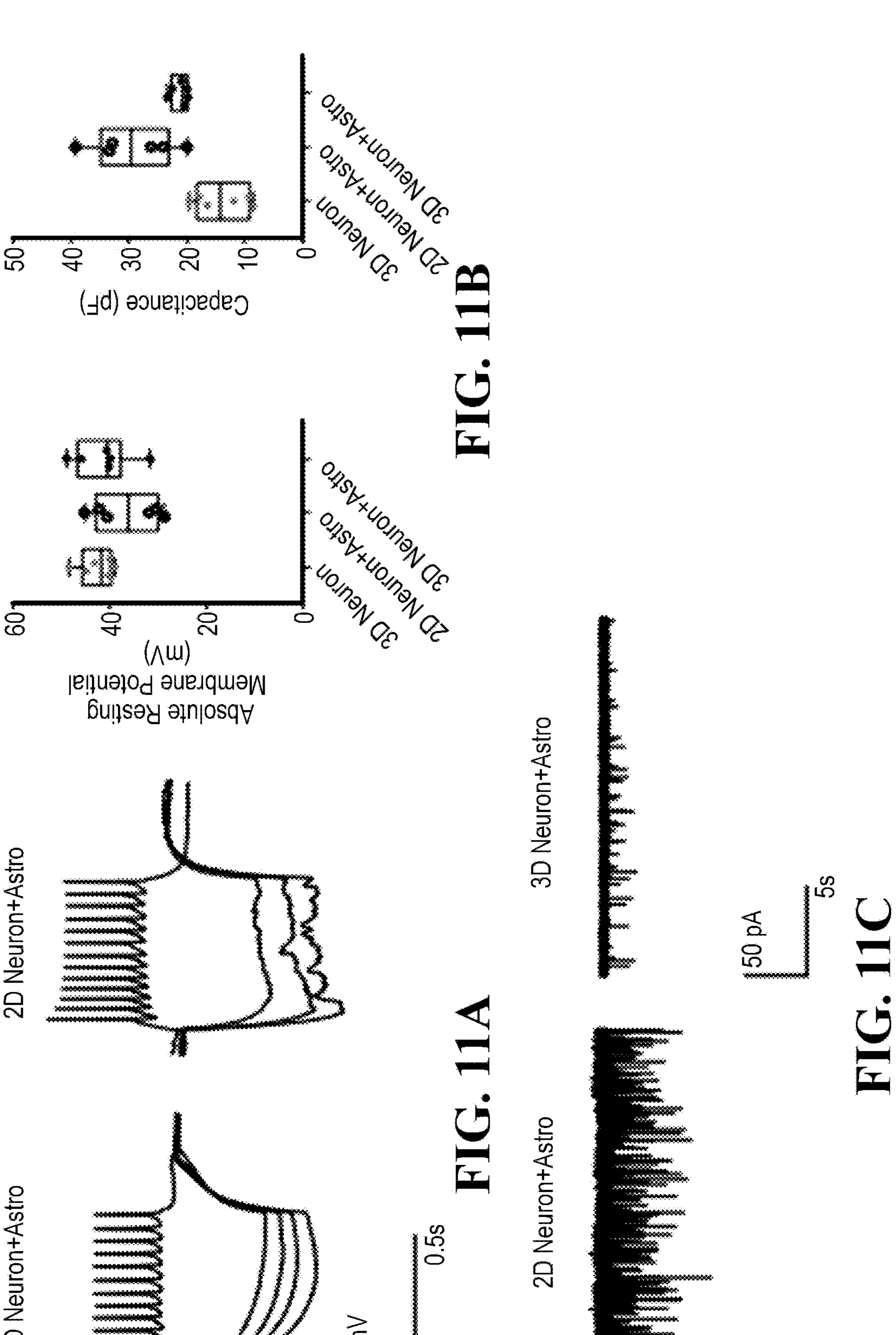
FIGS. 11A-11C: Electrophysiological properties of 3D cultured/co-cultured or 2D co-cultured iN cells. Human iN cells cultured with or without mouse astrocytes in 3D hydrogels (7.36 mg/ml Matrigel) and co-cultured with mouse astrocytes on 2D surfaces. Electrophysiological measurements on iN cell cultures with and without astrocytes in 3D hydrogels were conducted at day 45 and 36, respectively. Electrophysiological measurements on iN cell co-cultures on 2D surfaces were conducted at day 44.

To characterize the differences between 2D and 3D cultures of iN cells, we performed global transcriptome analysis and observed clear differences between these cultures at both the 1-week and 5-week time points (FIG. 1*c*, Table 4, 5). Maintaining healthy neural tissues for an extended amount of time promotes neuronal maturity[13,22], and we therefore focused our analysis on tissues at the 5-week time point. Gene set enrichment analysis (GSEA) showed more enriched neurological processes present in 3D cultured iN cells than in 2D ones at five weeks, whereas 2D cultures were enriched for apoptosis and oxidative stress, indicative of their poor health (FIG. 7*a*). We validated a subset of these genes by qPCR (=FIG. 7*b*). This is supported by gene ontology (GO) analysis for up- and down-regulated genes with p<0.001 (FIG. 1*f*). This trend was not significantly affected by batch-to-batch variation in Matrigel (FIGS. 8A-8C). Given this trend, we next tested whether increasing the concentration of Matrigel would further enhance for neurological processes, and we found an incremental improvement (FIGS. 8D, 8E). The ability to study the electrophysiological properties in a 3D culture system is desirably for downstream genetic studies, and we therefore analyzed the expression of genes involved in channel activity and the electrophysiological properties of these tissues. The 3D cultures of iN cells showed increased expression of a number of genes involved in channel activity, and we found that these cells, unlike their 2D counterparts, were capable of firing repetitive action potentials and displayed spontaneous excitatory postsynaptic currents (sEPSCs) (FIGS. 9A-9C). To further develop the cellular composition of our 3D cultures, we co-cultured iN cells with mouse astrocytes, which support neuronal processes and functions[18,19,27] (FIG. 1*b*) and performed bulk RNA-seq (reads from mouse astrocytes were filtered out, see FIG. 10*a* and methods). We observed global transcriptome differences between 2D and 3D co-cultures of iN cells at both the 1-week and 5-week time points (FIG. 1*d*, Table 6), and a substantial number of the significantly upregulated genes in 3D co-culture conditions were also upregulated in iN cells cultured in 3D without mouse astrocytes (FIG. 1*e*). Although cells in both 3D and 2D co-cultures at longer time points are electrophysiologically active (Supplementary FIG. 6), GO analysis of significantly up- and down regulated genes (p<0.001) at five weeks revealed more enriched neurological processes present in iN cells co-cultured in 3D versus 2D (FIG. 1*g*). The co-cultured 3D tissues showed clear transcriptional differences from pure iN 3D cultures and upregulation of genes involved in neurological processes (Supplementary FIG. 5*b, c*). We therefore used co-cultured 3D tissues for further analysis.

The following tables may be accessed in Tekin et al. “Effects of 3D culting conditions on the transcriptomic profile of stem-cell-derived neurons,” Nature Biomedical Engineering, 2: 540-554 (2018), which is herein incorporated by reference, specifically Supplemental Tables 2-3 and 11 that form part of the Supplementary Information of said paper and which may be accessed at doi.org/10.1038/s41551-018-0219-9.

Table 4 (Tekin Table 11): Differentially expressed genes at 1 week between iN cells cultured in 4.6 mg/ml Matrigel and iN cells cultured on 2D.

Table 5 (Tekin Table 2): Differentially expressed genes at 5 week between iN cells cultured in 4.6 mg/ml Matrigel and iN cells cultured on 2D.

Table 6 (Tekin Table 3): Differentially expressed genes at 5 week between iN cells co-cultured with mouse astrocytes in 4.6 mg/ml Matrigel and iN cells co-cultured with mouse astrocytes on 2D.

Example 3. Influence of HA on Transcriptome of 3D Co-Cultured iN Cells

Figure 2C:
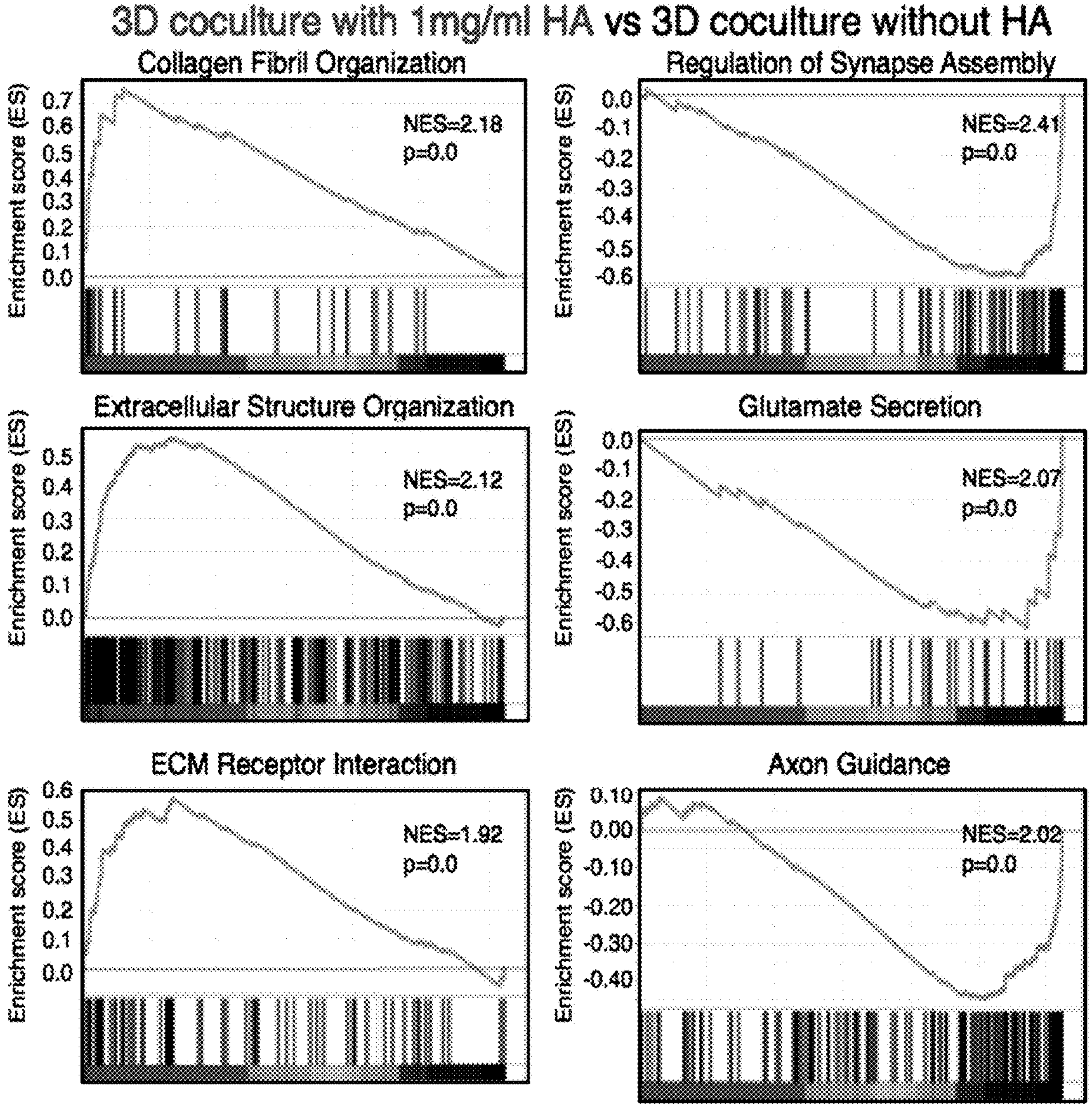
Figure 12:
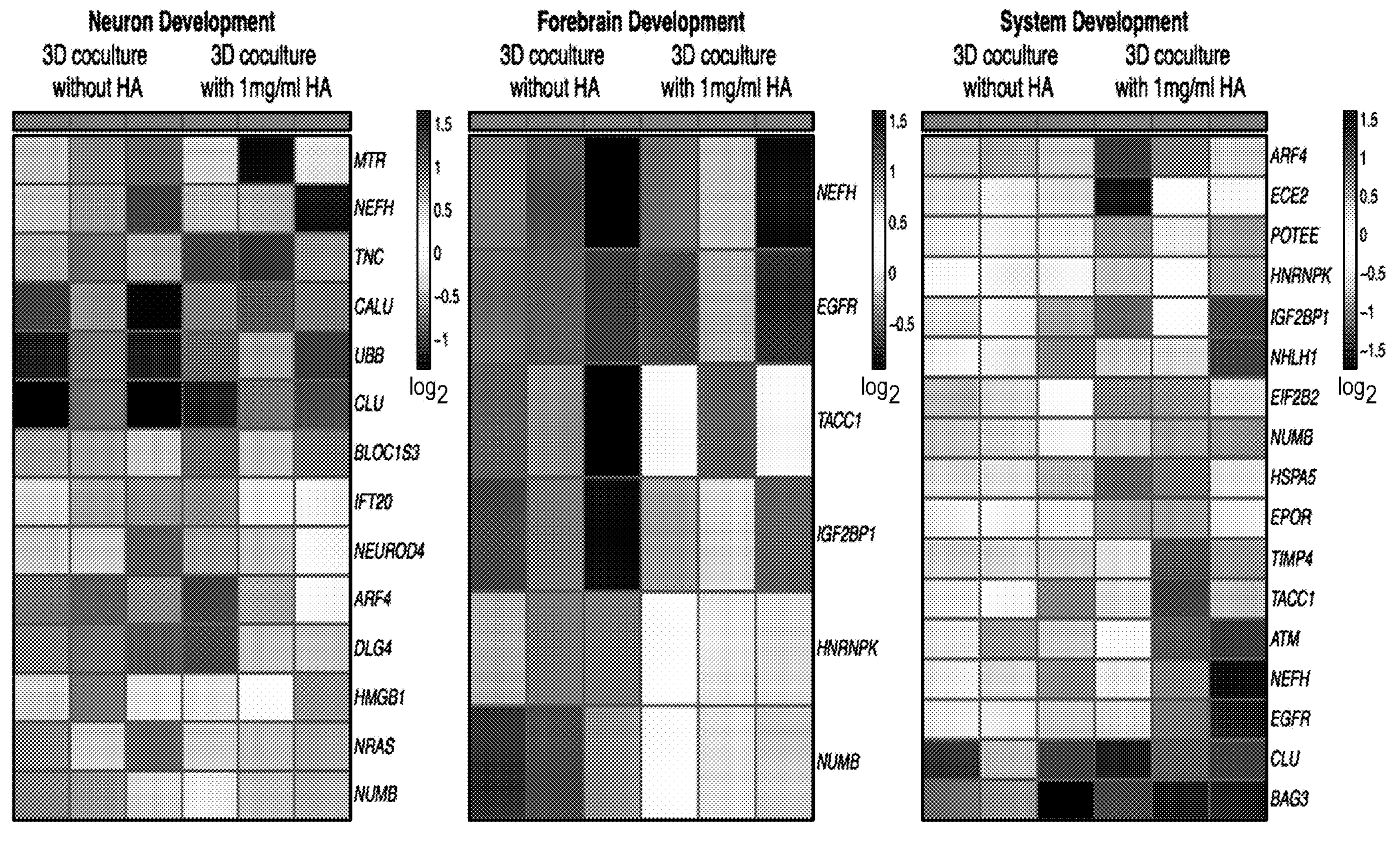
FIG. 12: Analysis of gene expression profiles of human iN cells co-cultured in Matrigel with HA. Relative expression of significantly ($p<0.05$) upregulated genes in iN cells co-cultured in 3D (7.36 mg/ml) Matrigel with HA compared to iN cells co-cultured in 3D (7.36 mg/ml) Matrigel without HA associated with neuron development, forebrain development and central nervous system development biological processes.

Previous neural tissue engineering approaches have incorporated HA, a non-sulfated glycosaminoglycan, into the matrix to mimic biological conditions 26,28-31, but the influence of HA has not been characterized by genome-wide profiling before. We incorporated a high molecular weight (~1.5-1.8×106 Da) HA at two different concentrations in our tissue system (FIG. 2*a*) and then performed bulk RNA-seq at 5 weeks. The presence of HA resulted in significant differences in the transcriptome of iN cells (FIG. 2*b*). GSEA and GO analysis showed that cells cultured in the absence of HA were more enriched for neurological processes, whereas the presence of HA lead to enrichment in non-neuronal biological processes (FIG. 2*c, d*, Table 2). Given previous reports of increased transcription of some neuronal genes in the presence of HA 29, we specifically looked at the expression of genes involved in neuron development, forebrain development, central nervous system development, and channel activity. We find expression of some genes, including DLG4, NEUROD4, and CLU, do show elevated expression in the presence of HA (FIG. 2*e*, FIG. 12). To gain a global view of the effect of HA on gene expression, we compared the transcriptome of our engineered tissues with and without HA to the human brain transcriptome of four different subregions (V1C: primary visual cortex (striate cortex, area V1/17); DFC: dorsolateral prefrontal cortex; A1C: primary auditory cortex (core); M1C: primary motor cortex (area M1, area 4)) at four fetal developmental stages (12 post-conceptual weeks (pcw), 16 pcw, 19 pcw and 37 pcw). We found that the presence of HA broadly decreased the correlation between the transcriptome of 3D co-cultured iN cells to the human brain developmental transcriptome, although correlations to 37 pcw did not fit this trend (FIG. 2*f*).

TABLE 2

Figure 2D:
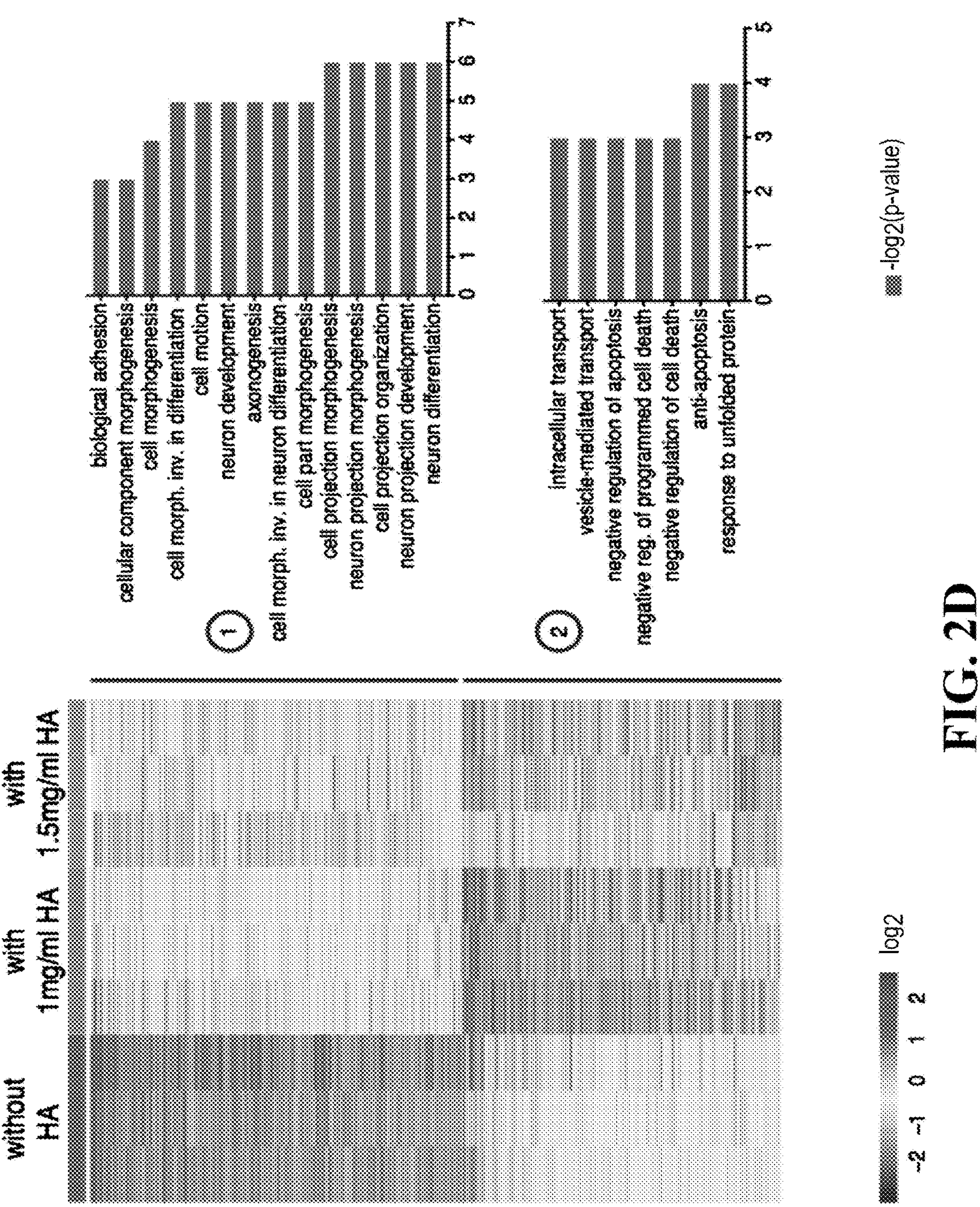
Figure 2E:
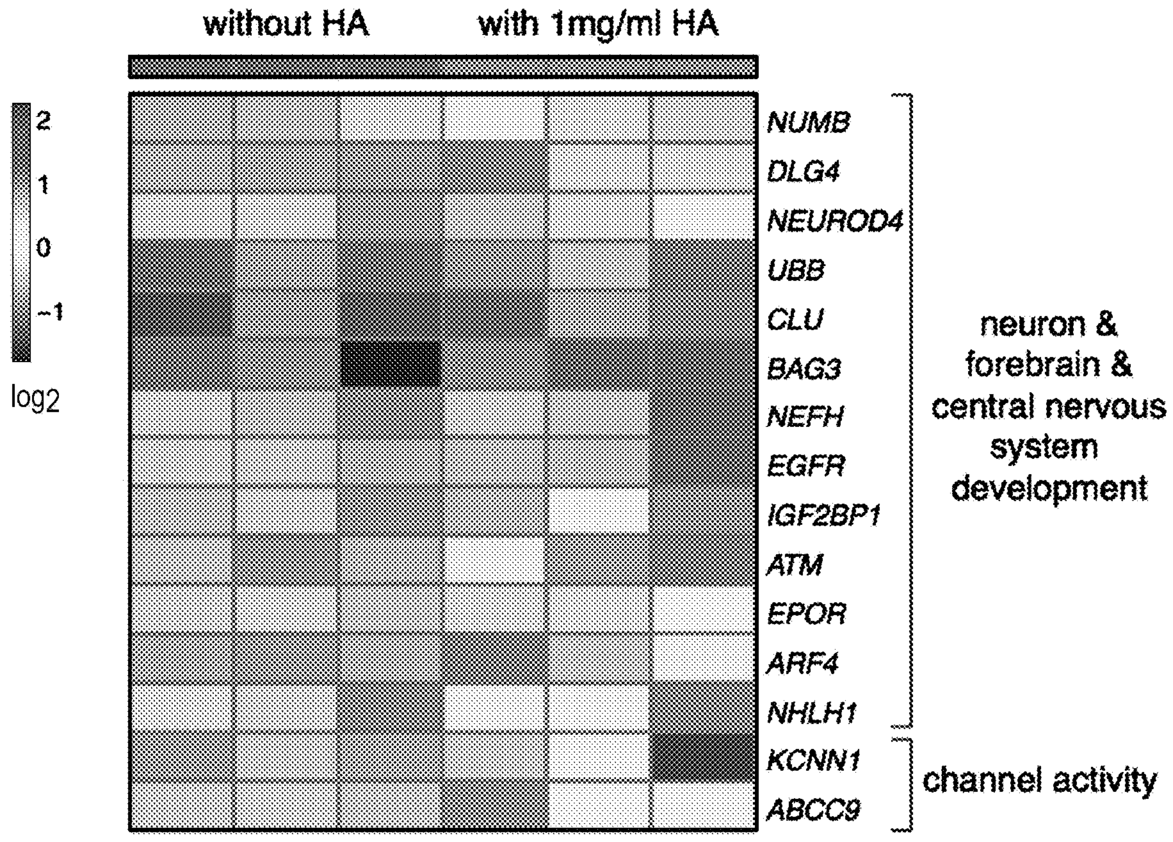
Figure 2F:
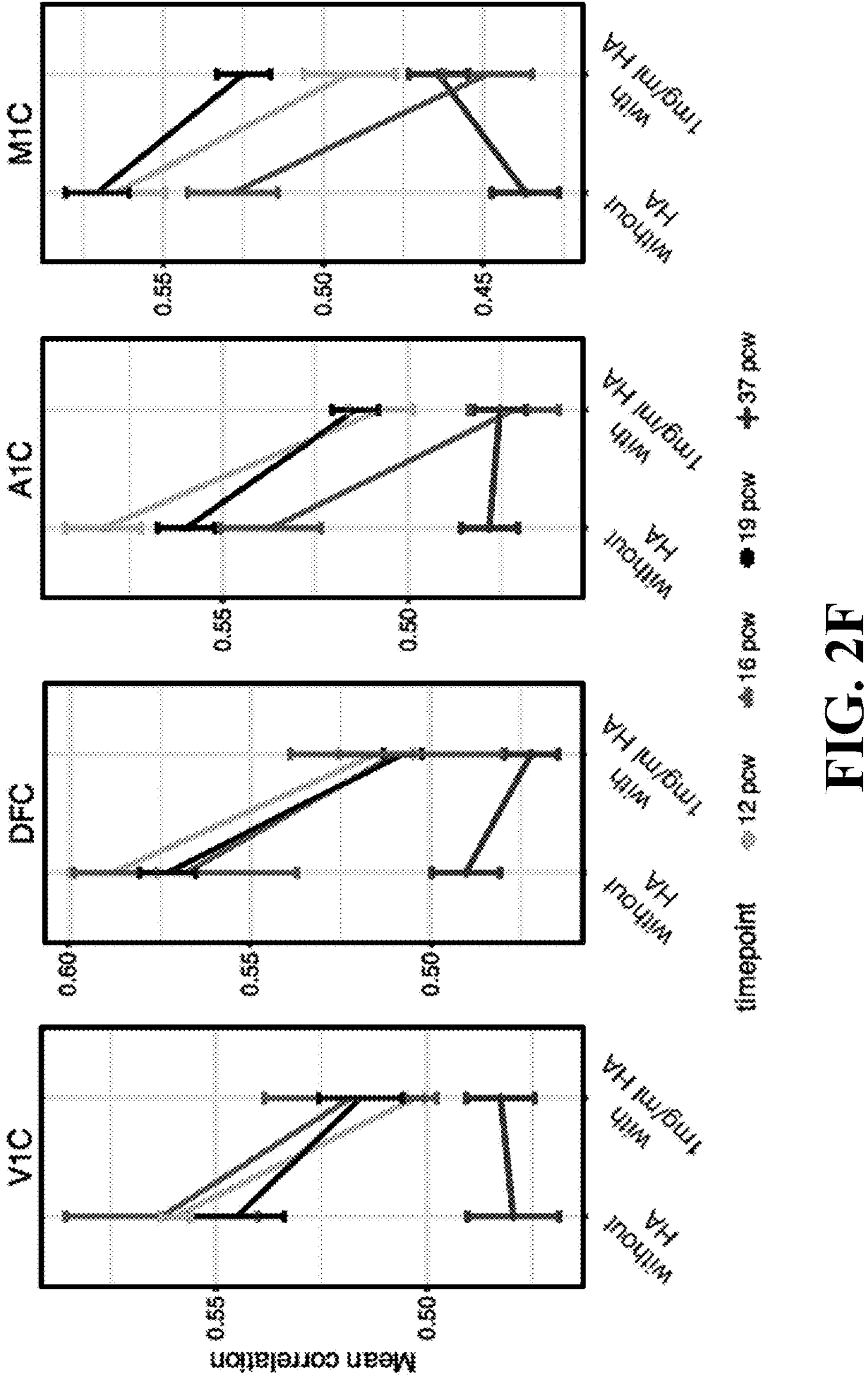

Genes in each cluster for heatmap in FIG. 2d.

| Gene Name | CL # |
|---|---|
| MTRNR2L8 | 1 |
| MTRNR2L2 | 1 |
| NEFL | 1 |
| ALCAM | 1 |
| STMN1 | 1 |
| NEFM | 1 |

TABLE 2-continued

Genes in each cluster for heatmap in FIG. 2d.

| Gene Name | CL # |
|---|---|
| STMN2 | 1 |
| ISL1 | 1 |
| DPYSL2 | 1 |
| MTRNR2L1 | 1 |
| TUBB | 1 |
| KIFAP3 | 1 |
| GNG2 | 1 |
| DDAH1 | 1 |
| TUBA1A | 1 |
| PRKACB | 1 |
| TUBB3 | 1 |
| TMEFF2 | 1 |
| CALM2 | 1 |
| GAP43 | 1 |
| VAT1L | 1 |
| RTN1 | 1 |
| FXYD6 | 1 |
| SEMA3C | 1 |
| RAP1GDS1 | 1 |
| TUBB2A | 1 |
| TUBB4A | 1 |
| ANK2 | 1 |
| AASDHPPT | 1 |
| DNM3 | 1 |
| C20orf112 | 1 |
| UBE2E3 | 1 |
| MAB21L1 | 1 |
| ATP6V1G2 | 1 |
| ACOT7 | 1 |
| PAFAH1B3 | 1 |
| SPTAN1 | 1 |
| FEZ1 | 1 |
| SYT1 | 1 |
| TUBB2B | 1 |
| RPL21 | 1 |
| PTPRS | 1 |
| CLASP2 | 1 |
| EFR3B | 1 |
| SRSF3 | 1 |
| BTF3L4 | 1 |
| CRIP2 | 1 |
| TTC3 | 1 |
| TSC22D1 | 1 |
| GSTA4 | 1 |
| TBCB | 1 |
| ZNF770 | 1 |
| YWHAB | 1 |
| CRMP1 | 1 |
| CHGA | 1 |
| KIF21A | 1 |
| MAPK8 | 1 |
| MAPT | 1 |
| LPPR2 | 1 |
| ATP1A3 | 1 |
| SYT13 | 1 |
| CD24 | 1 |
| PKIA | 1 |
| PCDHA4 | 1 |
| NPDC1 | 1 |
| CALM3 | 1 |
| B3GALT2 | 1 |
| FGF13 | 1 |
| DCTN1 | 1 |
| MARCKSL1 | 1 |
| ZCCHC12 | 1 |
| SPON1 | 1 |
| SLC16A14 | 1 |
| PBX1 | 1 |
| DCX | 1 |
| SPOCK1 | 1 |
| PTBP2 | 1 |
| ACLY | 1 |
| DZIP3 | 1 |
| KIF2A | 1 |
| SERPINI1 | 1 |
| NAP1L3 | 1 |

TABLE 2-continued

Genes in each cluster for heatmap in FIG. 2d.

| Gene Name | CL # |
|---|---|
| RAB10 | 1 |
| C1orf216 | 1 |
| ATP6V0E2 | 1 |
| SNCA | 1 |
| ELAVL2 | 1 |
| ATP6V1A | 1 |
| RAB3B | 1 |
| CD200 | 1 |
| SLC30A9 | 1 |
| PAPSS1 | 1 |
| BLCAP | 1 |
| EPHA3 | 1 |
| DNER | 1 |
| NSG1 | 1 |
| HSBP1 | 1 |
| NCALD | 1 |
| MAB21L2 | 1 |
| RND3 | 1 |
| SMARCAD1 | 1 |
| RAP1B | 1 |
| CLSTN3 | 1 |
| SEPT5-GP1BB | 1 |
| DPYSL3 | 1 |
| ZFAND5 | 1 |
| PFN2 | 1 |
| GNAI1 | 1 |
| SCD5 | 1 |
| KIF3C | 1 |
| FAM5C | 1 |
| UBQLN1 | 1 |
| CDH10 | 1 |
| NSF | 1 |
| CA10 | 1 |
| TRIM2 | 1 |
| DSTN | 1 |
| SH3GL2 | 1 |
| PHACTR3 | 1 |
| CXCR4 | 1 |
| TMEM59L | 1 |
| SCMH1 | 1 |
| TMSB15A | 1 |
| DKK3 | 1 |
| ANK3 | 1 |
| LY6H | 1 |
| PCSK1N | 1 |
| SIX1 | 1 |
| TMEFF1 | 1 |
| CDH8 | 1 |
| CAPN1 | 1 |
| MAGED4B | 1 |
| CTNNA2 | 1 |
| P2RX3 | 1 |
| KLHL13 | 1 |
| TPPP3 | 1 |
| RPAP3 | 1 |
| LMO3 | 1 |
| SEMA3D | 1 |
| NGFRAP1 | 1 |
| PGM2L1 | 1 |
| STMN3 | 1 |
| CORO1A | 1 |
| ZNF260 | 1 |
| ATP9A | 1 |
| PIP4K2B | 1 |
| FLRT3 | 1 |
| NHLH2 | 1 |
| SCN2A | 1 |
| MYO5A | 1 |
| PEBP1 | 1 |
| TANC2 | 1 |
| NME1-NME2 | 1 |
| EPHB1 | 1 |
| PPP2R3C | 1 |
| SREBF2 | 1 |
| TOMM20 | 1 |
| ATL1 | 1 |

TABLE 2-continued

| Genes in each cluster for heatmap in FIG. 2d. | |
|---|---|
| Gene Name | CL # |
| NLGN4X | 1 |
| EEF1G | 1 |
| ABCA7 | 1 |
| ZBED1 | 1 |
| ATRX | 1 |
| APC | 1 |
| SEMA3E | 1 |
| SNX14 | 1 |
| CELSR2 | 1 |
| RCHY1 | 1 |
| NEUROG2 | 1 |
| NAP1L1 | 1 |
| CPNE8 | 1 |
| CHRDL1 | 1 |
| MTRNR2L3 | 1 |
| CORO7 | 1 |
| PCSK1 | 1 |
| STAU2 | 1 |
| TSPAN2 | 1 |
| GABRA3 | 1 |
| SMIM18 | 1 |
| USP5 | 1 |
| SEPW1 | 1 |
| WTAP | 1 |
| CBX3 | 1 |
| PPA2 | 1 |
| SLC8A1 | 1 |
| HPCAL4 | 1 |
| PAFAH1B2 | 1 |
| FSTL5 | 1 |
| BZW2 | 1 |
| NKRF | 1 |
| FKBP3 | 1 |
| EYA1 | 1 |
| SULT4A1 | 1 |
| TRO | 1 |
| JUP | 1 |
| B3GNT1 | 1 |
| SYP | 1 |
| C12orf68 | 1 |
| APBB1 | 1 |
| KLHL11 | 1 |
| MARCKS | 1 |
| SLC23A2 | 1 |
| ATP2B1 | 1 |
| TM7SF2 | 1 |
| SH3BGRL | 1 |
| CGGBP1 | 1 |
| PCDH10 | 1 |
| DGKB | 1 |
| CALB1 | 1 |
| B3GALNT1 | 1 |
| DCLK1 | 1 |
| ERC1 | 1 |
| KIAA1598 | 1 |
| REEP1 | 1 |
| PRNP | 1 |
| SNRPE | 1 |
| PCDH9 | 1 |
| MOAP1 | 1 |
| MTRNR2L10 | 1 |
| LPHN1 | 1 |
| HSD11B1L | 1 |
| DOK4 | 1 |
| CXADR | 1 |
| NIPSNAP3A | 1 |
| NCS1 | 1 |
| PLXNA4 | 1 |
| NR2C2 | 1 |
| AZI2 | 1 |
| ZFP90 | 1 |
| CNST | 1 |
| NDUFC2 | 1 |
| LOC642366 | 1 |
| OGT | 1 |
| LPPR4 | 1 |

TABLE 2-continued

| Genes in each cluster for heatmap in FIG. 2d. | |
|---|---|
| Gene Name | CL # |
| ELMOD1 | 1 |
| GPS1 | 1 |
| PIK3R3 | 1 |
| DMD | 1 |
| CDO1 | 1 |
| ALDH2 | 1 |
| PCDH17 | 1 |
| MAPK10 | 1 |
| RAC3 | 1 |
| NRG1 | 1 |
| KLHL22 | 1 |
| LRSAM1 | 1 |
| ASTN1 | 1 |
| SUMO3 | 1 |
| UBXN2B | 1 |
| GRIA4 | 1 |
| LRRC40 | 1 |
| GNG4 | 1 |
| KLHL23 | 1 |
| LSAMP | 1 |
| DIRAS2 | 1 |
| HPCAL1 | 1 |
| NELL1 | 1 |
| TMEM35 | 1 |
| PLEC | 1 |
| TRIM36 | 1 |
| PFDN4 | 1 |
| RCN2 | 1 |
| ICA1L | 1 |
| YWHAG | 1 |
| DOPEY2 | 1 |
| ZNF148 | 1 |
| INA | 1 |
| USP33 | 1 |
| PPFIA2 | 1 |
| RPL39 | 1 |
| ARHGEF12 | 1 |
| ITFG1 | 1 |
| MTRNR2L6 | 1 |
| GPM6A | 1 |
| RIMKLB | 1 |
| KIF3A | 1 |
| NUDT11 | 1 |
| KIAA0513 | 1 |
| SNCG | 1 |
| PAK7 | 1 |
| UGP2 | 1 |
| GARNL3 | 1 |
| SRSF6 | 1 |
| UBC | 2 |
| SERPINH1 | 2 |
| UBB | 2 |
| GAPDH | 2 |
| CLU | 2 |
| FTL | 2 |
| CRYAB | 2 |
| FLNC | 2 |
| HSPB1 | 2 |
| P4HA1 | 2 |
| AHNAK | 2 |
| SRPR | 2 |
| CALU | 2 |
| COPB2 | 2 |
| HSPA6 | 2 |
| MALAT1 | 2 |
| RPS2P32 | 2 |
| MIAT | 2 |
| ARF4 | 2 |
| SF3A3 | 2 |
| GPRC5C | 2 |
| HSPA5 | 2 |
| ARL1 | 2 |
| HSPA1B | 2 |
| P4HA2 | 2 |
| SH3BGR | 2 |
| BAG3 | 2 |

TABLE 2-continued

Genes in each cluster for heatmap in FIG. 2d.

| Gene Name | CL # |
|---|---|
| SEC31A | 2 |
| KLHL15 | 2 |
| JMJD6 | 2 |
| PPP1R15A | 2 |
| HSPH1 | 2 |
| HMGB2 | 2 |
| SPARC | 2 |
| SLC3A2 | 2 |
| MED8 | 2 |
| PMEL | 2 |
| NEU1 | 2 |
| MFAP4 | 2 |
| DNAJB1 | 2 |
| PRRC1 | 2 |
| DNAJC3 | 2 |
| M6PR | 2 |
| NEAT1 | 2 |
| TXNL4B | 2 |
| PQLC2 | 2 |
| AGT | 2 |
| UBA52 | 2 |
| TUBA1C | 2 |
| NOL6 | 2 |
| SEC24C | 2 |
| CCDC47 | 2 |
| DLG4 | 2 |
| GANAB | 2 |
| SRP54 | 2 |
| DUSP13 | 2 |
| SPTY2D1 | 2 |
| TMX2 | 2 |
| SUPT5H | 2 |
| USP36 | 2 |
| NCSTN | 2 |
| COPA | 2 |
| NRAS | 2 |
| WBP5 | 2 |
| CHPF | 2 |
| YIF1A | 2 |
| BMS1 | 2 |
| KAT7 | 2 |
| SDE2 | 2 |
| KRT8 | 2 |
| RECQL | 2 |
| DCAF13 | 2 |
| SLC20A1 | 2 |
| CRABP2 | 2 |
| DDX17 | 2 |
| ATAD3B | 2 |
| GNG5 | 2 |
| SIKE1 | 2 |
| MGAT5 | 2 |
| ALG3 | 2 |
| SRP68 | 2 |
| TIMP4 | 2 |
| PPP1R3C | 2 |
| TMEM70 | 2 |
| CD63 | 2 |
| ADIPOR1 | 2 |
| PGM3 | 2 |
| NOLC1 | 2 |
| LOC100272217 | 2 |
| HNRNPA1P10 | 2 |
| CAPG | 2 |
| DSP | 2 |
| TIMP1 | 2 |
| HNRNPH3 | 2 |
| YIPF5 | 2 |
| FNDC3B | 2 |
| FBXW11 | 2 |
| CALCB | 2 |
| ZNF445 | 2 |
| GDF15 | 2 |
| ENO3 | 2 |
| NPC2 | 2 |
| B2M | 2 |

TABLE 2-continued

Genes in each cluster for heatmap in FIG. 2d.

| Gene Name | CL # |
|---|---|
| GBF1 | 2 |
| ATL3 | 2 |
| GLUL | 2 |
| TRMT112 | 2 |
| HBP1 | 2 |
| KDELR3 | 2 |
| DDX39A | 2 |
| GNPDA1 | 2 |
| AP5Z1 | 2 |
| LAS1L | 2 |
| EIF3M | 2 |
| CALCRL | 2 |
| SH3BGRL3 | 2 |
| STK17B | 2 |
| SERP1 | 2 |
| PES1 | 2 |
| GOSR2 | 2 |
| ANXA5 | 2 |
| TMX1 | 2 |
| SUPT6H | 2 |
| EMG1 | 2 |
| DDIT3 | 2 |
| SQSTM1 | 2 |
| NR1D1 | 2 |
| WDR36 | 2 |
| SEC23IP | 2 |
| DAD1 | 2 |
| PURA | 2 |
| POTEE | 2 |
| NGDN | 2 |
| PER1 | 2 |
| IGF2BP1 | 2 |
| CALCA | 2 |
| SLC44A2 | 2 |
| KDELR2 | 2 |
| PRELID1 | 2 |
| POTEM | 2 |
| EMC7 | 2 |
| POLR2A | 2 |
| ANXA2P2 | 2 |
| TNFRSF10D | 2 |
| SETD7 | 2 |
| UROD | 2 |
| ZNF695 | 2 |
| SLC35F6 | 2 |
| FSTL1 | 2 |
| SNHG1 | 2 |
| TCF4 | 2 |
| HSPA1A | 2 |
| GOLGA5 | 2 |
| NXF1 | 2 |
| DNHD1 | 2 |
| EIF2B2 | 2 |
| GNL2 | 2 |
| GFPT1 | 2 |
| ABCF1 | 2 |
| LINC00599 | 2 |
| ECM1 | 2 |
| UBE4A | 2 |
| SNX2 | 2 |
| NUDT7 | 2 |
| SPG7 | 2 |
| NUP214 | 2 |
| SRCAP | 2 |
| GDAP2 | 2 |
| COL1A1 | 2 |
| PPP1R11 | 2 |
| SLC35A2 | 2 |
| RNMT | 2 |
| YES1 | 2 |
| GRN | 2 |
| SPTLC1 | 2 |
| MOSPD1 | 2 |
| CTSL1 | 2 |
| CCKBR | 2 |
| AVL9 | 2 |

TABLE 2-continued

| Genes in each cluster for heatmap in FIG. 2d. | |
|---|---|
| Gene Name | CL # |
| EXOSC1 | 2 |
| GOLT1B | 2 |
| HSPB8 | 2 |
| P4HB | 2 |
| BET1L | 2 |
| SERF2 | 2 |
| SCPEP1 | 2 |
| SLC7A6 | 2 |
| SLC31A1 | 2 |
| GMPS | 2 |
| HM13 | 2 |
| TOX4 | 2 |
| DLK1 | 2 |
| ATM | 2 |
| C11orf24 | 2 |
| QRICH1 | 2 |
| SON | 2 |
| DNAH3 | 2 |
| IFT20 | 2 |
| SEC61A1 | 2 |
| ACP5 | 2 |
| EYA3 | 2 |
| NDUFAF3 | 2 |
| AQP3 | 2 |
| TPD52L1 | 2 |
| HERPUD2 | 2 |
| RPUSD2 | 2 |
| IGFBP5 | 2 |
| HK2 | 2 |
| UTP20 | 2 |
| BRD2 | 2 |
| CTNND1 | 2 |
| PRPF3 | 2 |
| TNC | 2 |
| CLIC1 | 2 |
| NARS | 2 |
| TMEM120B | 2 |
| SRA1 | 2 |
| MYBBP1A | 2 |
| ZKSCAN8 | 2 |
| C22orf28 | 2 |
| PLIN2 | 2 |
| MMS19 | 2 |
| DPP9 | 2 |
| AKAP2 | 2 |
| PRRC2C | 2 |
| LRRC59 | 2 |
| RHOC | 2 |
| IKBKAP | 2 |
| PDHX | 2 |
| CDK5RAP3 | 2 |
| ACTN1 | 2 |
| DDX6 | 2 |
| VPRBP | 2 |
| DOLK | 2 |
| SRPRB | 2 |
| SLC25A51 | 2 |
| BNIP3 | 2 |
| JAM3 | 2 |
| CDS2 | 2 |
| FABP3 | 2 |
| SMCR8 | 2 |
| PLTP | 2 |

CL: Cluster

Example 4. Transcriptome Profiles can be Tuned by Using Composite Hydrogels

Figure 3A:
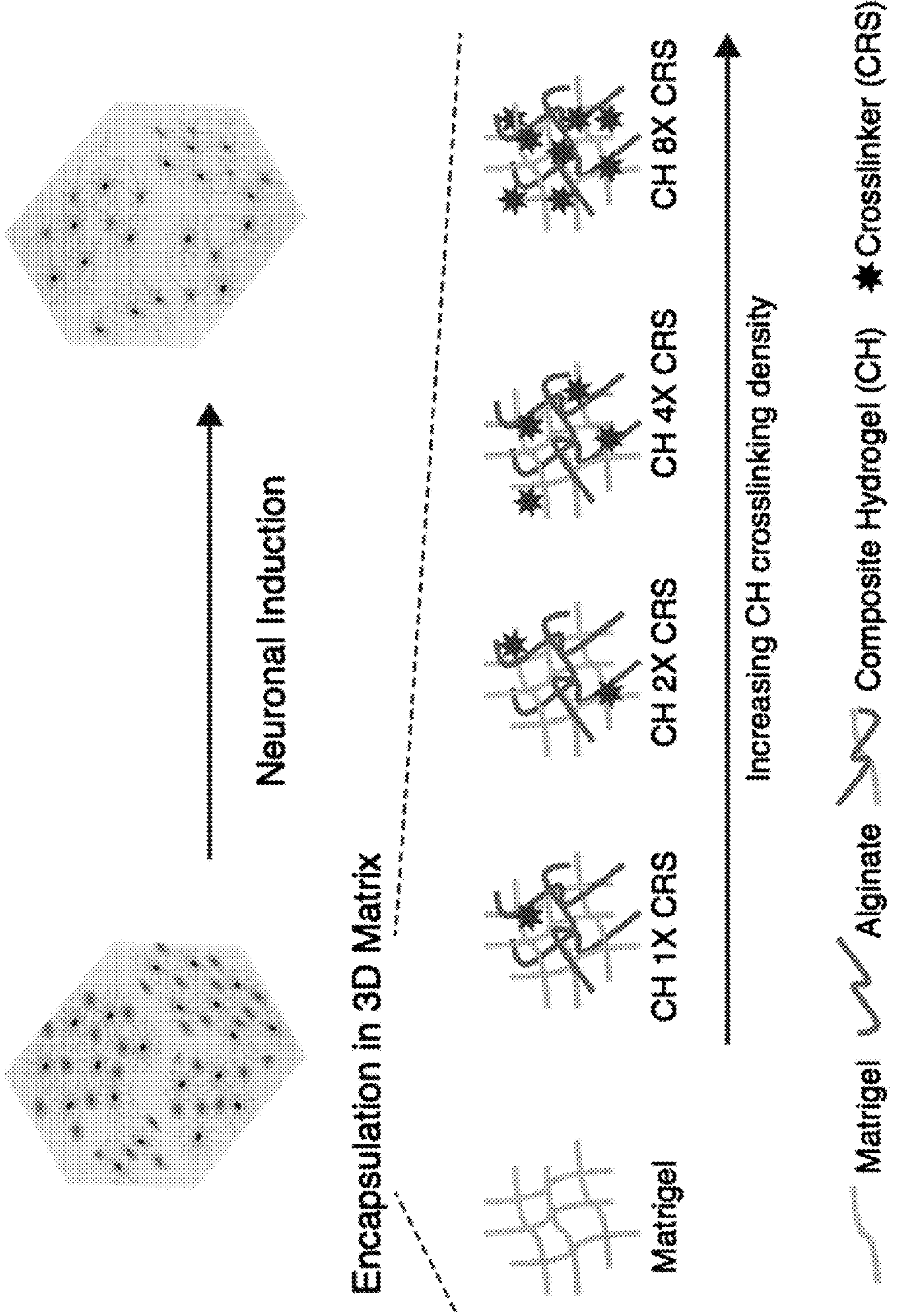
Figure 3B:
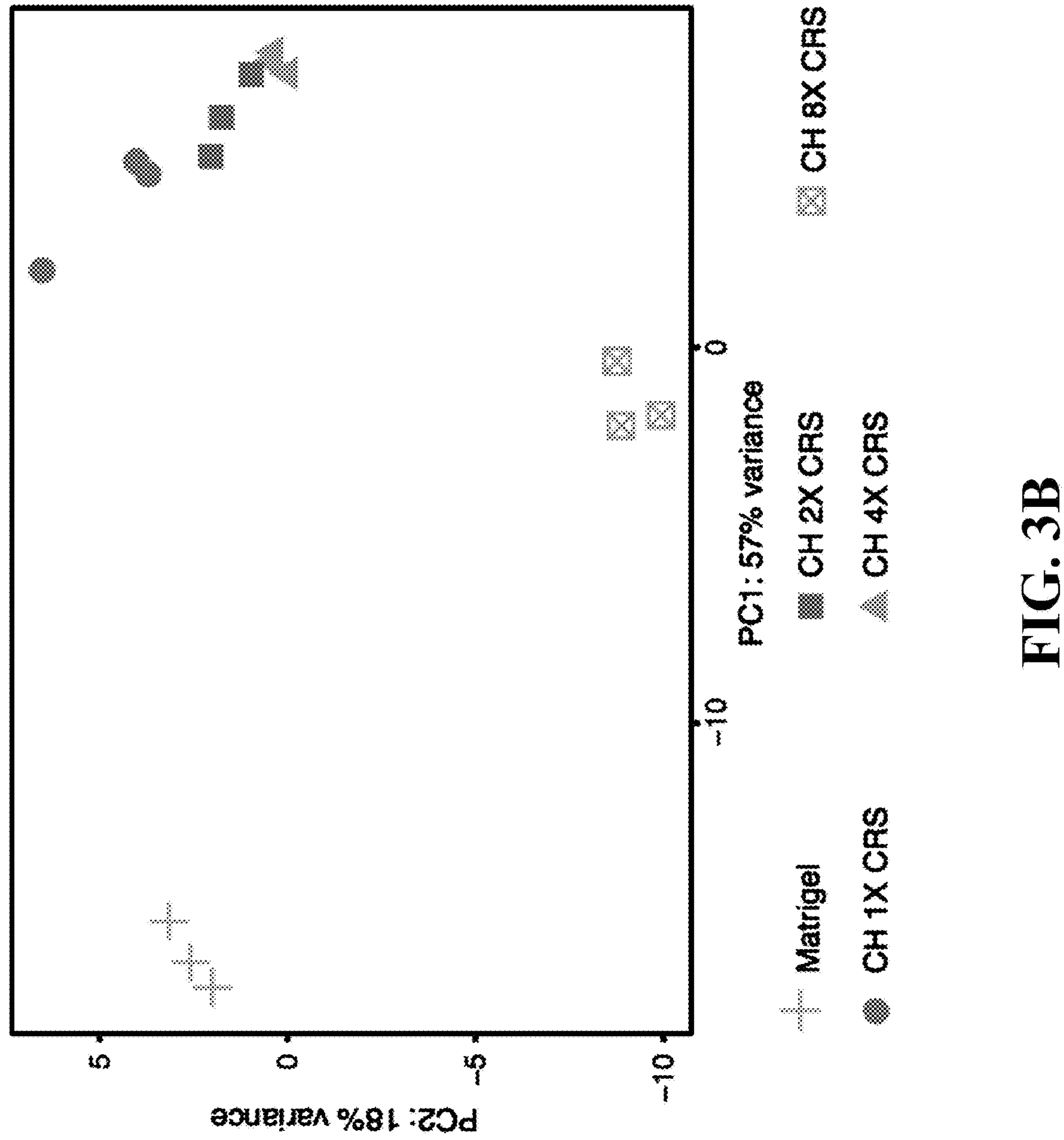
Figure 3C:
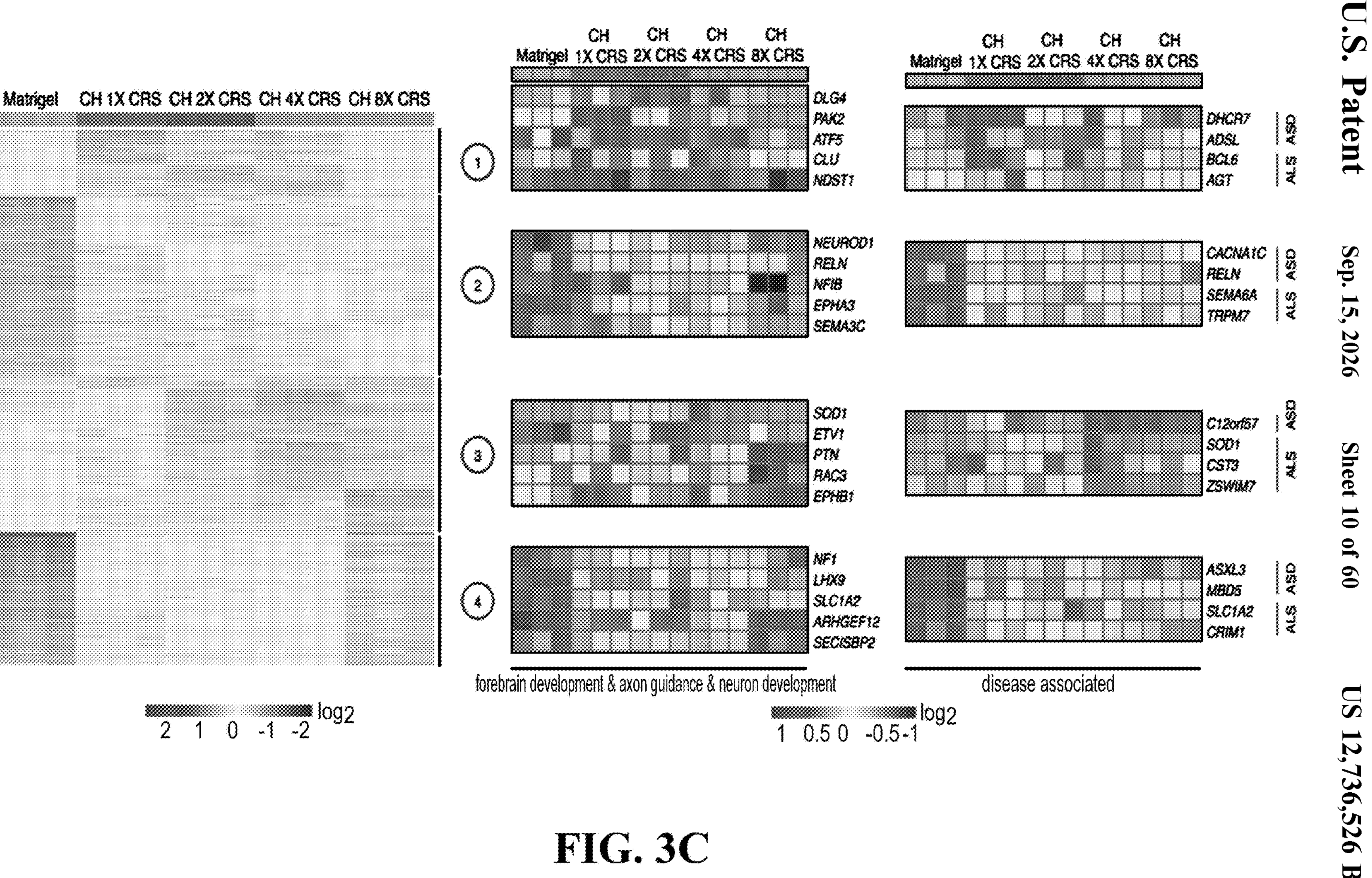
Figure 13A:
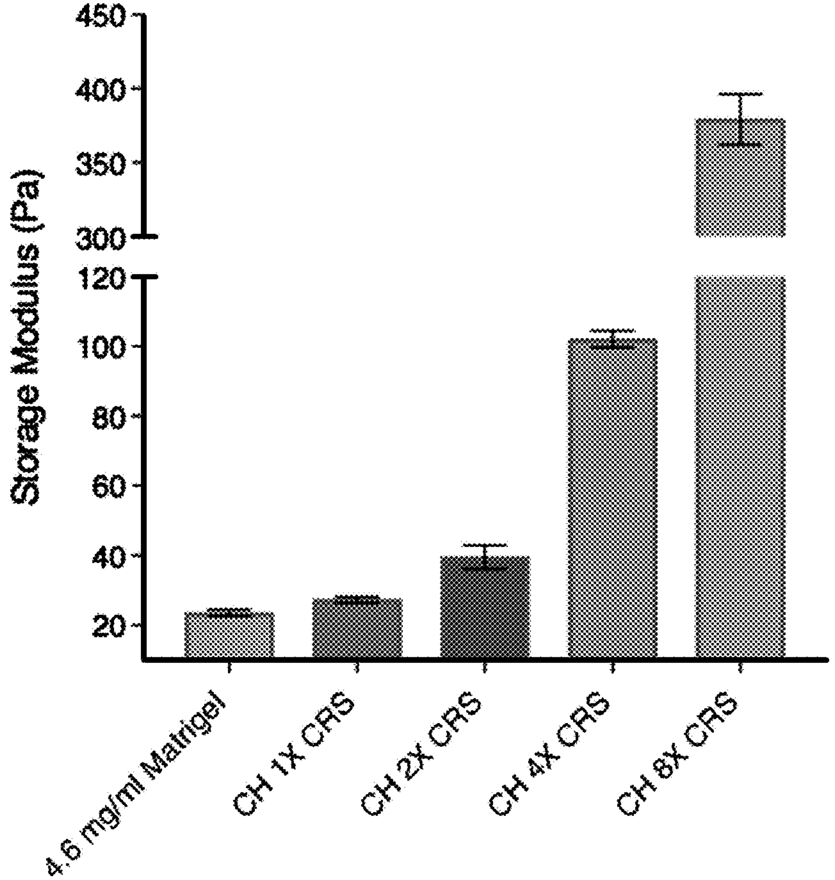
FIGS. 13A-13D: Mechanical properties of Matrigel and composite hydrogels (CHs) and analysis of gene expression profiles of human iN cells co-cultured in Matrigel or composite hydrogels (CHs).
Figure 13B:
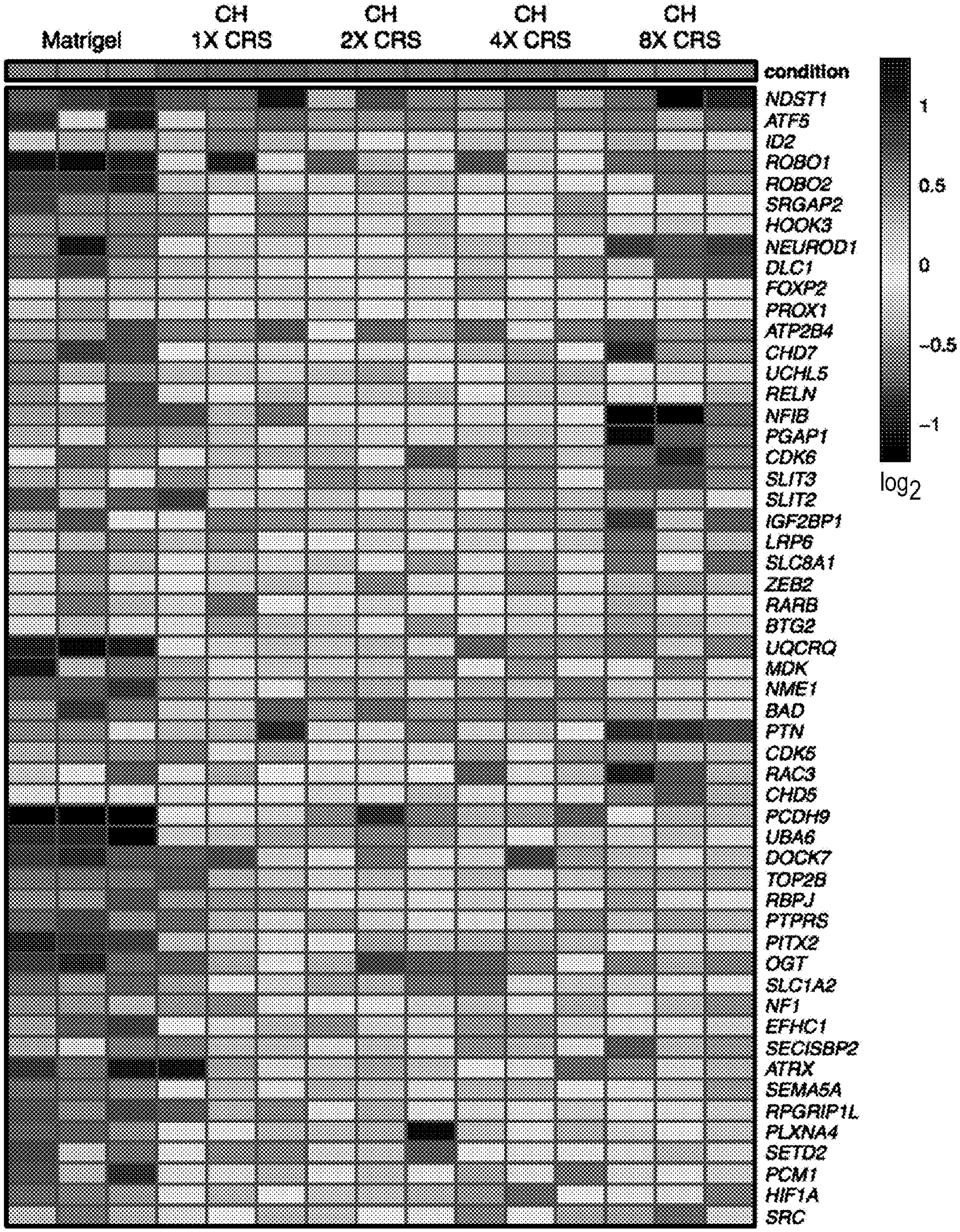
Figure 13C:
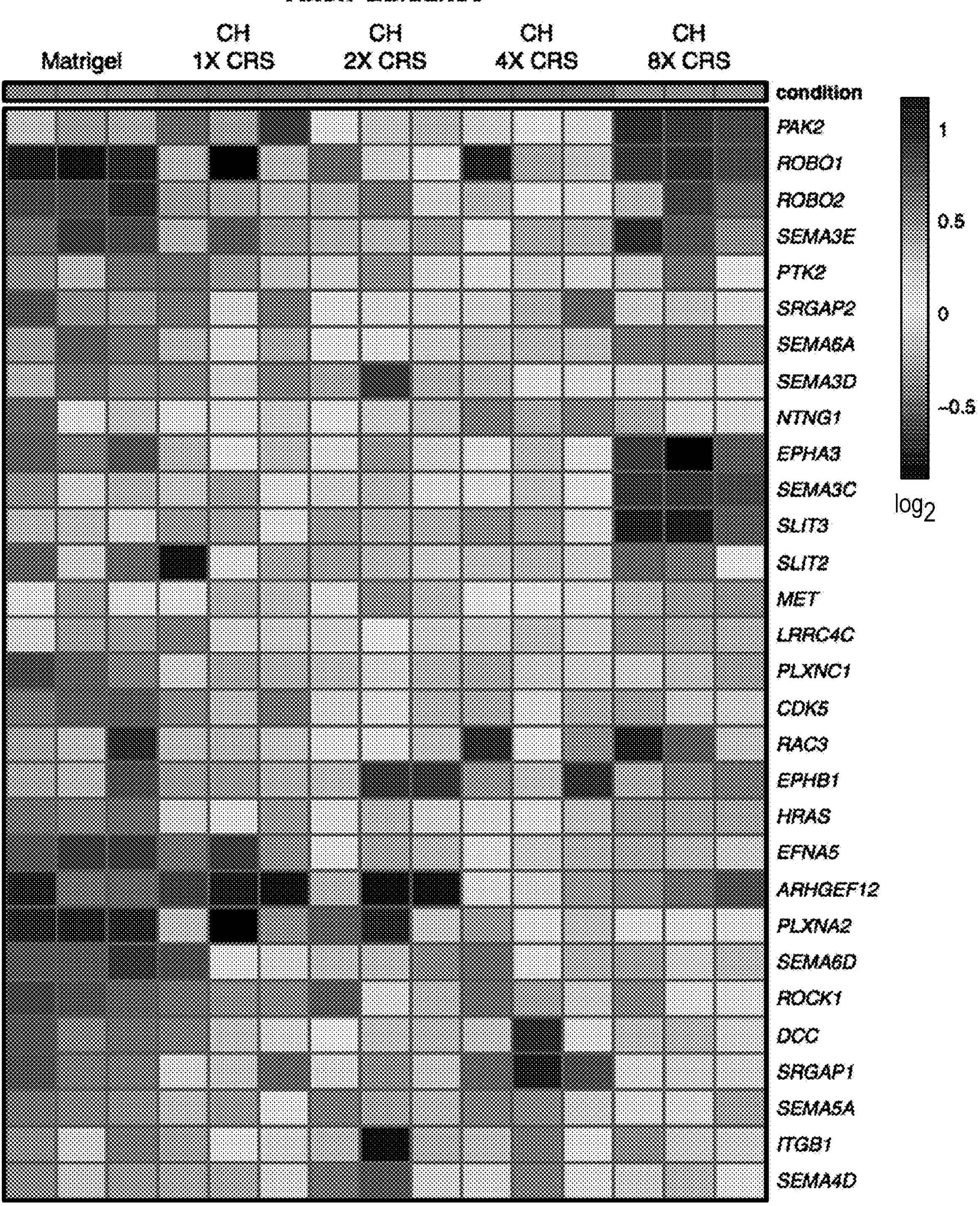
Figure 13D:
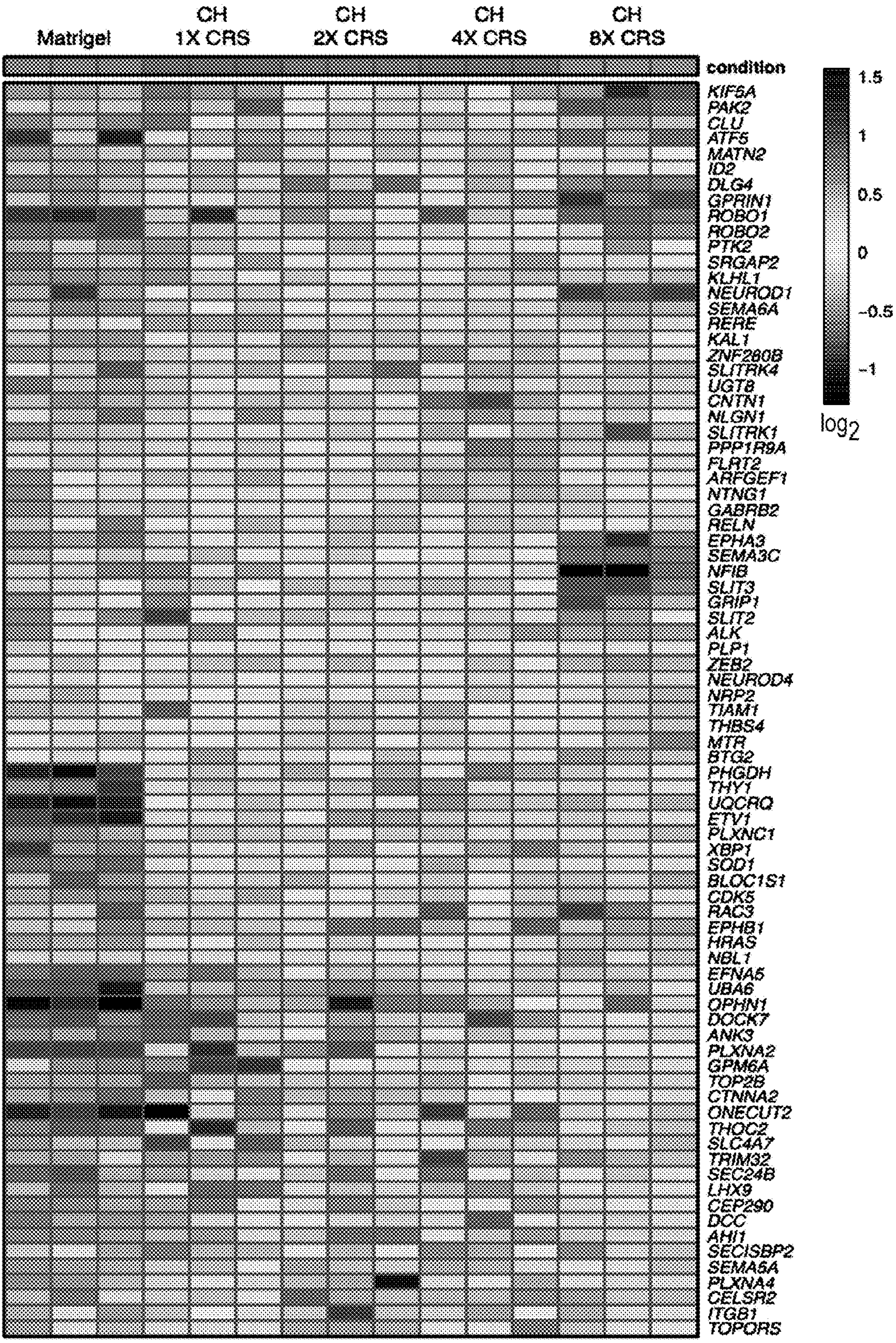
Figures 14A, 14B:
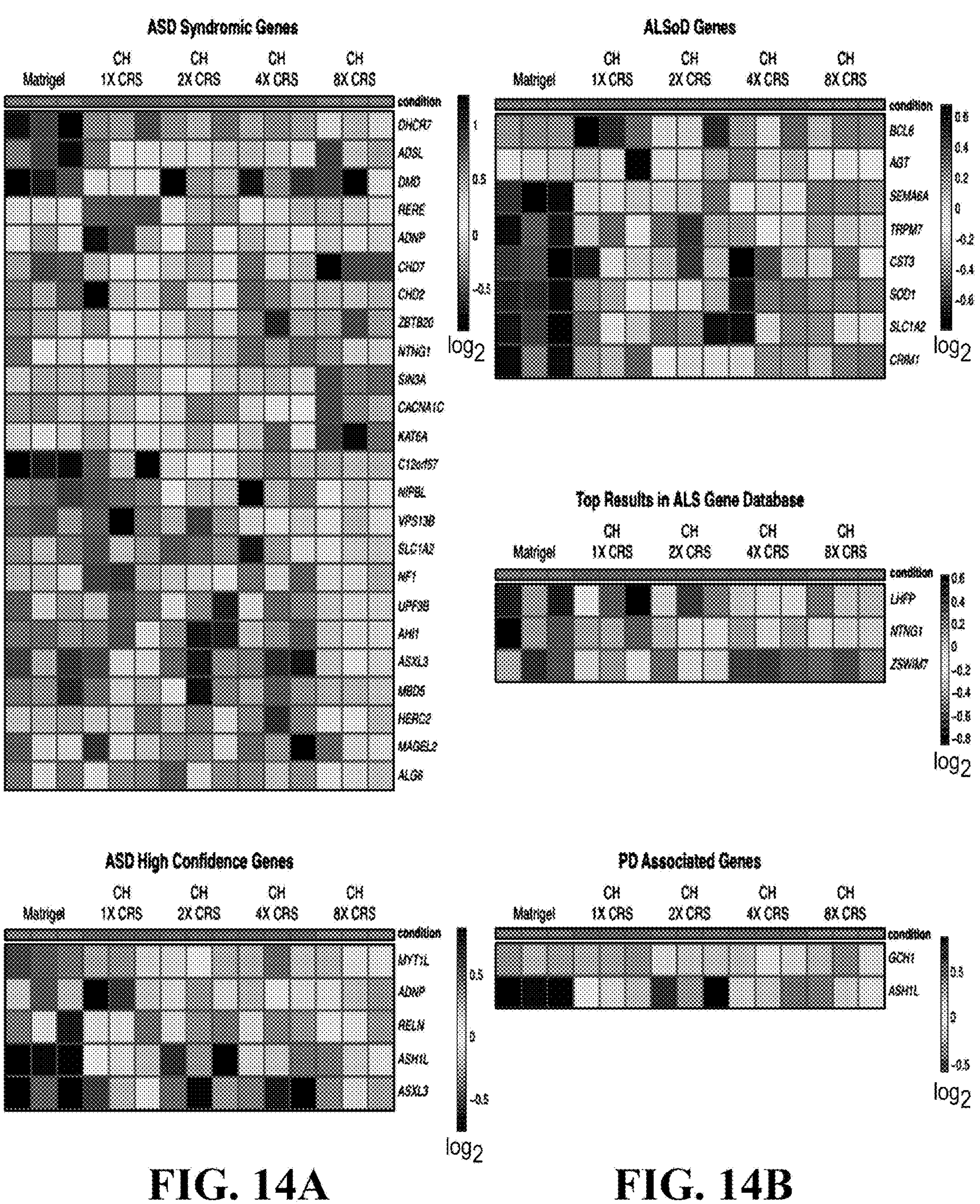
FIGS. 14A-14B: Expression profiles of disease-associated genes in iN cells co-cultured in Matrigel or composite hydrogels (CHs). Relative expression levels of (FIG. 14*a*) Autism Spectrum Disorder (ASD)-associated syndromic genes (from https://gene.sfari.org/autdb/GSGeneList.do?c=S) and ASD-associated high confidence genes (https://gene.sfari.org/autdb/GSGeneList.do?c=1), (FIG. 14*b*) Amyotrophic Lateral Sclerosis (ALS)-associated genes from ALS Online Database (ALSoD) (Abel, O. et al. Human Mutation 33, 1345-1351, (2012)) (http://alsod.iop.kcl.ac.uk/misc/dataDownload.aspx #C1), ALS-associated genes which are top results in ALS Gene Database (Lill, C. M. et al. Amyotrophic Lateral Sclerosis 12, 238-249, (2011)) (http://www.alsgene.org/top_results) and Parkinson's Disease-associated genes (Nalls, M. A. et al. Nature Genetics 46, 989 (2014)). (http://www.pdgene.org/top_results) in iN cells co-cultured within either Matrigel (4.6 mg/ml) or CH formed with varying amounts of crosslinker (CRS), $CaCl_2$ (1×: 3.125 mM; 2×: 6.25 mM; 4×: 12.5 mM; 8×: 25 mM) (n=3 for each condition). Differential expression was processed between co-cultures in CHs and co-culture in Matrigel. Differentially expressed genes with $p<0.01$ and $\log_2$ (fold change)<−1 or $\log_2$ (fold change)>1 were used for intersecting with the disease-associated gene sets.
Figure 15:
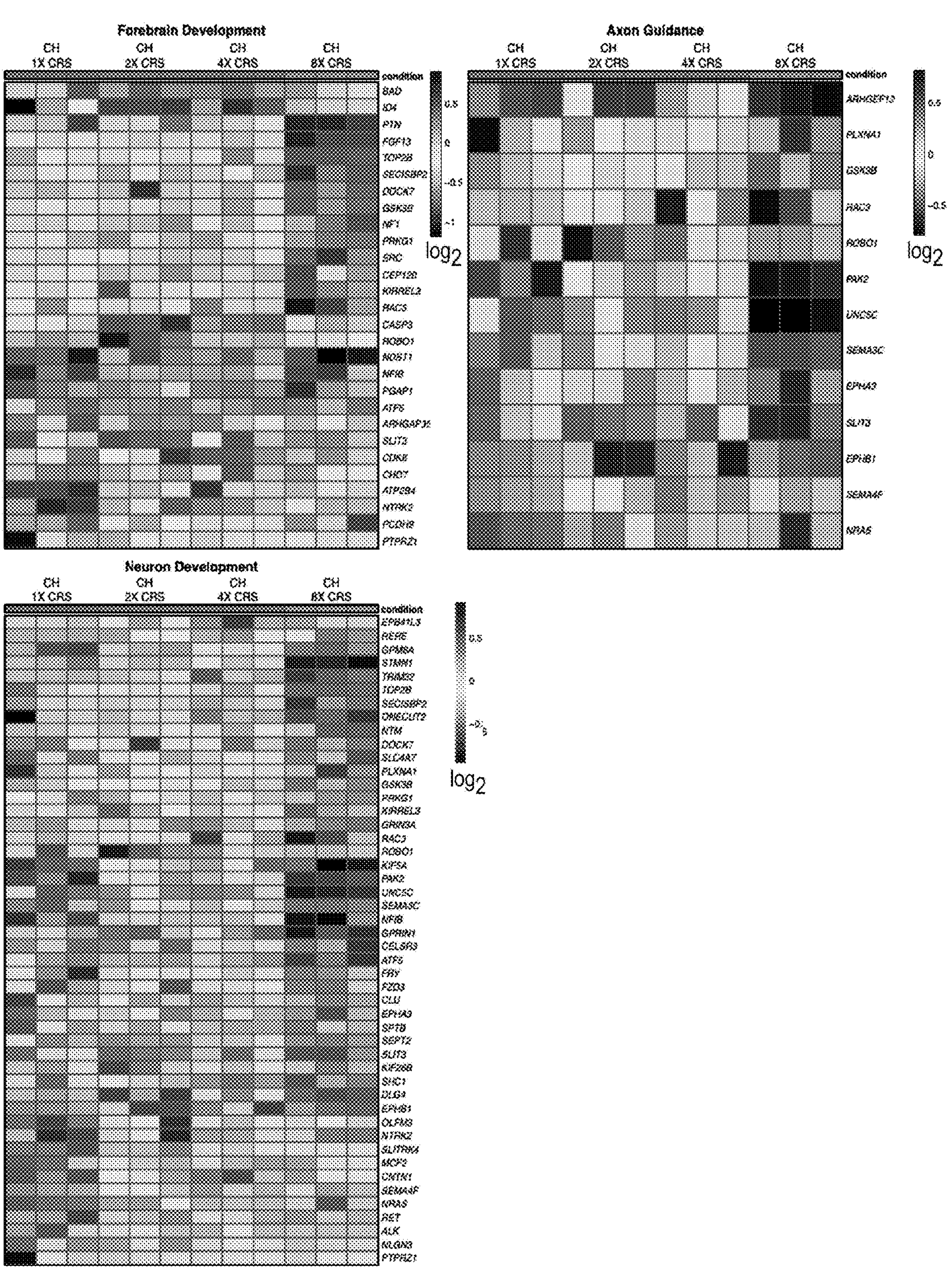
FIG. 15: Analysis of the effect of varying amounts of CRS in CHs on expression of genes involved in neuronal processes. Relative expression of genes involved in forebrain development process, axon guidance pathway and neuron development process in iN cells co-cultured within CHs formed with varying amounts of $CaCl_2$. (1×: 3.125 mM; 2×: 6.25 mM; 4×: 12.5 mM; 8×: 25 mM). Differential expression analysis was performed as described in FIG. 3*d* and differentially expressed genes with $p<0.05$ and $\log_2$ (fold change) <−0.75 or $\log_2$ (fold change)>0.75 were further used for intersecting with the gene sets of neuronal processes.

Differentiation of cells in 3D tissues and their gene expression profiles can be affected by the mechanical stiffness of the matrix[29,32-35] providing an avenue for creation of tunable engineered tissues. As increasing the concentration of Matrigel had minimal effect, we explored how a composite hydrogel (CH) consisting of alginate and Matrigel affected gene expression profiles (FIG. 3*a*). Alginate networks can be created in the Matrigel through addition of a crosslinker (calcium), the concentration of which can be increased to produce a stiffer matrix[33] (FIG. 13*a*). We performed bulk RNA-seq on co-cultured iN cells at week 5 in Matrigel and in CH with increasing amounts of crosslinker. PCA showed clear transcriptomic differences in the CH relative to Matrigel alone, although the global gene expression profiles with intermediate levels of crosslinker were not strongly separated from each other (FIG. 3*b*). Global differential expression analysis between the transcriptome of iN cells in CHs versus in Matrigel hydrogel showed four distinct clusters of genes with different patterns of expression, containing a number of genes relevant to human neurological disease such as amyotrophic lateral sclerosis (ALS) (e.g., SOD1) and autism spectrum disorder (ASD) (e.g., ADSL) (FIG. 3*c*, FIGS. 14A, 14B, Table 3). We also looked at the differential expression of genes involved in forebrain development, axon guidance, and neuron development biological processes (FIG. 3*c*, FIGS. 13B-13D). To analyze the effect of increasing crosslinker concentration in CHs on the gene expression profile of iN cells, we performed differential expression analysis of our RNA-seq data relative to CH with the lowest level of crosslinker, focusing on differentially expressed genes involved in forebrain development, axon guidance, and neuron development biological processes (FIG. 3*d*, FIG. 15). Neuronal transcripts such as DLG4, NFIB, and UNC5C are less expressed in iN cells co-cultured in CH with high levels of crosslinker than in iN cells co-cultured in other CHs (FIG. 3*d*, FIG. 15). Although raising crosslinker concentration in CHs increased expression of ARHGEF12, GSK3B, SLC4A7, and GPM6A, neuronal genes such as ID4 and BAD are more highly expressed in iN cells co-cultured in CHs with intermediate levels of crosslinker than in iN cells co-cultured in CH with low or high levels crosslinker (FIG. 3*d*, FIG. 15).

Figure 3E:
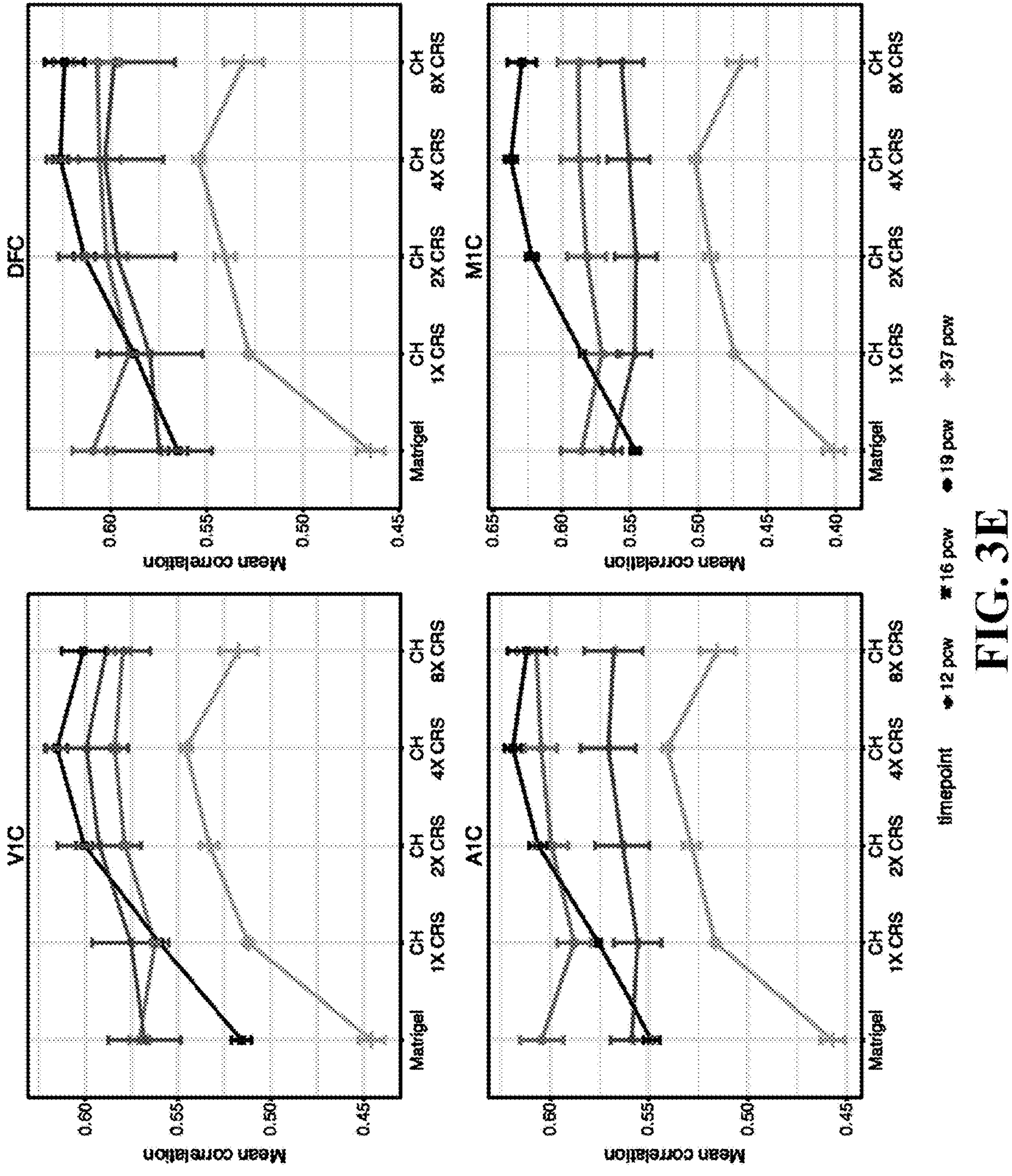
Figures 16A, 16B:
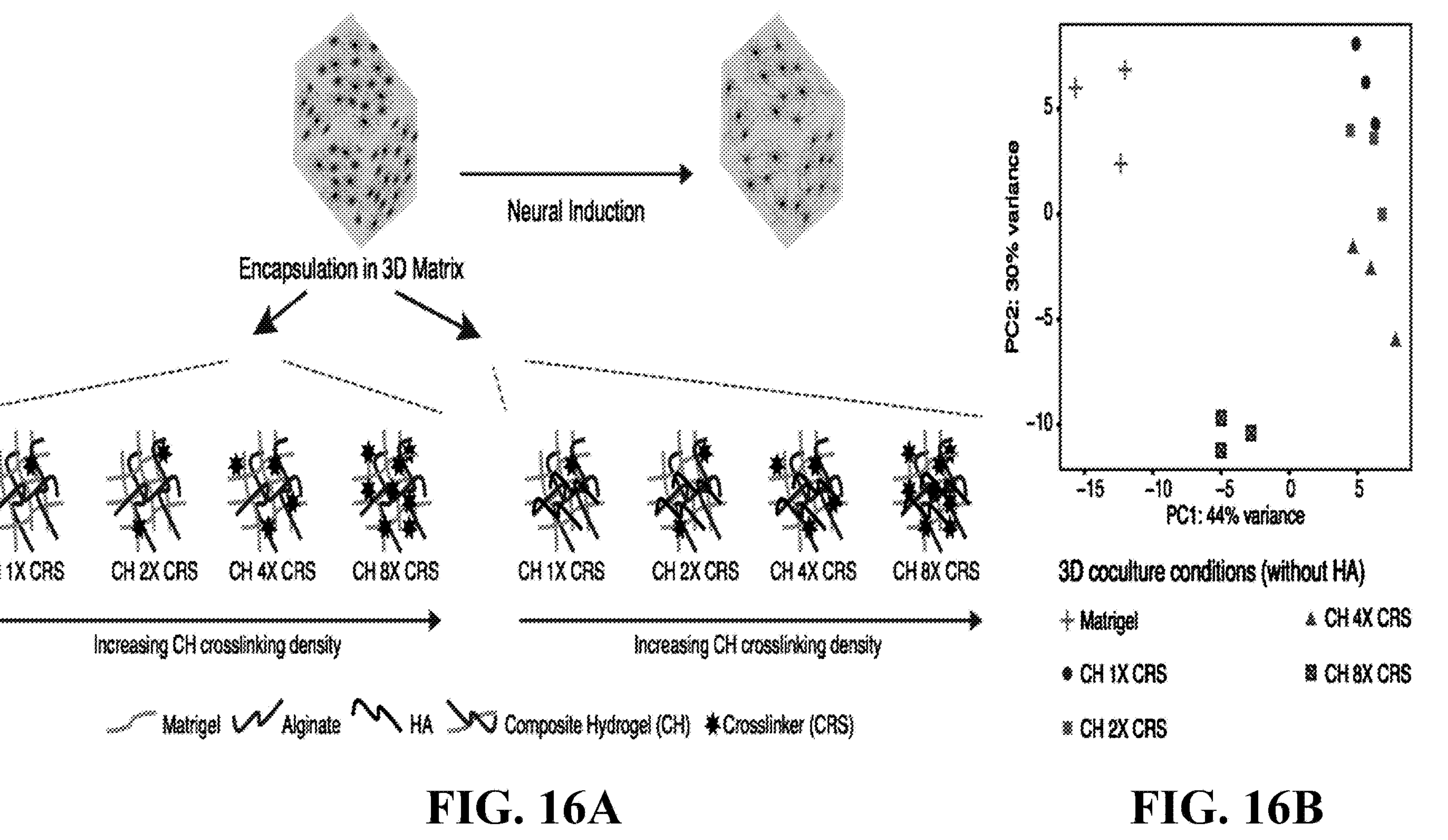
FIGS. 16A-16C: Analysis of the effect of HA on the transcriptome of 3D co-cultured human iN cells in CHs with varying amounts of CRS.
Figure 16C:
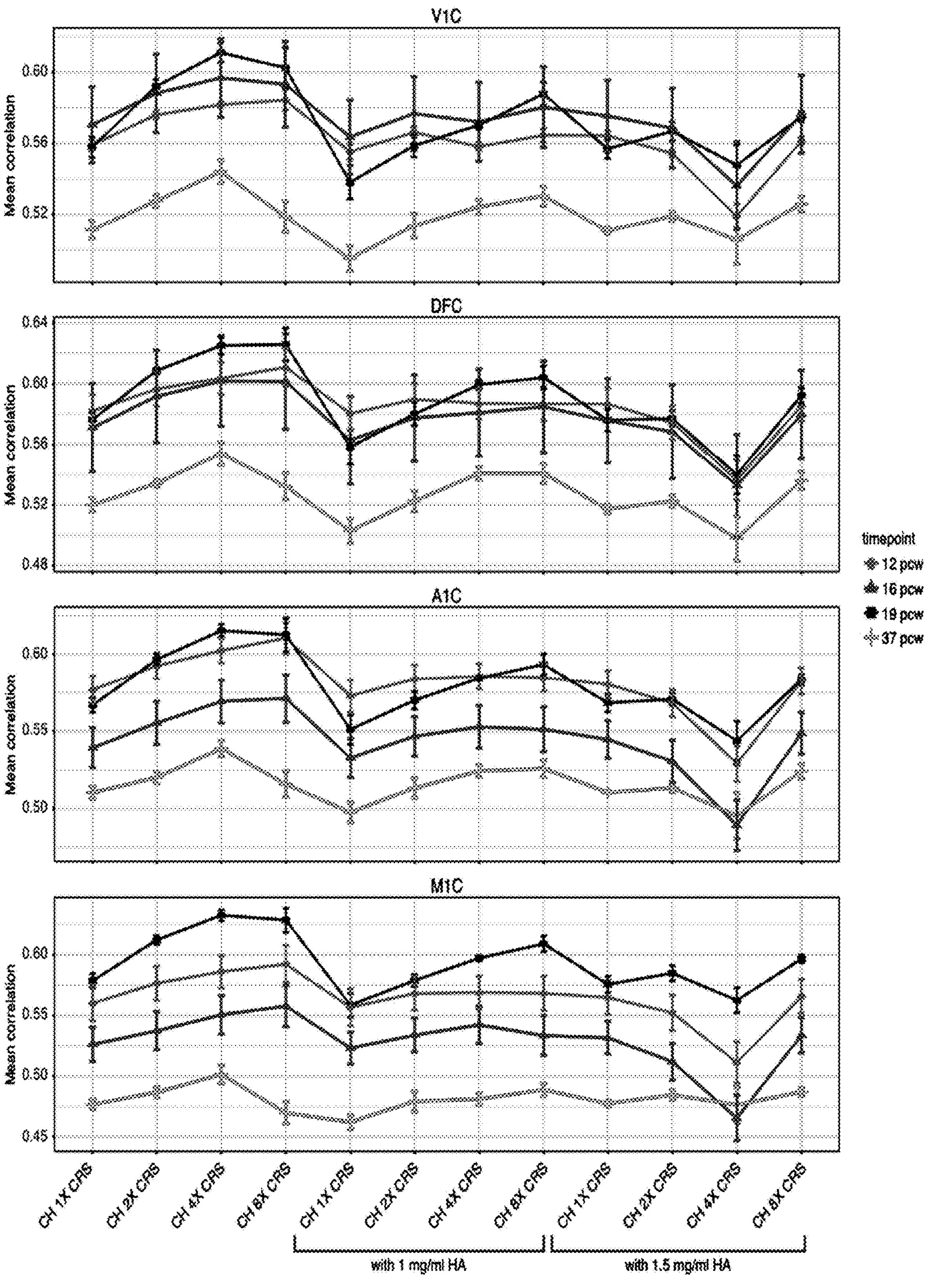
Figures 17A, 17B, 17C:
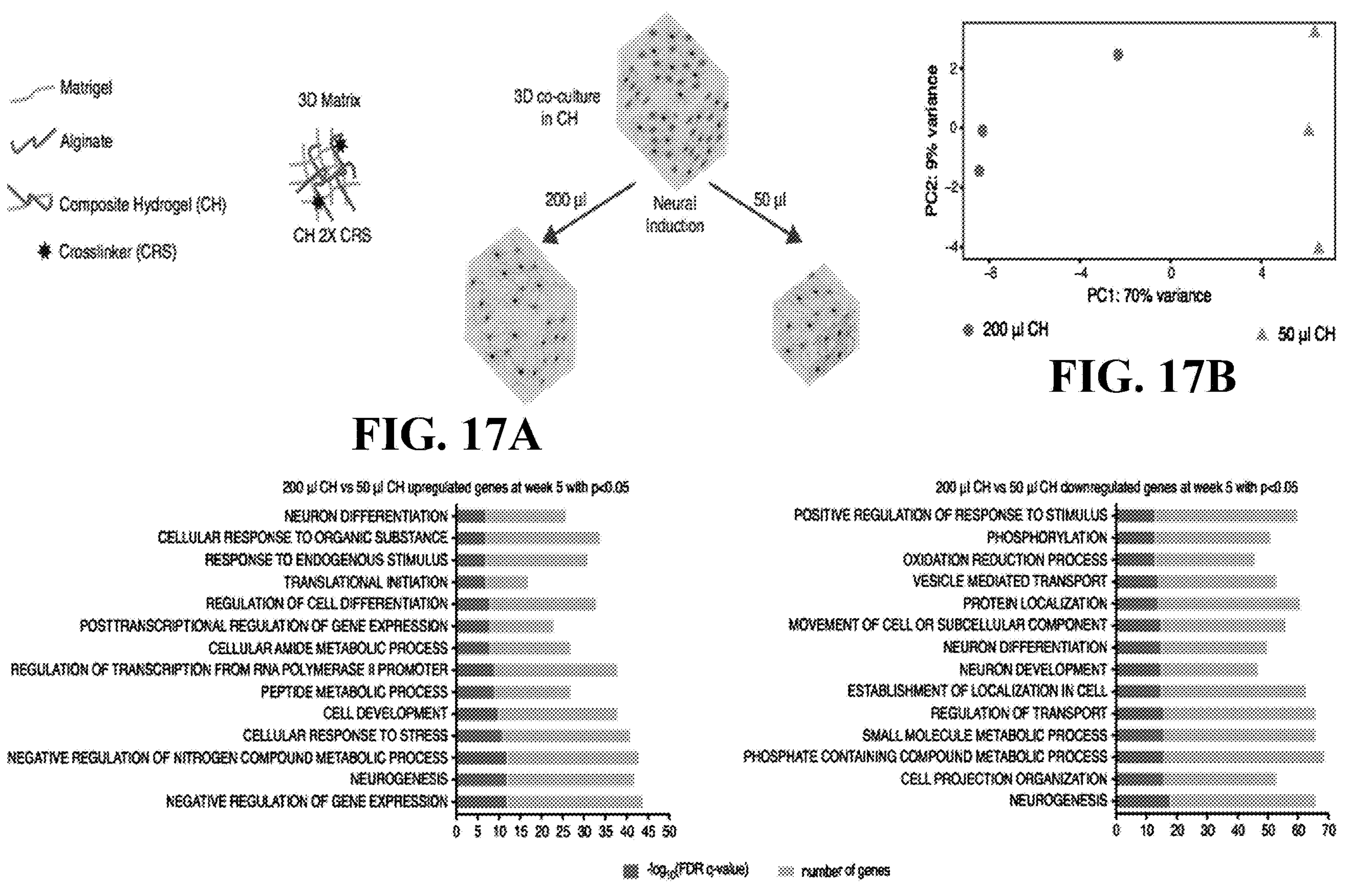
FIGS. 17A-17D: Influence of varying the volume of CH on gene expression in 3D co-cultured human iN cells.
Figure 17D:
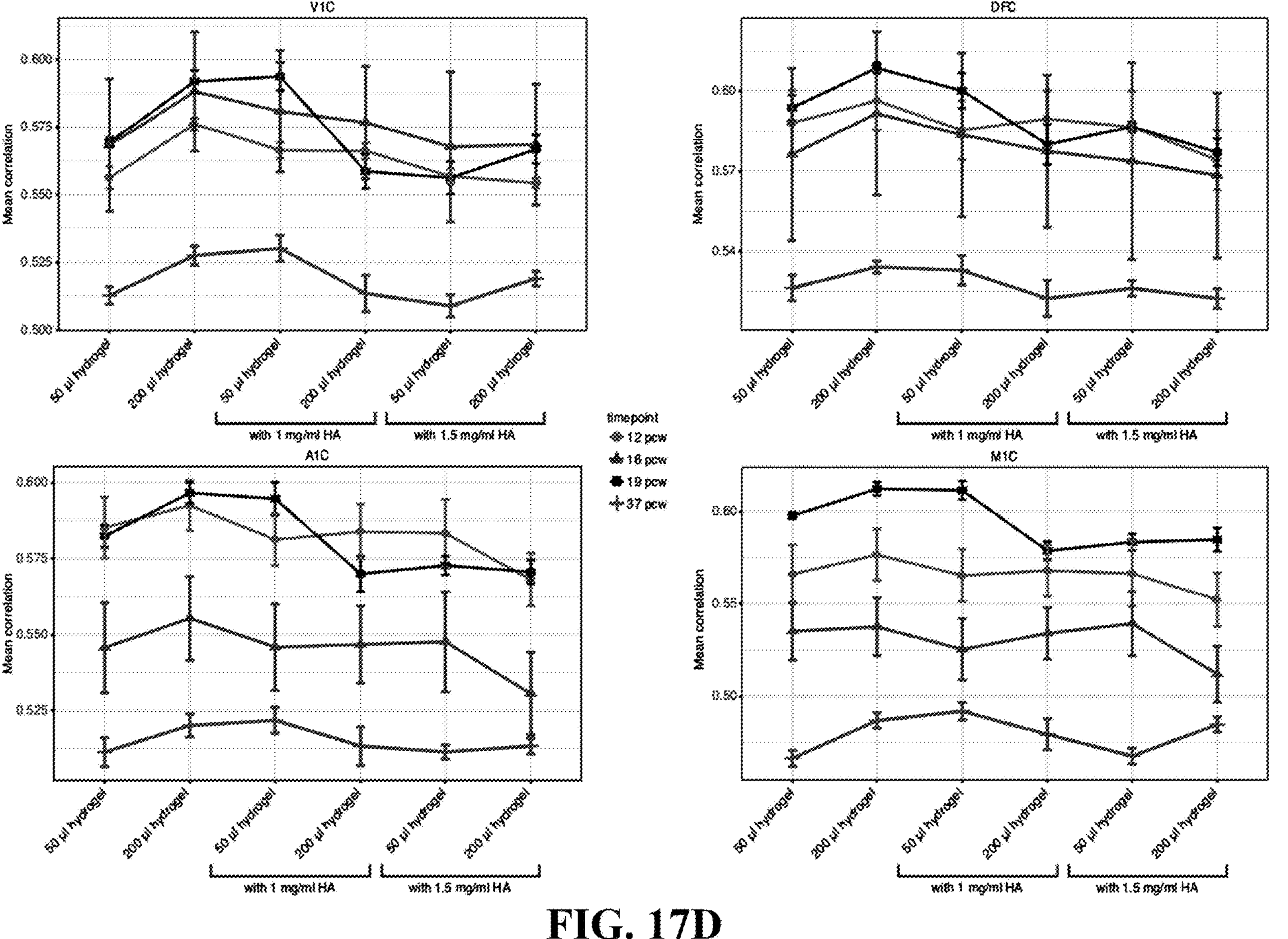

We further examined the influence of co-culturing iN cells in Matrigel hydrogel and CHs for five weeks by comparing their transcriptome to a panel of human brain transcriptome samples. For all four subregions tested, we observed a positive trend in the correlation between the transcriptome of co-cultured iN cells to the human brain transcriptome at later developmental time points (19 pcw and 37 pcw) when moving from Matrigel to CH with increasing levels of crosslinker (FIG. 3*e*). Although there are some exceptions to this trend, in most cases, CH was an improvement over Matrigel alone. At the earliest developmental time point (12 pcw), gene expression of iN cells co-cultured in Matrigel alone correlates more closely with the human data. To determine genes driving increased correlation to human brain transcriptome at later developmental time points (19 pcw and 37 pcw) moving from Matrigel to CH 4× crosslinker, we scored each gene (see Methods) and generated rank lists for each time point (19 pcw and 37 pcw) and brain region (V1C, DFC, A1C and M1C), where high scoring genes have similar expression levels in human brain developmental transcriptome and CH 4× crosslinker condition, and different expression levels in human brain developmental transcriptome and Matrigel condition (Tables 7-30). GO analysis for high scoring genes (rank score>3) for each brain region at 19 pcw showed enrichment for neuronal-related processes, while high scoring genes (rank score>3) for each brain region at 37 pcw demonstrated enrichment for extracellular matrix-related processes (Tables 7-30). Additionally, we investigated how the presence of HA and increased cell density in CH impacts gene expression profiles. In agreement with our previous findings, adding HA to the CH decreased the correlation between the transcriptome of co-cultured iN cells to the human brain transcriptome, whereas increasing cell density lead to similar trends (FIGS. 16A-16C). We also investigated the effect of varying the volume of CH with or without HA on the gene expression profile of co-cultured iN cells and found that decreasing the volume improved the enrichment of neurological processes while marginally decreasing the correlation to the human brain transcriptome (FIGS. 17A-17D).

Figure 18:
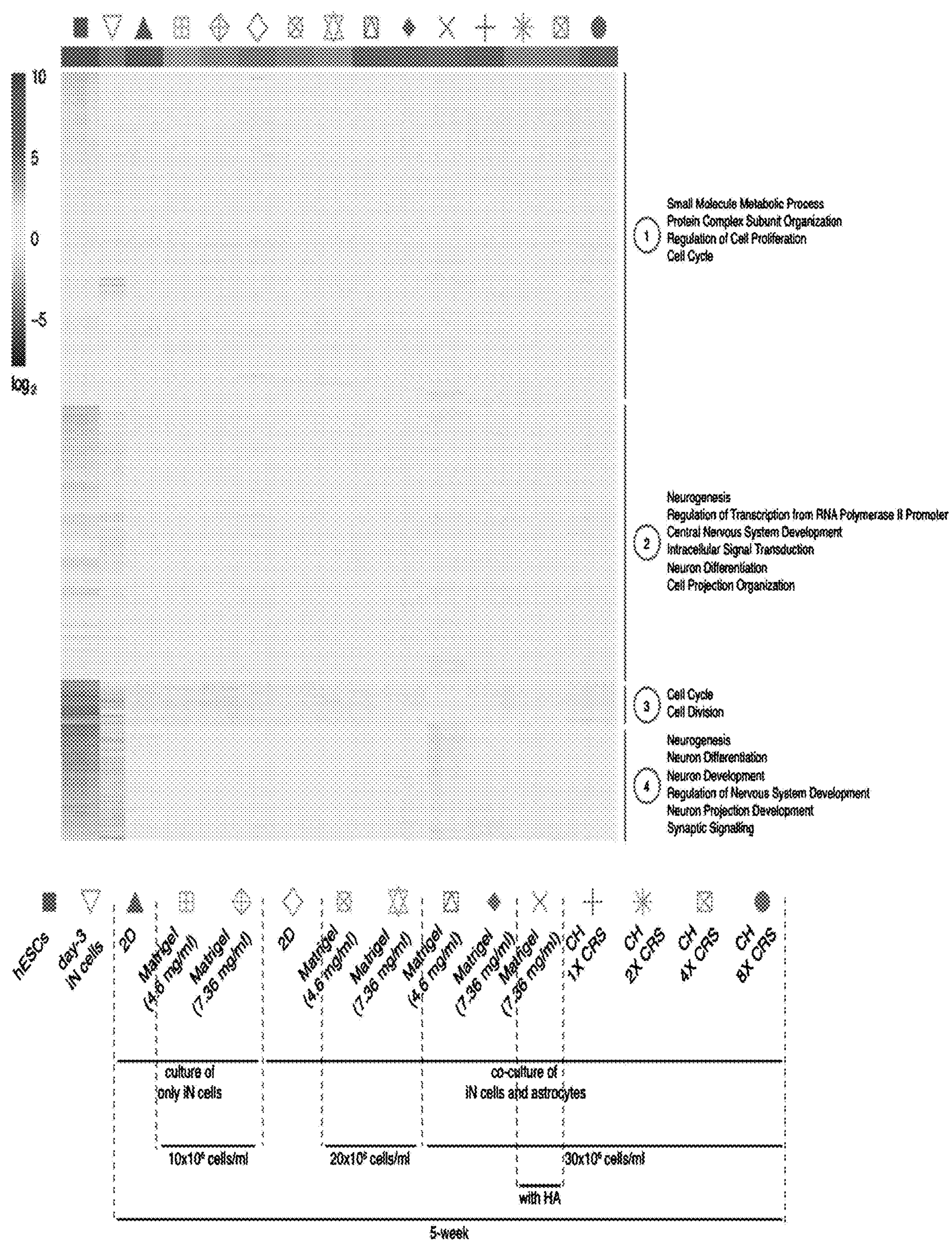
FIG. 18: Gene expression clusters of iN cells cultured/co-cultured in different culturing conditions relative to hESCs. Differential expression was performed for each condition relative to hESCs (n=3 for each condition, except n=2 for condition of day 3 iN cells) (symbols are shown at the bottom of the figure). Differentially expressed genes for each condition relative to hESCs with $p<0.01$ and $\log_2$ (fold change)<−2 or $\log_2$ (fold change)>2 were used. Differentially expressed genes for all conditions were then combined. Heatmap displays the relative expression of combined genes as 4 clusters in iN cells cultured or co-cultured with mouse astrocytes in various conditions and in hESCs. Representative enriched GO terms for genes in each cluster are shown.

To compare broadly across all conditions tested, we performed differential expression analysis of all conditions relative to stem cells. In agreement with our previous results, we find that stem cells are enriched for cell cycle and cell divisions processes and depleted for neurogenesis and neuronal developmental processes. 2D cultures show marginal differences, whereas 3D cultures, with the exception of the HA condition, show the opposite pattern, with enrichment for neuronal-related processes and reduced expression of cell cycle and cell division genes (FIG. 18, Table 31).

Figure 4B:
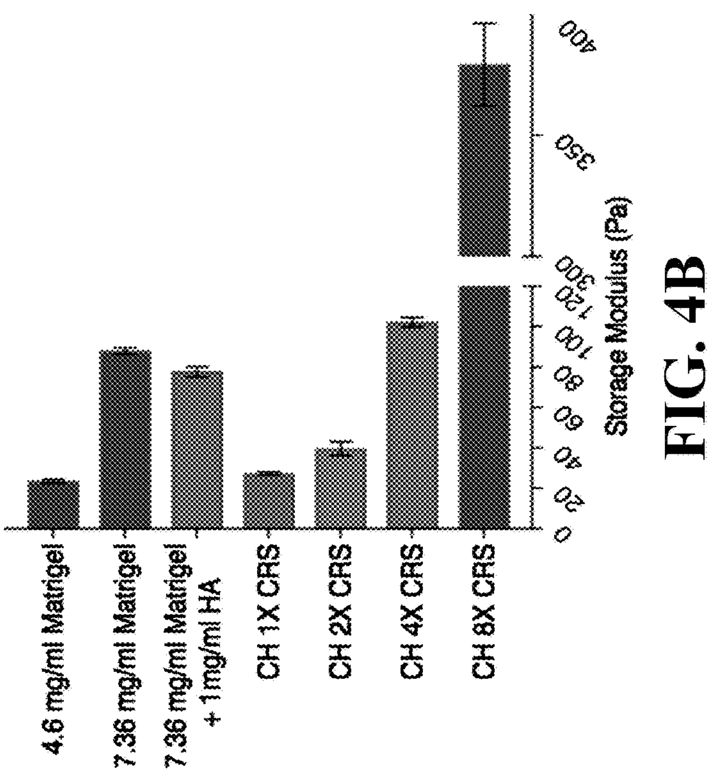
FIGS. 4A-4D: Global comparison of effects of culture conditions on human iN cells and mechanical properties of encapsulating hydrogels.
Figure 4A:
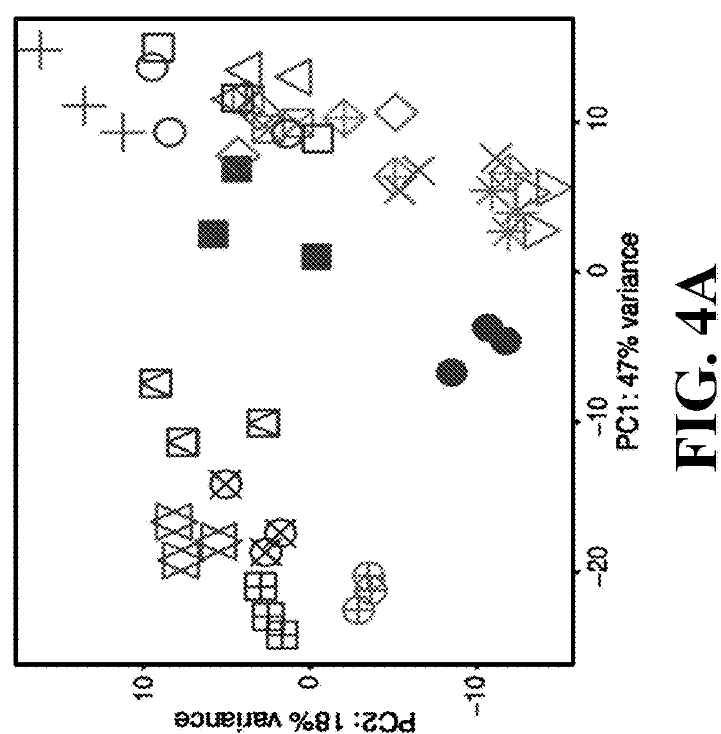
Figure 4C:
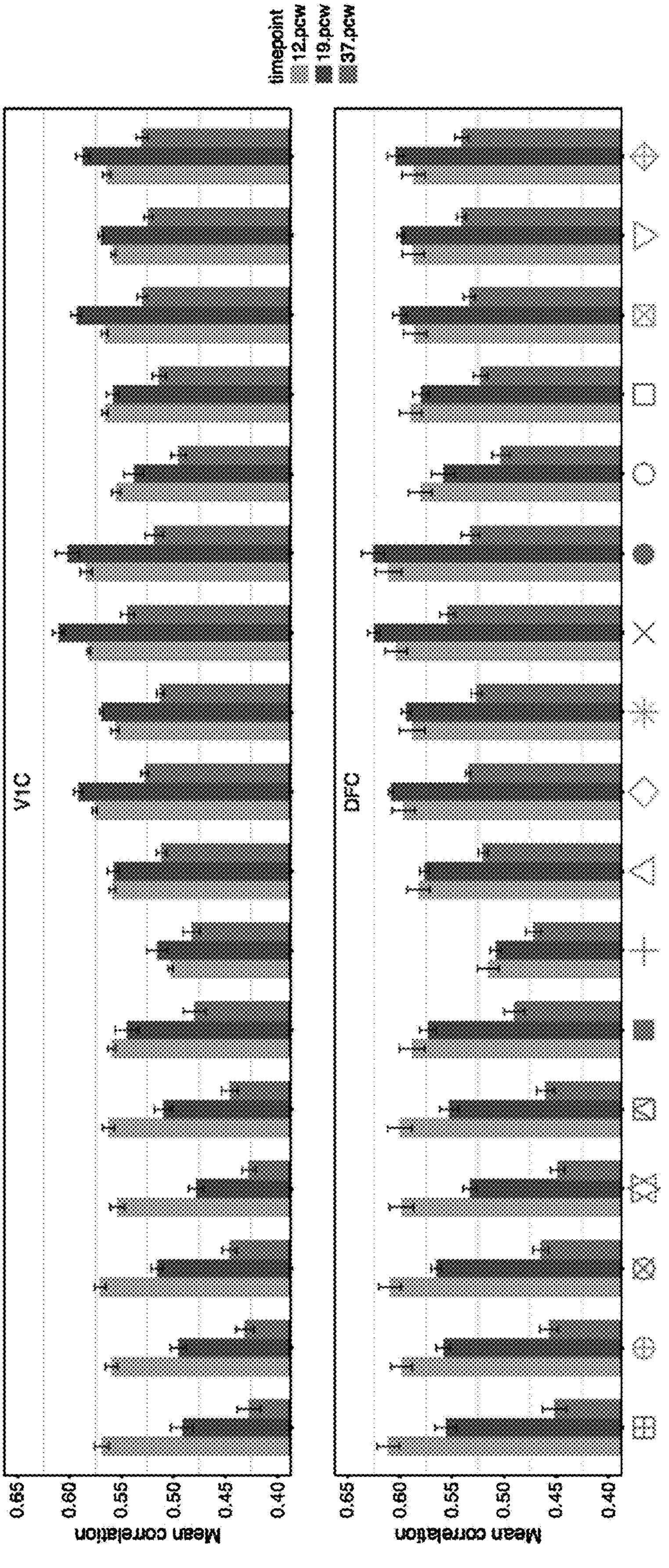
Figure 4D:
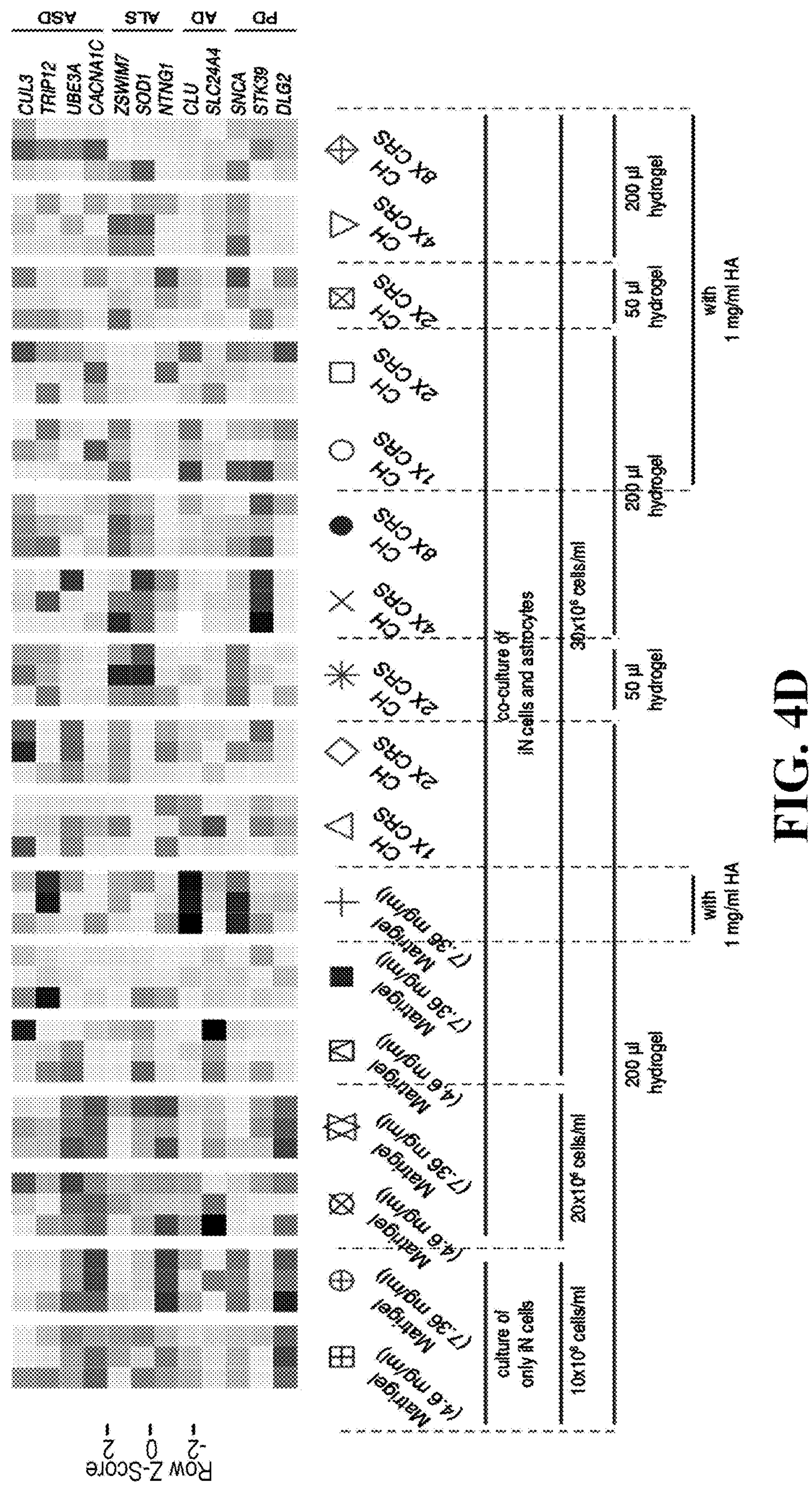

We next compared the transcriptomes of the 3D tissues under all conditions using PCA, which showed transcriptomic differences among various conditions (FIG. 4*a*). We also compared the mechanical properties of encapsulating hydrogels, which displayed storage modulus differences among various hydrogels used (FIG. 4*b*, FIG. 19). We profiled the mean correlation between the transcriptome of the 3D tissues to the human brain transcriptome (FIG. 4*c*, FIG. 19*a*). Moving from Matrigel conditions to CH conditions increased the correlation to four subregions at later developmental time points (19 pcw and 37 pcw) while decreasing the difference between the correlations at the early developmental time point (12 pcw) and late developmental time point (37 pcw). Addition of HA to CHs broadly decreased the correlation to four subregions at three developmental time points (12 pcw, 19 pcw and 37 pcw) relative to their corresponding CHs without HA. We observed the highest correlations to four subregions at 19 pcw and 37 pcw developmental time points with CH with 4× crosslinker. In addition, expression levels of a number of genes associated with neurological diseases varied across 3D conditions (FIG. 4*d*, FIG. 19*b*). These results suggest that 3D tissues could serve as substrates for studying various neurological diseases while providing transcriptomic correlation to the human brain subregions at different developmental time points.

TABLE 3

Genes in each cluster for heatmap in FIG. 3c.

| Gene Name | CL # |
|---|---|
| UBC | 1 |
| SCD | 1 |
| SCG2 | 1 |
| B2M | 1 |
| CDS2 | 1 |
| DHCR24 | 1 |
| NDST1 | 1 |
| GPI | 1 |
| ANXA6 | 1 |
| DHCR7 | 1 |
| PDLIM3 | 1 |
| ZFHX3 | 1 |
| KIF5A | 1 |
| WDR1 | 1 |
| PCDHGB4 | 1 |
| EPB41L1 | 1 |
| YARS | 1 |

TABLE 3-continued

Genes in each cluster for heatmap in FIG. 3c.

| Gene Name | CL # |
|---|---|
| SGK196 | 1 |
| AVL9 | 1 |
| MTHFD2 | 1 |
| FDFT1 | 1 |
| SERPINE2 | 1 |
| WARS | 1 |
| ANXA2 | 1 |
| DDC | 1 |
| UCP2 | 1 |
| TMEM130 | 1 |
| BCL6 | 1 |
| ETV5 | 1 |
| PAK2 | 1 |
| SPARC | 1 |
| TBRG1 | 1 |
| AHNAK | 1 |
| GSTP1 | 1 |
| ASS1 | 1 |
| C20orf27 | 1 |
| QPCT | 1 |
| MBNL2 | 1 |
| TMPPE | 1 |
| MSN | 1 |
| HLA-B | 1 |
| NMB | 1 |
| RASL11B | 1 |
| DUSP6 | 1 |
| SPHKAP | 1 |
| GSTO1 | 1 |
| CKMT1A | 1 |
| SYVN1 | 1 |
| GNL3 | 1 |
| CSRP1 | 1 |
| GGH | 1 |
| TMEM14A | 1 |
| GNG10 | 1 |
| MMD2 | 1 |
| LOC100129361 | 1 |
| RNF220 | 1 |
| TRIM67 | 1 |
| QDPR | 1 |
| CHRNB4 | 1 |
| KLHDC8B | 1 |
| PSMB8 | 1 |
| STEAP3 | 1 |
| SHC4 | 1 |
| SNX10 | 1 |
| UBL7 | 1 |
| RNF167 | 1 |
| CRYL1 | 1 |
| CTBP1 | 1 |
| CLIC1 | 1 |
| CISD2 | 1 |
| PPM1L | 1 |
| SPRY4 | 1 |
| COPS7A | 1 |
| CLU | 1 |
| ECEL1 | 1 |
| ATF5 | 1 |
| TBC1D3B | 1 |
| GPX3 | 1 |
| MINA | 1 |
| KAT7 | 1 |
| MATN2 | 1 |
| CMBL | 1 |
| VOPP1 | 1 |
| NIM1 | 1 |
| SLC18B1 | 1 |
| TPPP3 | 1 |
| WLS | 1 |
| HLA-C | 1 |
| DYSF | 1 |
| SLC25A1 | 1 |
| ID2 | 1 |
| STYK1 | 1 |
| COMT | 1 |

TABLE 3-continued

Genes in each cluster for heatmap in FIG. 3c.

| Gene Name | CL # |
|---|---|
| TMEM189-UBE2V1 | 1 |
| ENPP2 | 1 |
| FAM84A | 1 |
| SVEP1 | 1 |
| FAM65A | 1 |
| SMAD9 | 1 |
| TMEM30B | 1 |
| TRUB2 | 1 |
| DNAJC16 | 1 |
| RHEBL1 | 1 |
| EIF4E3 | 1 |
| UFD1L | 1 |
| SYNPR | 1 |
| HBEGF | 1 |
| MTHFS | 1 |
| MGAT3 | 1 |
| ANXA5 | 1 |
| AGT | 1 |
| RPS6 | 1 |
| ATP6V1G1 | 1 |
| DDX17 | 1 |
| RPL13A | 1 |
| DLG4 | 1 |
| CNRIP1 | 1 |
| SHMT2 | 1 |
| CARS | 1 |
| SLC3A2 | 1 |
| DDIT3 | 1 |
| IGFBP4 | 1 |
| SNX17 | 1 |
| PKIG | 1 |
| BCS1L | 1 |
| SDHD | 1 |
| ADSL | 1 |
| GPRIN1 | 1 |
| AUP1 | 1 |
| MKX | 1 |
| SCRG1 | 1 |
| ZNF664 | 1 |
| HIST1H2BK | 1 |
| PSMD9 | 1 |
| RHOC | 1 |
| CD163L1 | 1 |
| BBIP1 | 1 |
| NFXL1 | 1 |
| MGRN1 | 1 |
| ATF3 | 1 |
| HNRNPUL2-BSCL2 | 1 |
| TP53I13 | 1 |
| SLC1A5 | 1 |
| ACYP1 | 1 |
| CSK | 1 |
| SFXN5 | 1 |
| SLC45A1 | 1 |
| BRMS1 | 1 |
| GNPDA1 | 1 |
| ATRAID | 1 |
| MIR7-3HG | 1 |
| RAB30 | 1 |
| MLX | 1 |
| VILL | 1 |
| CCNF | 1 |
| PLCG1 | 1 |
| DUSP26 | 1 |
| SLC7A3 | 1 |
| RNF185 | 1 |
| TRIB3 | 1 |
| SESN2 | 1 |
| PCED1A | 1 |
| CKB | 1 |
| HTR3A | 1 |
| CPE | 1 |
| COX7A2L | 1 |
| SAP18 | 1 |
| WRB | 1 |
| LAPTM4B | 1 |

TABLE 3-continued

Genes in each cluster for heatmap in FIG. 3c.

| Gene Name | CL # |
|---|---|
| GLRX | 1 |
| HERPUD1 | 1 |
| NELFE | 1 |
| REXO2 | 1 |
| EEF1A2 | 1 |
| LY6E | 1 |
| LOC401397 | 1 |
| SUPT4H1 | 1 |
| BACH2 | 1 |
| ZNF497 | 1 |
| CTSL1 | 1 |
| BLVRB | 1 |
| CYB5A | 1 |
| DLL3 | 1 |
| GALNT14 | 1 |
| KCNQ2 | 1 |
| STX1B | 1 |
| BTBD11 | 1 |
| MGMT | 1 |
| MANEAL | 1 |
| SYT17 | 1 |
| PPP2R2C | 1 |
| PSME1 | 1 |
| ZKSCAN8 | 1 |
| HS3ST1 | 1 |
| SLC22A18 | 1 |
| SEPN1 | 1 |
| CRNDE | 1 |
| RAD23A | 1 |
| C11orf95 | 1 |
| TMEM164 | 1 |
| BOLA3 | 1 |
| UPF1 | 1 |
| SFXN4 | 1 |
| NUDT5 | 1 |
| CDH6 | 1 |
| A2M | 1 |
| MAOA | 1 |
| TAGLN2 | 1 |
| PCDHA10 | 1 |
| SYN3 | 1 |
| LRRTM2 | 1 |
| CECR1 | 1 |
| CSMD1 | 1 |
| NGB | 1 |
| TXNIP | 2 |
| ROBO1 | 2 |
| FSIP2 | 2 |
| EGFEM1P | 2 |
| ROBO2 | 2 |
| PDZRN3 | 2 |
| VCAN | 2 |
| SEMA3E | 2 |
| MACF1 | 2 |
| ARRDC3 | 2 |
| EYS | 2 |
| EXOC5 | 2 |
| ST8SIA1 | 2 |
| CDR1 | 2 |
| LOC100271836 | 2 |
| GPCPD1 | 2 |
| LYST | 2 |
| ARRDC4 | 2 |
| PCDHB2 | 2 |
| ZNF655 | 2 |
| ZFP62 | 2 |
| LOC100272216 | 2 |
| CNTN5 | 2 |
| C7orf55-LUC7L2 | 2 |
| PHLDB1 | 2 |
| SMA4 | 2 |
| SPC25 | 2 |
| PTPRD | 2 |
| ZNF518A | 2 |
| THSD7B | 2 |
| DMD | 2 |

TABLE 3-continued

Genes in each cluster for heatmap in FIG. 3c.

| Gene Name | CL # |
|---|---|
| CSRNP2 | 2 |
| U2SURP | 2 |
| ZBTB41 | 2 |
| CCDC144B | 2 |
| FMNL3 | 2 |
| ZNF204P | 2 |
| PTK2 | 2 |
| SRGAP2 | 2 |
| LOC150776 | 2 |
| NYAP2 | 2 |
| CCNJ | 2 |
| TBC1D3F | 2 |
| SH3BP5 | 2 |
| LOC100132247 | 2 |
| MYO6 | 2 |
| UBN2 | 2 |
| FRAS1 | 2 |
| SRGAP2C | 2 |
| ZNF780A | 2 |
| LRRC37A4P | 2 |
| FKBP15 | 2 |
| TBC1D15 | 2 |
| GRIK1 | 2 |
| PFKFB3 | 2 |
| MIR600HG | 2 |
| POLR2J2 | 2 |
| CSMD3 | 2 |
| ZNF711 | 2 |
| CACNA1E | 2 |
| HOOK3 | 2 |
| DENND1B | 2 |
| AMOTL1 | 2 |
| KDM5A | 2 |
| RFX7 | 2 |
| KLHL1 | 2 |
| FNBP4 | 2 |
| LOC595101 | 2 |
| VSNL1 | 2 |
| CLOCK | 2 |
| ESCO1 | 2 |
| GABPB1-AS1 | 2 |
| NEUROD1 | 2 |
| FXR1 | 2 |
| TET1 | 2 |
| ETAA1 | 2 |
| GOLGA6L5 | 2 |
| DOPEY1 | 2 |
| LIN28B | 2 |
| TTN | 2 |
| RBBP5 | 2 |
| NCAPG | 2 |
| DENND4C | 2 |
| SEMA6A | 2 |
| IGDCC3 | 2 |
| RPS6KB1 | 2 |
| ZNF253 | 2 |
| DLC1 | 2 |
| DIP2A | 2 |
| KIAA0754 | 2 |
| SMA5 | 2 |
| LHFP | 2 |
| REM2 | 2 |
| ZNF876P | 2 |
| RANBP17 | 2 |
| ATR | 2 |
| RERE | 2 |
| PGM5P2 | 2 |
| CACNG3 | 2 |
| NAA38 | 2 |
| RP1-177G6.2 | 2 |
| C7orf60 | 2 |
| CHRM3 | 2 |
| PRPF4B | 2 |
| SEMA3D | 2 |
| SLC16A3 | 2 |
| FOXP2 | 2 |

TABLE 3-continued

Genes in each cluster for heatmap in FIG. 3c.

| Gene Name | CL # |
|---|---|
| FAM35A | 2 |
| ZNF781 | 2 |
| RPS6KC1 | 2 |
| ECT2 | 2 |
| NR2C1 | 2 |
| PROX1 | 2 |
| LOC286437 | 2 |
| CRABP2 | 2 |
| SS18 | 2 |
| PCMTD1 | 2 |
| DCUN1D1 | 2 |
| ZNF26 | 2 |
| RORA | 2 |
| PCDHB4 | 2 |
| MYT1L | 2 |
| ZNF124 | 2 |
| XKR9 | 2 |
| CEP350 | 2 |
| DOCK4 | 2 |
| FLJ31306 | 2 |
| TTF1 | 2 |
| ADNP | 2 |
| RALGAPB | 2 |
| STARD9 | 2 |
| PIGW | 2 |
| BCAS3 | 2 |
| C2orf68 | 2 |
| PTCHD2 | 2 |
| HERC2P4 | 2 |
| TP53INP1 | 2 |
| LOC440300 | 2 |
| ZSCAN2 | 2 |
| GLCE | 2 |
| QKI | 2 |
| LOC284581 | 2 |
| SETBP1 | 2 |
| ST6GAL2 | 2 |
| TEAD1 | 2 |
| ERCC6L2 | 2 |
| PRR26 | 2 |
| SSFA2 | 2 |
| VPS13A | 2 |
| AGO1 | 2 |
| SLC25A29 | 2 |
| TNRC6B | 2 |
| SRSF1 | 2 |
| GOLGB1 | 2 |
| DGKB | 2 |
| CHRDL1 | 2 |
| NCOR1 | 2 |
| EYA1 | 2 |
| PRICKLE2 | 2 |
| KIAA1109 | 2 |
| RND3 | 2 |
| TCERG1 | 2 |
| DMXL1 | 2 |
| C5orf30 | 2 |
| ZNF407 | 2 |
| TRPM7 | 2 |
| CPNE8 | 2 |
| GPBP1L1 | 2 |
| BTRC | 2 |
| XRN1 | 2 |
| PIAS1 | 2 |
| ZNF281 | 2 |
| CUL1 | 2 |
| HELZ | 2 |
| PLA2G4B | 2 |
| KLHL29 | 2 |
| KAL1 | 2 |
| ARHGAP21 | 2 |
| CNOT1 | 2 |
| NEGR1 | 2 |
| HDHD2 | 2 |
| UG0898H09 | 2 |
| MID1 | 2 |

TABLE 3-continued

Genes in each cluster for heatmap in FIG. 3c.

| Gene Name | CL # |
|---|---|
| ZNF404 | 2 |
| ATP2B4 | 2 |
| SEC23IP | 2 |
| LMO3 | 2 |
| PIGN | 2 |
| ZNF382 | 2 |
| LOC100133331 | 2 |
| PDXDC2P | 2 |
| USO1 | 2 |
| HCFC2 | 2 |
| PRTG | 2 |
| CHD7 | 2 |
| ZNF616 | 2 |
| UCHL5 | 2 |
| ZNF17 | 2 |
| ZNF765 | 2 |
| MDM4 | 2 |
| TAF1B | 2 |
| MAGI1 | 2 |
| MIOS | 2 |
| ZNF737 | 2 |
| FAM171B | 2 |
| MDGA1 | 2 |
| MLLT4 | 2 |
| ZNF280B | 2 |
| AGBL4 | 2 |
| LCORL | 2 |
| AACSP1 | 2 |
| LRBA | 2 |
| CEP78 | 2 |
| YEATS2 | 2 |
| ZNF436 | 2 |
| SHPRH | 2 |
| CCDC14 | 2 |
| ARFIP1 | 2 |
| PTCD3 | 2 |
| USP24 | 2 |
| UNC80 | 2 |
| PRMT10 | 2 |
| PILRB | 2 |
| LEO1 | 2 |
| MXD1 | 2 |
| SMEK2 | 2 |
| SLITRK4 | 2 |
| PDCD6IP | 2 |
| HSPA4L | 2 |
| CKAP2 | 2 |
| KIAA1211 | 2 |
| MIR100HG | 2 |
| IFT80 | 2 |
| ZNF880 | 2 |
| NECAB1 | 2 |
| RIMS2 | 2 |
| ZNF121 | 2 |
| ABCC8 | 2 |
| ZFYVE16 | 2 |
| CPD | 2 |
| ZNF808 | 2 |
| UGT8 | 2 |
| AMMECR1 | 2 |
| ZNF611 | 2 |
| RBFOX1 | 2 |
| PPP2R3A | 2 |
| PCDHGB7 | 2 |
| ADNP2 | 2 |
| G3BP2 | 2 |
| CNTN1 | 2 |
| PAPOLA | 2 |
| EFR3B | 2 |
| PNISR | 2 |
| JAK1 | 2 |
| MTMR6 | 2 |
| FAM122B | 2 |
| FAR1 | 2 |
| ZNF160 | 2 |
| LOC388692 | 2 |

TABLE 3-continued

Genes in each cluster for heatmap in FIG. 3c.

| Gene Name | CL # |
|---|---|
| ZNF468 | 2 |
| SORBS2 | 2 |
| PYROXD1 | 2 |
| DCUN1D4 | 2 |
| ARHGAP12 | 2 |
| KRIT1 | 2 |
| LOC642366 | 2 |
| NCAN | 2 |
| CHD2 | 2 |
| ZNF433 | 2 |
| NINL | 2 |
| HAUS3 | 2 |
| ZNF701 | 2 |
| FAM179B | 2 |
| MGC27345 | 2 |
| PDK1 | 2 |
| ZFP30 | 2 |
| KLF10 | 2 |
| ZNF254 | 2 |
| DMTF1 | 2 |
| FAM117B | 2 |
| DCLRE1C | 2 |
| ZDHHC17 | 2 |
| CACUL1 | 2 |
| UNC119 | 2 |
| ZBTB20 | 2 |
| C2orf69 | 2 |
| ZNF608 | 2 |
| WDR33 | 2 |
| ZNF772 | 2 |
| C21orf91 | 2 |
| NLGN1 | 2 |
| ZKSCAN7 | 2 |
| CWC27 | 2 |
| CCND2 | 2 |
| LOC729737 | 2 |
| HAUS6 | 2 |
| ZNF493 | 2 |
| TNRC6A | 2 |
| CCDC91 | 2 |
| UBE2D1 | 2 |
| SLITRK1 | 2 |
| PPP1R9A | 2 |
| UBXN7 | 2 |
| NBPF14 | 2 |
| ZNF211 | 2 |
| CCNT2 | 2 |
| SLCO1A2 | 2 |
| GPR85 | 2 |
| RBBP9 | 2 |
| KLHL28 | 2 |
| ZNF813 | 2 |
| MYO1B | 2 |
| BIRC2 | 2 |
| FAM126B | 2 |
| SUCO | 2 |
| PTPN12 | 2 |
| PIK3CB | 2 |
| ZNF93 | 2 |
| PCDHB3 | 2 |
| EDEM3 | 2 |
| SMCHD1 | 2 |
| TIMP3 | 2 |
| TARBP1 | 2 |
| KDM3A | 2 |
| ZNF350 | 2 |
| FLRT2 | 2 |
| CSMD2 | 2 |
| HACE1 | 2 |
| UHRF1BP1L | 2 |
| TSTD2 | 2 |
| ZNF10 | 2 |
| NFYB | 2 |
| NOL4 | 2 |
| ZNF654 | 2 |
| ADAM10 | 2 |

TABLE 3-continued

Genes in each cluster for heatmap in FIG. 3c.

| Gene Name | CL # |
|---|---|
| DLGAP3 | 2 |
| TRIP11 | 2 |
| PCF11 | 2 |
| ZNF28 | 2 |
| PAPOLG | 2 |
| FBN3 | 2 |
| DHX40 | 2 |
| ARFGEF1 | 2 |
| BMS1 | 2 |
| ZNF75D | 2 |
| LOC202181 | 2 |
| ZNF708 | 2 |
| HK2 | 2 |
| NTNG1 | 2 |
| GABRB2 | 2 |
| ONECUT1 | 2 |
| AKAP13 | 2 |
| DNMT3B | 2 |
| MED23 | 2 |
| TRAM1 | 2 |
| ZNF226 | 2 |
| TNRC6C | 2 |
| ZNF546 | 2 |
| ATM | 2 |
| USP6 | 2 |
| ZNF37A | 2 |
| MAGI2-AS3 | 2 |
| KIAA0556 | 2 |
| ZNF549 | 2 |
| NOS1AP | 2 |
| SDK1 | 2 |
| ZNF287 | 2 |
| ZNF844 | 2 |
| CSGALNACT2 | 2 |
| CREBZF | 2 |
| ZNF345 | 2 |
| RELN | 2 |
| SKIDA1 | 2 |
| NIN | 2 |
| PLOD1 | 2 |
| ZNF529 | 2 |
| TMEM254 | 2 |
| ZNF443 | 2 |
| ZNF440 | 2 |
| FASTKD1 | 2 |
| WDR75 | 2 |
| KCNN3 | 2 |
| MIER2 | 2 |
| MAPK7 | 2 |
| ZNF624 | 2 |
| KLHL8 | 2 |
| DCAF17 | 2 |
| MGA | 2 |
| ZNF141 | 2 |
| ZBTB11 | 2 |
| SPECC1 | 2 |
| PLEKHM1P | 2 |
| C4orf21 | 2 |
| ZNF571 | 2 |
| KCNIP4-IT1 | 2 |
| ATF7IP | 2 |
| KLHL13 | 2 |
| EPHA3 | 2 |
| SEMA3C | 2 |
| ETNK1 | 2 |
| NFIB | 2 |
| RGS4 | 2 |
| PGAP1 | 2 |
| IFI16 | 2 |
| ZNF652 | 2 |
| AKAP2 | 2 |
| SLC5A7 | 2 |
| ZNF460 | 2 |
| ZNF385D | 2 |
| KALRN | 2 |
| KDM4C | 2 |

TABLE 3-continued

Genes in each cluster for heatmap in FIG. 3c.

| Gene Name | CL # |
|---|---|
| ST18 | 2 |
| CDK6 | 2 |
| FGD4 | 2 |
| ZEB1 | 2 |
| KLHL24 | 2 |
| SPON1 | 2 |
| ARHGEF2 | 2 |
| SESN3 | 2 |
| NUMA1 | 2 |
| PHTF2 | 2 |
| BBX | 2 |
| SIN3A | 2 |
| GUCY1A2 | 2 |
| KRT8 | 2 |
| PAPPA | 2 |
| SLIT3 | 2 |
| CPEB4 | 2 |
| VCPIP1 | 2 |
| FLNB | 2 |
| LOC100216546 | 2 |
| TRAPPC11 | 2 |
| CACNA1C | 2 |
| SLC7A5P2 | 2 |
| PMEL | 2 |
| ABCA1 | 2 |
| SKIL | 2 |
| LOC100190986 | 2 |
| STXBP5L | 2 |
| NOMO3 | 2 |
| GPRASP1 | 2 |
| GMPS | 2 |
| DNM3OS | 2 |
| PTPRG | 2 |
| ZNF43 | 2 |
| ARHGAP28 | 2 |
| LPP | 2 |
| RFX3 | 2 |
| KAT6A | 2 |
| NDST4 | 2 |
| RNF138P1 | 2 |
| P4HA1 | 2 |
| ZNF704 | 2 |
| CBLB | 2 |
| ALDOC | 2 |
| PAN2 | 2 |
| AGPAT4-IT1 | 2 |
| RICTOR | 2 |
| GRIP1 | 2 |
| SV2C | 2 |
| LOC286467 | 2 |
| LIG4 | 2 |
| BCL2L11 | 2 |
| SLIT2 | 2 |
| SOCS6 | 2 |
| UTRN | 2 |
| LOC613037 | 2 |
| MKLN1 | 2 |
| HDAC9 | 2 |
| NCOA3 | 2 |
| PLGLB1 | 2 |
| ZDHHC20 | 2 |
| IGF2BP1 | 2 |
| GPATCH2L | 2 |
| TMX3 | 2 |
| MYEF2 | 2 |
| STARD4-AS1 | 2 |
| QSER1 | 2 |
| DOCK10 | 2 |
| LINC00478 | 2 |
| LRP6 | 2 |
| DSC2 | 2 |
| ARHGAP24 | 2 |
| TPBG | 2 |
| ZNF3 | 2 |
| GPATCH8 | 2 |
| PCDHB15 | 2 |

TABLE 3-continued

Genes in each cluster for heatmap in FIG. 3c.

| Gene Name | CL # |
|---|---|
| AMOT | 2 |
| RC3H1 | 2 |
| ALK | 2 |
| ATAD2B | 2 |
| MET | 2 |
| SLC8A1 | 2 |
| OPRK1 | 2 |
| B3GNT5 | 2 |
| EVI2A | 2 |
| LRRC4C | 2 |
| N4BP2L2-IT2 | 2 |
| PDE1A | 2 |
| FLJ45340 | 2 |
| TMC3 | 2 |
| FAM208A | 2 |
| PLP1 | 2 |
| POC1B | 2 |
| AGO4 | 2 |
| PDE4C | 2 |
| LEPR | 2 |
| INO80D | 2 |
| ADAMTS20 | 2 |
| METTL14 | 2 |
| GPR18 | 2 |
| IKZF4 | 2 |
| PPP2R1B | 2 |
| KIAA1324L | 2 |
| DLG1 | 2 |
| RYR1 | 2 |
| POLI | 2 |
| NRSN1 | 2 |
| SLC30A7 | 2 |
| ZEB2 | 2 |
| GOLGA6L9 | 2 |
| RARB | 2 |
| VCAM1 | 2 |
| ZFP112 | 2 |
| BMS1P2 | 2 |
| BMS1P6 | 2 |
| CEP192 | 2 |
| CDH7 | 2 |
| LOC286184 | 2 |
| ZNF555 | 2 |
| ERCC6L | 2 |
| RALGAPA2 | 2 |
| ZNF471 | 2 |
| NEUROD4 | 2 |
| FTX | 2 |
| NRP2 | 2 |
| RXRG | 2 |
| GPC5 | 2 |
| MDN1 | 2 |
| PTPRH | 2 |
| RBM41 | 2 |
| PCDHB13 | 2 |
| ST3GAL1 | 2 |
| KLRAP1 | 2 |
| ITGA9 | 2 |
| RGS5 | 2 |
| BMS1P1 | 2 |
| BMS1P5 | 2 |
| IFIT2 | 2 |
| TIAM1 | 2 |
| PAX3 | 2 |
| TK2 | 2 |
| ZNF85 | 2 |
| FAM208B | 2 |
| THBS4 | 2 |
| FBXO30 | 2 |
| PARP11 | 2 |
| KLHL4 | 2 |
| NR1H2 | 2 |
| LOC100133920 | 2 |
| TMEM196 | 2 |
| MTR | 2 |
| SGK494 | 2 |

TABLE 3-continued

Genes in each cluster for heatmap in FIG. 3c.

| Gene Name | CL # |
|---|---|
| PCDHA9 | 2 |
| ABCD2 | 2 |
| HLA-DPA1 | 2 |
| ZNF525 | 2 |
| MUC20 | 2 |
| POU6F2 | 2 |
| ITCH | 2 |
| DSP | 2 |
| ANKRD44 | 2 |
| BTG2 | 2 |
| BNIP2 | 2 |
| EXOC6B | 2 |
| SETD7 | 2 |
| ACAT2 | 3 |
| ATF4 | 3 |
| TMEM97 | 3 |
| NME2 | 3 |
| INSIG1 | 3 |
| LSS | 3 |
| FDPS | 3 |
| MVD | 3 |
| SEC11C | 3 |
| PHGDH | 3 |
| C14orf1 | 3 |
| THY1 | 3 |
| GOT1 | 3 |
| UQCRQ | 3 |
| PMP22 | 3 |
| ETV1 | 3 |
| CACNG4 | 3 |
| PCYT2 | 3 |
| FABP3 | 3 |
| RPS26 | 3 |
| LAMTOR4 | 3 |
| CYSTM1 | 3 |
| PLXNC1 | 3 |
| TRMT112 | 3 |
| HIST2H2BE | 3 |
| CBS | 3 |
| RAMP1 | 3 |
| CHAC1 | 3 |
| ZFAS1 | 3 |
| NSDHL | 3 |
| CST3 | 3 |
| NOL3 | 3 |
| TIMM8B | 3 |
| DANCR | 3 |
| COX14 | 3 |
| CYB561 | 3 |
| MVK | 3 |
| MDK | 3 |
| RPS18 | 3 |
| RPS5 | 3 |
| RPL31 | 3 |
| RPL17 | 3 |
| RPS14 | 3 |
| RPLP1 | 3 |
| RPS15A | 3 |
| C17orf76-AS1 | 3 |
| RPS15 | 3 |
| RPL19 | 3 |
| RPS10 | 3 |
| RPSA | 3 |
| RPL41 | 3 |
| MYL6 | 3 |
| RPL34 | 3 |
| RPL38 | 3 |
| RPS8 | 3 |
| RPL10A | 3 |
| RPS7 | 3 |
| RPL35A | 3 |
| HINT1 | 3 |
| RPS19 | 3 |
| PSMA7 | 3 |
| RPS11 | 3 |
| UBL5 | 3 |

TABLE 3-continued

Genes in each cluster for heatmap in FIG. 3c.

| Gene Name | CL # |
|---|---|
| RPL29 | 3 |
| FAU | 3 |
| RPL18A | 3 |
| COX7A2 | 3 |
| RPS2 | 3 |
| RPL27A | 3 |
| GPX1 | 3 |
| GAS5 | 3 |
| RPL36 | 3 |
| RPL27 | 3 |
| RPL23A | 3 |
| RPL11 | 3 |
| RPL12 | 3 |
| RPS17L | 3 |
| RPS17 | 3 |
| UQCR11 | 3 |
| RPS12 | 3 |
| RPL35 | 3 |
| RPL26 | 3 |
| RPS27 | 3 |
| RPS16 | 3 |
| NME1 | 3 |
| COX6A1 | 3 |
| NDUFS7 | 3 |
| COX7B | 3 |
| RPS29 | 3 |
| C1QBP | 3 |
| GPX4 | 3 |
| NDUFB9 | 3 |
| NDUFA13 | 3 |
| C14orf2 | 3 |
| RPS21 | 3 |
| PSMB6 | 3 |
| BAD | 3 |
| ANAPC11 | 3 |
| TRAPPC5 | 3 |
| PRELID1 | 3 |
| NDUFB2 | 3 |
| COX5B | 3 |
| RPL37 | 3 |
| EIF3K | 3 |
| NDUFAB1 | 3 |
| C12orf57 | 3 |
| PHPT1 | 3 |
| RPAIN | 3 |
| TMEM14B | 3 |
| NDUFB7 | 3 |
| FAM96B | 3 |
| SNRPD2 | 3 |
| HMGN1 | 3 |
| SSR4 | 3 |
| FAM216A | 3 |
| NDUFB6 | 3 |
| RPS28 | 3 |
| C16orf13 | 3 |
| NUTF2 | 3 |
| TCEB2 | 3 |
| TMED3 | 3 |
| HIST1H4C | 3 |
| MRPL12 | 3 |
| MRPL21 | 3 |
| SLIRP | 3 |
| POLR2F | 3 |
| SIVA1 | 3 |
| NDUFA2 | 3 |
| SF3B5 | 3 |
| SELK | 3 |
| C11orf31 | 3 |
| MRPL34 | 3 |
| MRPL20 | 3 |
| TMA7 | 3 |
| BASP1 | 3 |
| LINC00493 | 3 |
| TSTD1 | 3 |
| MIEN1 | 3 |
| MXRA7 | 3 |

TABLE 3-continued

Genes in each cluster for heatmap in FIG. 3c.

| Gene Name | CL # |
|---|---|
| ZNHIT1 | 3 |
| HAX1 | 3 |
| MRPL14 | 3 |
| COA3 | 3 |
| TOMM7 | 3 |
| LSM7 | 3 |
| ECSIT | 3 |
| EIF4EBP1 | 3 |
| ROMO1 | 3 |
| ZNF32 | 3 |
| SNHG15 | 3 |
| TOMM6 | 3 |
| ATP5I | 3 |
| CD9 | 3 |
| EMG1 | 3 |
| MEA1 | 3 |
| PTOV1 | 3 |
| MRPS24 | 3 |
| KRTCAP2 | 3 |
| XBP1 | 3 |
| NDUFS6 | 3 |
| CDK4 | 3 |
| MPC1 | 3 |
| IGFBP5 | 3 |
| SNHG8 | 3 |
| ALKBH7 | 3 |
| MYEOV2 | 3 |
| PRPF31 | 3 |
| CCDC167 | 3 |
| MRPS12 | 3 |
| CCDC23 | 3 |
| DBNDD2 | 3 |
| TIMM13 | 3 |
| IFI27L2 | 3 |
| EBP | 3 |
| TXNL4A | 3 |
| MRPL27 | 3 |
| NPRL2 | 3 |
| NXT1 | 3 |
| NPC2 | 3 |
| LSMD1 | 3 |
| NDUFAF2 | 3 |
| MRPS11 | 3 |
| HSD17B10 | 3 |
| RPL26L1 | 3 |
| ARL16 | 3 |
| MRPL13 | 3 |
| RPL21 | 3 |
| BOK | 3 |
| MRPL55 | 3 |
| C9orf16 | 3 |
| CMTM3 | 3 |
| HDDC2 | 3 |
| MED31 | 3 |
| AIP | 3 |
| WBSCR22 | 3 |
| LSM3 | 3 |
| RUNDC3A | 3 |
| ATOX1 | 3 |
| MRPL52 | 3 |
| MEF2BNB | 3 |
| UBE2T | 3 |
| ASNA1 | 3 |
| ZNF771 | 3 |
| HADH | 3 |
| TMCC3 | 3 |
| WDR74 | 3 |
| TMSB4X | 3 |
| TMSB10 | 3 |
| RPL37A | 3 |
| RPL13AP5 | 3 |
| RPL32 | 3 |
| RPL18 | 3 |
| RPS24 | 3 |
| RPL24 | 3 |
| RPS3A | 3 |

TABLE 3-continued

Genes in each cluster for heatmap in FIG. 3c.

| Gene Name | CL # |
|---|---|
| RPL7A | 3 |
| RPL23 | 3 |
| GABARAP | 3 |
| PFDN5 | 3 |
| RPS3 | 3 |
| RPL8 | 3 |
| RPL30 | 3 |
| TXN | 3 |
| COX6B1 | 3 |
| RPL39 | 3 |
| SOD1 | 3 |
| NDUFS5 | 3 |
| UBA52 | 3 |
| COX8A | 3 |
| RPS20 | 3 |
| RPS9 | 3 |
| NDUFB8 | 3 |
| PSMD8 | 3 |
| MGST3 | 3 |
| NDUFB11 | 3 |
| RNF7 | 3 |
| NDUFS3 | 3 |
| MRPS21 | 3 |
| OCIAD2 | 3 |
| ATP5G1 | 3 |
| RNASEK | 3 |
| RPS19BP1 | 3 |
| PCBP2 | 3 |
| FIS1 | 3 |
| DGUOK | 3 |
| MRPL41 | 3 |
| NDUFS8 | 3 |
| ATP5J2 | 3 |
| NHP2 | 3 |
| WDR82 | 3 |
| FAM229B | 3 |
| NUDT14 | 3 |
| CAPNS1 | 3 |
| MRPL51 | 3 |
| C19orf60 | 3 |
| TRAPPC1 | 3 |
| POLR2I | 3 |
| MRPS34 | 3 |
| RNF181 | 3 |
| RPL28 | 3 |
| PC | 3 |
| GNAZ | 3 |
| C4orf48 | 3 |
| SUMF2 | 3 |
| POLR2G | 3 |
| OST4 | 3 |
| NDUFA7 | 3 |
| BUD31 | 3 |
| NTMT1 | 3 |
| TRAPPC2L | 3 |
| NDUFB4 | 3 |
| PDRG1 | 3 |
| RPS27L | 3 |
| C19orf70 | 3 |
| UXT | 3 |
| ZSWIM7 | 3 |
| DBI | 3 |
| C7orf55 | 3 |
| AP2S1 | 3 |
| C6orf1 | 3 |
| TEX264 | 3 |
| NAA10 | 3 |
| COMTD1 | 3 |
| C1orf122 | 3 |
| TMEM208 | 3 |
| PRADC1 | 3 |
| TRAPPC3 | 3 |
| SLC35B1 | 3 |
| SDHB | 3 |
| STRA13 | 3 |
| TCTEX1D2 | 3 |

TABLE 3-continued

Genes in each cluster for heatmap in FIG. 3c.

| Gene Name | CL # |
|---|---|
| PSAT1 | 3 |
| POLR2J | 3 |
| DGCR6L | 3 |
| CD81 | 3 |
| NOP10 | 3 |
| AURKAIP1 | 3 |
| RNF157 | 3 |
| DGCR6 | 3 |
| UBE2Q1 | 3 |
| PET100 | 3 |
| DNPH1 | 3 |
| C6orf106 | 3 |
| NOSIP | 3 |
| ANKRD39 | 3 |
| FAM96A | 3 |
| MNF1 | 3 |
| UROD | 3 |
| SNRNP25 | 3 |
| TIMM17B | 3 |
| C19orf10 | 3 |
| ARHGDIG | 3 |
| C19orf53 | 3 |
| SCNM1 | 3 |
| PSME2 | 3 |
| BLOC1S1 | 3 |
| LYRM4 | 3 |
| PSMG3 | 3 |
| CSTB | 3 |
| LOC100505761 | 3 |
| PTRHD1 | 3 |
| MRPL24 | 3 |
| MDP1 | 3 |
| RRAGC | 3 |
| SAT2 | 3 |
| EMC6 | 3 |
| SDHAF1 | 3 |
| NOP16 | 3 |
| SERPINB6 | 3 |
| DDT | 3 |
| PAM16 | 3 |
| PTS | 3 |
| LINC00116 | 3 |
| APOA1BP | 3 |
| OVCA2 | 3 |
| DALRD3 | 3 |
| MRTO4 | 3 |
| B4GALT2 | 3 |
| PSMB10 | 3 |
| S100A13 | 3 |
| VEGFB | 3 |
| NTHL1 | 3 |
| LSM6 | 3 |
| SPPL3 | 3 |
| LSM10 | 3 |
| NME3 | 3 |
| IFI6 | 3 |
| MED30 | 3 |
| EIF3B | 3 |
| TMEM141 | 3 |
| RHOB | 3 |
| COA6 | 3 |
| PGRMC2 | 3 |
| TSSC4 | 3 |
| ZNF282 | 3 |
| DACT3 | 3 |
| TIMP2 | 3 |
| TRPT1 | 3 |
| ATP5E | 3 |
| COX7C | 3 |
| NDUFA4 | 3 |
| MIF | 3 |
| MYL12B | 3 |
| RPL9 | 3 |
| RPL21P28 | 3 |
| TPT1 | 3 |
| COX6C | 3 |

TABLE 3-continued

Genes in each cluster for heatmap in FIG. 3c.

| Gene Name | CL # |
|---|---|
| SEPW1 | 3 |
| NDUFA12 | 3 |
| CRIP2 | 3 |
| USMG5 | 3 |
| FABP5 | 3 |
| EEF1B2 | 3 |
| UQCRH | 3 |
| SQLE | 3 |
| ATP5O | 3 |
| NDUFA11 | 3 |
| RPLP2 | 3 |
| PTN | 3 |
| NDUFS4 | 3 |
| NDUFB1 | 3 |
| COMMD6 | 3 |
| UQCR10 | 3 |
| SNRPG | 3 |
| LY6H | 3 |
| CISD1 | 3 |
| NDUFA1 | 3 |
| PRDX4 | 3 |
| IDI1 | 3 |
| RAB33A | 3 |
| LGI2 | 3 |
| MINOS1 | 3 |
| HEBP2 | 3 |
| BEX5 | 3 |
| CDK5 | 3 |
| PIN1 | 3 |
| RAC3 | 3 |
| EPHB1 | 3 |
| C11orf73 | 3 |
| HRAS | 3 |
| BAIAP3 | 3 |
| SC5DL | 3 |
| DCXR | 3 |
| MRPL33 | 3 |
| BMPER | 3 |
| NBL1 | 3 |
| CCDC107 | 3 |
| CDHR1 | 3 |
| KLF6 | 3 |
| GPR26 | 3 |
| CMC2 | 3 |
| LPCAT1 | 3 |
| PIEZO2 | 3 |
| RHOQ | 3 |
| HSPB11 | 3 |
| NUDT16L1 | 3 |
| LIN7B | 3 |
| DNAJC19 | 3 |
| C8orf59 | 3 |
| ISCU | 3 |
| GCHFR | 3 |
| CD320 | 3 |
| GCAT | 3 |
| HIST3H2A | 3 |
| MMP24 | 3 |
| NSMCE4A | 3 |
| GPR50 | 3 |
| GNPTG | 3 |
| HSD17B7 | 3 |
| ZFAND2A | 3 |
| HAGHL | 3 |
| MZT2B | 3 |
| PEMT | 3 |
| COX17 | 3 |
| NIT2 | 3 |
| GAMT | 3 |
| MSRB1 | 3 |
| ITGAE | 3 |
| SLC22A17 | 3 |
| CERS6-AS1 | 3 |
| ADAP1 | 3 |
| LAMTOR2 | 3 |
| C11orf48 | 3 |

TABLE 3-continued

Genes in each cluster for heatmap in FIG. 3c.

| Gene Name | CL # |
|---|---|
| HENMT1 | 3 |
| MRPL54 | 3 |
| EXOSC8 | 3 |
| EPCAM | 3 |
| SPIN2B | 3 |
| EBF3 | 3 |
| PDLIM1 | 3 |
| C1orf233 | 3 |
| SHC3 | 3 |
| RBP4 | 3 |
| POLR2H | 3 |
| MRPL36 | 3 |
| TMEM126A | 3 |
| FAM134B | 3 |
| POLE4 | 3 |
| TMEM163 | 3 |
| TMEM117 | 3 |
| ECI1 | 3 |
| SLC22A4 | 3 |
| STK24 | 3 |
| SELM | 3 |
| SLC25A33 | 3 |
| UBAC1 | 3 |
| CALY | 3 |
| MCAT | 3 |
| GCH1 | 3 |
| CHD5 | 3 |
| FAM108C1 | 3 |
| CCDC74A | 3 |
| SNX7 | 3 |
| ADAM11 | 3 |
| CENPV | 3 |
| DUX2 | 3 |
| HS3ST2 | 3 |
| SLC4A5 | 3 |
| PTPRR | 3 |
| PXMP2 | 3 |
| SLC1A6 | 3 |
| C8orf76 | 3 |
| HES6 | 3 |
| ENDOG | 3 |
| PDXP | 3 |
| SST | 3 |
| AK5 | 3 |
| THOC6 | 3 |
| TTC9 | 3 |
| EPS8L1 | 3 |
| SPATS2L | 3 |
| ME1 | 3 |
| CBLN1 | 3 |
| ZBTB8OS | 3 |
| MAP2K2 | 3 |
| UGDH-AS1 | 4 |
| MTRNR2L2 | 4 |
| KCNQ1OT1 | 4 |
| MTRNR2L8 | 4 |
| ASTN2 | 4 |
| SHISA9 | 4 |
| MAPK8 | 4 |
| ZNF770 | 4 |
| ORC4 | 4 |
| MALAT1 | 4 |
| MTRNR2L1 | 4 |
| ANKRD36B | 4 |
| ABCC9 | 4 |
| LOC646214 | 4 |
| LOC100131257 | 4 |
| ANKRD36 | 4 |
| UBQLN1 | 4 |
| PCDH9 | 4 |
| BAZ2B | 4 |
| CCDC88A | 4 |
| PLEKHA5 | 4 |
| MGEA5 | 4 |
| ZNF638 | 4 |
| ZMYM2 | 4 |

TABLE 3-continued

Genes in each cluster for heatmap in FIG. 3c.

| Gene Name | CL # |
|---|---|
| ZNF91 | 4 |
| ATP8A1 | 4 |
| AKAP9 | 4 |
| LOC643406 | 4 |
| ANKRD12 | 4 |
| PCSK1 | 4 |
| EFNA5 | 4 |
| NKTR | 4 |
| REXO1L1 | 4 |
| ARHGEF12 | 4 |
| RGPD2 | 4 |
| PDK3 | 4 |
| USP34 | 4 |
| MTRNR2L3 | 4 |
| UBA6 | 4 |
| PLEC | 4 |
| LUC7L3 | 4 |
| ISLR2 | 4 |
| TRIM36 | 4 |
| ARHGEF11 | 4 |
| UBLCP1 | 4 |
| GREB1L | 4 |
| GOLGA4 | 4 |
| KIF2A | 4 |
| OPHN1 | 4 |
| GPRIN3 | 4 |
| DOCK7 | 4 |
| PCLO | 4 |
| TTC14 | 4 |
| ANK3 | 4 |
| CPSF6 | 4 |
| DST | 4 |
| N4BP2L2 | 4 |
| PLXNA2 | 4 |
| GPM6A | 4 |
| TOP2B | 4 |
| NEUROG2 | 4 |
| ODF2L | 4 |
| NIPBL | 4 |
| LOC441081 | 4 |
| WSB1 | 4 |
| SEMA6D | 4 |
| SNRPE | 4 |
| RBPJ | 4 |
| YME1L1 | 4 |
| RCHY1 | 4 |
| MAB21L3 | 4 |
| ZNF780B | 4 |
| CACNA2D1 | 4 |
| SRSF3 | 4 |
| SENP6 | 4 |
| SENP7 | 4 |
| KLHL11 | 4 |
| RBM33 | 4 |
| PCDH11X | 4 |
| VPS13C | 4 |
| DENND4A | 4 |
| UGGT2 | 4 |
| SMC3 | 4 |
| ZNF260 | 4 |
| PPP6R3 | 4 |
| CCDC90B | 4 |
| RASGEF1B | 4 |
| MTRNR2L10 | 4 |
| GRIA2 | 4 |
| KIAA1551 | 4 |
| CDC42BPA | 4 |
| ROCK1 | 4 |
| SCAF11 | 4 |
| CCSER1 | 4 |
| MARCH7 | 4 |
| SCAPER | 4 |
| CASD1 | 4 |
| ZNF644 | 4 |
| VPS13B | 4 |
| CHD9 | 4 |

TABLE 3-continued

Genes in each cluster for heatmap in FIG. 3c.

| Gene Name | CL # |
|---|---|
| SRSF6 | 4 |
| PTPRS | 4 |
| CTNNA2 | 4 |
| RC3H2 | 4 |
| BOD1L1 | 4 |
| ANKRD20A9P | 4 |
| HSPH1 | 4 |
| ACAP2 | 4 |
| SIM1 | 4 |
| PHF3 | 4 |
| L2HGDH | 4 |
| DMXL2 | 4 |
| TMSB15A | 4 |
| ZMYM5 | 4 |
| ARID4A | 4 |
| NEMF | 4 |
| KPNA5 | 4 |
| SMC6 | 4 |
| BCAS2 | 4 |
| ERV3-1 | 4 |
| ONECUT2 | 4 |
| LOC440297 | 4 |
| KCNH7 | 4 |
| MTRNR2L6 | 4 |
| ALMS1 | 4 |
| CCDC144C | 4 |
| RHOT1 | 4 |
| RIF1 | 4 |
| PITX2 | 4 |
| THOC2 | 4 |
| IFT81 | 4 |
| BRWD3 | 4 |
| RBBP6 | 4 |
| DZIP3 | 4 |
| ASH1L | 4 |
| BDP1 | 4 |
| PNRC2 | 4 |
| MIAT | 4 |
| EBF2 | 4 |
| PHIP | 4 |
| GNRHR2 | 4 |
| PUS7L | 4 |
| PIBF1 | 4 |
| TMEM212 | 4 |
| ITSN1 | 4 |
| PKN2 | 4 |
| C6orf170 | 4 |
| MTPAP | 4 |
| VPS13D | 4 |
| HTATSF1 | 4 |
| KIAA0513 | 4 |
| ERP44 | 4 |
| PRPF39 | 4 |
| ZNF33B | 4 |
| OGT | 4 |
| LOC100131564 | 4 |
| TMF1 | 4 |
| KCNIP4 | 4 |
| PNN | 4 |
| CNTNAP5 | 4 |
| RASAL2 | 4 |
| SLC4A7 | 4 |
| TRIM32 | 4 |
| RFC1 | 4 |
| CLK1 | 4 |
| TIA1 | 4 |
| PCNXL4 | 4 |
| SEC24B | 4 |
| ZCCHC11 | 4 |
| PDE4B | 4 |
| EP400 | 4 |
| PHF20 | 4 |
| PTPRT | 4 |
| C5orf42 | 4 |
| FER | 4 |
| SYT13 | 4 |

TABLE 3-continued

Genes in each cluster for heatmap in FIG. 3c.

| Gene Name | CL # |
|---|---|
| MLL3 | 4 |
| PCDH7 | 4 |
| TENM4 | 4 |
| CTDSPL2 | 4 |
| ZNF148 | 4 |
| EHBP1 | 4 |
| LTV1 | 4 |
| LHX9 | 4 |
| CEP290 | 4 |
| ARID4B | 4 |
| ZMYM4 | 4 |
| TTC30B | 4 |
| LRRN3 | 4 |
| ARL15 | 4 |
| SLC1A2 | 4 |
| CDK17 | 4 |
| HERC2P2 | 4 |
| TERF1 | 4 |
| CEP85L | 4 |
| LOC100506123 | 4 |
| MTMR3 | 4 |
| SOGA3 | 4 |
| PPA2 | 4 |
| SUV420H1 | 4 |
| DCC | 4 |
| ZNF248 | 4 |
| CCNL2 | 4 |
| ABCA5 | 4 |
| FAM135A | 4 |
| PAR-SN | 4 |
| CALB1 | 4 |
| WDR17 | 4 |
| NF1 | 4 |
| RBM12B | 4 |
| UPF3B | 4 |
| DDHD1 | 4 |
| SLC23A2 | 4 |
| UBA5 | 4 |
| UHRF2 | 4 |
| CHD1 | 4 |
| FAM214A | 4 |
| SMG1P1 | 4 |
| NTS | 4 |
| EPPK1 | 4 |
| ARID2 | 4 |
| C2CD5 | 4 |
| AHI1 | 4 |
| PRPF19 | 4 |
| SRP19 | 4 |
| PXK | 4 |
| MYO16 | 4 |
| DENND6A | 4 |
| SRGAP1 | 4 |
| ENC1 | 4 |
| RAD17 | 4 |
| ZUFSP | 4 |
| EFHC1 | 4 |
| SOCS4 | 4 |
| KIAA1841 | 4 |
| GINM1 | 4 |
| PBDC1 | 4 |
| PPP1R12B | 4 |
| ZNF587 | 4 |
| SECISBP2 | 4 |
| ATRX | 4 |
| LRRC7 | 4 |
| CASP8AP2 | 4 |
| PCDH1 | 4 |
| ZNF791 | 4 |
| ERLEC1 | 4 |
| FAT3 | 4 |
| FAM172A | 4 |
| GOLGA8A | 4 |
| SEMA5A | 4 |
| ZNF37BP | 4 |
| RPGRIP1L | 4 |

TABLE 3-continued

Genes in each cluster for heatmap in FIG. 3c.

| Gene Name | CL # |
|---|---|
| KDM5C | 4 |
| HERC3 | 4 |
| KDM5B | 4 |
| CAND1 | 4 |
| SLC17A6 | 4 |
| ATP6V1C1 | 4 |
| CLASP1 | 4 |
| USP47 | 4 |
| ASXL3 | 4 |
| PLXNA4 | 4 |
| DNTTIP2 | 4 |
| ZKSCAN1 | 4 |
| NEK1 | 4 |
| LINC00599 | 4 |
| SMARCAD1 | 4 |
| ANKRD50 | 4 |
| KIAA1107 | 4 |
| KAT6B | 4 |
| SLC16A14 | 4 |
| CCSER2 | 4 |
| PDS5B | 4 |
| LRRC40 | 4 |
| OPA1 | 4 |
| JMJD1C | 4 |
| PIK3R3 | 4 |
| ELAVL2 | 4 |
| GOLGA8B | 4 |
| SUCLA2 | 4 |
| TTC17 | 4 |
| DIP2C | 4 |
| ZNF441 | 4 |
| CELSR2 | 4 |
| PHYHIPL | 4 |
| FEM1C | 4 |
| ZNF84 | 4 |
| RIMKLB | 4 |
| ITGB1 | 4 |
| PRR14L | 4 |
| ANO6 | 4 |
| TMEFF1 | 4 |
| ASCC3 | 4 |
| REV3L | 4 |
| CDC37L1 | 4 |
| MAP4K5 | 4 |
| NHLRC2 | 4 |
| HTT | 4 |
| TTBK2 | 4 |
| CAPN7 | 4 |
| ZNF33A | 4 |
| FOCAD | 4 |
| RSF1 | 4 |
| SETD2 | 4 |
| ZNF800 | 4 |
| CNOT10 | 4 |
| TOPORS | 4 |
| USP15 | 4 |
| RAB3IP | 4 |
| RNF219 | 4 |
| SRRM2 | 4 |
| ANKRD52 | 4 |
| CCDC82 | 4 |
| GRM8 | 4 |
| NLN | 4 |
| TAF2 | 4 |
| ZNF286B | 4 |
| ZNF268 | 4 |
| TFAP2A | 4 |
| NUCB2 | 4 |
| CWC22 | 4 |
| SPEN | 4 |
| ZFC3H1 | 4 |
| NOVA1 | 4 |
| FAM49A | 4 |
| GPC2 | 4 |
| SOAT1 | 4 |
| NAV2 | 4 |

TABLE 3-continued

Genes in each cluster for heatmap in FIG. 3c.

| Gene Name | CL # |
|---|---|
| KTN1 | 4 |
| UBR5 | 4 |
| LYPLAL1 | 4 |
| ADCY7 | 4 |
| ABCD3 | 4 |
| PIK3C2A | 4 |
| METAP1 | 4 |
| SEMA4D | 4 |
| NBN | 4 |
| USP48 | 4 |
| MBD5 | 4 |
| INTS8 | 4 |
| ZNF618 | 4 |
| TBCK | 4 |
| BAI3 | 4 |
| ZFP1 | 4 |
| SWT1 | 4 |
| CEP70 | 4 |
| TRAPPC13 | 4 |
| ZNF334 | 4 |
| RGS17 | 4 |
| AP1G1 | 4 |
| LRRC16B | 4 |
| POLR3GL | 4 |
| HIPK3 | 4 |
| ZNF836 | 4 |
| ZNF429 | 4 |
| FAM120A | 4 |
| ESF1 | 4 |
| KIAA1430 | 4 |
| NAA35 | 4 |
| ZNF484 | 4 |
| KIAA1731 | 4 |
| RALGPS1 | 4 |
| CD46 | 4 |
| SULF2 | 4 |
| PJA2 | 4 |
| GTF2I | 4 |
| PHF6 | 4 |
| DNM1L | 4 |
| PCM1 | 4 |
| FBXO11 | 4 |
| HIF1A | 4 |
| HECTD1 | 4 |
| WDR7 | 4 |
| ADSS | 4 |
| RANBP6 | 4 |
| GMFB | 4 |
| PXDN | 4 |
| HERC2 | 4 |
| PPP1R12A | 4 |
| TRAM1L1 | 4 |
| UBE2W | 4 |
| ZNF83 | 4 |
| PANX1 | 4 |
| ZNF841 | 4 |
| ZFP37 | 4 |
| UGP2 | 4 |
| SPIN4 | 4 |
| ZNF14 | 4 |
| FAM178A | 4 |
| TMEM132A | 4 |
| ZNF700 | 4 |
| PPIG | 4 |
| CLIP1 | 4 |
| CRIM1 | 4 |
| PPIL4 | 4 |
| ACAP3 | 4 |
| HPCAL1 | 4 |
| DPP8 | 4 |
| ZNF790 | 4 |
| ZNF669 | 4 |
| CCDC112 | 4 |
| ZNF415 | 4 |
| AKD1 | 4 |
| HERC4 | 4 |
| MAGEL2 | 4 |
| ZNF354A | 4 |
| SRC | 4 |
| ZNF470 | 4 |
| ALG6 | 4 |
| FLNA | 4 |
| MSH2 | 4 |
| FAM160A2 | 4 |
| ANAPC4 | 4 |
| ZSCAN29 | 4 |
| XPA | 4 |
| ZNF180 | 4 |
| BNC2 | 4 |
| ZNF12 | 4 |
| MTERFD3 | 4 |
| USP1 | 4 |
| MBIP | 4 |
| EMC2 | 4 |
| MTHFR | 4 |
| SNHG6 | 4 |
| LINC00643 | 4 |

CL: Cluster

The influence of co-culturing iN cells in Matrigel hydrogel and CHs for five weeks was assessed by comparing their transcriptome to a panel of human brain transcriptome samples. For all four subregions tested, a positive trend was observed in the correlation between the transcriptome of co-cultured iN cells to the human brain transcriptome at later developmental time points (19 pcw and 37 pcw) when moving from Matrigel to CH with increasing levels of crosslinker (FIG. 3*e*). Although there are some exceptions to this trend, in most cases, CH was an improvement over Matrigel alone. At the earliest developmental time point (12 pcw), gene expression of iN cells co-cultured in Matrigel alone correlates more closely with the human data. To determine genes driving increased correlation to human brain transcriptome at later developmental time points (19 pcw and 37 pcw) moving from Matrigel to CH 4× crosslinker, each gene was scored and rank lists were generated for each time point (19 pcw and 37 pcw) and brain region (V1C, DFC, A1C and M1C), where high scoring genes have similar expression levels in human brain developmental transcriptome and CH 4× crosslinker condition, and different expression levels in human brain developmental transcriptome and Matrigel condition (Tables 7-30). GO analysis for high scoring genes (rank score>3) for each brain region at 19 pcw showed enrichment for neuronal-related processes, while high scoring genes (rank score>3) for each brain region at 37 pcw demonstrated enrichment for extracellular matrix-related processes (Tables 7-30). Additionally, the presence of HA and increased cell density in CH was investigated for impacts on gene expression profiles. Adding HA to the CH decreased the correlation between the transcriptome of co-cultured iN cells to the human brain transcriptome, whereas increasing cell density lead to similar trends (FIGS. 16A-16C). The effect of varying the volume of CH with or without HA on the gene expression profile of co-cultured iN cells was investigated. Decreasing the volume improved the enrichment of neurological processes while marginally decreasing the correlation to the human brain transcriptome (FIGS. 17A-17D).

The following tables may be accessed in Tekin et al. “Effects of 3D culturing conditions on the transcriptomic profile of stem-cell-derived neurons,” Nature Biomedical Engineering, 2: 540-554 (2018), which is herein incorporated by reference, specifically Supplemental Tables 1 and 6-14 that form part of the Supplementary Information of said paper and which may be accessed at doi.org/10.1038/s41551-018-0219-9.

Tables 7-9 (Table 7 corresponding to Tekin Table 6|Genes with rank score, Table 8 corresponding to Tekin Tabl 6|GO genes score>3, and Table 9 corresponding to Tekin Table 6|GO genes score<−3): Genes ranked based on their squared log fold change in iN cells co-cultured (at total cell concentration 20×10$^6$ cells/ml) in Matrigel (4.6 mg/ml) compared to the V1C brain region at 19 pcw, normalized by the squared log fold change of iN cells co-cultured (at total cell concentration 20×10$^6$ cells/ml) in CH 4×CRS compared to the V1C brain region at 19 pcw, as well as Gene Ontology results for genes with score>3 and for genes with score<−3.

Tables 10-12 (Table 10 corresponding to Tekin Table 7|Genes with ranked score, Table 11 corresponding to Tekin Table 7|GO genes score>3, and Table 12 corresponding to Tekin Table 7|GO gene score<−3): Genes ranked based on their squared log fold change in iN cells co-cultured (at total cell concentration 20×10$^6$ cells/ml) in Matrigel (4.6 mg/ml) compared to the V1C brain region at 37 pcw, normalized by the squared log fold change of iN cells co-cultured (at total cell concentration 20×10$^6$ cells/ml) in CH 4×CRS compared to the V1C brain region at 37 pcw, as well as Gene Ontology results for genes with score>3 and for genes with score<−3.

Tables 13-15 (Table 13 corresponding to Tekin Table 8|Genes with ranke score, Table 14 corresponding to Tekin Table 8|GO genes score>3, and Table 15 corresponding to Tekin Table 8|GO genes score<−3): Genes ranked based on their squared log fold change in iN cells co-cultured (at total cell concentration 20×10$^6$ cells/ml) in Matrigel (4.6 mg/ml) compared to the DFC brain region at 19 pcw, normalized by the squared log fold change of iN cells co-cultured (at total cell concentration 20×10$^6$ cells/ml) in CH 4×CRS compared to the DFC brain region at 19 pcw, as well as Gene Ontology results for genes with score>3 and for genes with score<−3.

Tables 16-18 (Table 16 corresponding to Tekin Table 9|Genes with rank score, Table 17 corresponding to Tekin Table 9|GO genes with gene score>3, and Table 18 corresponding to Tekin Table 9|GO genes with score<−3): Genes ranked based on their squared log fold change in iN cells co-cultured (at total cell concentration 20×10$^6$ cells/ml) in Matrigel (4.6 mg/ml) compared to the DFC brain region at 37 pcw, normalized by the squared log fold change of iN cells co-cultured (at total cell concentration 20×10$^6$ cells/ml) in CH 4×CRS compared to the DFC brain region at 37 pcw, as well as Gene Ontology results for genes with score>3 and for genes with score<−3.

Tables 19-21 (Table 19 corresponding to Tekin Table 10|Genes with ranked scores, Table 20 corresponding to Tekin Table 10|GO gene scores>3, Table 21 corresponding to Tekin Table 10|GO gene scores<−3): Genes ranked based on their squared log fold change in iN cells co-cultured (at total cell concentration 20×10$^6$ cells/ml) in Matrigel (4.6 mg/ml) compared to the A1C brain region at 19 pcw, normalized by the squared log fold change of iN cells co-cultured (at total cell concentration 20×10$^6$ cells/ml) in CH 4×CRS compared to the A1C brain region at 19 pcw, as well as Gene Ontology results for genes with score>3 and for genes with score<−3.

Tables 22-24 (Table 22 corresponding to Tekin Table 1, Table 23 corresponding to Tekin Table 11|GO gene score>3 and Table 24 corresponding to Tekin Table 11|GO genes score<−3, respectively): Genes ranked based on their squared log fold change in iN cells co-cultured (at total cell concentration 20×10$^6$ cells/ml) in Matrigel (4.6 mg/ml) compared to the A1C brain region at 37 pcw, normalized by the squared log fold change of iN cells co-cultured (at total cell concentration 20×10$^6$ cells/ml) in CH 4×CRS compared to the A1C brain region at 37 pcw, as well as Gene Ontology results for genes with score>3 and for genes with score<−3.

Tables 25-27 (Table 25 corresponding to Tekin Table 12|genes with rank score, Table 26 corresponding to Table 12|GO genes score>3, and Table 27 corresponding to Table 12|GO genes score<−3, respectively): Genes ranked based on their squared log fold change in iN cells co-cultured (at total cell concentration 20×10$^6$ cells/ml) in Matrigel (4.6 mg/ml) compared to the M1C brain region at 19 pcw, normalized by the squared log fold change of iN cells co-cultured (at total cell concentration 20×10$^6$ cells/ml) in CH 4×CRS compared to the M1C brain region at 19 pcw, as well as Gene Ontology results for genes with score>3 and for genes with score<−3.

Tables 28-30 (Tekin Table 13|Genes with rank score, Table 13|GO genes score>3, and Table 13|GO gene score<−3, respectively): Genes ranked based on their squared log fold change in iN cells co-cultured (at total cell concentration 20×10$^6$ cells/ml) in Matrigel (4.6 mg/ml) compared to the M1C brain region at 37 pcw, normalized by the squared log fold change of iN cells co-cultured (at total cell concentration 20×10$^6$ cells/ml) in CH 4×CRS compared to the M1C brain region at 37 pcw, as well as Gene Ontology results for genes with score>3 and for genes with score<−3.

Figures 20A, 20B:
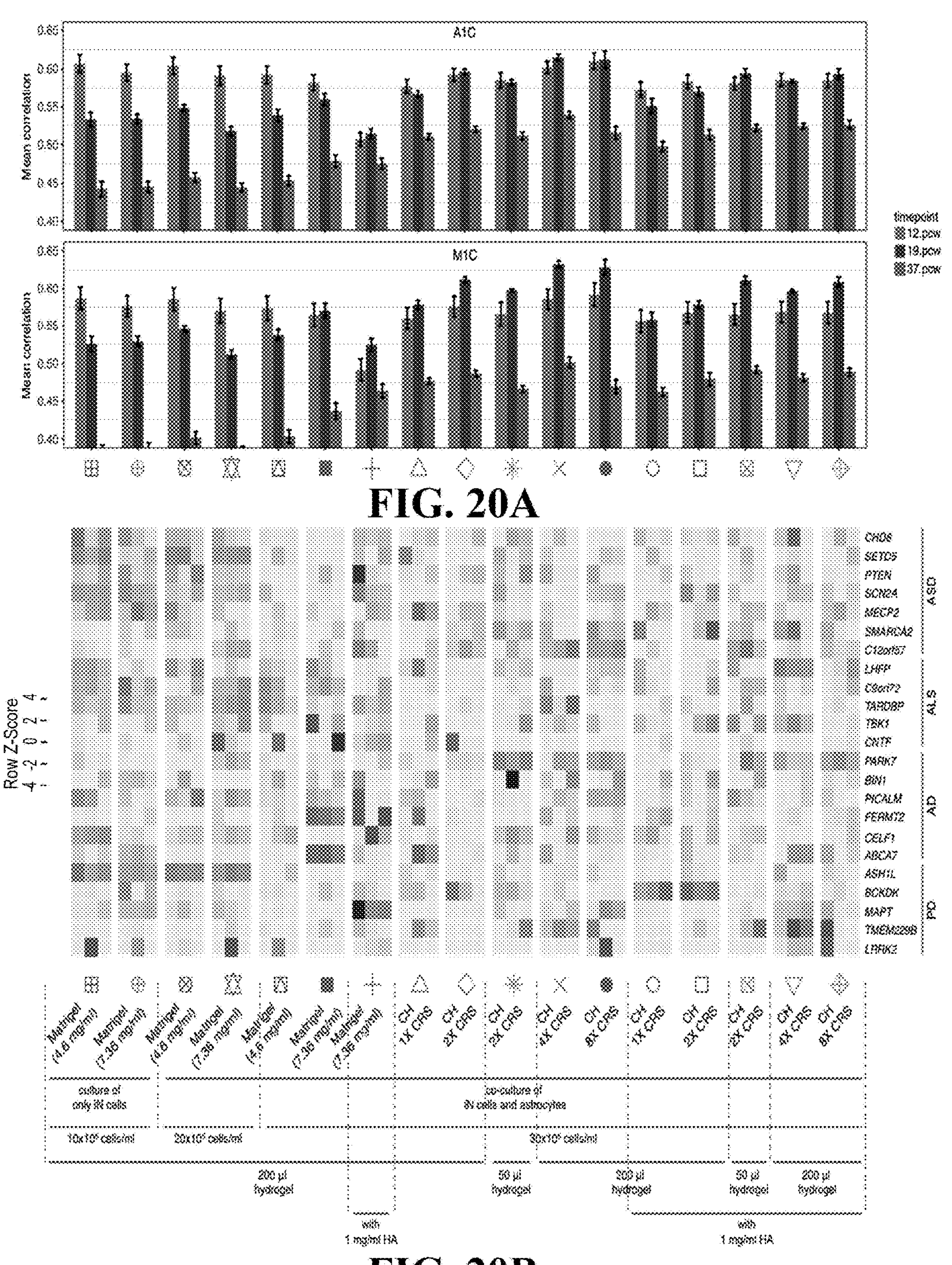
FIGS. 20A-20B: Global comparison of effects of culture conditions on human iN cells.

Table 31 (Tekin Table 14): Genes in each cluster for heatmap in FIG. 20B.

Example 5. Generation of 3D Neural Tissues with Human Cell Components

Figure 5A:
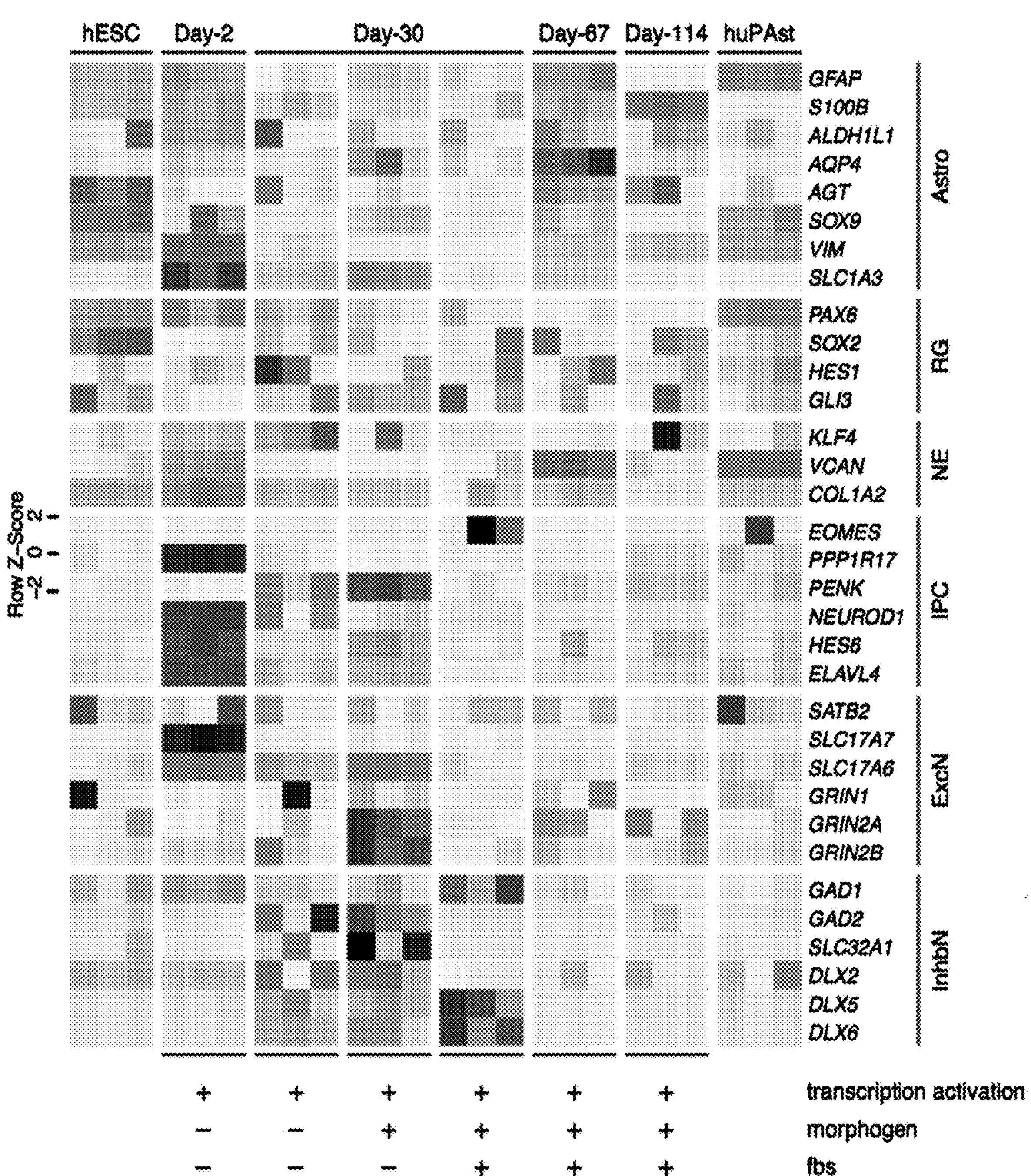
FIGS. 5A-5L: Generation of 3D neural tissues composed of human iN and astrocytic cells.
Figures 5B, 5C, 5D, 5E:
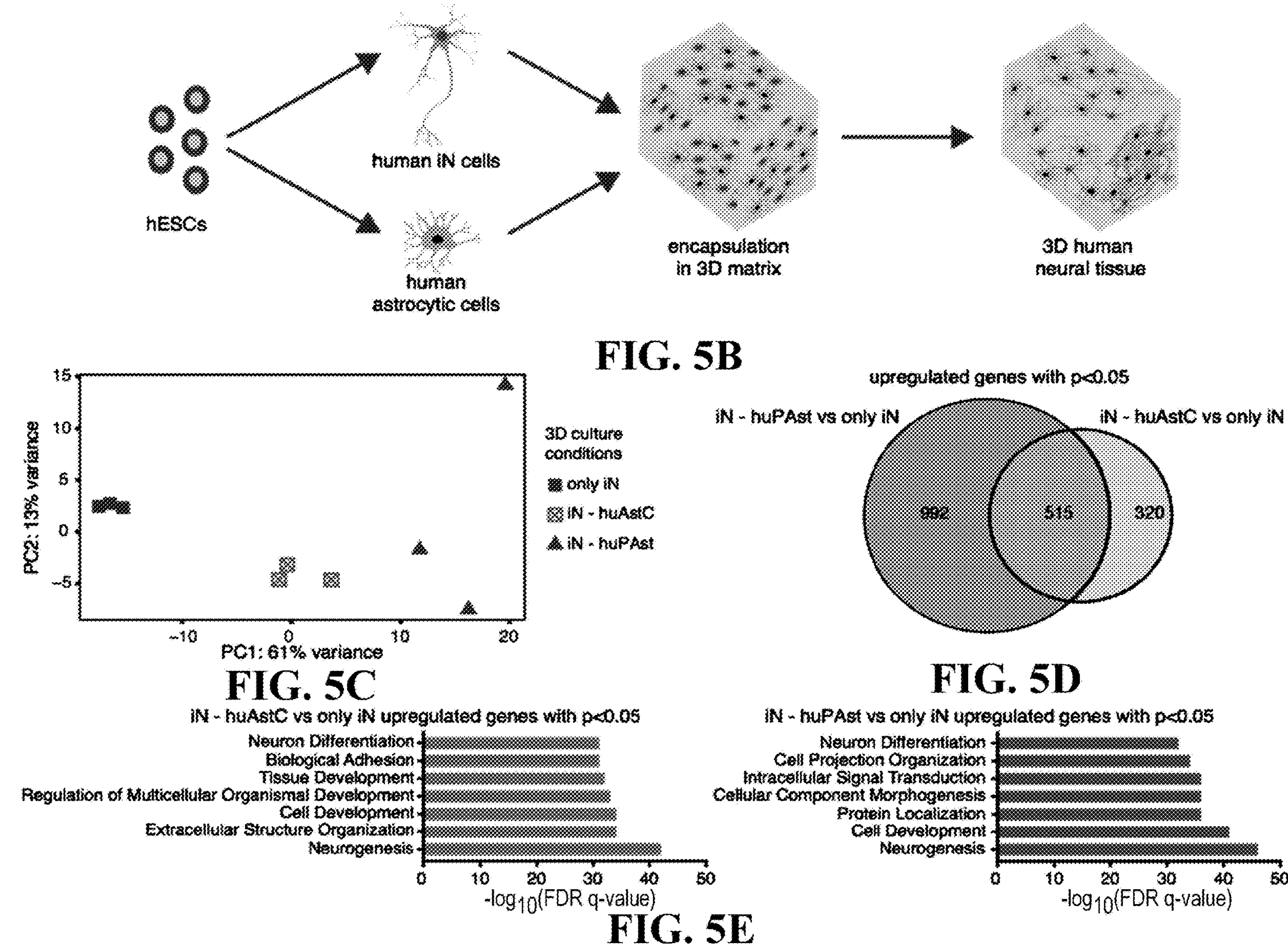
Figures 21A, 21B:
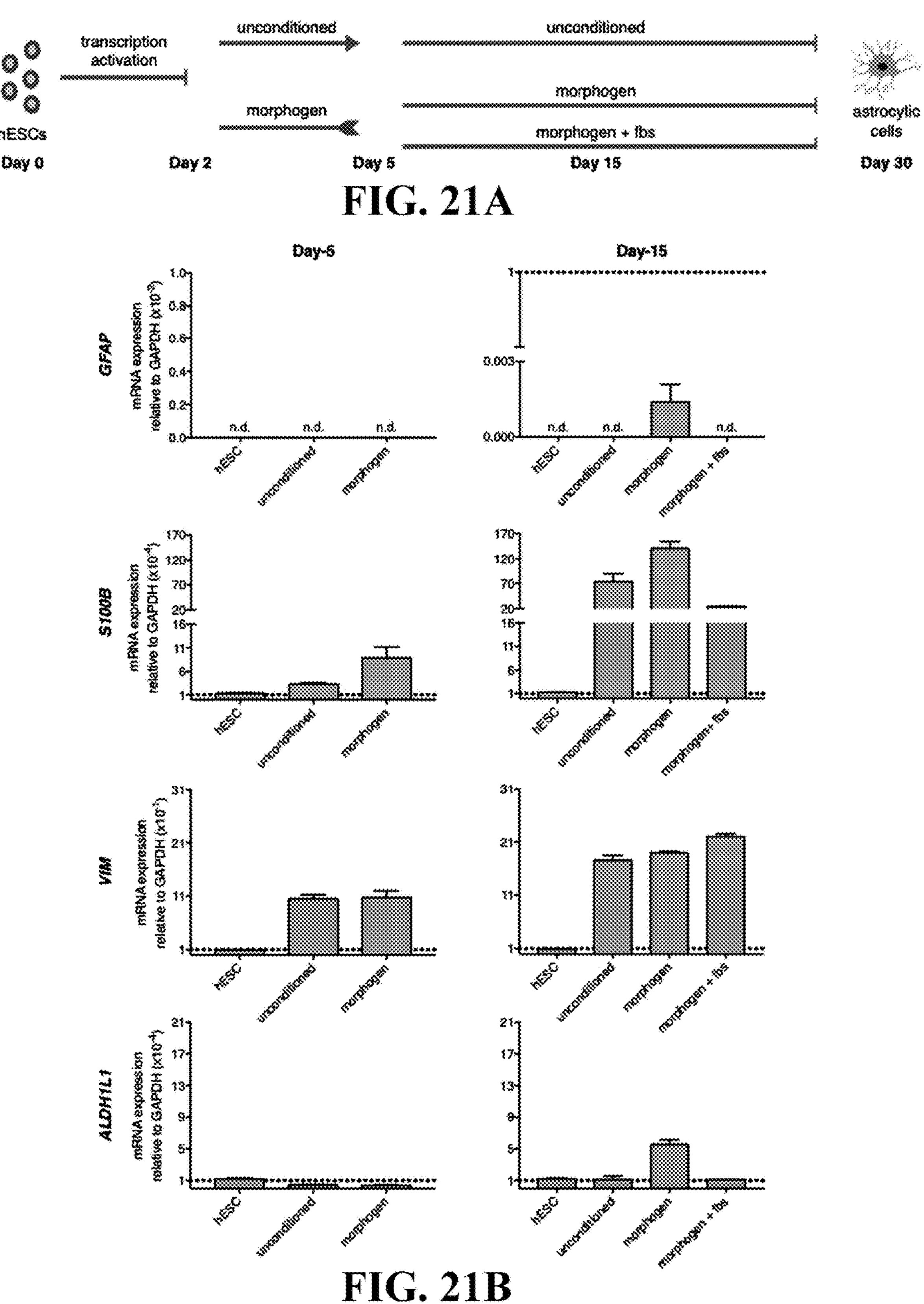
FIGS. 21A-21B: Derivation of human astrocytic cells directly derived from hESCs.
Figure 22:
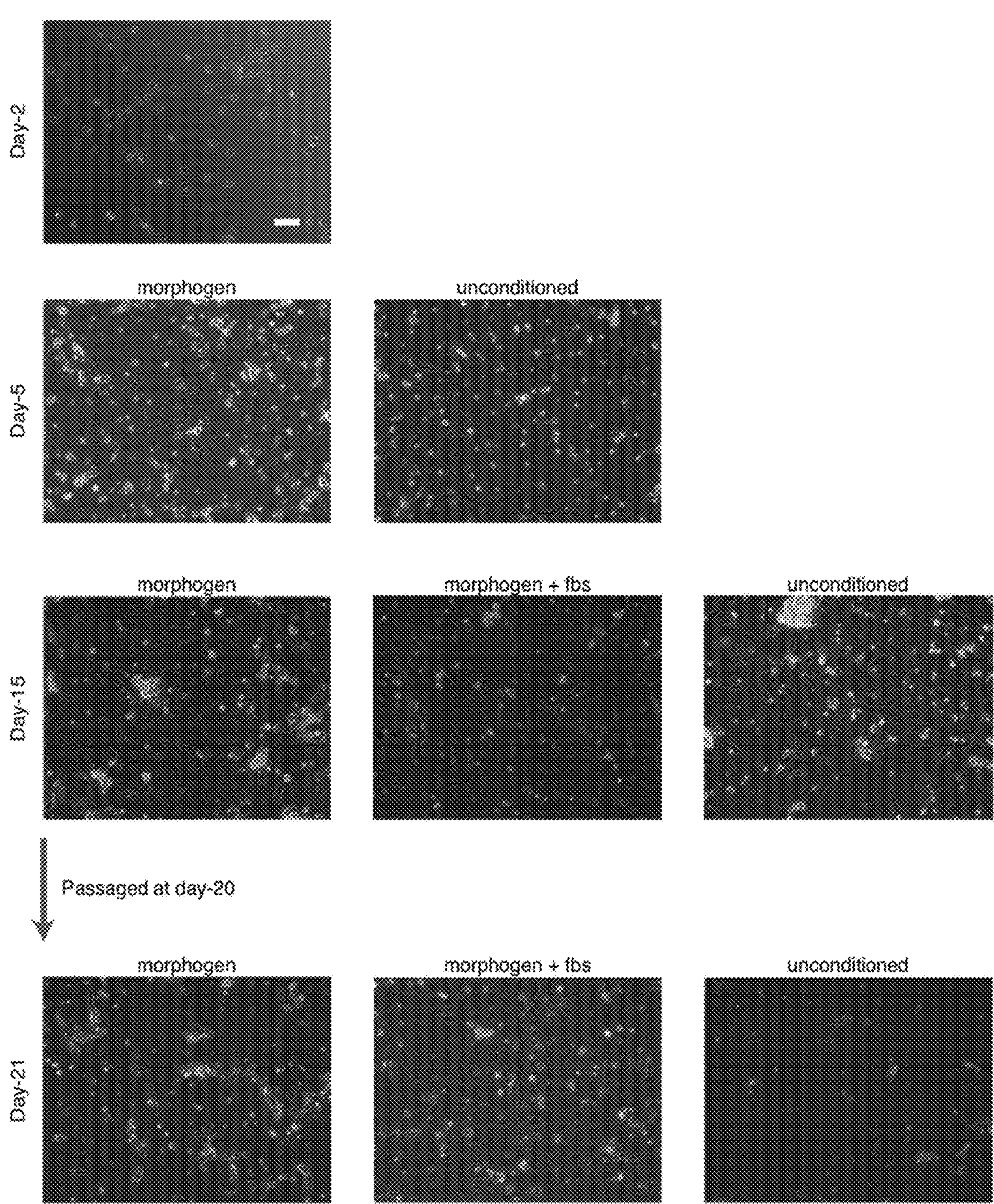
FIG. 22: Passaging removes neuron-like cells formed during derivation of astrocytic cells from hESCs. Representative phase images of cells at day-2, day-5, day-15 and day-21 of differentiation protocols described in FIG. 5*a* and FIG. 21*a*. Passaging cells in all conditions at day 20 removed neuron-like cells formed along with astrocytic cells during derivation protocols. Scale bar, 100 μm.
Figures 23A, 23B:
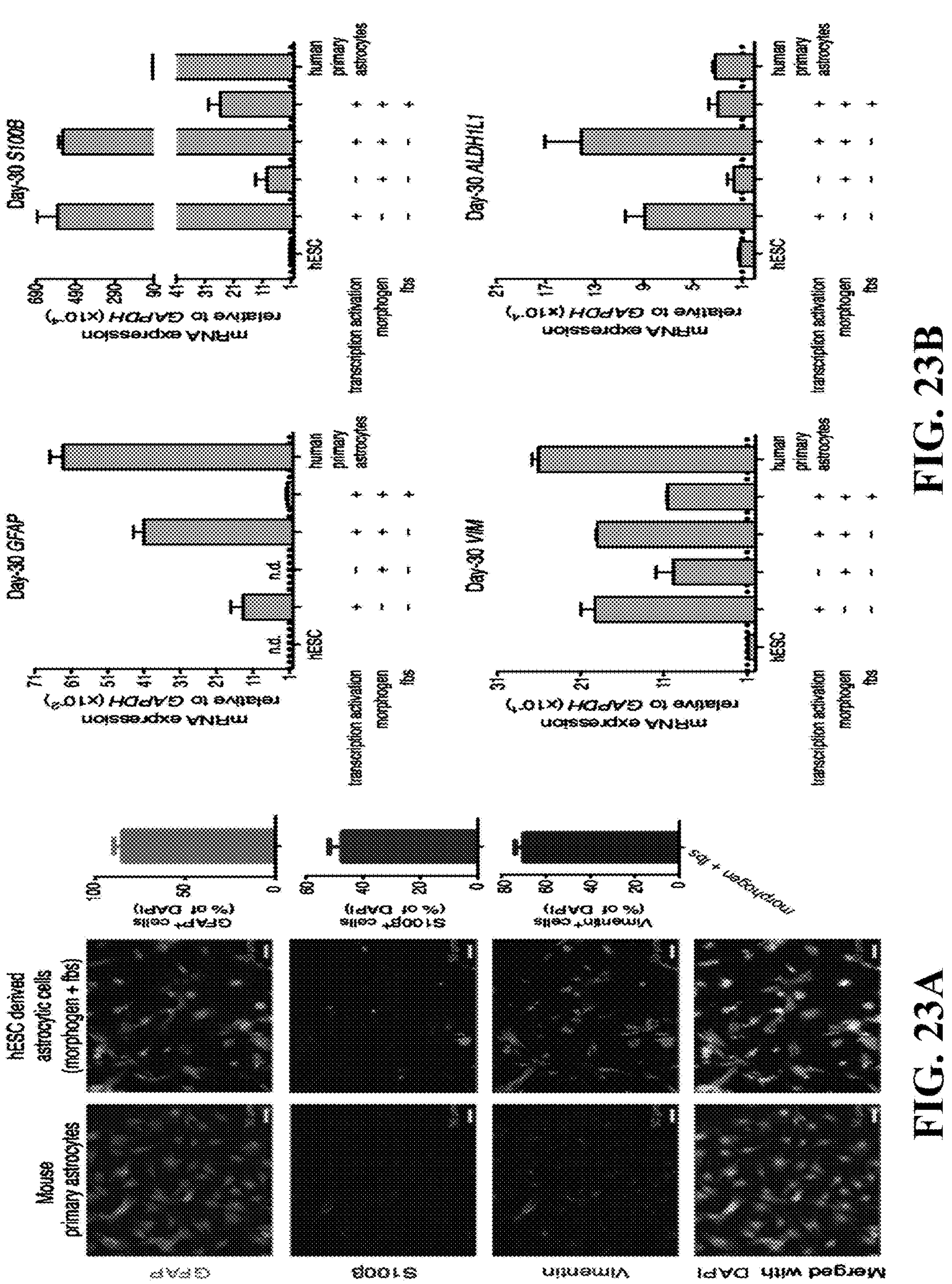
FIGS. 23A-23C: Characterization of human astrocytic cells derived from hESCs.
Figure 23C:
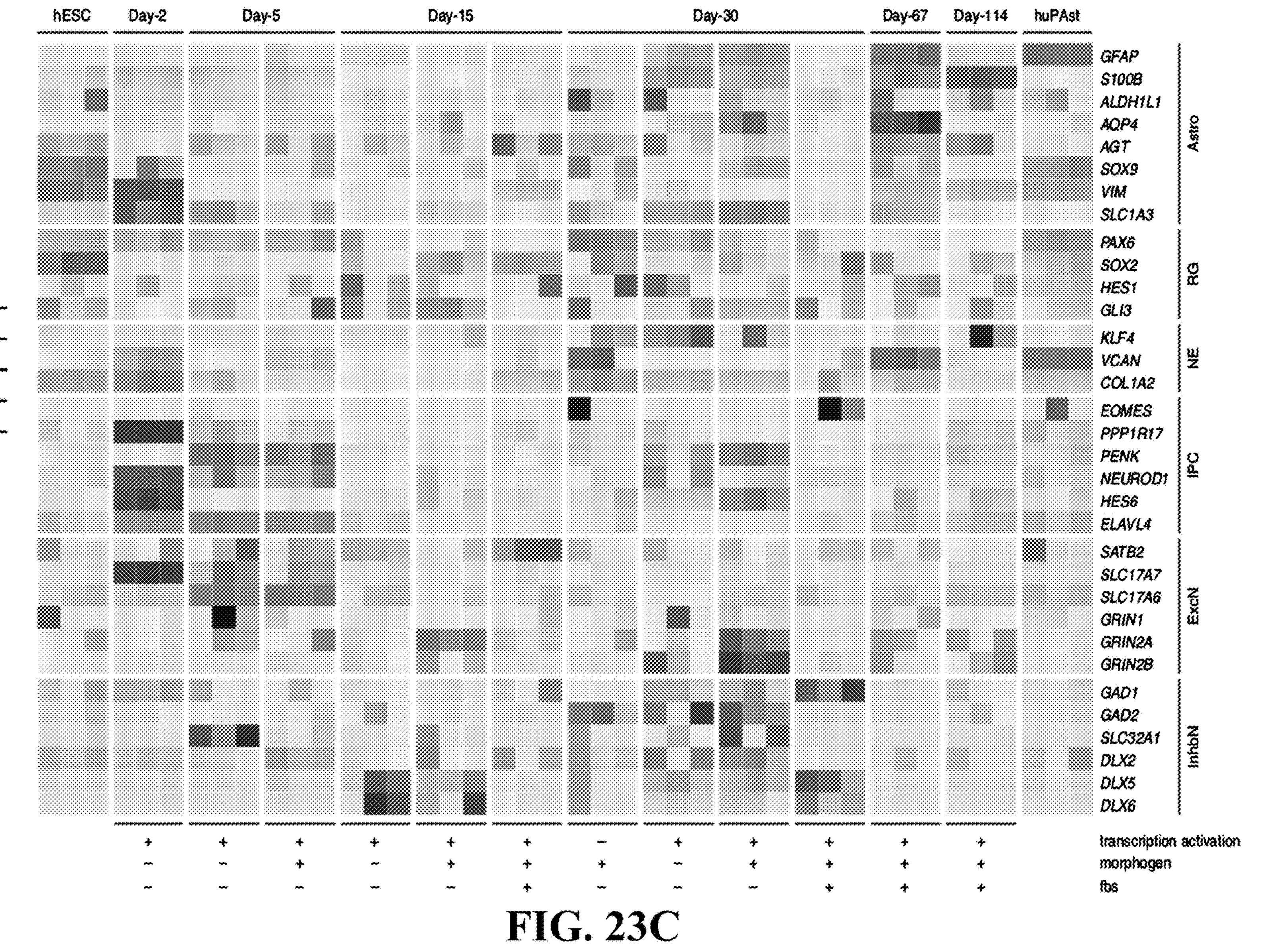
Figures 24A, 24B, 24C:
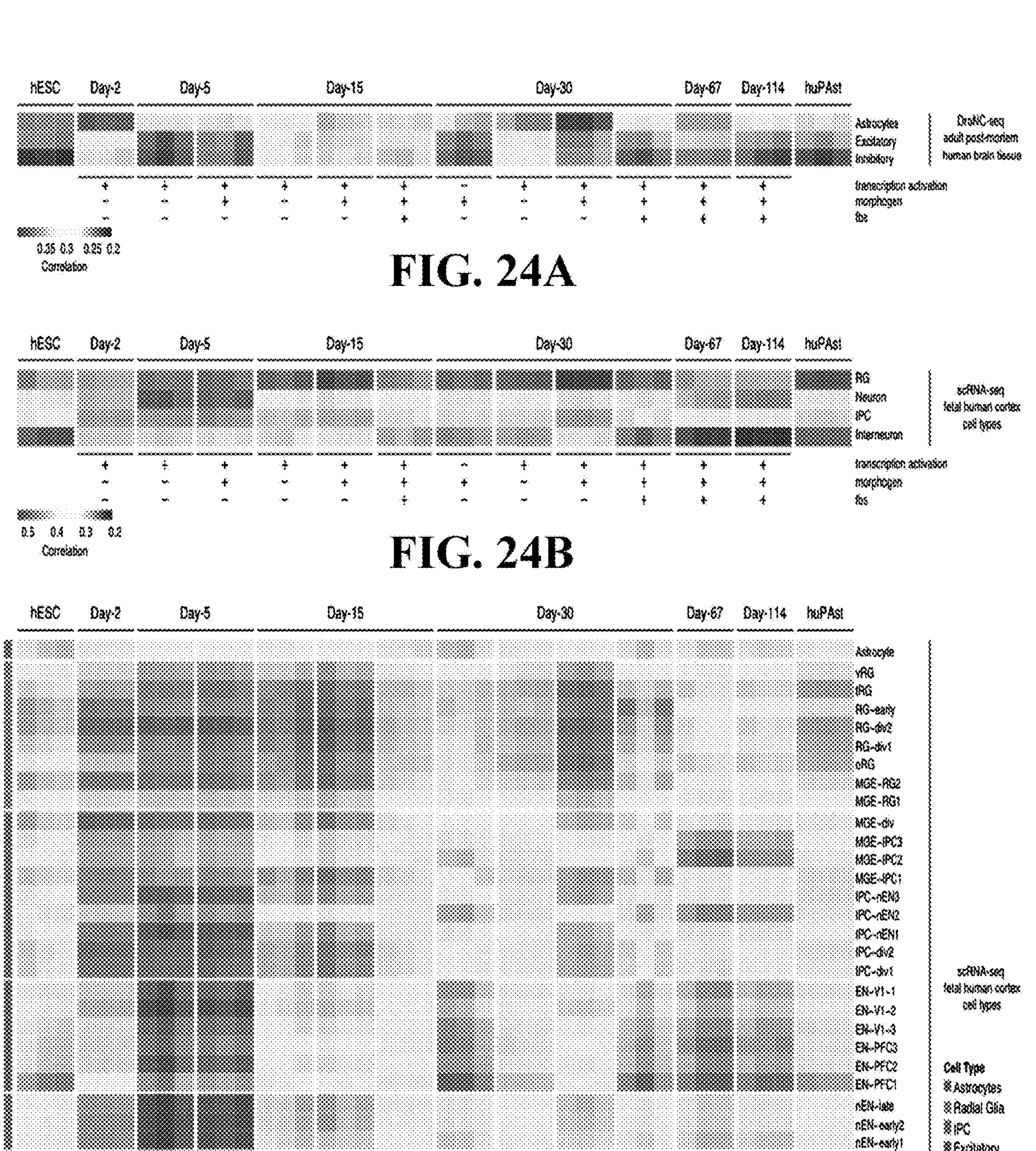
FIGS. 24A-24E: Transcriptomic correlation of cells in astrocytic cell differentiation protocols to cell types in human brain and characterization of co-culture of human iN cells with human astrocytic cells. Pearson's correlations between bulk RNA-seq data of cells in astrocytic cell differentiation protocols (involved transcription factors (NGN1 and NGN2) used for neural induction, a morphogen (cntf, ciliary neurotrophic factor) and fetal bovine serum (fbs)) at different time points as well as undifferentiated hESCs and human primary astrocytes (huPAst) were used as controls (n=3 for all conditions) (columns) and (FIG. 24*a*) cell types (Excitatory Neurons, Inhibitory Neurons, and Astrocytes) defined by DroNC-seq (single-nucleus RNA sequencing with droplet technology) in the adult post-mortem human brain tissue (Habib, N. et al. Nature Methods 14, 955, (2017)) (rows) and (FIG. 24*b*) cell types (Int-Neu: Interneurons; IPC: Intermediate Progenitor Cells; RG: Radial Glia cells) defined by single-cell RNA sequencing (scRNA-seq) in the human fetal cortex (Pollen, A. A. et al. Cell 163, 55-67, (2015)) (rows) and (FIG. 24*c*) cell types defined by scRNA-seq in the human fetal cortex (Nowakowski, T. J. et al. Science 358, 1318-1323, (2017)) (rows). EN: Excitatory Neuron; PFC: Prefrontal Cortex; V1: Primary Visual Cortex; IN: Inhibitory Neuron; CGE: Caudal Ganglionic Eminence; MGE: Medial Ganglionic Eminence; IPC: Intermediate Progenitor Cells; RG: Radial Glia cells. See also Table 32 for descriptions of cell type clusters defined by scRNA-seq in the human fetal cortex (Nowakowski, T. J. et al. Science 358, 1318-1323, (2017)).

To better represent the cell composition of the human brain in our 3D tissues, we developed a method to derive human astrocytic cells directly from hESCs and used this to engineer 3D tissues of co-cultured human iN and astrocytic cells. It was previously reported that overexpression of NGN1/2 in stem cells leads to a transient neural progenitor state before the cells turn into iN cells 18, which we hypothesized could be exploited to derive human astrocytic cells. We developed a method to induce formation of astrocytic cells by terminating NGN1/2 overexpression and adding a morphogen, ciliary neurotrophic factor (cntf), at day 2, followed by passaging cells at day 20 to eliminate neuron-like cells (FIGS. 21*a*, 22). The majority of the cells thus derived were GFAP+, S100β+, and Vimentin+ at day 35, comparable to mouse astrocytes (FIG. 23*a*). We also analyzed the expression of GFAP, S100B, VIM, and ALDH1L1 by qPCR for cells exposed to derivation protocols without any passaging at days 5, 15, and 30 using undifferentiated hESCs, hESCs only exposed to morphogen, and human primary astrocytes as controls (FIG. 21*b*, FIG. 23*b*). GFAP expression was not detectable in undifferentiated hESCs and in hESCs only exposed to morphogen but when morphogen was added following transcriptional activation, GFAP levels increased. Similarly, expression of S100B, VIM, and ALDH1L1 also gradually increased from day 5 to day 30 during the differentiation protocol (FIG. 21*b*, FIG. 23*b*). The addition of fetal bovine serum (fbs), which is frequently used to derive astrocytes 36,37, decreased, but did not abolish, the expression of all genes tested (FIG. 23*b*). However, fbs aided in the passaging steps of these cells for further expansion and was therefore included in the differentiation protocol. We also performed bulk RNA-seq throughout the course of astrocytic cell differentiation and observed that expression levels of a number of astrocyte marker genes gradually increased starting from day 15 and by day 30 reached levels similar to that of human primary astrocytes. Moreover, these expression levels were still high at day 67 and day 114 in conditions combining transcription activation, morphogen, and fbs, whereas undifferentiated hESCs and hESCs only exposed to morphogen lacked high expression levels for the majority of astrocyte marker genes (FIG. 5*a*, FIG. 23*c*). Consistent with our qPCR results, addition of fbs decreased expression levels of astrocyte marker genes at day 30, whereas expression levels of these marker genes was high at day 67 and day 114 for the same condition (FIG. 5*a*, FIG. 23*c*). Comparison to single-cell RNA-seq (scRNA-seq) datasets of fetal human cortex38,39 and single-nuclei RNA-seq dataset of adult human brain40 showed similar trends: gradually increasing correlations to astrocytes in adult human brain (FIG. 24*a*) and fetal human cortex (FIG. 24*c*) from day 15 to day 30, particularly for conditions with transcription activation and morphogen. Addition of fbs decreased this trend (FIG. 24*a*). We also analyzed expression levels of marker genes of other cell types, such as radial glia (RG), intermediate progenitor cells (IPC), excitatory neurons, and inhibitory neurons, among the samples throughout the course of astrocytic cell differentiation (FIG. 5*a*, FIG. 23*c*), and derived transcriptomic correlations between these samples and corresponding cell types in fetal human cortex and adult human brain (FIGS. 24A-24C). Although these comparisons suggest there is some heterogeneity in the populations of cells arising from the astrocytic cell differentiation protocols at the transcriptomic level, immunostaining, qPCR and RNA-seq profiles of marker genes support the identity of these cells as astrocytic, and we therefore co-cultured them in 3D tissues with iN cells for further experiments (FIG. 5*b*).

TABLE 32

Description of abbreviations for cell type clusters defined by scRNA-seq in the human fetal cortex (Nowakowski et al., 2017).

| Cell Type Cluster Name | Description |
|---|---|
| EN-PFC1 | Early Born Deep Layer/subplate Excitatory Neuron PFC |
| EN-PFC2 | Early and Late Born Excitatory Neuron PFC |
| EN-PFC3 | Early and Late Born Excitatory Neuron PFC |
| EN-V1-3 | Excitatory Neuron V1 - late born |
| EN-V1-2 | Early and Late Born Excitatory Neuron V1 |
| EN-V1-1 | Early Born Deep Layer/subplate Excitatory Neuron V1 |
| nEN-early1 | Newborn Excitatory Neuron - early born |
| nEN-early2 | Newborn Excitatory Neuron - early born |
| nEN-late | Newborn Excitatory Neuron - late born |
| IN-CTX-CGE1 | CGE/LGE-derived inhibitory neurons |
| IN-CTX-CGE2 | CGE/LGE-derived inhibitory neurons |
| IN-CTX-MGE1 | MGE-derived Ctx inhibitory neuron, Germinal Zone Enriched |
| IN-CTX-MGE2 | MGE-derived Ctx inhibitory neuron, Cortical Plate-enriched |
| IN-STR | Striatal neurons |
| nIN1 | MGE newborn neurons |
| nIN2 | MGE newborn neurons |
| nIN3 | MGE newborn neurons |
| nIN4 | MGE newborn neurons |
| nIN5 | MGE newborn neurons |
| IPC-div1 | Dividing Intermediate Progenitor Cells RG-like |
| IPC-div2 | Intermediate Progenitor Cells RG-like |
| IPC-nEN1 | Intermediate Progenitor Cells EN-like |
| IPC-nEN2 | Intermediate Progenitor Cells EN-like |
| IPC-nEN3 | Intermediate Progenitor Cells EN-like |
| MGE-IPC1 | MGE Progenitors |
| MGE-IPC2 | MGE Progenitors |
| MGE-IPC3 | MGE Progenitors |
| MGE-div | dividing MGE Progenitors |
| Astrocyte | Astrocyte |
| MGE-RG1 | MGE Radial Glia 1 |
| MGE-RG2 | MGE Radial Glia 2 |
| oRG | Outer Radial Glia |
| RG-div1 | Dividing Radial Glia (G2/M-phase) |
| RG-div2 | Dividing Radial Glia (S-phase) |
| RG-early | early RG |
| tRG | Truncated Radial Glia |
| vRG | Ventricular Radial Glia |

Figure 24D:
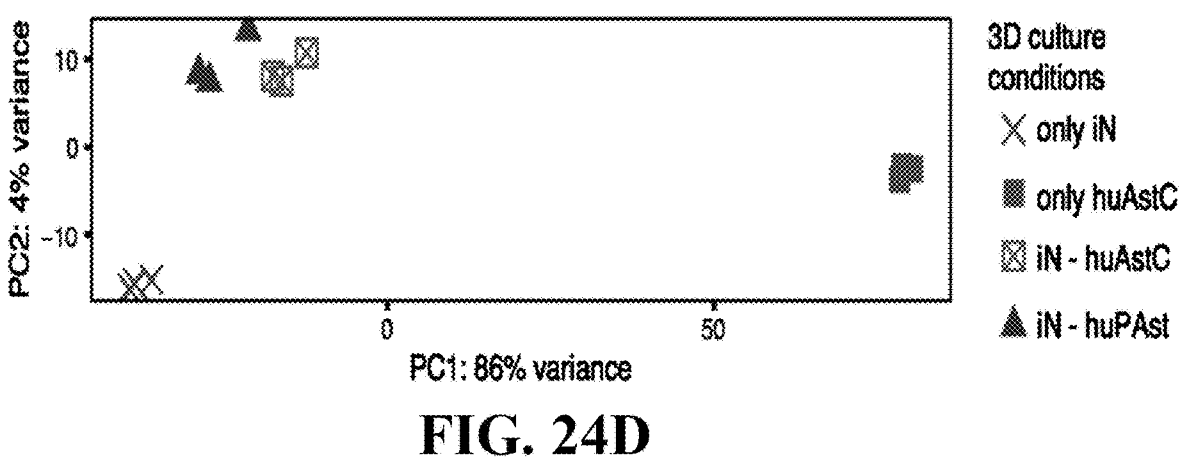
Figure 24E:
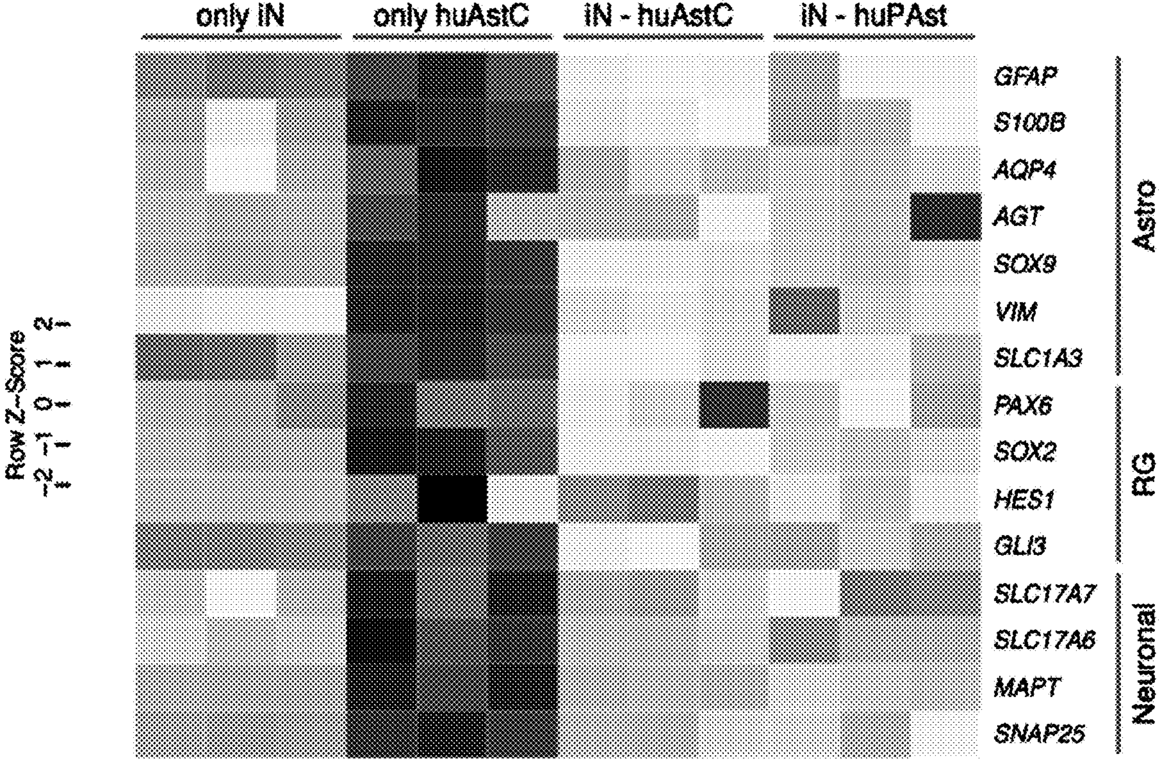

To examine the impact of astrocytic cells on iN cells, we compared the gene expression profiles of iN cells co-cultured with differentiated astrocytic cells, human primary astrocytes, or cultured without any astrocytic cells. We performed fluorescent-activated cell sorting (FACS) of iN cells from all cultures at week 5 with minimal cell contamination from astrocytic cells or human primary astrocytes (FIGS. 24D, 24E). Gene expression profiling showed that astrocytic cells cause gene expression differences in iN cells close to that caused by human primary astrocytes (FIGS. 5C-5E), further supporting the astrocytic-like cell fate arising from our differentiation protocol.

Figure 5G:
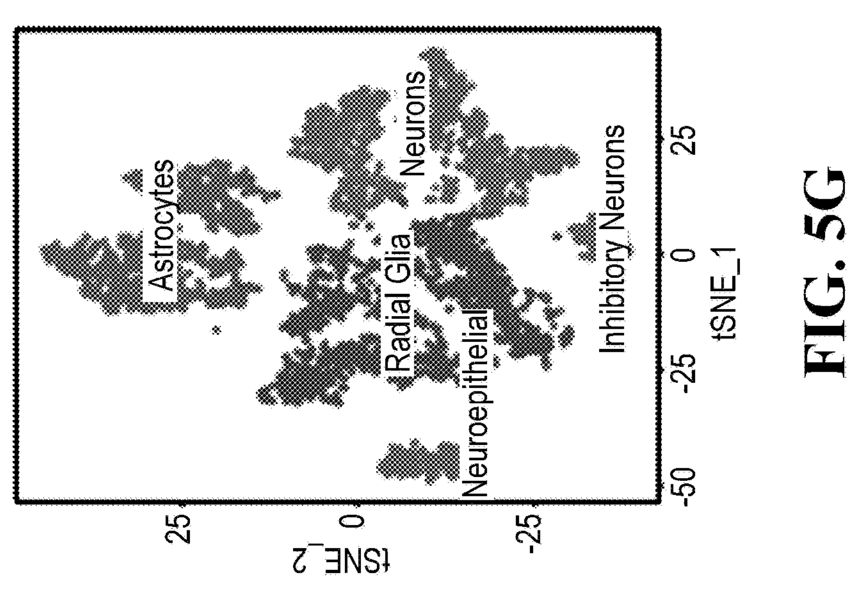
Figure 5F:
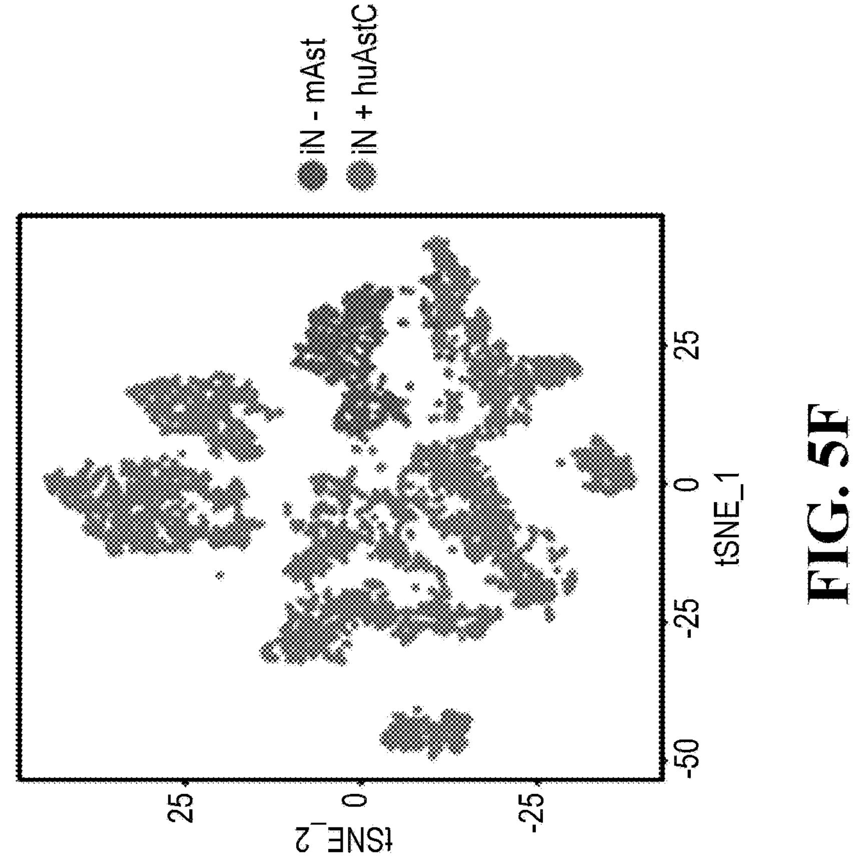
Figures 25A, 25B:
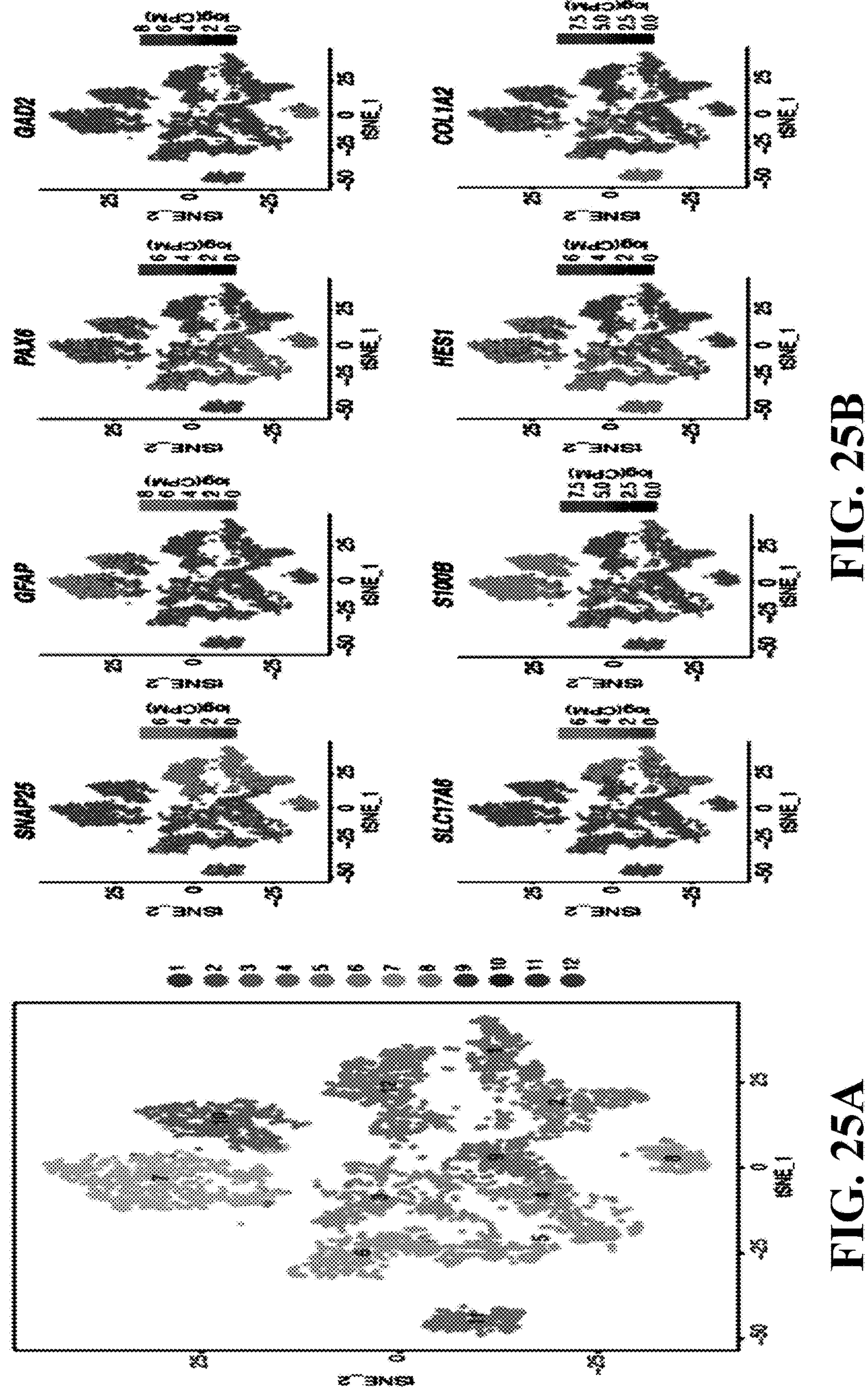
FIGS. 25A-25G: Analysis of scRNA-seq data.
Figure 25C:
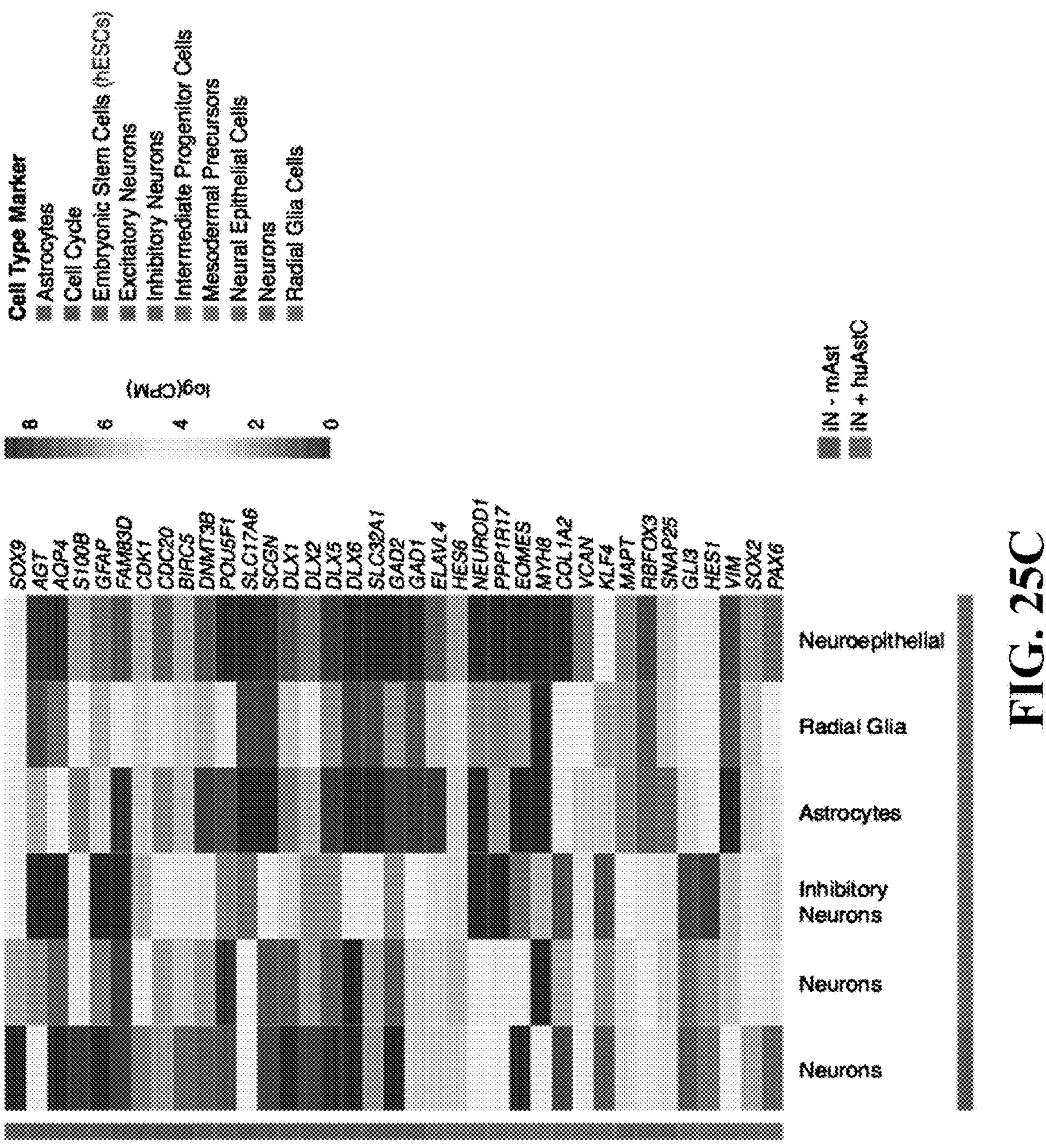
Figure 25D:
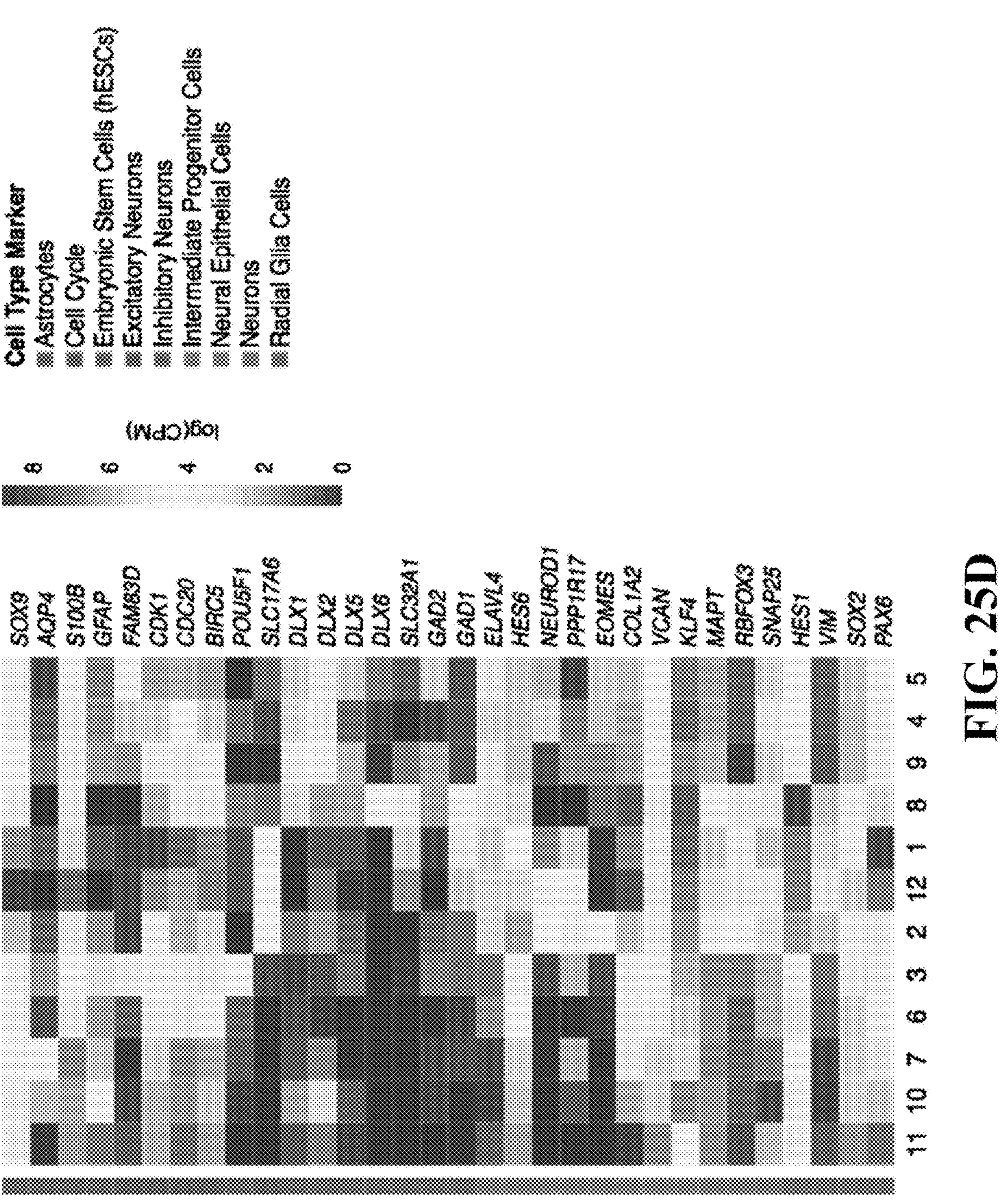

To further explore the cell fates and transcriptional profiles of the cells in our tissues, we performed single-cell sequencing on 3D co-cultures of human iN cells with mouse astrocytes and with human astrocytic cells in CH 4× cross-linker at week 5. We performed clustering on scRNA-seq profiles of human cells in both 3D co-cultures and identified 12 clusters (FIG. 5*f*, FIG. 25*a*), and using various cell type marker genes (FIGS. 25B-25D) we classified 5 main clusters of cell types: neurons, astrocytes, inhibitory neurons, RG, and neuroepithelial (FIG. 5*g*). iN cells co-cultured with mouse astrocytes contained only neuron cells (only reads aligning to the human genome were analyzed), whereas iN cells co-cultured with human astrocytic cells contained cells from clusters of neurons, astrocytes, inhibitory neurons, RG, and neuroepithelial (FIG. 5*h*), suggesting that the astrocytic cell differentiation protocol generates other transcriptionally distinct cell types in addition to astrocytes, which was also observed in bulk RNA-seq (FIG. 5*a*, Supplementary FIG. 18*c*, FIGS. 24A-24C).

Figures 5H, 5I, 5J, 5K:
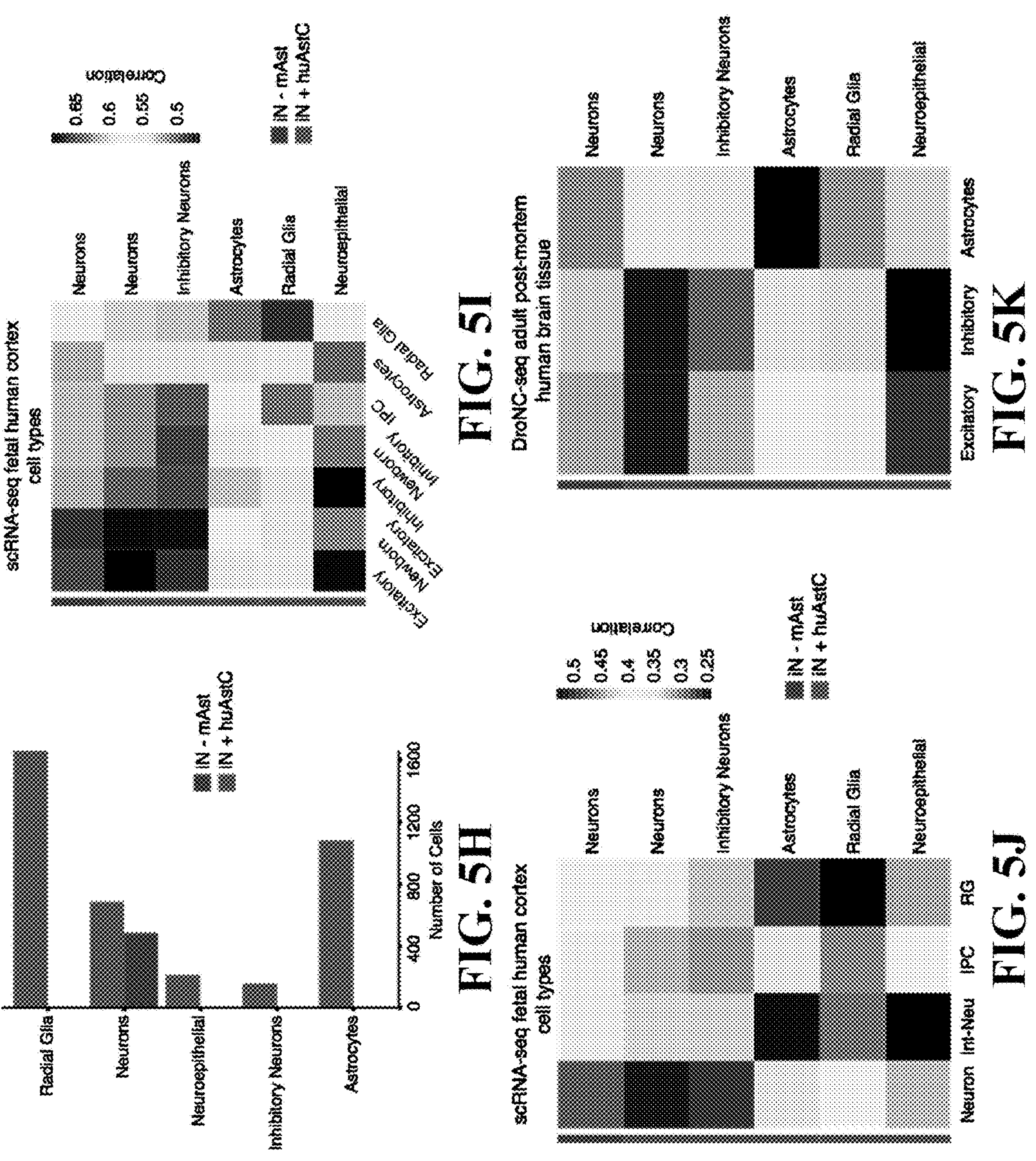
Figure 5L:
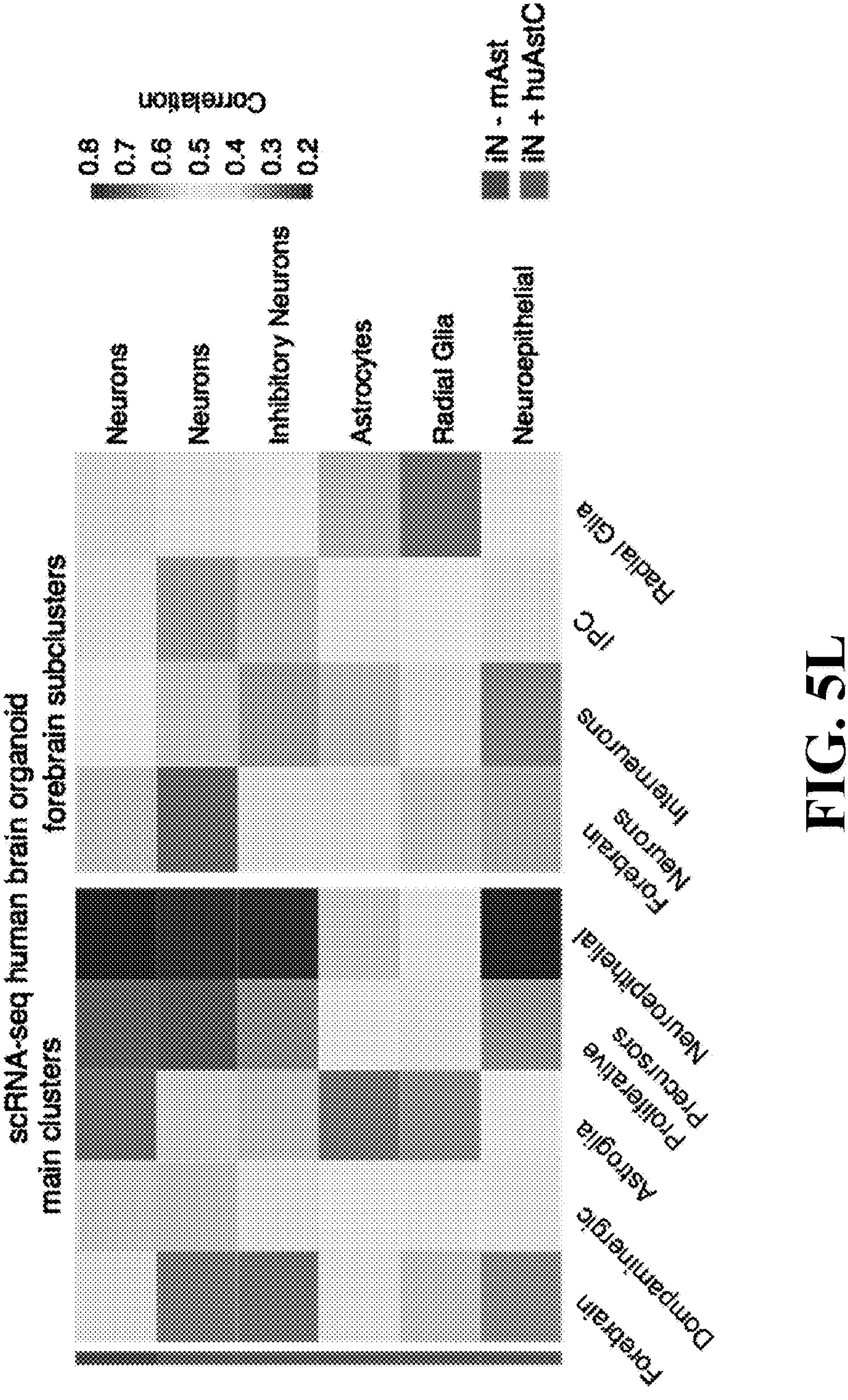
Figures 25E, 25F, 25G:
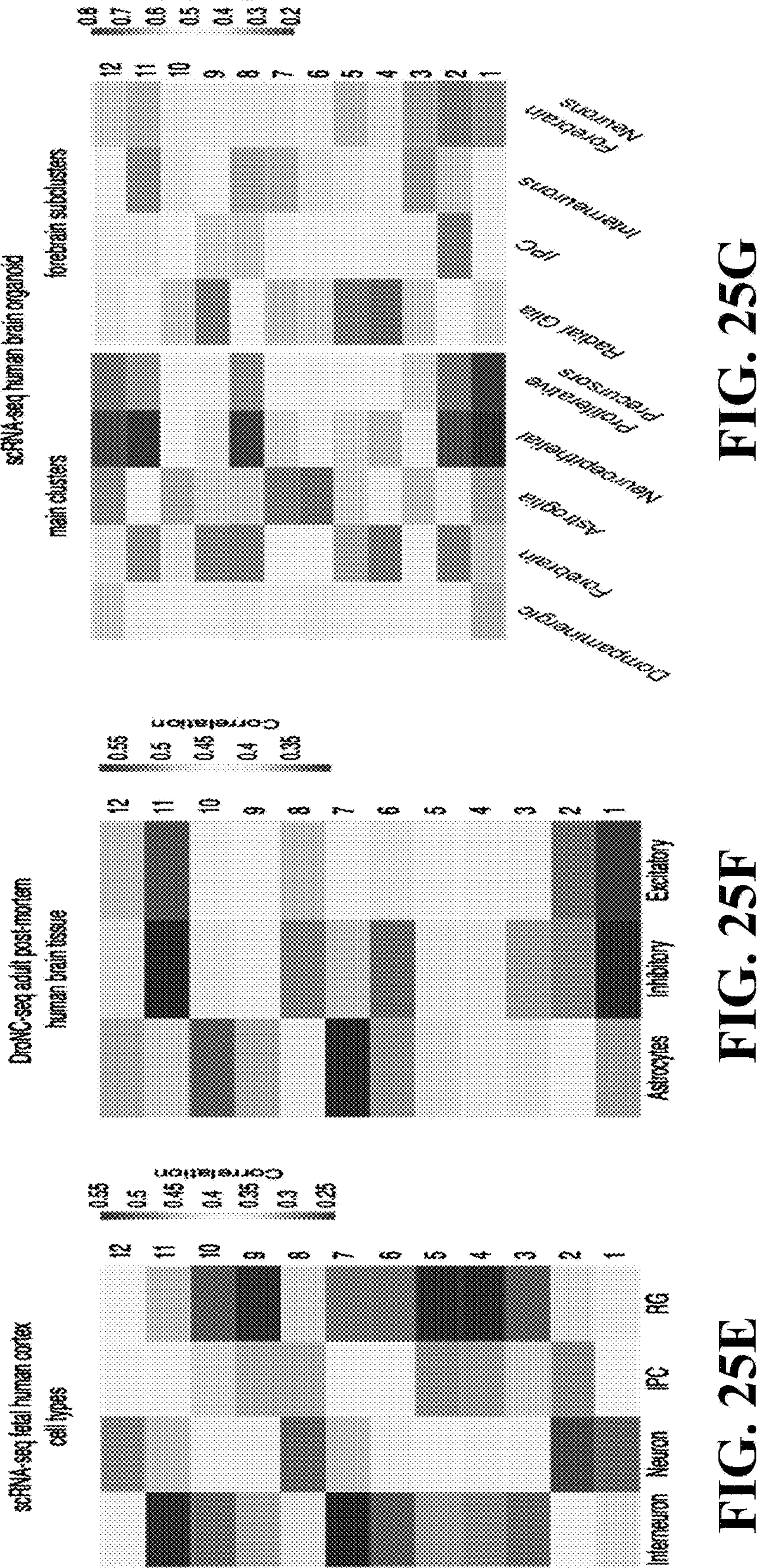
Figures 26A, 26B:
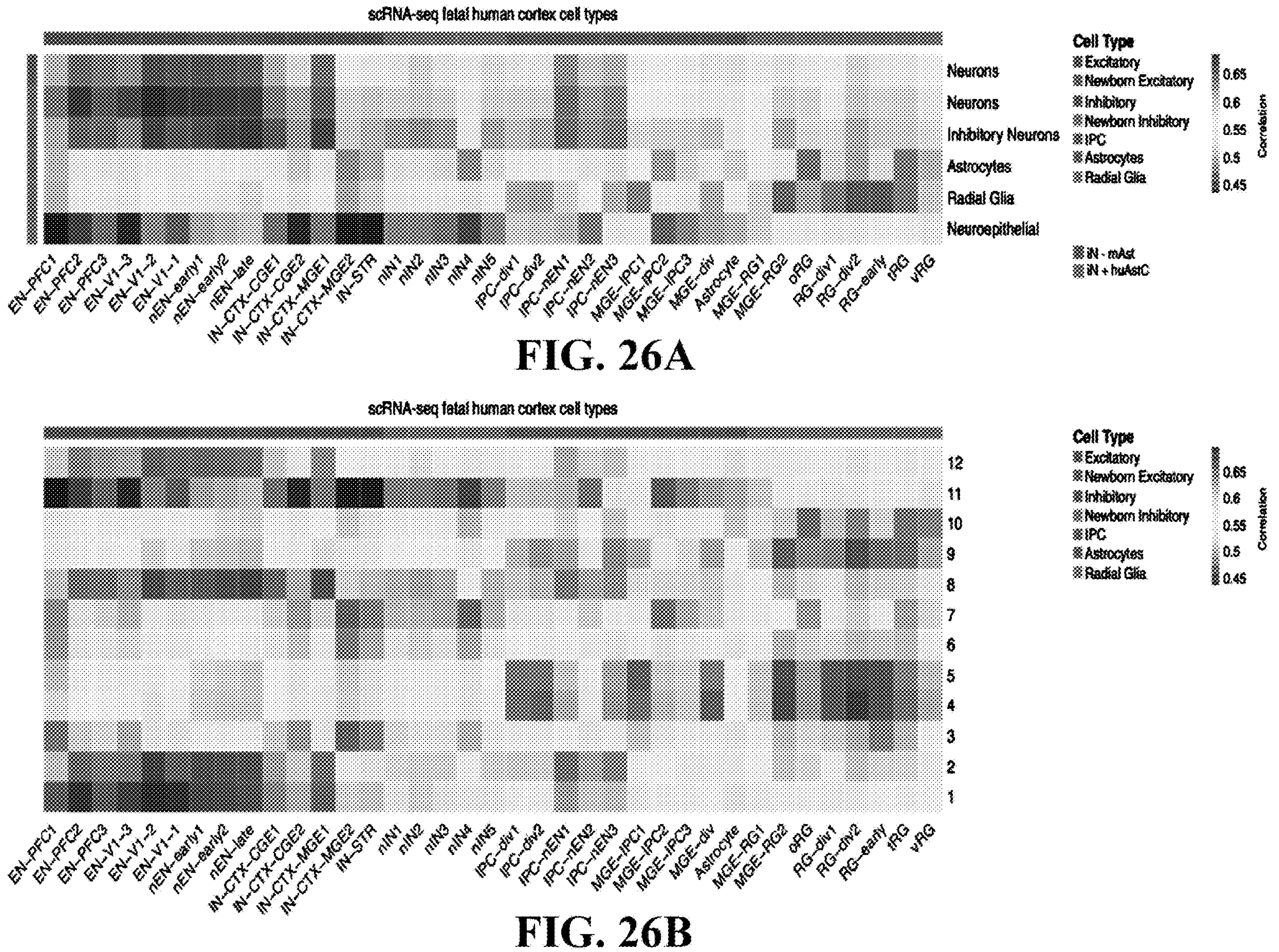
FIGS. 26A-26F: Comparison of scRNA-seq data of 3D neural tissues and scRNA-seq data of six-month-old human brain organoids to scRNA-seq data of fetal human cortex.
Figures 26C, 26D, 26E, 26F:
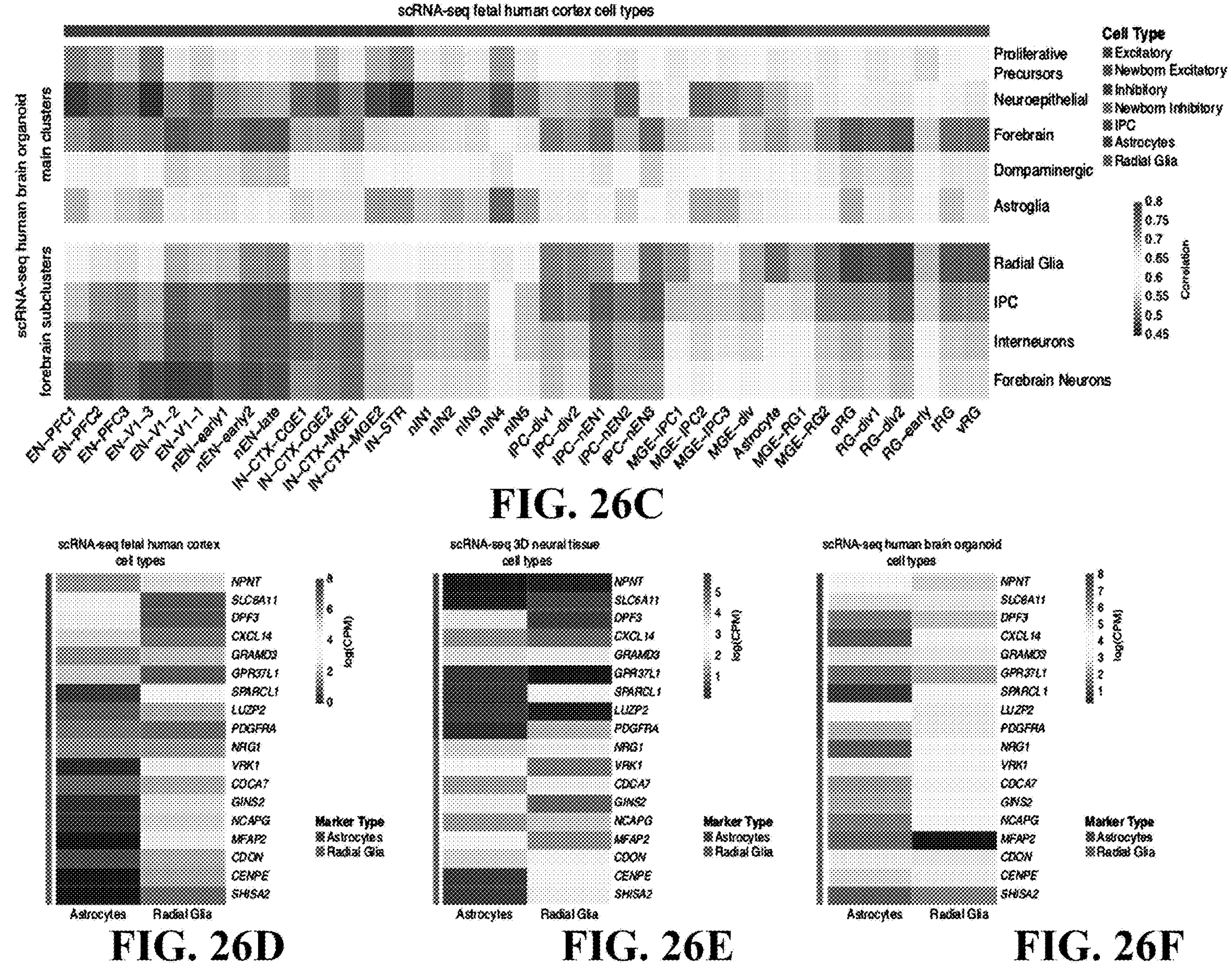
Figures 28A, 28B, 28C, 28D, 28E:
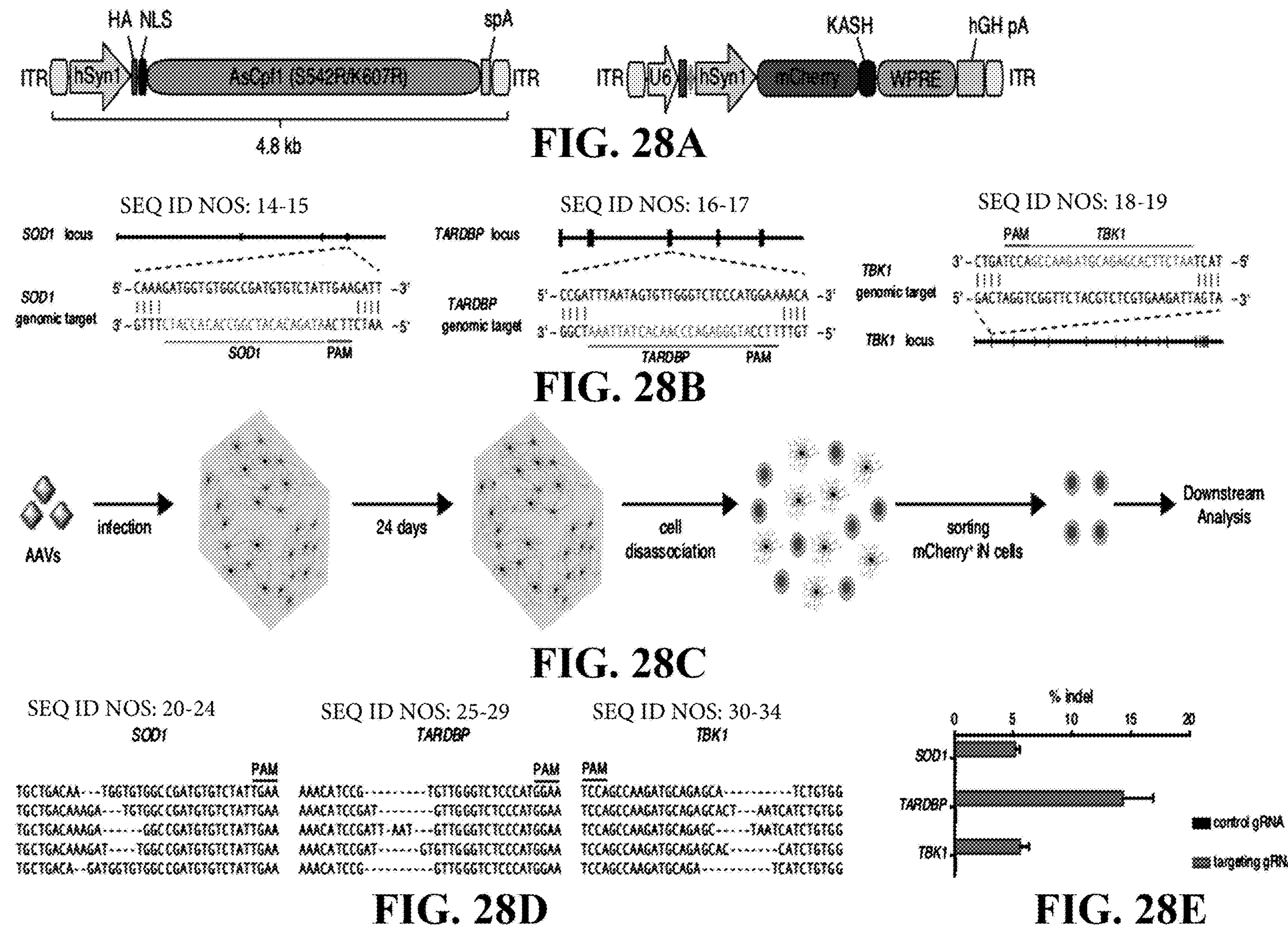
FIGS. 28A-28E: Perturbation of disease-implicated genes in 3D tissues composed of human iN and astrocytic cells.

It was next examined whether cell type clusters we identified in our 3D tissues transcriptionally resemble their counterparts in human brain by comparing our data to scRNA-seq datasets of fetal human cortex38,39 and single-nuclei RNA-seq datasets of adult human brain40. Although we see some expression of marker genes for IPCs, the transcriptomic correlation of our neurons cluster to neurons in the fetal human cortex is higher than its correlation to IPCs in fetal human cortex (FIGS. 5I, 5J, FIG. 25*e*, FIGS. 26A, 26B). Moreover, our neurons cluster showed a high transcriptomic correlation to different types of excitatory neurons in the fetal human cortex data, such as early and late born excitatory neurons in the primary visual cortex (EN-V1-2) and prefrontal cortex (EN-PFC2), and in the adult human brain (FIGS. 5I, 5K, FIG. 20*f*, Supplementary FIG. 26*a,b*). In addition, the gene expression profile of our RG cluster correlates more with RG cells in the fetal human cortex, such as early RG (RG-early), dividing RG (RG-div2), and medial ganglionic eminence RG (MGE-RG2), which can give rise to inhibitory neurons39 (FIGS. 5I, 5J, FIG. 25*e*, FIGS. 26A, 26B). Although our inhibitory neurons cluster transcriptionally correlates with both inhibitory neuron types (such as IN-CTX-MGE 1; MGE-derived cortex inhibitory neurons) and excitatory neuron types identified in the fetal human cortex (FIG. 5*i*, Supplementary FIG. 26*a,b*), in the adult human brain, it correlates most highly with inhibitory neurons (FIG. 5*k*, FIG. 25*f*). Similarly, although our astrocyte cluster correlates more highly with RG cells than with astrocytes in the fetal human cortex (FIG. 5*i*, FIGS. 26A, 26B), its transcriptome correlation with astrocytes in the adult human brain is higher than its correlation to other cell types (FIG. 5*k*, FIG. 25*f*). This trend is also observed in comparisons between scRNA-seq data from six-month-old human brain organoids16 and scRNA-seq data from the fetal human cortex39 (FIG. 26*c*). To explore this further, we performed differential expression analysis between astrocytes and RG cells in the scRNA-seq dataset of the human fetal cortex39 and identified the top 9 astrocyte-specific genes and top 9 RG-specific genes based on log fold change (FIG. 26*d*). The average expression levels of these genes in the astrocyte and RG clusters in our 3D tissue and in data from the six-month-old human brain organoids varies between these cell types (FIGS. 26E, 26F), indicating that in both our 3D tissues and the human brain organoids, astrocytic-like cells are present, but they are not transcriptionally homogenous. Taken together, these results demonstrated that cell types in our 3D tissue transcriptionally resemble their analogues in fetal human cortex and adult human brain. Finally, comparison between scRNA-seq profiles of our 3D tissues and scRNA-seq dataset of six-month-old human brain organoids16 revealed that our cell type clusters show transcriptome correlation with their counterparts in six-month-old human brain organoids (FIG. 5I, FIG. 25*g*).

Example 6. CRISPR-Mediated Genome Editing in Engineered 3D Neural Tissues

As a proof-of-concept, we tested the feasibility of performing CRISPR-mediated genome editing in our engineered 3D neural tissues in a disease context. Using Cpf1-mediated genome editing via AAV-based gene delivery[41,42], we targeted SOD1, TARDBP and TBK1, genes implicated in ALS and frontotemporal dementia (FTD)[43-46]. We identified indels in three independently targeted loci and found ~5%, ~14%, and ~6% indel formation in SOD1, TARDBP, and TBK1, respectively (FIG. 27, 28). These results show that our 3D human neural tissue system can be combined with genome-engineering and gene-delivery tools to perturb genes implicated in neurodegenerative diseases.

Discussion 3D neural tissues have the potential to be tractable models for studying the human brain and neurological disorders, but to achieve this potential, they must closely reflect the cell composition, ECM, and gene expression profiles of the human brain. Here we analyzed how the transcriptome of iN cells in 3D tissues relates to the human brain transcriptome and is affected by a number of tissue engineering variables. Furthermore, we developed an approach to generate co-cultured iN and astrocytic cells derived from hESCs in a 3D matrix that could be tuned to reflect different transcriptomic states of the human developing brain transcriptome, which will be helpful for the rapid generation of complex neurological disease models.

To gain a global view of the brain-like properties of these engineered tissues, we compared the transcriptomes of cells cultured in 3D versus 2D and found more enriched neuronal biological processes in iN cells cultured in 3D Matrigel than 2D cultured cells (FIG. 1*f*), which was not affected by batch-to-batch variation in Matrigel (FIGS. 8A-8C). In addition, transcriptome profiling showed enriched apoptotic and oxidative stress biological processes in 2D cultures compared to 3D cultures and 3D cultures enabled electrophysiological measurements (FIGS. 7A, 7B, 9A-9C), both suggesting that iN cells in 3D cultures were healthier than cells in 2D cultures, although we did not directly test cell viability. In addition, we co-cultured iN cells with mouse astrocytes both in 3D and on 2D. Although iN cells in both co-cultures were electrophysiologically active at later timepoints, the transcriptome of 3D co-cultured iN cells was more enriched in neuronal biologically processes than that of iN cells on 2D, indicating 3D tissues offer a closer approximation to the biology than 2D tissues. Varying cell seeding densities or independent components of the encapsulating matrix (e.g., laminin, collagens, or synthetic hydrogels) may lead to different characteristics of the iN cells, avenues which could be explored in future functional studies.

Engineered neural tissues can be made more brain-like by adding other ECM components, such as HA, which has been shown to promote better replication of the brain microenvironment 29-31. Under the conditions we tested, however, incorporation of HA in our 3D Matrigel co-cultures of iN cells did not strongly improve the correlation with the transcriptome of the human developing brain, although some individual neuronal transcripts as well as genes associated with neurological diseases were upregulated (FIG. 2*e* and FIG. 4*c*). We chose to use a high-molecular weight HA and incorporated it in a high concentration of Matrigel (which showed a storage modulus closed to Matrigel without HA due to the uncrosslinked state of HA in Matrigel) to minimize its diffusion from the hydrogel structures while maintaining its natural state 26,28. However, other variables (such as chemical modifications, concentration, and the source of HA 47,48) or shorter culture times (such as 1 week) that were not tested may have a greater impact on gene expression. Given that high-molecular weight HA is thought to inhibit remyelination following central nervous system (CNS) injury 26,49, introducing HA into hydrogels could impede expression of genes involved in neuronal development.

Matrix stiffness in engineered tissues can also impact cellular properties and can be increased in a pure Matrigel hydrogel simply by increasing the concentration of Matrigel 33,50. Alternatively, in a CH, stiffness can be increased by increasing the amount of crosslinker while holding the concentration of alginate and Matrigel constant 33. We therefore investigated whether developing 3D co-cultures of iN cells within CHs of Matrigel and alginate improved the transcriptomic correlation to human brain samples. Alginate is a naturally occurred polysaccharide, composed of mannuronic acid and guluronic acid with no cell adhesion ligands, that can be crosslinked to form a network within Matrigel through addition of divalent cations such as calcium (Ca+2) 33. We demonstrated that increasing the crosslinking of the alginate network in CHs (which lead to an increase in storage modulus) can tune the correlation of the transcriptome of 3D co-cultured iN cells to the transcriptome of particular sub-regions of the human brain at specific developmental stages. Furthermore, modulating the amount of crosslinker and/or the volume of the CH led to gene expression changes in specific neuronal transcripts, including DLG4, GRIN3A, and SOD1 as well as changes in expression levels of genes associated with neurological diseases (FIGS. 3A-3E and FIG. 4*c*). As HA was previously integrated in crosslinked alginate hydrogels 51, we incorporated HA in CHs of Matrigel and alginate and, in agreement with our other results, found it had little effect. It will be informative to analyze the effects of changing the hydrogel volume or removing the Matrigel on cellular state to better understand how these parameters impact gene expression.

To better model cell composition in human brain within our 3D tissues, we first developed a method to derive human astrocytic cells directly from hESCs. We exploited a previously reported transient neural progenitor state of stem cells induced by overexpression of neurogenins 18 to differentiate cells towards an astrocytic phenotype. Immunostaining, qPCR, and bulk RNA-seq showed that the derived astrocytic cells express astrocyte markers and that this expression increases over time. By day 15, we could detect the expression of marker genes for astrocytic cells, inhibitory neurons, and RG, offering the potential to rapidly create 3D tissues with controlled composition of these cell types by generating reporter cell lines using these markers. Using single-cell RNA sequencing, we evaluated the gene expression profiles of the cells arising from our differentiation protocols and compared these to published transcriptional datasets of fetal and adult human brain as well as human brain organoids. We found that the cells present in our 3D co-cultured tissues broadly reflect their counterparts in the human brain, and we observed interesting similarities between the gene expression profiles in our system and in human brain organoids as they relate to the human brain data. Overall, these results suggest that we were able to generate relevant cell types, but further functional studies are required to fully characterize these astrocytic cells and inhibitory neurons in our system and it will be informative to test additional differentiation protocols (such as use of other transcription factors or small molecules) to further expand the cells types that can be studied in this system.

Our method of deriving both iN and astrocytic cells from the same pool of hESCs allows for the rapid creation of engineered tissues with an isogenic background. These 3D tissues composed of iN cells (at day 35) and astrocytic cells (at day 118) exhibit transcriptional profiles that correlate with relevant cell types in the human brain as well as with six-month-old human brain organoids, suggesting this system may be a faster alternative to organoids. To show the potential for studying the genetics of neurodegenerative diseases in our 3D neural tissues, we perturbed three genes implicated in ALS and FTD using Cpf152 directly in iN cells, and observed at least 5% indel formation rates for each gene. Directly injecting AAV mixtures within 3D tissues instead of mixing with culture medium could be tested in future studies to improve indel rates. This approach could be extended by independently targeting astrocytic cells within 3D tissues by using the GFAP promoter in gene editing constructs.

Despite the potential for this approach as a scalable method for interrogating the genetics of brain disorders, there are a number of limitations and challenges. All 3D tissue models are limited in their ability to recapitulate complex environmental features, such as the interplay between the immune system and the central nervous system, vasculature and the signals that are distributed through this network, and aging. Nevertheless, as the technology and our understanding of the brain advances, it should be possible to develop increasingly complex tissues that contain multiple cell types that develop over time.

REFERENCES

1 Bulik-Sullivan, B. et al. An atlas of genetic correlations across human diseases and traits. Nature Genetics 47, 1236-+, doi:10.1038/ng.3406 (2015).

2 Quadrato, G., Brown, J. & Arlotta, P. The promises and challenges of human brain organoids as models of neuropsychiatric disease. Nature Medicine 22, 1220-1228, doi:10.1038/nm.4214 (2016).

3 Lambert, J. C. et al. Meta-analysis of 74,046 individuals identifies 11 new susceptibility loci for Alzheimer's disease. Nature Genetics 45, 1452-U1206, doi:10.1038/ng.2802 (2013).

4 McCarro, S. A., Feng, G. P. & Hyman, S. E. Genome-scale neurogenetics: methodology and meaning. Nature Neuroscience 17, 756-763, doi: 10.1038/nn.3716 (2014).

5 Gandhi, S. & Wood, N. W. Genome-wide association studies: the key to unlocking neurodegeneration? Nature Neuroscience 13, 789-794, doi: 10.1038/nn.2584 (2010).

6 Choi, S. H. et al. A three-dimensional human neural cell culture model of Alzheimer's disease. Nature 515, 274-U293, doi:10.1038/naturel3800 (2014).

7 Tang-Schomer, M. D. et al. Bioengineered functional brain-like cortical tissue. Proceedings of the National Academy of Sciences of the United States of America 111, 13811-13816, doi:10.1073/pnas.1324214111 (2014).

8 Schwartz, M. P. et al. Human pluripotent stem cell-derived neural constructs for predicting neural toxicity. Proceedings of the National Academy of Sciences of the United States of America 112, 12516-12521, doi:10.1073/pnas.1516645112 (2015).

9 Kim, S. H. et al. Anisotropically organized three-dimensional culture platform for reconstruction of a hippocampal neural network. Nature Communications 8, doi: 10.1038/ncommsl4346 (2017).

10 Grealish, S. et al. Human ESC-Derived Dopamine Neurons Show Similar Preclinical Efficacy and Potency to Fetal Neurons when Grafted in a Rat Model of Parkinson's Disease. Cell Stem Cell 15, 653-665, doi:10.1016/j.stem.2014.09.017 (2014).

11 Dimos, J. T. et al. Induced pluripotent stem cells generated from patients with ALS can be differentiated into motor neurons. Science 321, 1218-1221, doi: 10.1126/science. 1158799 (2008).

12 Pasca, A. M. et al. Functional cortical neurons and astrocytes from human pluripotent stem cells in 3D culture. Nature Methods 12, 671-+, doi:10.1038/nmeth.3415 (2015).

13 Lancaster, M. A. et al. Cerebral organoids model human brain development and microcephaly. Nature 501, 373-+, doi:10.1038/naturel2517 (2013).

14 Qian, X. Y. et al. Brain-Region-Specific Organoids Using Mini-bioreactors for Modeling ZIKV Exposure. Cell 165, 1238-1254, doi:10.1016/j.cell.2016.04.032 (2016).

15 Kraehenbuehl, T. P., Langer, R. & Ferreira, L. S. Three-dimensional biomaterials for the study of human pluripotent stem cells. Nature Methods 8, 731-736, doi:10.1038/nmeth.1671 (2011).

16 Quadrato, G. et al. Cell diversity and network dynamics in photosensitive human brain organoids. Nature 545, 48-+, doi:10.1038/nature22047 (2017).

17 Camp, J. G. et al. Human cerebral organoids recapitulate gene expression programs of fetal neocortex development. Proceedings of the National Academy of Sciences of the United States of America 112, 15672-15677, doi: 10.1073/pnas.1520760112 (2015).

18 Busskamp, V. et al. Rapid neurogenesis through transcriptional activation in human stem cells. Molecular Systems Biology 10 (2014).

19 Zhang, Y. S. et al. Rapid Single-Step Induction of Functional Neurons from Human Pluripotent Stem Cells. Neuron 78, 785-798, doi:10.1016/j.neuron.2013.05.029 (2013).

20 Pang, Z. P. P. et al. Induction of human neuronal cells by defined transcription factors. Nature 476, 220-U122, doi: 10.1038/naturel0202 (2011).

21 Chanda, S. et al. Generation of Induced Neuronal Cells by the Single Reprogramming Factor ASCL1. Stem Cell Reports 3, 282-296, doi:10.1016/j.stemcr.2014.05.020 (2014).

22 Lam, R. S., Topfer, F. M., Wood, P. G., Busskamp, V. & Bamberg, E. Functional Maturation of Human Stem Cell-Derived Neurons in Long-Term Cultures. Plos One 12, doi:10.1371/journal.pone.0169506 (2017).

23 Yi, F. et al. Autism-associated SHANK3 haploinsufficiency causes I-h channelopathy in human neurons. Science 352, doi:10.1126/science.aaf2669 (2016).

24 Huang, Y.-W. A., Zhou, B., Wernig, M. & Südhof, T. C. ApoE2, ApoE3, and ApoE4 Differentially Stimulate APP Transcription and Aβ Secretion. Cell 168, 427-441.e421, doi:http://doi.org/10.1016/j.cell.2016.12.044 (2017).

25 Carlson, A. L. et al. Generation and transplantation of reprogrammed human neurons in the brain using 3D microtopographic scaffolds. Nature Communications 7, doi:10.1038/ncomms10862 (2016).

26 Lau, L. W., Cua, R., Keough, M. B., Haylock-Jacobs, S. & Yong, V. W. OPINION Pathophysiology of the brain extracellular matrix: a new target for remyelination. Nature Reviews Neuroscience 14, 722-729, doi: 10.1038/nrn3550 (2013).

27 Tang, X. et al. Astroglial cells regulate the developmental timeline of human neurons differentiated from induced pluripotent stem cells. Stem Cell Research 11, 743-757, doi:10.1016/j.scr.2013.05.002 (2013).

28 Margolis, R. U., Margolis, R. K., Chang, L. B. & Preti, C. Glycosaminoglycans of brain during development. Biochemistry 14, 85-88, doi:10.1021/bi00672a014 (1975).

29 Bozza, A. et al. Neural differentiation of pluripotent cells in 3D alginate-based cultures. Biomaterials 35, 4636-4645, doi:10.1016/j.biomaterials.2014.02.039 (2014).

30 Brannvall, K. et al. Enhanced neuronal differentiation in a three-dimensional collagen-hyaluronan matrix. Journal of Neuroscience Research 85, 2138-2146, doi:10.1002/jnr.21358 (2007).

31 Seidlits, S. K. et al. The effects of hyaluronic acid hydrogels with tunable mechanical properties on neural progenitor cell differentiation. Biomaterials 31, 3930-3940, doi:10.1016/j.biomaterials.2010.01.125 (2010).

32 Khetan, S. et al. Degradation-mediated cellular traction directs stem cell fate in covalently crosslinked three-dimensional hydrogels. Nature Materials 12, 458-465, doi:10.1038/nmat3586 (2013).

33 Chaudhuri, O. et al. Extracellular matrix stiffness and composition jointly regulate the induction of malignant phenotypes in mammary epithelium. Nature Materials 13, 970-978, doi: 10.1038/nmat4009 (2014).

34 Chaudhuri, O. et al. Hydrogels with tunable stress relaxation regulate stem cell fate and activity. Nature Materials 15, 326-+, doi:10.1038/nmat4489 (2016).

35 Huebsch, N. et al. Harnessing traction-mediated manipulation of the cell/matrix interface to control stem-cell fate. Nature Materials 9, 518-526, doi:10.1038/nmat2732 (2010).

36 Shaltouki, A., Peng, J., Liu, Q. Y., Rao, M. S. & Zeng, X. M. Efficient Generation of Astrocytes from Human Pluripotent Stem Cells in Defined Conditions. Stem Cells 31, 941-952, doi:10.1002/stem.1334 (2013).

37 Chojnacki, A. & Weiss, S. Production of neurons, astrocytes and oligodendrocytes from mammalian CNS stem cells. Nature Protocols 3, 935-940, doi:10.1038/nprot.2008.55 (2008).

38 Pollen, A. A. et al. Molecular Identity of Human Outer Radial Glia during Cortical Development. Cell 163, 55-67, doi:10.1016/j.cell.2015.09.004 (2015).

39 Nowakowski, T. J. et al. Spatiotemporal gene expression trajectories reveal developmental hierarchies of the human cortex. Science 358, 1318-1323, doi:10.1126/science.aap8809 (2017).

40 Habib, N. et al. Massively parallel single-nucleus RNA-seq with DroNc-seq. Nature Methods 14, 955-+, doi: 10.1038/nmeth.4407 (2017).

41 Zetsche, B. et al. Multiplex gene editing by CRISPR-Cpf1 using a single crRNA array. Nature Biotechnology 35, 31-34, doi:10.1038/nbt.3737 (2017).

42 Zetsche, B. et al. Cpf1 Is a Single RNA-Guided Endonuclease of a Class 2 CRISPR-Cas System. Cell 163, 759-771, doi:10.1016/j.cell.2015.09.038 (2015).

43 Renton, A. E., Chio, A. & Traynor, B. J. State of play in amyotrophic lateral sclerosis genetics. Nature Neuroscience 17, 17-23, doi: 10.1038/nn.3584 (2014).

44 Katz, J. S., Katzberg, H. D., Woolley, S. C., Marklund, S. L. & Andersen, P. M. Combined fulminant frontotemporal dementia and amyotrophic lateral sclerosis associated with an I113T SOD1 mutation. Amyotrophic Lateral Sclerosis 13, 567-569, doi:10.3109/17482968.2012.678365 (2012).

45 Mackenzie, I. R. A., Rademakers, R. & Neumann, M. TDP-43 and FUS in amyotrophic lateral sclerosis and frontotemporal dementia. Lancet Neurology 9, 995-1007, doi:10.1016/s1474-4422(10)70195-2 (2010).

46 Freischmidt, A. et al. Haploinsufficiency of TBK1 causes familial ALS and fronto-temporal dementia. Nature Neuroscience 18, 631-+, doi: 10.1038/nn.4000 (2015).

47 Burdick, J. A. & Prestwich, G. D. Hyaluronic Acid Hydrogels for Biomedical Applications. Advanced Materials 23, H41-H56, doi:10.1002/adma.201003963 (2011).

48 Brigham, M. D. et al. Mechanically Robust and Bioadhesive Collagen and Photocrosslinkable Hyaluronic Acid Semi-Interpenetrating Networks. Tissue Engineering Part A 15, 1645-1653, doi:10.1089/ten.tea.2008.0441 (2009).

49 Back, S. A. et al. Hyaluronan accumulates in demyelinated lesions and inhibits oligodendrocyte progenitor maturation. Nature Medicine 11, 966-972, doi: 10.1038/nm1279 (2005).

50 Zaman, M. H. et al. Migration of tumor cells in 3D matrices is governed by matrix stiffness along with cell-matrix adhesion and proteolysis. Proceedings of the National Academy of Sciences of the United States of America 103, 10889-10894, doi: 10.1073/pnas.0604460103 (2006).

51 Catanzano, O. et al. Alginate-hyaluronan composite hydrogels accelerate wound healing process. Carbohydrate Polymers 131, 407-414, doi:10.1016/j.carbpol.2015.06.081 (2015).

52 Gao, L. Y. et al. Engineered Cpf1 variants with altered PAM specificities. Nature Biotechnology 35, 789-792, doi: 10.1038/nbt.3900 (2017).
53 Patel, A. P. et al. Single-cell RNA-seq highlights intratumoral heterogeneity in primary glioblastoma. Science 344, 1396-1401, doi: 10.1126/science. 1254257 (2014).
54 Zheng, G. X. Y. et al. Massively parallel digital transcriptional profiling of single cells. Nature Communications 8, doi: 10.1038/ncomms 14049 (2017).
55 Picelli, S. et al. Full-length RNA-seq from single cells using Smart-seq2. Nature Protocols 9, 171-181, doi: 10.1038/nprot.2014.006 (2014).
56 Li, B. & Dewey, C. N. RSEM: accurate transcript quantification from RNA-Seq data with or without a reference genome. Bmc Bioinformatics 12, doi:10.1186/1471-2105-12-323 (2011).
57 Dobin, A. et al. STAR: ultrafast universal RNA-seq aligner. Bioinformatics 29, 15-21, doi:10.1093/bioinformatics/bts635 (2013).
58 Love, M. I., Huber, W. & Anders, S. Moderated estimation of fold change and dispersion for RNA-seq data with DESeq2. Genome Biology 15, doi:10.1186/s13059-014-0550-8 (2014).
59 Subramanian, A., Kuehn, H., Gould, J., Tamayo, P. & Mesirov, J. P. GSEA-P: A desktop application for Gene Set Enrichment Analysis. Bioinformatics 23, 3251-3253, doi:10.1093/bioinformatics/btm369 (2007).
60 Abel, O., Powell, J. F., Andersen, P. M. & Al-Chalabi, A. ALSoD: A user-friendly online bioinformatics tool for amyotrophic lateral sclerosis genetics. Human Mutation 33, 1345-1351, doi:10.1002/humu.22157 (2012).
61 Lill, C. M., Abel, O., Bertram, L. & Al-Chalabi, A. Keeping up with genetic discoveries in amyotrophic lateral sclerosis: The ALSoD and ALSGene databases. Amyotrophic Lateral Sclerosis 12, 238-249, doi:10.3109/17482968.2011.584629 (2011).
62 Van Cauwenberghe, C., Van Broeckhoven, C. & Sleegers, K. The genetic landscape of Alzheimer disease: clinical implications and perspectives. Genetics in Medicine 18, 421-430, doi:10.1038/gim.2015.117 (2016).
63 Nalls, M. A. et al. Large-scale meta-analysis of genome-wide association data identifies six new risk loci for Parkinson's disease. Nature Genetics 46, 989-+, doi: 10.1038/ng.3043 (2014).
64 Satija, R., Farrell, J. A., Gennert, D., Schier, A. F. & Regev, A. Spatial reconstruction of single-cell gene expression data. Nature Biotechnology 33, 495-U206, doi:10.1038/nbt.3192 (2015).
65 Shekhar, K. et al. Comprehensive Classification of Retinal Bipolar Neurons by Single-Cell Transcriptomics. Cell 166, 1308-+, doi:10.1016/j.cell.2016.07.054 (2016).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A tractable neural tissue culture, comprising a three-dimensional (3D) matrix, the 3D matrix comprising neuronal and/or glial cells cultured from a stem cell, a biological supporting material comprising a proliferation inhibitor, and one or more crosslinker, wherein the biological supporting material is a composite hydrogel comprising an basement membrane matrix and alginate;

wherein the concentration of the basement membrane matrix is about 1 mg/mL to about 10 mg/mL;

wherein the concentration of alginate is about 1 mg/mL to about 10 mg/mL;

wherein the concentration of the one or more crosslinker is about 1 mM to about 30 mM; and wherein the basement membrane matrix consists of laminin, collagen IV, growth factors, heparin sulfate proteoglycans, entactin, and nidogen.

2. The tractable neural tissue culture of claim 1, wherein the one or more crosslinker is independently selected from the group consisting of calcium chloride (CaCl2), zinc sulfate, aluminum chloride, and barium chloride.

3. The tractable neural tissue culture of claim 1, wherein the concentration of alginate is about 5 mg/mL.

4. The tractable neural tissue culture of claim 1, wherein the concentration of the basement membrane matrix is about 4.4 mg/mL, about 4.6 mg/mL, about 7.36 mg/mL, about 8.5 mg/mL, or about 10 mg/mL.

5. The tractable neural tissue culture of claim 1, wherein the alginate is a salt alginate such as sodium alginate, potassium alginate, or calcium alginate.

6. A tractable neural tissue culture, comprising a 3D matrix, the 3D matrix comprising neuronal and/or glial cells cultured from a stem cell, a biological supporting material comprising a proliferation inhibitor, and one or more calcium crosslinkers, wherein the biological supporting material is a composite hydrogel comprising an basement membrane matrix and alginate;

wherein the concentration of the basement membrane matrix is about 1 mg/mL to about 10;

wherein the concentration of alginate is about 1 mg/mL to about 10 mg/mL;

wherein the concentration of the one or more crosslinker is about 1 mM to about 30 mM;

wherein the 3D matrix comprises hyaluronic acid;

wherein the basement membrane matrix consists of laminin, collagen IV, growth factors, heparin sulfate proteoglycans, entactin, and nidogen, and wherein one or more genes in the neuronal and/or glial cells have increased or decreased expression relative to cells in a two-dimensional or another 3D matrix.

7. The tractable neural tissue culture of claim 6, wherein the one or more crosslinker is independently selected from the group consisting of calcium chloride (CaCl2), zinc sulfate, aluminum chloride, and barium chloride.

8. The tractable neural tissue culture of claim 6, wherein the concentration of the alginate is about 5 mg/mL.

9. The tractable neural tissue culture of claim 6, wherein the concentration of the basement membrane matrix is about 4.4 mg/mL, about 4.6 mg/mL, about 7.36 mg/mL, about 8.5 mg/mL, or about 10 mg/mL.

10. The tractable neural tissue culture of claim 6, wherein the glial cells are human astrocytes.

11. The tractable neural tissue culture of claim 6, wherein the neuronal cells are selected from the group consisting of glutamatergic neurons, GABAergic neurons, dopaminergic neurons, microglia, oligodendrocytes, motor neurons, and bipolar neurons.

12. The tractable neural tissue culture of claim 1, wherein the proliferation inhibitor is 1-β-D-Arabinofuranosylcytosin (Ara-C).

13. The tractable neural tissue culture of claim 6, wherein the alginate is a salt alginate such as sodium alginate, potassium alginate, or calcium alginate.

14. A method of generating a tractable neural tissue culture, comprising:

(a) culturing a stem cell on a two-dimensional plate, (b) inducing differentiation of the stem cell into neuronal and/or glial cells, and (c) detaching and encapsulating the neuronal and/or glial cells in a three dimensional (3D) matrix comprising decreasing the distance of a gene expression profile of the neuronal tissue culture as compared to a target tissue by modulating the density or stiffness of the three dimensional (3D) matrix, wherein the 3D matrix comprises neuronal and/or glial cells cultured from a stem cell, a biological supporting material comprising a proliferation inhibitor, and one or more crosslinker;

wherein the biological supporting material is a composite hydrogel comprising an basement membrane matrix and alginate;

wherein the concentration of the basement membrane matrix is about 1 mg/mL to about 10;

wherein the concentration of alginate is about 1 mg/mL to about 10 mg/mL;

wherein the concentration of the one or more crosslinker is about 1 mM to about 30 mM; and wherein the basement membrane matrix consists of laminin, collagen IV, growth factors, heparin sulfate proteoglycans, entactin, and nidogen.

15. The method of claim 14, wherein the concentration of the alginate is from about 5 mg/mL.

16. The method of claim 14, wherein the one or more crosslinker is independently selected from the group consisting of calcium chloride (CaCl2), zinc sulfate, aluminum chloride, and barium chloride.

17. The method of claim 14, wherein the 3D matrix further comprises hyaluronic acid.

18. The method of claim 14, wherein step (c) further comprises co-culturing the neuronal cells with astrocytes.

19. The method of claim 14, wherein the stem cell expresses one or more transcription factors that drives neuronal differentiation selected from the group consisting of NGN1, NGN2, Neurod1, Ascl1, Dlx2, SOX10, OLIG2, NKX6.2, Isl1, Lhx3, Phox2a, Brn2, Myt1l, Neurogenin-1, and Neurogenin-2.

20. The method of claim 14, wherein the neuronal cells are selected from the group consisting of one or more of glutamatergic neuron, GABAergic neuron, dopaminergic neuron, microglial cell, oligodendrocyte, motor neuron, and bipolar neuron.

21. The method of claim 14, wherein the proliferation inhibitor suppresses proliferation of undifferentiated stem cells.

22. The method of claim 21, wherein the proliferation inhibitor is 1-β-D-Arabinofuranosylcytosin (Ara-C).

23. A method for identifying a candidate agent for treating a neurological disease, comprising:

(a) providing a tractable neural tissue culture comprising a three-dimensional (3D) matrix, the 3D matrix comprising a biological supporting material comprising a proliferation inhibitor, and one or more crosslinker, (b) contacting the tractable neural tissue culture with a test compound, and (c) detecting the expression and/or activity of one or more genes associated with the neurological disease, wherein an increase or decrease of the one or more genes associated with the neurological disease indicates that the agent is effective for treating the neurological disease;

wherein the biological supporting material is a composite hydrogel comprising an basement membrane matrix and alginate;

wherein the concentration of the basement membrane matrix is about 1 mg/mL to about 10;

wherein the concentration of alginate is about 1 mg/mL to about 10 mg/mL;

wherein the concentration of the one or more crosslinker is about 1 mM to about 30 mM; and wherein the basement membrane matrix consists of laminin, collagen IV, growth factors, heparin sulfate proteoglycans, entactin, and nidogen.

24. The method of claim 23, wherein the neurological disease is Alzheimer's disease (AD), Parkinson's disease (PD), Amyotrophic lateral sclerosis (ALS), Autism spectrum disorder (ASD), Frontotemporal Dementia (FTD), X-linked mental disorder, epilepsy, hyperekplexia, Neuropathic pain, Chronic spinal cord injuries, Huntington's disease, spinal muscular atrophy (SMA), spinal and bulbar muscular atrophy (SBMA), a brain cancer, a neurodegenerative disease, a psychiatric or cognitive disorder, or an autoimmune disease.

25. The method of claim 24, wherein the neurological disease is FTD, and the one or more genes are SOD1, TARDBP, and TBK1.

26. The method of claim 24, wherein the neurological disease is ASD, and the one or more genes are CLU3, TRIP12, UBE3A, CACNA1C, CHD8, SETD5, PTEN, SCN2A, MECP2, SMARCA2, and C12orf57.

27. The method of claim 24, wherein the neurological disease is ALS, and the one or more genes are ZSWIM7, SOD1, NTNG1, LHFP, C9orf72, TARDBP, TBK1, and CNTF.

28. The method of claim 24, wherein the neurological disease is AD, and the one or more genes are CLU, SLC24A4, PARK7, BIN1, PICALM, FERMT2, CELF1, and ABCA7.

29. The method of claim 24, wherein the neurological disease is PD, and the one or more genes are SNCA, STK39, DLG2, ASH1L, BCKDK, MAPT, TMEM229B, and LRRK2.

30. The tractable tissue culture of claim 1, wherein the neuronal cells have been modified to express a CRISPR-Cas protein.

31. A method of identifying a gene associated with a neurological disease, comprising:

introducing one or more guide RNAs into the tractable neural tissue culture of claim 30, in which the neuronal cells are either expressing a CRISPR-Cas9 protein or have the CRISPR-Cas9 protein or a nucleic acid encoding the CRISPR-Cas9 protein introduced simultaneously or sequentially with the guide RNAs, wherein the guide RNAs target one or more endogenous genes; and assaying for a phenotype indicative of a neurological disease in the modified neuronal cells to identify a gene associated with the neurological disease.

32. A method for identifying a gene associated with a phenotype of neuronal cells, comprising:

introducing a library of guide RNAs into the tractable neural tissue culture of claim 30, in which the neuronal cells are either expressing a CRISPR-Cas9 protein or have the CRISPR-Cas9 protein or a nucleic acid encoding the CRISPR-Cas9 protein introduced simultaneously or sequentially with the guide RNAs, wherein the guide RNAs target a plurality of endogenous genes;

selecting the neuronal cells based on a pre-determined phenotype; and sequencing guide RNAs present in the selected neuronal cells, wherein the enrichment or depletion of guide RNAs are quantified and/or ranked to identify a gene associated with the pre-determined phenotype.

33. The method of claim 32, further comprising measuring one or more biological characteristics of the neuronal cells.

34. The method of claim 33, wherein the one or more biological characteristics are electrophysiological property, activity based on calcium imaging, and phenotype readout based on fluorescent and bioluminescent imaging.

* * * * *